US011895913B2

(12) United States Patent
Parham et al.

(10) Patent No.: US 11,895,913 B2
(45) Date of Patent: Feb. 6, 2024

(54) MATERIALS FOR ORGANIC LIGHT EMITTING DEVICES

(71) Applicant: Merck Patent GmbH, Darmstadt (DE)

(72) Inventors: Amir Hossain Parham, Darmstadt (DE); Anja Jatsch, Darmstadt (DE); Thomas Eberle, Darmstadt (DE); Tobias Grossmann, Shanghai (CN); Jonas Valentin Kroeber, Darmstadt (DE); Lars Dobelmann-Mara, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 17/994,035

(22) Filed: Nov. 25, 2022

(65) Prior Publication Data

US 2023/0125939 A1 Apr. 27, 2023

Related U.S. Application Data

(63) Continuation of application No. 16/808,515, filed on Mar. 4, 2020, now Pat. No. 11,626,561, which is a continuation of application No. 15/308,749, filed as application No. PCT/EP2015/000705 on Apr. 1, 2015, now Pat. No. 10,622,565.

(30) Foreign Application Priority Data

May 5, 2014 (EP) .................................... 14001573

(51) Int. Cl.
| | |
|---|---|
| H01L 51/50 | (2006.01) |
| H10K 85/60 | (2023.01) |
| C07D 403/14 | (2006.01) |
| C07D 409/14 | (2006.01) |
| C07D 407/14 | (2006.01) |
| H10K 85/30 | (2023.01) |
| C07D 251/24 | (2006.01) |
| C07D 403/04 | (2006.01) |
| C07D 405/04 | (2006.01) |
| C07D 405/10 | (2006.01) |
| C07D 405/14 | (2006.01) |
| C07D 409/04 | (2006.01) |
| C07D 487/04 | (2006.01) |
| C07D 491/06 | (2006.01) |
| C07D 495/04 | (2006.01) |
| C09K 11/02 | (2006.01) |
| C09K 11/06 | (2006.01) |
| H10K 50/11 | (2023.01) |
| H10K 50/16 | (2023.01) |
| H10K 50/18 | (2023.01) |
| H10K 50/12 | (2023.01) |
| H10K 101/10 | (2023.01) |

(52) U.S. Cl.
CPC ......... *H10K 85/654* (2023.02); *C07D 251/24* (2013.01); *C07D 403/04* (2013.01); *C07D 403/14* (2013.01); *C07D 405/04* (2013.01); *C07D 405/10* (2013.01); *C07D 405/14* (2013.01); *C07D 407/14* (2013.01); *C07D 409/04* (2013.01); *C07D 409/14* (2013.01); *C07D 487/04* (2013.01); *C07D 491/06* (2013.01); *C07D 495/04* (2013.01); *C09K 11/025* (2013.01); *C09K 11/06* (2013.01); *H10K 85/342* (2023.02); *H10K 85/615* (2023.02); *H10K 85/622* (2023.02); *H10K 85/624* (2023.02); *H10K 85/626* (2023.02); *H10K 85/657* (2023.02); *H10K 85/6572* (2023.02); *H10K 85/6574* (2023.02); *H10K 85/6576* (2023.02); *C09K 2211/1007* (2013.01); *C09K 2211/1029* (2013.01); *C09K 2211/185* (2013.01); *H10K 50/11* (2023.02); *H10K 50/121* (2023.02); *H10K 50/16* (2023.02); *H10K 50/18* (2023.02); *H10K 2101/10* (2023.02)

(58) Field of Classification Search
USPC ................ 428/690, 917; 313/504, 505, 506; 257/40, E51.05, E51.026, E51.032, 257/E51.052; 548/304.1, 304.4, 418, 548/440, 444
See application file for complete search history.

(56) References Cited

U.S. PATENT DOCUMENTS

| | | | |
|---|---|---|---|
| 9,090,819 B2 | 7/2015 | Sugita et al. | |
| 9,334,260 B2 | 5/2016 | Parham et al. | |

(Continued)

FOREIGN PATENT DOCUMENTS

| | | | |
|---|---|---|---|
| CN | 102770427 A | 11/2012 | |
| CN | 103232843 A | 8/2013 | |

(Continued)

OTHER PUBLICATIONS

International Search Report for PCT/EP2015/000705 dated May 21, 2015.

(Continued)

*Primary Examiner* — Gregory D Clark
(74) *Attorney, Agent, or Firm* — Faegre Drinker Biddle & Reath LLP

(57) ABSTRACT

The present invention describes carbazole, dibenzofuran, dibenzothiophene and fluorene derivatives which are substituted by electron-deficient heteroaryl groups, in particular for use as triplet matrix materials in organic electroluminescent devices. The invention furthermore relates to a process for the preparation of the compounds according to the invention and to electronic devices comprising these compounds.

16 Claims, No Drawings

(56) References Cited

U.S. PATENT DOCUMENTS

| | | |
|---|---|---|
| 2011/0006670 A1 | 1/2011 | Katakura et al. |
| 2011/0057706 A1 | 3/2011 | Chou et al. |
| 2011/0309343 A1 | 12/2011 | Langer et al. |
| 2013/0035275 A1 | 2/2013 | Silvernail et al. |
| 2013/0062597 A1 | 3/2013 | Yoshida et al. |
| 2015/0214489 A1 | 7/2015 | Parham et al. |
| 2015/0228908 A1 | 8/2015 | Lee et al. |
| 2016/0181548 A1 | 6/2016 | Parham et al. |
| 2016/0248023 A1 | 8/2016 | Parham et al. |

FOREIGN PATENT DOCUMENTS

| | | | |
|---|---|---|---|
| CN | 103517906 A | 1/2014 | |
| CN | 105636959 A | 6/2016 | |
| EP | 2754661 A1 | 7/2014 | |
| JP | 2010-135467 A | 6/2010 | |
| JP | 2012-049518 A | 3/2012 | |
| JP | 2013-069905 A | 4/2013 | |
| KR | 10-2012-0104246 A | 9/2012 | |
| KR | 10-2013-0011955 A | 1/2013 | |
| KR | 10-2013-0130236 A | 12/2013 | |
| TW | 201134823 A | 10/2011 | |
| WO | WO 2006/128800 | * 12/2006 | ............ C09K 11/06 |
| WO | 2010/150593 A1 | 12/2010 | |
| WO | 2011/057706 A2 | 5/2011 | |
| WO | 2012/130709 A1 | 10/2012 | |
| WO | 2013/035275 A1 | 3/2013 | |
| WO | 2014/015931 A1 | 1/2014 | |
| WO | 2015/014434 A1 | 2/2015 | |
| WO | 2015/051869 A1 | 4/2015 | |

OTHER PUBLICATIONS

Japanese Office Action for Japanese Application No. 2016-567008 dated Dec. 5, 2018.

* cited by examiner

MATERIALS FOR ORGANIC LIGHT EMITTING DEVICES

This application is a continuation of U.S. application Ser. No. 16/808,515, filed Mar. 4, 2020, which is a continuation of U.S. application Ser. No. 15/308,749, filed Nov. 3, 2016, which is a National stage application (under 35 U.S.C. § 371) of PCT/EP2015/000705, filed Apr. 1, 2015, which claims benefit of European Application No. 14001573.6, filed May 5, 2014, all of which are incorporated herein by reference in their entirety.

The present invention describes carbazole, dibenzofuran, dibenzothiophene and fluorene derivatives which are substituted by electron-deficient heteroaromatic groups, in particular for use as triplet matrix materials in organic electroluminescent devices. The invention furthermore relates to a process for the preparation of the compounds according to the invention and to electronic devices comprising these compounds.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed are frequently organometallic complexes which exhibit phosphorescence instead of fluorescence. For quantum-mechanical reasons, an up to four-fold energy and power efficiency is possible using organometallic compounds as phosphorescence emitters. In general, there is still a need for improvement, for example with respect to efficiency, operating voltage and lifetime, in the case of OLEDs, in particular also in the case of OLEDs which exhibit phosphorescence.

The properties of phosphorescent OLEDs are not determined only by the triplet emitters employed. In particular, the other materials used, such as, for example, matrix materials, are also of particular importance here. Improvements in these materials may thus also result in significant improvements in the OLED properties.

In accordance with the prior art, use is made of, inter alia, carbazole derivatives (for example in accordance with WO 2014/015931), indolocarbazole derivatives (for example in accordance with WO 2007/063754 or WO 2008/056746) or indenocarbazole derivatives (for example in accordance with WO 2010/136109 or WO 2011/000455), in particular those which are substituted by electron-deficient heteroaromatic compounds, such as triazine, as matrix materials for phosphorescent emitters. Furthermore, for example, bis-dibenzofuran derivatives (for example in accordance with EP 2301926) are used as matrix materials for phosphorescent emitters. WO 2011/057706 discloses carbazole derivatives which are substituted by two triphenyltriazine groups. Further improvements are still desirable here, in particular with respect to the triplet level and to the sublimation stability. WO 2011/046182 discloses carbazole-arylene-triazine derivatives which are substituted on the triazine by a fluorenyl group. The characteristic feature of these compounds is the presence of the fluorenyl group. Compounds which do not contain a fluorenyl group as substituent are not disclosed. WO 2013/077352 discloses triazine derivates in which the triazine group is bonded to a dibenzofuran group via a divalent arylene group. These compounds are described as hole-blocking materials. A use of these materials as host for phosphorescent emitters is not described.

In general, there is still a need for improvement in these materials for use as matrix materials, in particular with respect to the lifetime, but also with respect to the efficiency and the operating voltage of the device.

The object of the present invention is the provision of compounds which are suitable for use in a phosphorescent or fluorescent OLED, in particular as matrix material. In particular, it is the object of the present invention to provide matrix materials which are suitable for red-, yellow- and green-phosphorescent OLEDs and optionally also for blue-phosphorescent OLEDs and which result in a long lifetime, good efficiency and a low operating voltage. The properties of the matrix materials in particular also have an essential influence on the lifetime and efficiency of the organic electroluminescent device.

Surprisingly, it has been found that electroluminescent devices which comprise compounds of the following formula (1) or formula (2) have improvements over the prior art, in particular on use as matrix material for phosphorescent dopants.

The present invention therefore relates to a compound of the following formula (1) or (2),

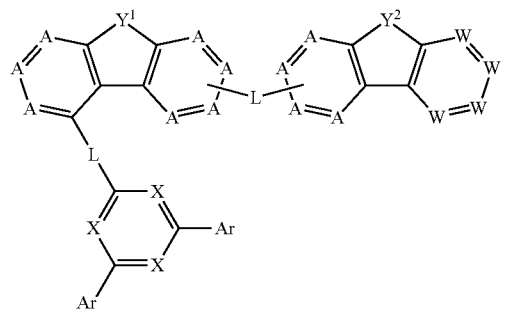

formula (1)

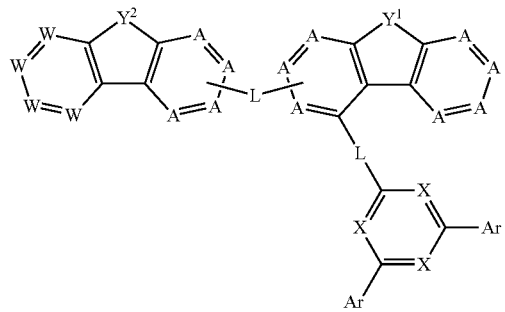

formula (2)

where the following applies to the symbols and indices used:

A is on each occurrence, identically or differently, CR or N, where a maximum of two groups A per ring, preferably a maximum of one group A per ring, stand for N and where A stands for C if a group L is bonded at this position;

W is on each occurrence, identically or differently, CR or N, where a maximum of two groups W stand for N, or two adjacent groups W together stand for a group of the following formula (3), where the compound of the formula (1) or formula (2) contans a maximum of one group of the formula (3),

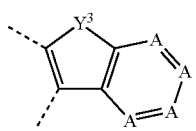

formula (3)

where the dashed bonds indicate the linking of this group and A has the meanings given above; with the proviso that the compound of the formula (2) does not contain a group of the formula (3) if $Y^1$ stands for $C(R)_2$;

X is on each occurrence, identically or differently, CR or N, with the proviso that at least one group X stands for N;

Ar is on each occurrence, identically or differently, an aromatic or heteroaromatic ring system having 5 to 30 aromatic ring atoms, which may be substituted by one or more radicals R;

$Y^1$, $Y^2$, $Y^3$ are on each occurrence, identically or differently, O, NR, S or $C(R)_2$, where the radical R which is bonded to N is not equal to H;

L is on each occurrence, identically or differently, a single bond or an aromatic or heteroaromatic ring system having 5 to 30 aromatic ring atoms, which may be substituted by one or more radicals R;

R is selected on each occurrence, identically or differently, from the group consisting of H, D, F, Cl, Br, I, CN, $NO_2$, $N(Ar^1)_2$, $N(R^1)_2$, $C(=O)Ar^1$, $C(=O)R^1$, $P(=O)(Ar^1)_2$, $P(Ar^1)_2$, $B(Ar^1)_2$, $Si(Ar^1)_3$, $Si(R^1)_3$, a straight-chain alkyl, alkoxy or thioalkyl group having 1 to 20 C atoms or a branched or cyclic alkyl, alkoxy or thioalkyl group having 3 to 20 C atoms or an alkenyl group having 2 to 20 C atoms, each of which may be substituted by one or more radicals $R^1$, where one or more non-adjacent $CH_2$ groups may be replaced by $R^1C=CR^1$, $Si(R^1)_2$, C=O, C=S, $C=NR^1$, P(=O)($R^1$), SO, $SO_2$, $NR^1$, O, S or $CONR^1$ and where one or more H atoms may be replaced by D, F, Cl, Br, I, CN or $NO_2$, an aromatic or heteroaromatic ring system having 5 to 40 aromatic ring atoms, which may in each case be substituted by one or more radicals $R^1$, an aryloxy or heteroaryloxy group having 5 to 40 aromatic ring atoms, which may be substituted by one or more radicals $R^1$, or an aralkyl or heteroaralkyl group having 5 to 40 aromatic ring atoms, which may be substituted by one or more radicals $R^1$; two substituents R which are bonded to the same carbon atom or to adjacent carbon atoms may optionally form a monocyclic or polycyclic, aliphatic, aromatic or heteroaromatic ring system here, which may be substituted by one or more radicals $R^1$;

$Ar^1$ is on each occurrence, identically or differently, an aromatic or heteroaromatic ring system having 5 to 30 aromatic ring atoms, which may be substituted by one or more non-aromatic radicals $R^1$; two radicals $Ar^1$ which are bonded to the same N atom, P atom or B atom may also be bridged to one another here by a single bond or a bridge selected from $N(R^1)$, $C(R^1)_2$, O or S;

$R^1$ is selected on each occurrence, identically or differently, from the group consisting of H, D, F, CN, an aliphatic hydrocarbon radical having 1 to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbon atoms; two or more adjacent substituents $R^1$ may form a mono- or polycyclic, aliphatic ring system with one another here.

Adjacent carbon atoms in the sense of the present invention are carbon atoms which are linked directly to one another.

The formulation that two or more radicals may form a ring with one another is, for the purposes of the present description, intended to be taken to mean, inter alia, that the two radicals are linked to one another by a chemical bond with formal cleaving-off of two hydrogen atoms. This is illustrated by the following scheme:

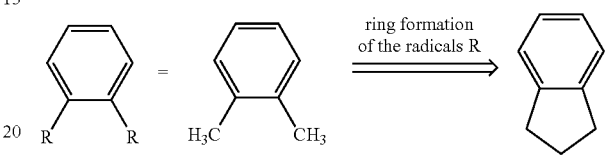

Furthermore, however, the above-mentioned formulation is also intended to be taken to mean that, in the case where one of the two radicals represents hydrogen, the second radical is bonded at the position at which the hydrogen atom was bonded, with formation of a ring. This is intended to be illustrated by the following scheme:

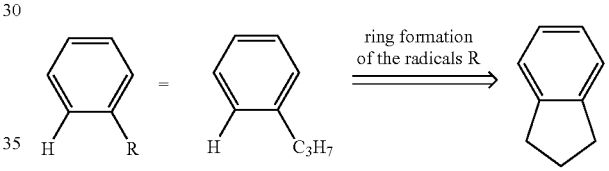

A condensed aryl group in the sense of the present invention is a group in which two or more aromatic groups are condensed, i.e. annellated, onto one another via a common edge, such as, for example, in naphthalene. By contrast, for example, fluorene is not a condensed aryl group in the sense of the present invention, since the two aromatic groups in fluorene do not have a common edge.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 40 C atoms in the ring system. A heteroaromatic ring system in the sense of this invention contains 1 to 40 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl, terphenyl, quaterphenyl or bipyridine, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{20}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-40 aromatic ring atoms, which may also in each case be substituted by the radicals mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or transindenofluorene, trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, W stands, identically or differently on each occurrence, for CR or two W stand for a group of the formula (3a) and the remaining W stand for CR, and A stands, identically or differently on each occurrence, for CR. Preference is thus given to the compounds of the following formulae (1a), (1b), (2a) and (2b),

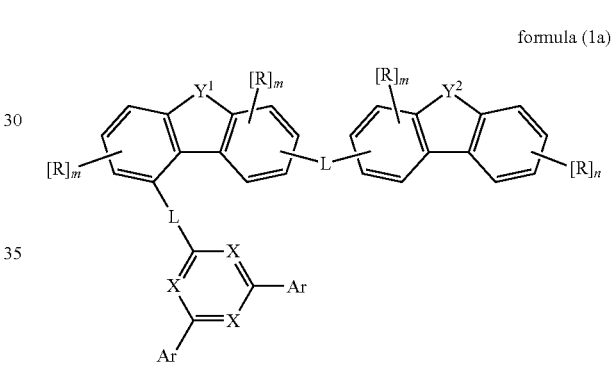

formula (1a)

formula (1b)

formula (2a)

formula (2b)

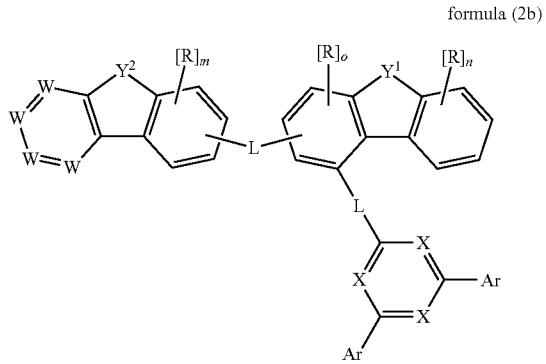

where:

two adjacent groups W together stand for a group of the following formula (3a) and the other two groups W stand for CR and preferably for CH, formula (3a)

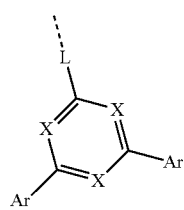

where the dashed bonds indicate the linking of this group;

n is on each occurrence, identically or differently, 0, 1, 2, 3 or 4;

m is on each occurrence, identically or differently, 0, 1, 2 or 3;

o is 0, 1 or 2;

the other symbols used have the meanings given above;

where compounds of the formula (2b) in which $Y^1$ stands for $CR^2$ are excluded from the invention.

In a preferred embodiment of the invention, at least two groups X stand for N, and the group X optionally remaining stands for CR, in particular for CH. In a particularly preferred embodiment of the invention, all groups X stand for N. It is thus particularly preferably a diaryltriazine group.

In a preferred embodiment of the invention, the following group,

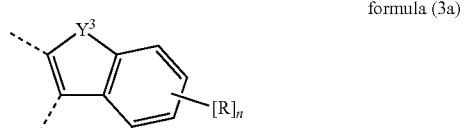

which is bonded in formulae (1) and (2) or the preferred embodiments is therefore selected from the following groups (HetAr-1), (HetAr-2) or (HetAr-3), (HetAr-1)

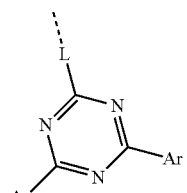

(HetAr-2)

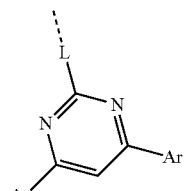

(HetAr-3)

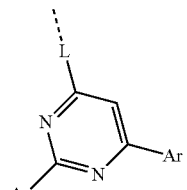

where L and Ar have the meanings given above and the dashed bond indicates the linking of this group.

In a further preferred embodiment of the invention, $Y^1$ and $Y^2$ stand, identically or differently on each occurrence, for O, NR, where the radical R bonded to the nitrogen is not equal to H, or S. It is preferred here for at least one of the groups $Y^1$ and/or $Y^2$ to stand for NR and for $Y^1$ in formula (2) to stand for O or S. In a particularly preferred embodiment of the invention, $Y^1$ and $Y^2$ stand, identically or differently, for O or NR, where the radical R bonded to the nitrogen is not equal to H, where $Y^1$ and $Y^2$ are preferably different. Very particularly preferably, $Y^1$ stands for O and $Y^2$ stands for NR, where the radical R bonded to the nitrogen is not equal to H.

In a further preferred embodiment of the invention, $Y^3$, if the compound contains a group of the formula (3), stands for O, NR, where the radical R bonded to the nitrogen is not equal to H, or $C(R)_2$, particularly preferably for NR, where the radical R bonded to the nitrogen is not equal to H, or $C(R)_2$ and very particularly preferably for $C(R)_2$.

If the compound according to the invention contains a group of the formula (3), this can be bonded in various positions. This is depicted diagrammatically below by the formulae (A) to (F) with reference to preferred embodiments in which the groups A and the other groups W stand for CR:

formula (A)

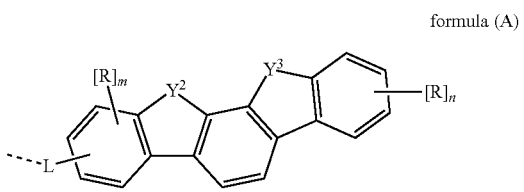

-continued

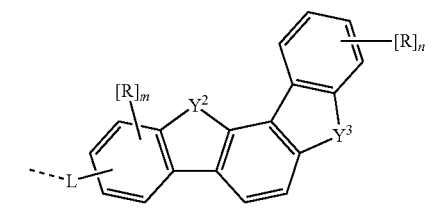
formula (B)

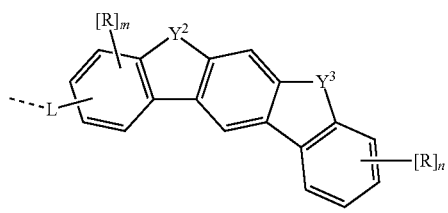
formula (C)

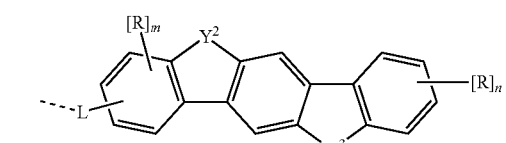
formula (D)

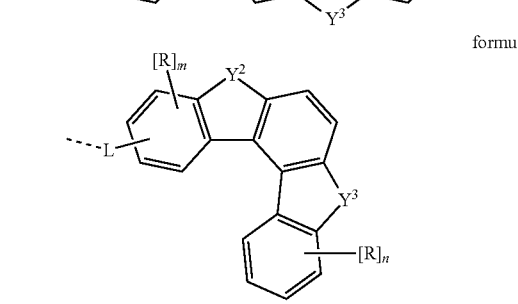
formula (E)

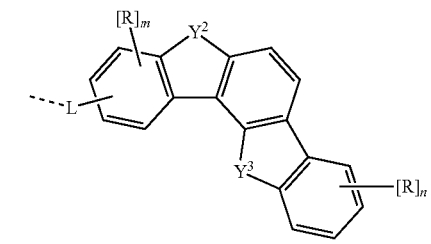
formula (F)

where the symbols and indices used have the meanings given above and the dashed bond represents the linking in the compound according to the invention.

In a further preferred embodiment of the invention, L stands, identically or differently on each occurrence, for a single bond or an aromatic or heteroaromatic ring system having 5 to 24 aromatic ring atoms, which may be substituted by one or more radicals R. L particularly preferably stands, identically or differently on each occurrence, for a single bond or an aromatic ring system having 6 to 12 aromatic ring atoms or a heteroaromatic ring system having 6 to 13 aromatic ring atoms, which may in each case be substituted by one or more radicals R, but is preferably unsubstituted. L very particularly preferably stands for a single bond. Examples of suitable aromatic or heteroaromatic ring systems L are selected from the group consisting of ortho-, meta- or para-phenylene, biphenyl, fluorene, pyridine, pyrimidine, triazine, dibenzofuran, dibenzothiophene and carbazole, each of which may be substituted by one or more radicals R, but is preferably unsubstituted.

In a further preferred embodiment of the invention, Ar stands, identically or differently on each occurrence, for an aromatic or heteroaromatic ring system having 6 to 24 aromatic ring atoms, preferably having 6 to 18 aromatic ring atoms, particularly preferably for an aromatic ring system having 6 to 12 aromatic ring atoms or a heteroaromatic ring system having 6 to 13 aromatic ring atoms, which may in each case be substituted by one or more radicals R, but is preferably unsubstituted. Examples of suitable groups Ar are selected from the group consisting of phenyl, ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals R, but is preferably unsubstituted.

Examples of suitable groups Ar are the structures Ar-1 to Ar-19 shown below,

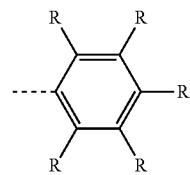
Ar-1

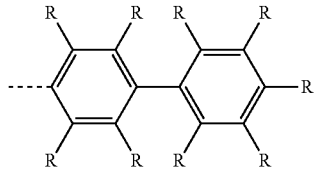
Ar-2

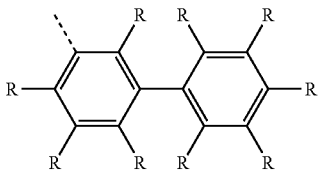
Ar-3

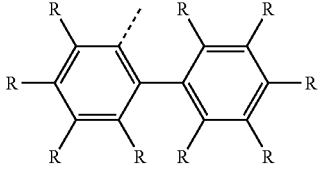
Ar-4

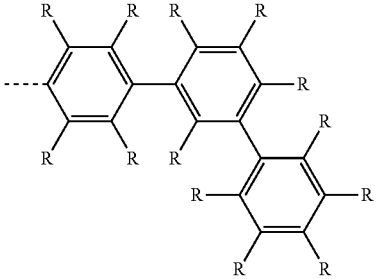
Ar-5

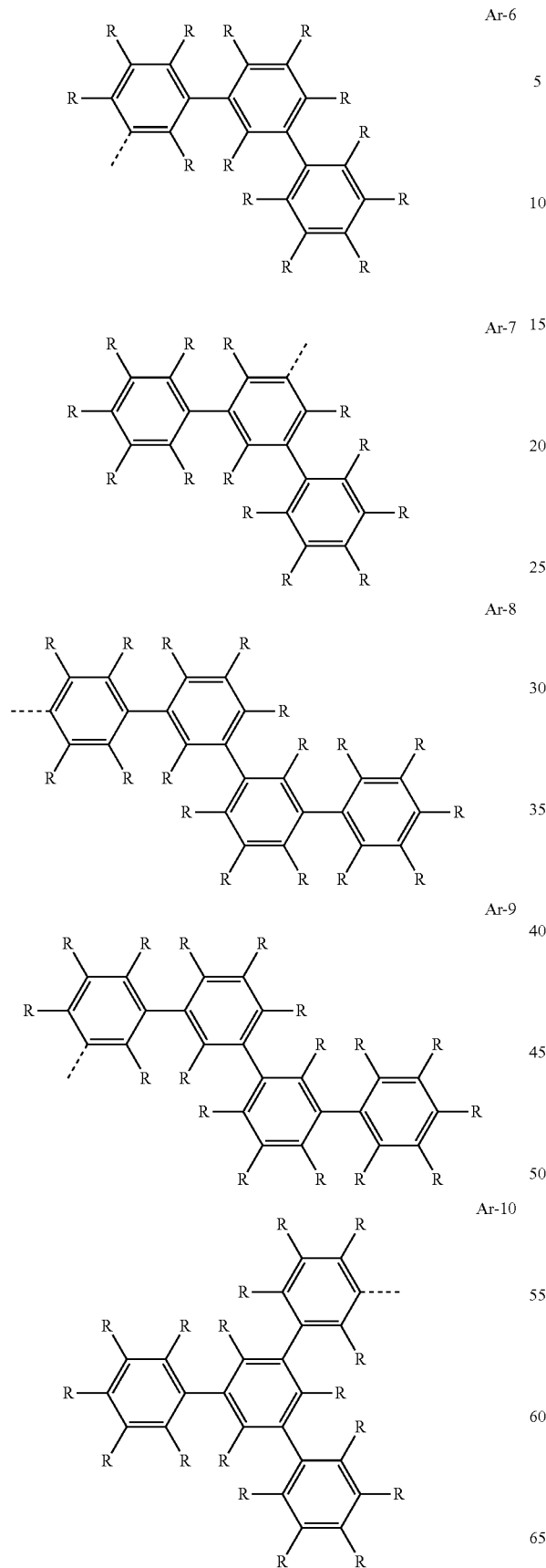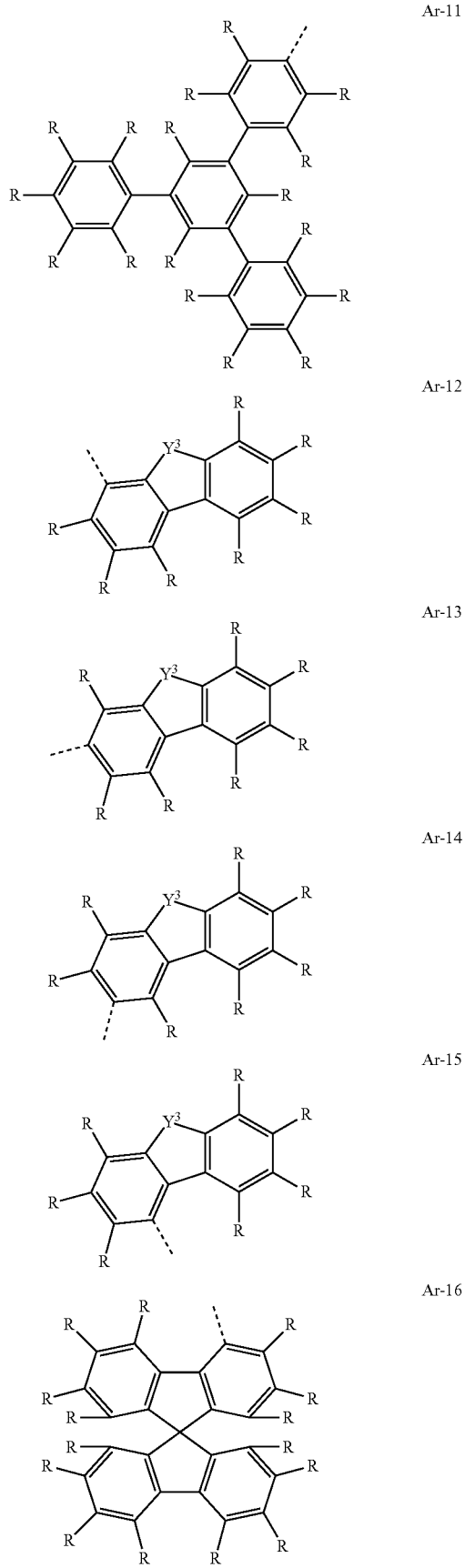

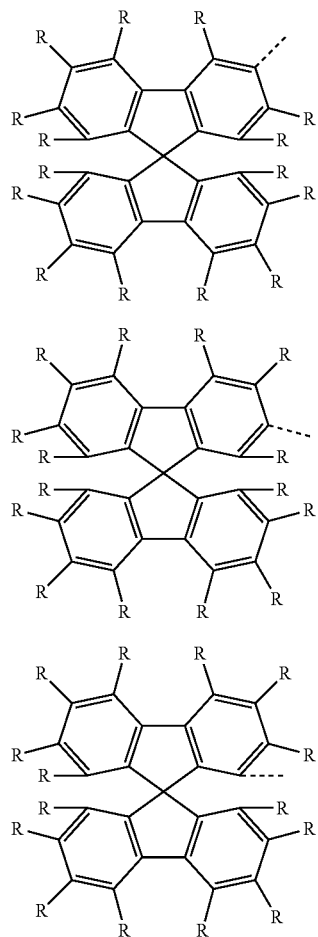

Ar-17

Ar-18

Ar-19 where $Y^3$ and R have the meanings given above and the dashed bond represents the bond to the six-membered heteroaryl ring group in formula (1) or formula (2).

In a further preferred embodiment of the invention, the index n in compounds of the formula (1a) or (2a) is 0, 1, 2 or 3, particularly preferably 0, 1 or 2 and very particularly preferably 0 or 1.

In still a further preferred embodiment of the invention, the index m in compounds of the formula (1a) or (2a) is 0, 1 or 2, particularly preferably 0 or 1 and very particularly preferably 0.

In still a further preferred embodiment of the invention, the index o in compounds of the formula (1a) or (2a) is 0 or 1, particularly preferably 0.

Preferred substituents R are described below. The preferred substituents here depend on whether they are bonded to A or W or to Ar or to $Y^1$, $Y^2$ or $Y^3$ and also depend on how $Y^1$, $Y^2$ and $Y^3$ are selected.

If A stands for CR or if W stands for CR or if the groups Ar are substituted by substituents R, these substituents R are then preferably selected from the group consisting of H, D, F, CN, N(Ar$^1$)$_2$, C(=O)Ar$^1$, P(=O)(Ar$^1$)$_2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals R$^1$, where one or more non-adjacent CH$_2$ groups may be replaced by O and where one or more H atoms may be replaced by D or F, an aromatic or heteroaromatic ring system having 5 to 24 aromatic ring atoms, which may in each case be substituted by one or more radicals R$^1$, but is preferably unsubstituted, or an aralkyl or heteroaralkyl group having 5 to 25 aromatic ring atoms, which may be substituted by one or more radicals R$^1$; two substituents R which are bonded to the same carbon atom or to adjacent carbon atoms may optionally form a monocyclic or polycyclic, aliphatic, aromatic or heteroaromatic ring system here, which may be substituted by one or more radicals R$^1$.

These substituents R are particularly preferably selected from the group consisting of H, D, F, CN, N(Ar$^1$)$_2$, a straight-chain alkyl group having 1 to 8 C atoms, preferably having 1, 2, 3 or 4 C atoms, or a branched or cyclic alkyl group having 3 to 8 C atoms, preferably having 3 or 4 C atoms, or an alkenyl group having 2 to 8 C atoms, preferably having 2, 3 or 4 C atoms, each of which may be substituted by one or more radicals R$^1$, but is preferably unsubstituted, or an aromatic or heteroaromatic ring system having 6 to 24 aromatic ring atoms, preferably having 6 to 18 aromatic ring atoms, particularly preferably having 6 to 13 aromatic ring atoms, which may in each case be substituted by one or more non-aromatic radicals R$^1$, but is preferably unsubstituted; two substituents R which are bonded to the same carbon atom or to adjacent carbon atoms may optionally form a monocyclic or polycyclic, aliphatic ring system here, which may be substituted by one or more radicals R$^1$, but is preferably unsubstituted.

The substituents R are very particularly preferably selected from the group consisting of H or an aromatic or heteroaromatic ring system having 6 to 18 aromatic ring atoms, preferably having 6 to 13 aromatic ring atoms, which may in each case be substituted by one or more non-aromatic radicals R$^1$, but is preferably unsubstituted. Examples of suitable substituents R are selected from the group consisting of phenyl, ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals R$^1$, but is preferably unsubstituted. Suitable structures R here are the same structures as depicted above for Ar-1 to Ar-19, where these structures are substituted by R$^1$ instead of R. For substituents R on the groups Ar, apart from the groups mentioned above, straight-chain alkyl groups having 1 to 4 C atoms or branched or cyclic alkyl groups having 3 to 6 C atoms are also particularly preferred.

If $Y^1$ or $Y^2$ or $Y^3$ stands for NR, the radical R which is bonded to this nitrogen atom preferably stands on each occurrence, identically or differently, for an aromatic or heteroaromatic ring system having 5 to 24 aromatic ring atoms, which may in each case be substituted by one or more radicals R$^1$, particularly preferably for an aromatic or heteroaromatic ring system having 6 to 18 aromatic ring atoms, which may be substituted by one or more radicals R$^1$. Examples of suitable substituents R are selected from the group consisting of phenyl, ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1,3,5-triazinyl, 4,6-diphenyl-1,3,5-triazinyl, 1-, 2-, 3- or 4-dibenzofuranyl, 1-, 2-, 3- or 4-dibenzothienyl and 1-, 2-, 3- or 4-carbazolyl, where the carbazolyl group is substituted on the nitrogen atom by a radical R$^1$ which is not equal to H or D. These groups may each be substituted by one or more radicals R$^1$ here, but are preferably unsubstituted. Suitable structures R here are the same structures as depicted above for Ar-1 to $Ar^{19}$, where these structures are substituted by $R^1$ instead of R.

If $Y^1$ or $Y^2$ or $Y^3$ stands for $C(R)_2$, the radicals R which are bonded to this carbon atom preferably stand on each occurrence, identically or differently, for a straight-chain alkyl group having 1 to 10 C atoms or a branched or cyclic alkyl group having 3 to 10 C atoms or an alkenyl group having 2 to 10 C atoms, each of which may be substituted by one or more radicals $R^1$, where one or more non-adjacent $CH_2$ groups may be replaced by 0 and where one or more H atoms may be replaced by D or F, or for an aromatic or heteroaromatic ring system having 5 to 24 aromatic ring atoms, which may in each case be substituted by one or more radicals $R^1$; the two substituents R may optionally form a monocyclic or polycyclic, aliphatic, aromatic or heteroaromatic ring system here, which may be substituted by one or more radicals $R^1$. Ring formation of the two substituents R forms a spiro system, for example a spirobifluorene or a derivative of a spirobifluorene, if the groups R stand for phenyl groups.

In a further preferred embodiment of the invention, $R^1$ is selected on each occurrence, identically or differently, from the group consisting of H, D, F, CN, an aliphatic hydrocarbon radical having 1 to 10 C atoms, preferably having 1, 2, 3 or 4 C atoms, or an aromatic or heteroaromatic ring system having 5 to 30 aromatic ring atoms, preferably having 5 to 24 aromatic ring atoms, particularly preferably having 5 to 13 aromatic ring atoms, which may be substituted by one or more alkyl groups, each having 1 to 4 carbon atoms, but is preferably unsubstituted.

If the compound according to the invention is substituted by aromatic or heteroaromatic groups R or R' or Ar or Ar', these preferably contain no aryl or heteroaryl groups having more than two aromatic six-membered rings condensed directly onto one another. The substituents particularly preferably contain absolutely no aryl or heteroaryl groups having six-membered rings condensed directly onto one another. This preference is due to the low triplet energy of such structures. Condensed aryl groups having more than two aromatic six-membered rings condensed directly onto one another which are nevertheless also suitable in accordance with the invention are phenanthrene and triphenylene, since these also have a high triplet level.

The preferences indicated above may occur individually or together. The preferences indicated above preferably occur together.

Preference is thus given to compounds of the above-mentioned formulae (1), (2), (1a), (1 b), (2a) and (2b) for which:
- X is, identically or differently on each occurrence, CR or N, where at least two groups X stand for N and any remaining group X stands for CR, in particular for CH;
- $Y^1$, $Y^2$ stand, identically or differently on each occurrence, for O, NR, where the radical R bonded to the nitrogen is not equal to H, or S; preferably, at least one of the groups $Y^1$ and/or $Y^2$ stands for NR and $Y^1$ in formulae (2), (2a) and (2b) stands for O or S here;
- $Y^3$ stands for O, NR, where the radical R bonded to the nitrogen is not equal to H, or $CR^2$;
- L stands, identically or differently on each occurrence, for a single bond or an aromatic or heteroaromatic ring system having 5 to 24 aromatic ring atoms, in particular having 6 to 12 aromatic ring atoms, which may be substituted by one or more radicals R, but is preferably unsubstituted;
- Ar stands, identically or differently on each occurrence, for an aromatic or heteroaromatic ring system having 6 to 24 aromatic ring atoms, which may be substituted by one or more radicals R, but is preferably unsubstituted;
- n in formula (1a), (1 b), (2a) or (2b) is, identically or differently on each occurrence, 0, 1, 2 or 3, preferably 0, 1 or 2;
- m in formula (1a), (1b), (2a) or (2b) is, identically or differently on each occurrence, 0, 1 or 2, preferably 0 or 1;
- o in formula (1a), (1 b), (2a) or (2b) is 0 or 1;
- R is selected, identically or differently on each occurrence, from the group consisting of H, D, F, CN, $N(Ar^1)_2$, $C(=O)Ar^1$, $P(=O)(Ar^1)_2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals $R^1$, where one or more non-adjacent $CH_2$ groups may be replaced by O and where one or more H atoms may be replaced by D or F, an aromatic or heteroaromatic ring system having 5 to 24 aromatic ring atoms, which may in each case be substituted by one or more radicals $R^1$, or an aralkyl or heteroaralkyl group having 5 to 25 aromatic ring atoms, which may be substituted by one or more radicals $R^1$; two substituents R which are bonded to the same carbon atom or to adjacent carbon atoms may optionally form a monocyclic or polycyclic, aliphatic, aromatic or heteroaromatic ring system here, which may be substituted by one or more radicals $R^1$;
- $R^1$ is defined as above.

Particular preference is given to compounds of the above-mentioned formulae (1), (2), (1a), (1 b), (2a) and (2b), for which:
- X is N;
- $Y^1$, $Y^2$ stand, identically or differently on each occurrence, for O or NR, where the radical R bonded to the nitrogen is not equal to H; preferably: $Y^1$ stands for O and $Y^2$ stands for NR, or $Y^1$ stands for NR and $Y^2$ stands for O, or $Y^1$ and $Y^2$ stand for NR;
- $Y^3$ stands for NR, where the radical R bonded to the nitrogen is not equal to H, or $CR_2$;
- L stands for a single bond;
- Ar stands, identically or differently on each occurrence, for an aromatic or heteroaromatic ring system having 6 to 18 aromatic ring atoms, preferably having 6 to 13 aromatic ring atoms, which may in each case be substituted by one or more radicals R, but is preferably unsubstituted;
- n in formulae (1a) to (2b) is on each occurrence, identically or differently, 0 or 1;
- in formulae (1a) to (2b) is 0;
- o in formulae (1a) to (2b) is 0;
- R is selected, identically or differently on each occurrence, from the group consisting of H, D, F, CN, $N(Ar^1)_2$, a straight-chain alkyl group having 1 to 8 C atoms, preferably having 1, 2, 3 or 4 C atoms, or a branched or cyclic alkyl group having 3 to 8 C atoms, preferably having 3 or 4 C atoms, or an alkenyl group having 2 to 8 C atoms, preferably having 2, 3 or 4 C atoms, each of which may be substituted by one or more radicals $R^1$, but is preferably unsubstituted, or an aromatic or heteroaromatic ring system having 6 to 24 aromatic ring atoms, preferably having 6 to 18 aromatic ring atoms, particularly preferably having 6 to 12 aromatic ring atoms, which may in each case be substituted by one or more non-aromatic radicals R$^1$, but is preferably unsubstituted; two substituents R which are bonded to the same carbon atom or to adjacent carbon atoms may optionally form a monocyclic or polycyclic, aliphatic ring system here, which may be substituted by one or more radicals R$^1$, but is preferably unsubstituted;

R$^1$ is defined as above.

The groups containing Y$^1$ and Y$^2$ are dibenzofuran derivatives for Y$^1$ or Y$^2$ =O, carbazole derivatives for Y$^1$ or Y$^2$=NR, dibenzothiophene derivatives for Y$^1$ or Y$^2$=S and fluorene derivatives for Y$^1$ or Y$^2$=C(R)$_2$. If the two radicals R in the CR$^2$ group form a ring with one another, a spiro system forms therefrom, for example a spirobifluorene derivative if the radicals R stand for phenyl.

These groups may be linked to one another in various positions and may be substituted in various positions. The numbering of the positions of the individual groups is depicted diagrammatically below by the formulae (4) and (5), where the compounds according to the invention arise through linking of the formulae (4) and (5) to one another via a group L:

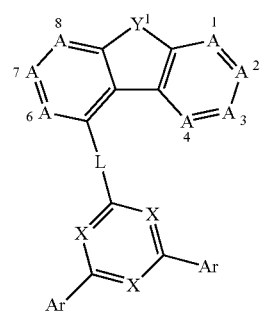

formula (4)

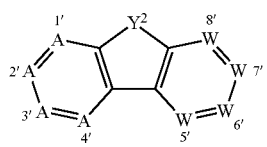

formula (5)

For compounds of the formula (1), the links 1-1', 1-2', 1-3', 1-4', 2-1', 2-2', 2-3', 2-4', 3-1', 3-2', 3-3', 3-4', 4-1', 4-2', 4-3' and 4-4' are thus suitable. A link 1-2' here, for example, means that the group of the formula (4) and the group of the formula (5) are linked to one another via a group L via the 1-position and 2'-position respectively.

For compounds of the formula (2), the links 6-1', 6-2', 6-3', 6-4', 7-1', 7-2', 7-3', 7-4', 8-1', 8-2', 8-3' and 8-4' are suitable.

In principle, all linking patterns indicated above can be combined with the preferences indicated above for the symbols and indices. The preferred linking pattern depends on the choice of Y$^1$ and Y$^2$.

If Y$^1$ stands for O, NR or S, the group of the formula (4) is preferably linked via the 1-position, the 2-position or the 3-position in formula (1) or via the 8-position in formula (2). The links 1-1', 1-2', 1-3', 1-4', 2-1', 2-2', 2-3', 2-4', 3-1', 3-2', 3-3' and 3-4' are thus preferred for compounds of the formula (1) where Y$^1$=O, NR or S and the links 8-1', 8-2', 8-3' and 8-4' are thus preferred for compounds of the formula (2).

Preferred embodiments of the compounds according to the invention are thus the compounds of the following formulae (6), (7), (8) and (9)

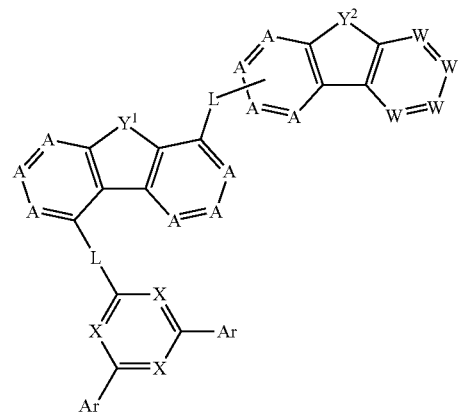

formula (6)

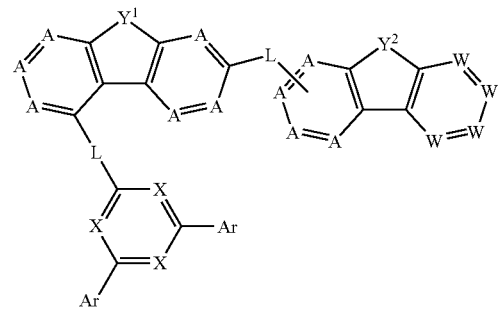

formula (7)

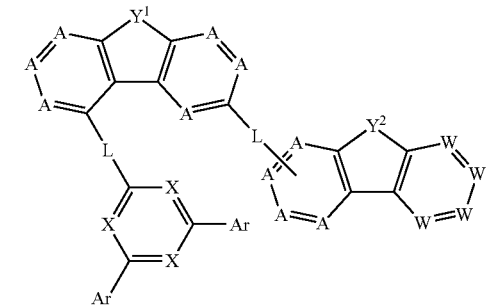

formula (8)

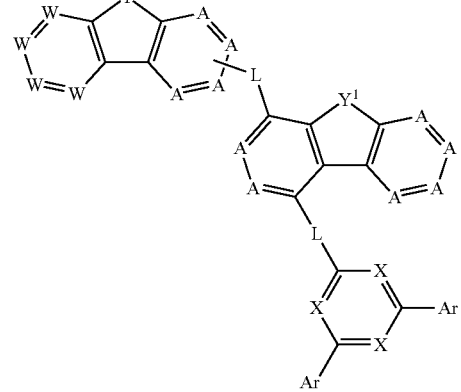

formula (9)

where Y$^1$ stands for O, NR or S, the other symbols used have the meanings given above and A preferably stands, identically or differently, for CR and W preferably stands, identically or differently on each occurrence, for CR or two groups W stand for a group of the formula (3) indicated above and the other groups W stand for CR. Particularly preferably, A and W stand, identically or differently on each occurrence, for CR.

If $Y^1$ stands for $C(R)_2$, the group of the formula (4) is preferably linked via the 2-position in formula (1) or via the 7-position in formula (2). The links 2-1', 2-2', 2-3' and 2-4' are thus preferred for compounds of the formula (1) where $Y^1=C(R)_2$ and the links 7-1', 7-2', 7-3' and 7-4' are thus preferred for compounds of the formula (2). For $Y=C(R)_2$, a compound of the formula (1) and not a compound of the formula (2), in particular, is involved. A preferred embodiment of the compounds according to the invention for $Y^1=CR^2$ is thus the compound of the following formula (10),

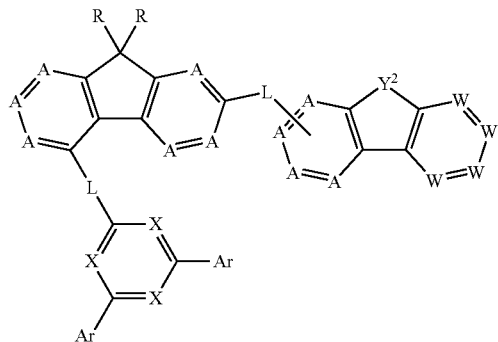

formula (10)

where the symbols used have the meanings given above and where A and W preferably stand, identically or differently on each occurrence, for CR.

If $Y^2$ stands for O, the group of the formula (5) is preferably linked via the 1'-, 3'- or 4'-position. The links 1-1', 1-3', 1-4', 2-1', 2-3', 2-4', 3-1', 3-3', 3-4', 4-1', 4-3' and 4-4' are thus preferred for compounds of the formula (1). The links 6-1', 6-3', 6-4', 7-1', 7-3', 7-4', 8-1', 8-3' and 8-4' are preferred for compounds of the formula (2).

If $Y^2$ stands for NR, the group of the formula (5) is preferably linked via the 2'- or 3'-position. The links 1-2', 1-3', 2-2', 2-3', 3-2', 3-3', 4-2' and 4-3' are thus preferred for compounds of the formula (1). The links 6-2', 6-3', 7-2', 7-3', 8-2' and 8-3' are preferred for compounds of the formula (2).

If $Y^2$ stands for S, the group of the formula (5) is preferably linked via the 1-, 2-, 3- or 4-position. The links 1-1', 1-2', 1-3', 1-4', 2-1', 2-2', 2-3', 2-4', 3-1', 3-2', 3-3', 3-4', 4-1', 4-2', 4-3' and 4-4' are thus preferred for compounds of the formula (1). The links 6-1', 6-2', 6-3', 6-4', 7-1', 7-2', 7-3', 7-4', 8-1', 8-2', 8-3' and 8-4' are preferred for compounds of the formula (2).

If $Y^2$ stands for $C(R)_2$, the group of the formula (5) is preferably linked via the 1'-, 2'- or 4'-position, particularly preferably via the 2'- or 4'-position.

The links 1-1', 2-1', 3-1', 4-1', 1-2', 2-2', 3-2', 4-2', 1-4', 2-4', 3-4' and 4-4' are thus preferred for compounds of the formula (1) and the links 6-1', 7-1', 8-1', 6-2', 7-2', 8-2', 6-4', 7-4' and 8-4' are thus preferred for compounds of the formula (2).

The precise preferred linking pattern for the groups $Y^2$ indicated above in each case depends on the group $Y^1$ used, as described above.

Preference is given to compounds of the formula (8) indicated above in which $Y^2$ stands for NR, O or S and the group of the formula (5) is linked via the 3'-position, in accordance with the following formula (8a) and preferably in accordance with the following formula (8b),

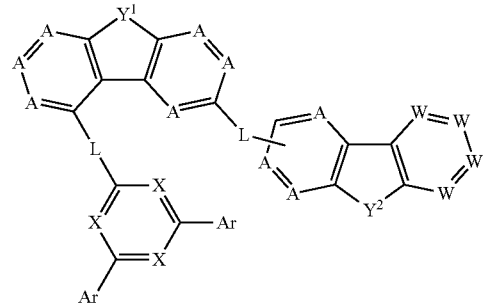

formula (8a)

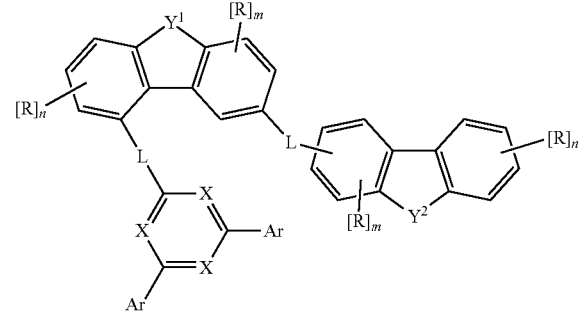

formula (8b)

where $Y^1$ stands for O, NR or S, $Y^2$ stands for NR, O or S and the other symbols and indices used have the meanings given above and in particular the meanings given as preferred and particularly preferred above.

Particular preference is thus given to the compounds of the following formula (8c),

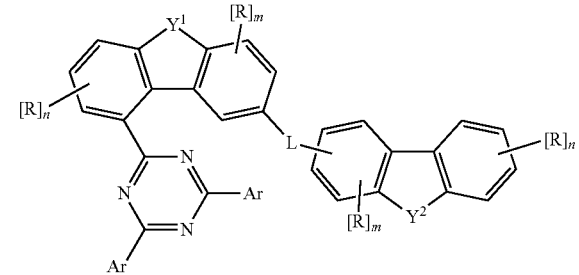

formula (8c)

where the following applies to the symbols and indices used:

$Y^1$, $Y^2$ stand, identically or differently on each occurrence, for O, NR, where the radical R bonded to the nitrogen is not equal to H, or S, with the proviso that at least one of the groups $Y^1$ and/or $Y^2$ stands for NR, and preferably stand for O or NR, where the radical R bonded to the nitrogen is not equal to H;

Ar stands, identically or differently on each occurrence, for an aromatic or heteroaromatic ring system having 6 to 24 aromatic ring atoms, preferably having 6 to 18 aromatic ring atoms, which may in each case be substituted by one or more radicals R, but is preferably unsubstituted;

n is, identically or differently on each occurrence, 0, 1, 2 or 3, preferably 0, 1 or 2, particularly preferably 0 or 1;

m is, identically or differently on each occurrence, 0, 1 or 2, preferably 0 or 1, particularly preferably 0;

is 0 or 1, particularly preferably 0;

R is selected, identically or differently on each occurrence, from the group consisting of H, D, F, CN, N(Ar$^1$)$_2$, C(=O)Ar$^1$, P(=O)(Ar$^1$)$_2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals R$^1$, where one or more non-adjacent CH$_2$ groups may be replaced by 0 and where one or more H atoms may be replaced by D or F, an aromatic or heteroaromatic ring system having 5 to 24 aromatic ring atoms, which may in each case be substituted by one or more radicals R$^1$, or an aralkyl or heteroaralkyl group having 5 to 25 aromatic ring atoms, which may be substituted by one or more radicals R$^1$; two substituents R which are bonded to the same carbon atom or to adjacent carbon atoms may optionally form a monocyclic or polycyclic, aliphatic, aromatic or heteroaromatic ring system here, which may be substituted by one or more radicals R$^1$; R is preferably selected, identically or differently on each occurrence, from the group consisting of H, D, F, CN, N(Ar$^1$)$_2$, a straight-chain alkyl group having 1 to 8 C atoms, preferably having 1, 2, 3 or 4 C atoms, or a branched or cyclic alkyl group having 3 to 8 C atoms, preferably having 3 or 4 C atoms, or an alkenyl group having 2 to 8 C atoms, preferably having 2, 3 or 4 C atoms, each of which may be substituted by one or more radicals R$^1$, but is preferably unsubstituted, or an aromatic or heteroaromatic ring system having 6 to 24 aromatic ring atoms, preferably having 6 to 18 aromatic ring atoms, particularly preferably having 6 to 12 aromatic ring atoms, which may in each case be substituted by one or more non-aromatic radicals R$^1$, but is preferably unsubstituted; two substituents R which are bonded to the same carbon atom or to adjacent carbon atoms may optionally form a monocyclic or polycyclic, aliphatic ring system here, which may be substituted by one or more radicals R$^1$, but is preferably unsubstituted.

R$^1$ here has the meanings given above and, if Y$^1$ and/or Y$^2$ stand(s) for NR, this radical R is preferably selected from the substituents as indicated above as preferred substituents on R.

Very particular preference is given to a compound of the following formula (8d), formula (8d)

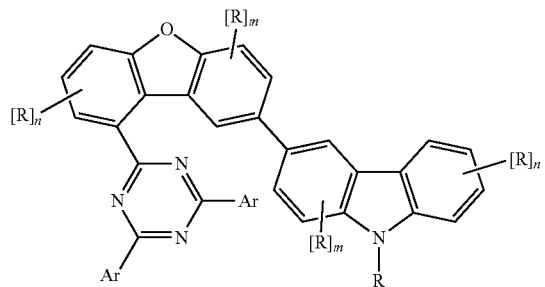

where the symbols and indices used have the meanings given under formula (8c) and the radical R bonded to the nitrogen stands for an aromatic or heteroaromatic ring system having 5 to 24 aromatic ring atoms, which may in each case be substituted by one or more radicals R$^1$, preferably for an aromatic or heteroaromatic ring system having 6 to 18 aromatic ring atoms, which may be substituted by one or more radicals R$^1$.

Examples of suitable compounds according to the invention are the structures shown below.

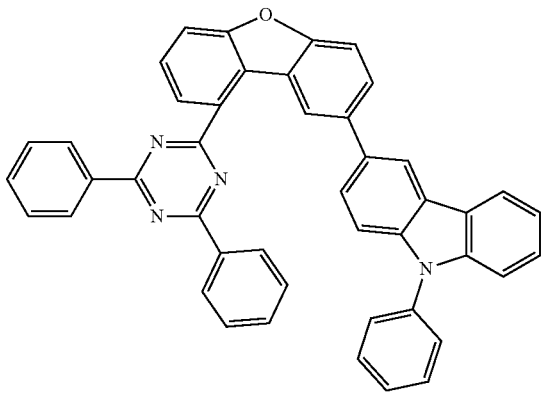

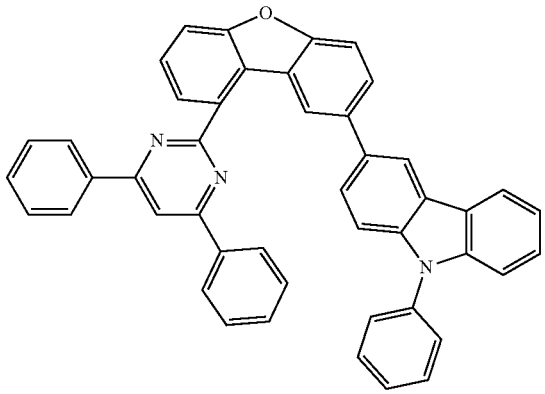

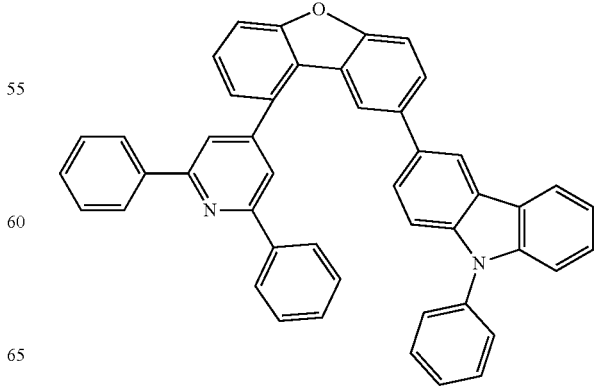

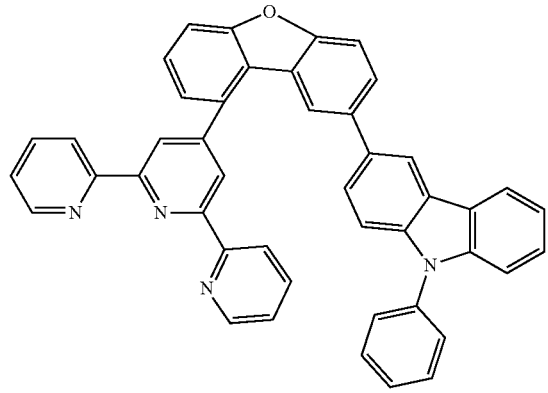
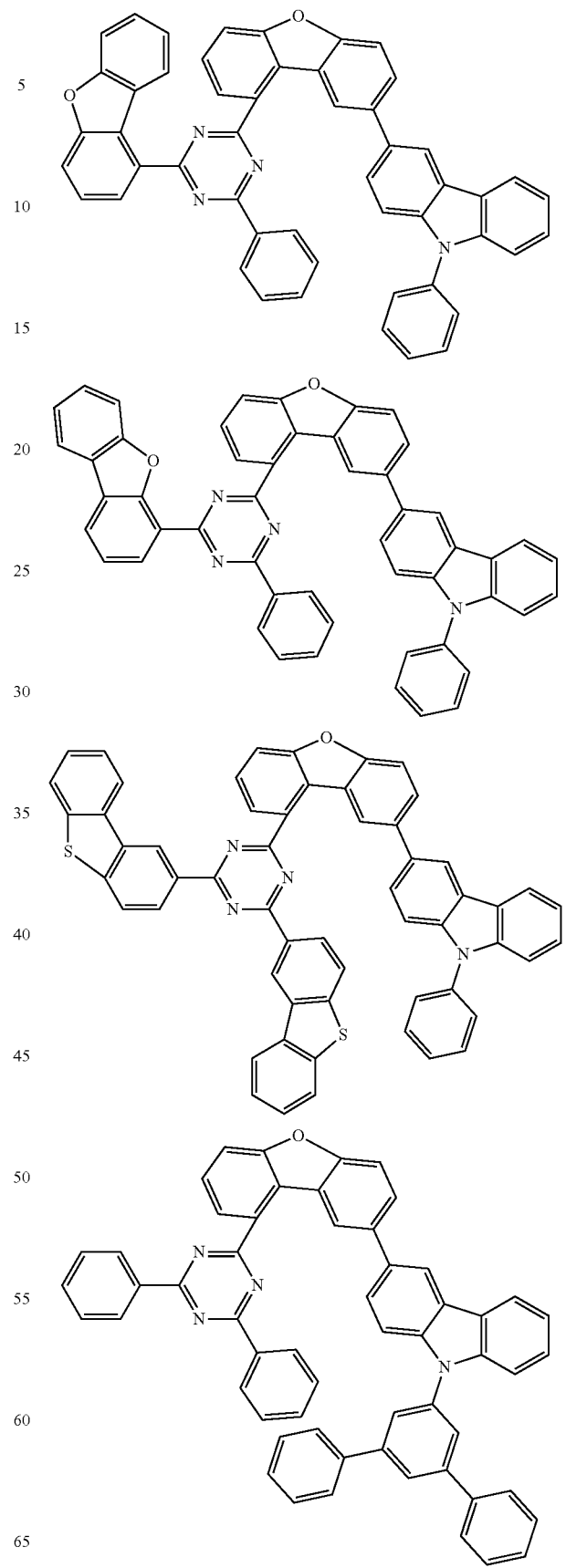

-continued
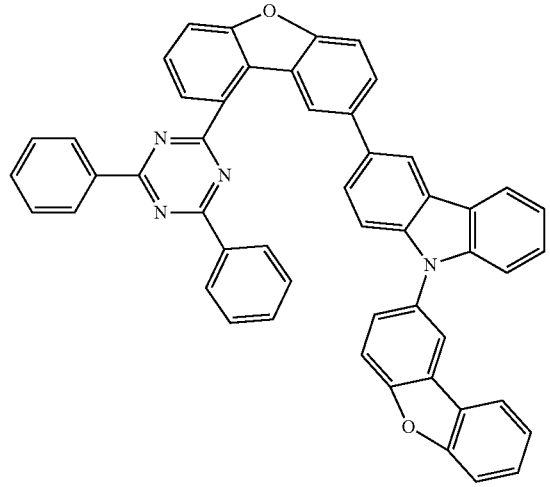
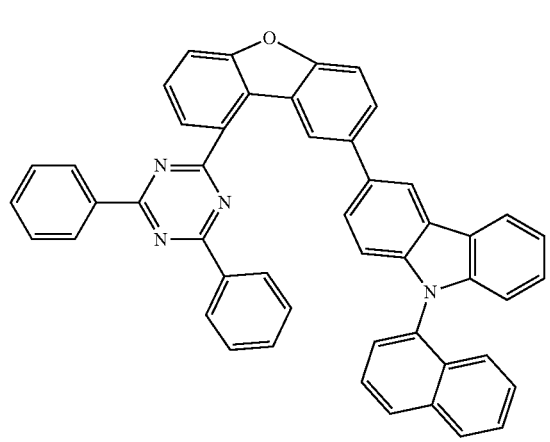
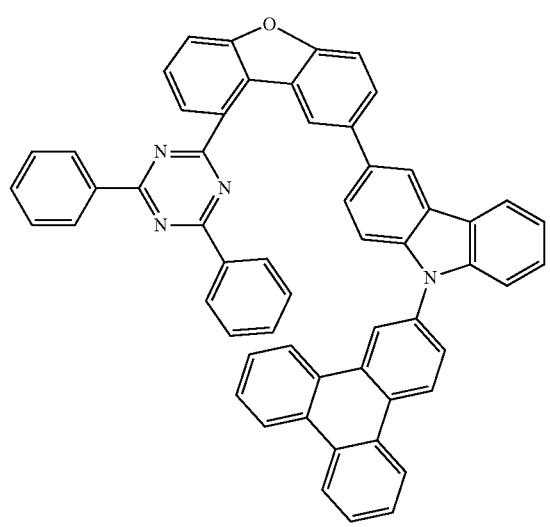
-continued
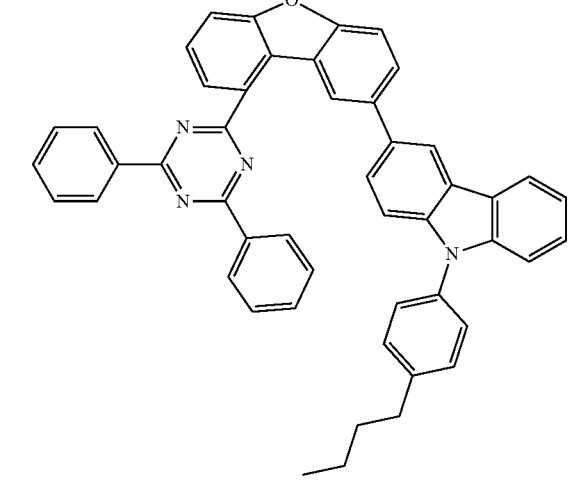
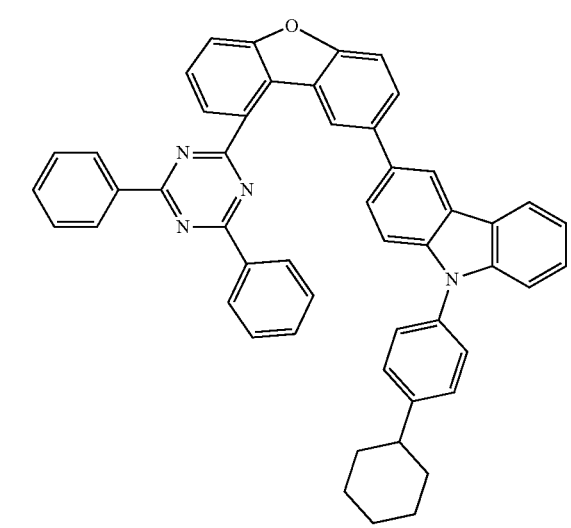
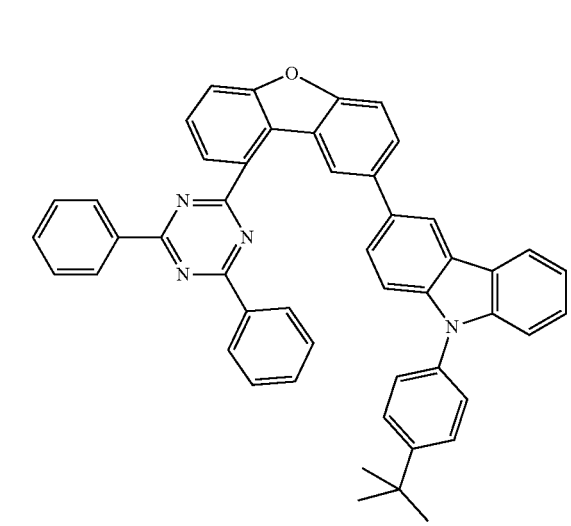

27
-continued
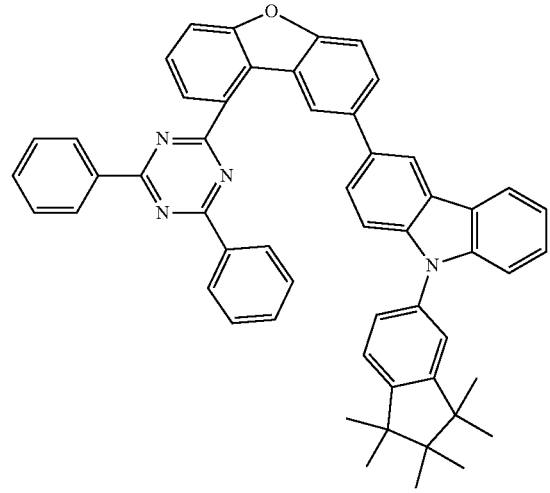
28
-continued
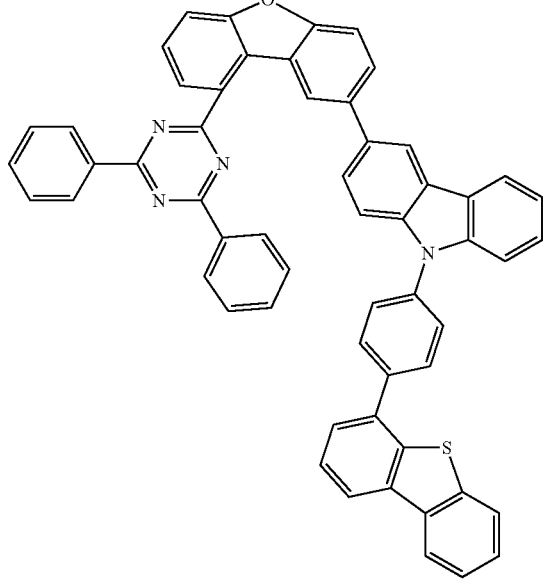
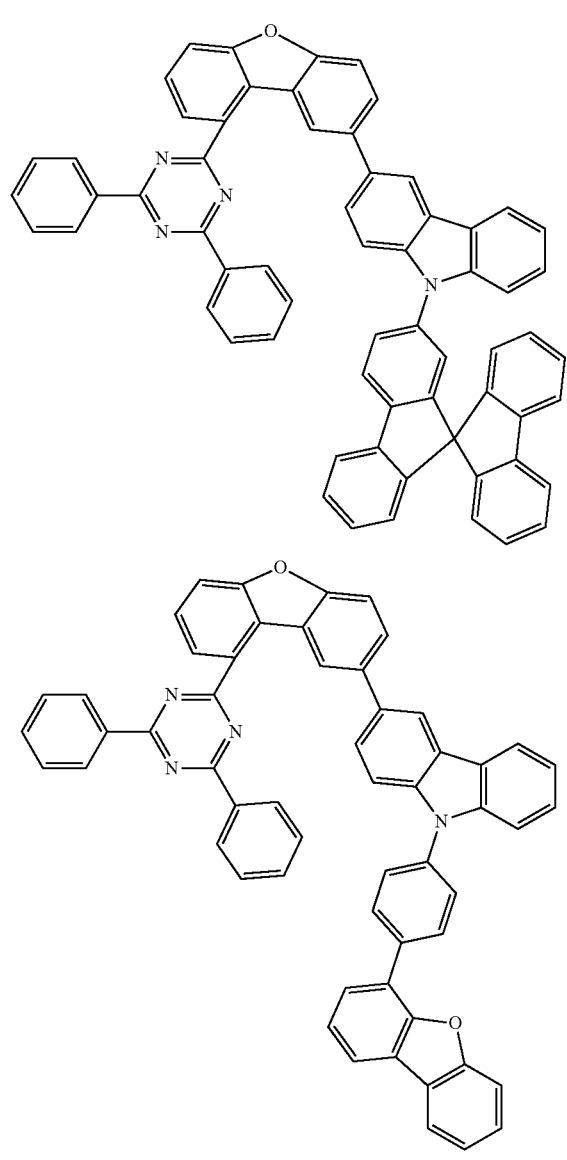
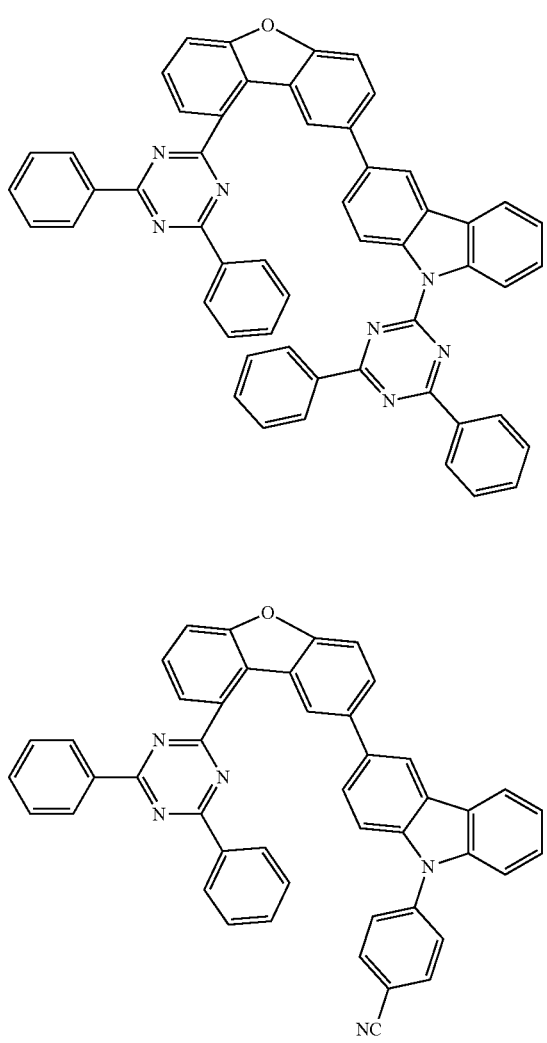

-continued
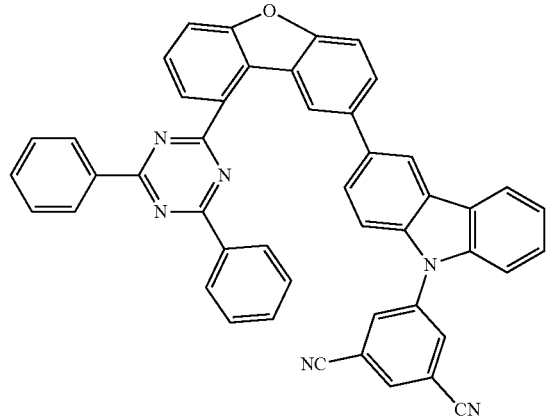
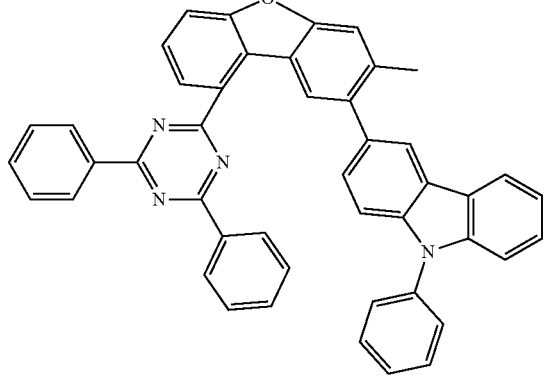
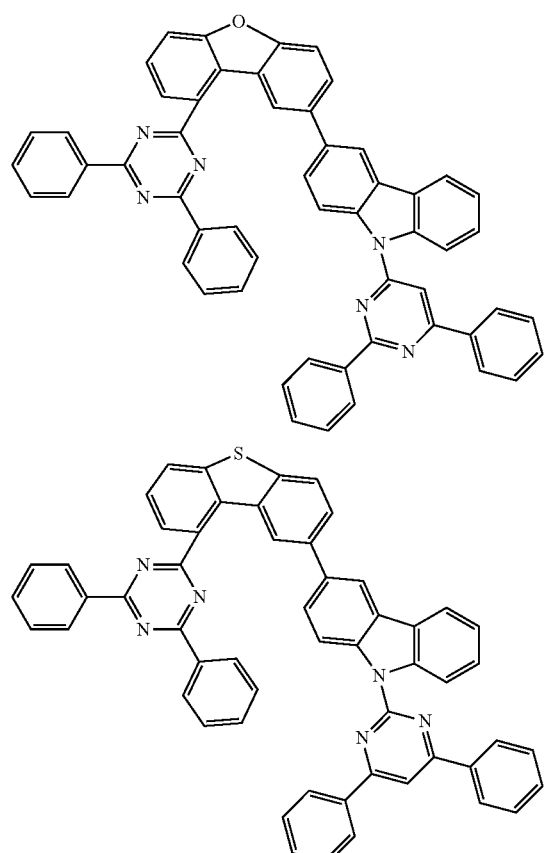
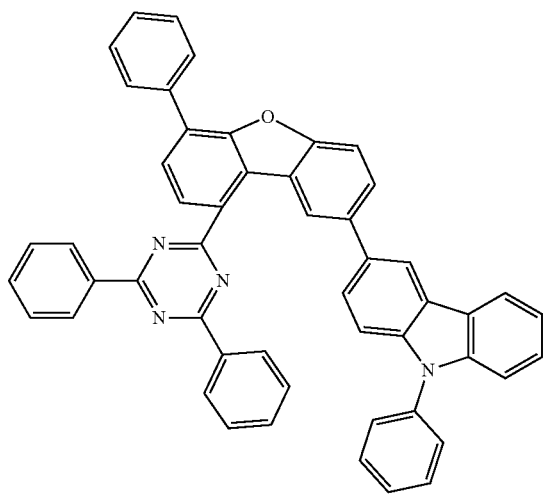
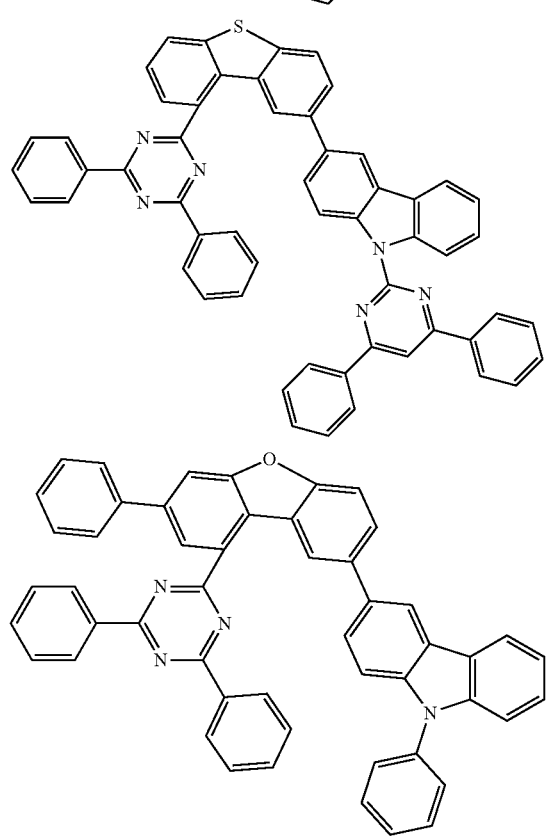
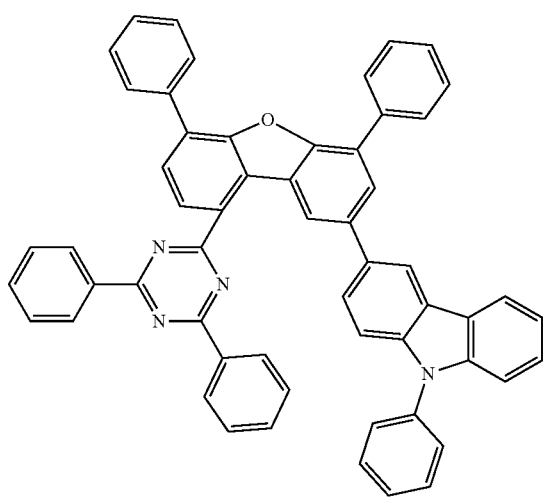

31
-continued
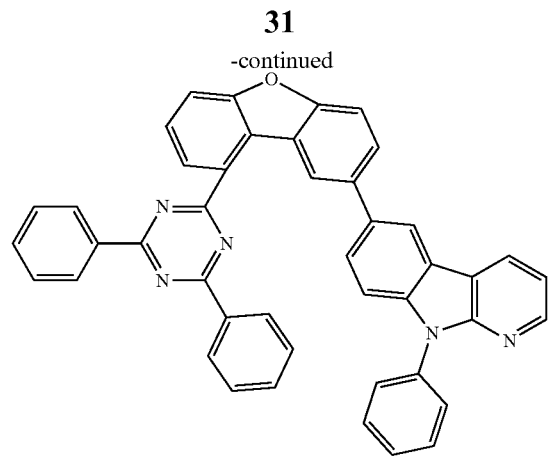
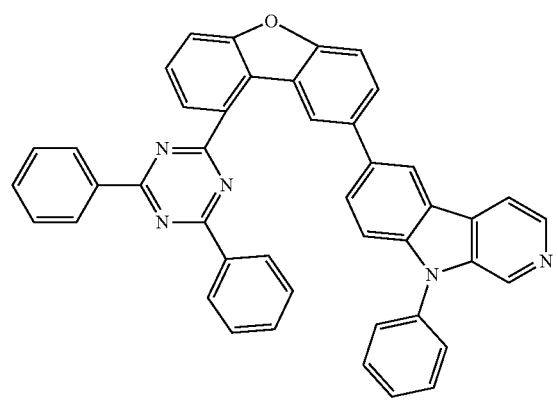
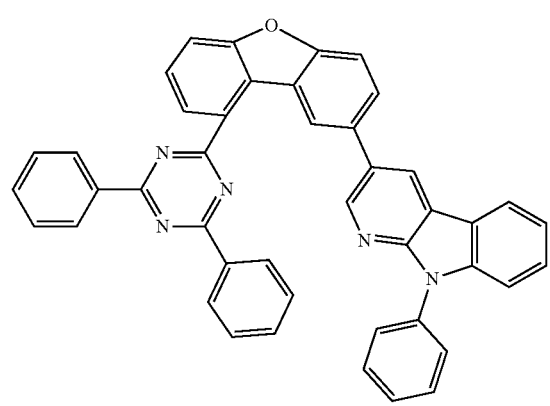
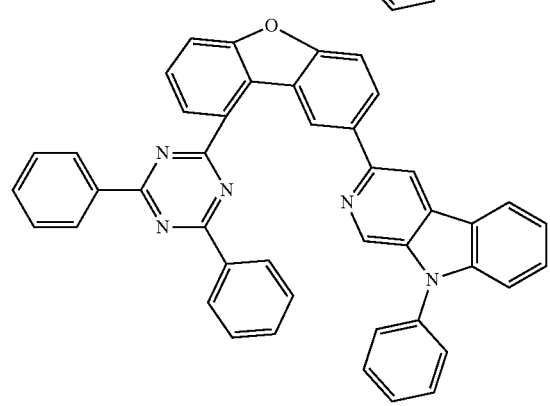
32
-continued
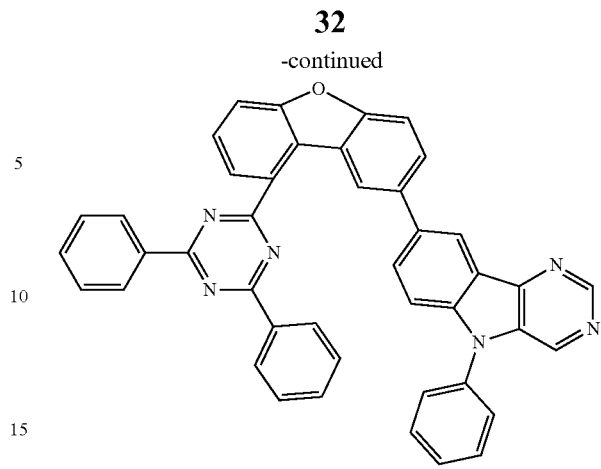
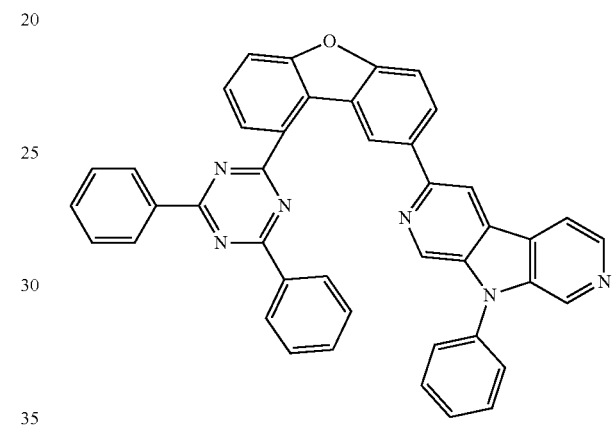
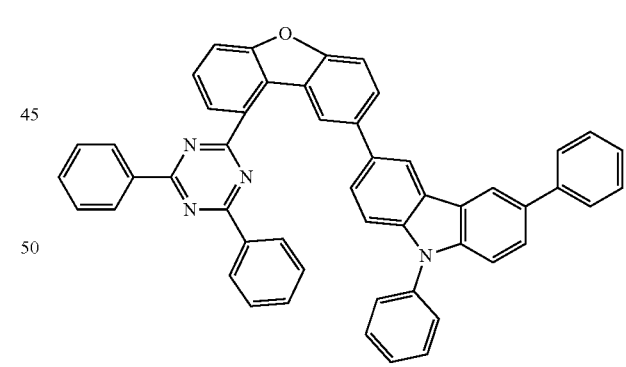
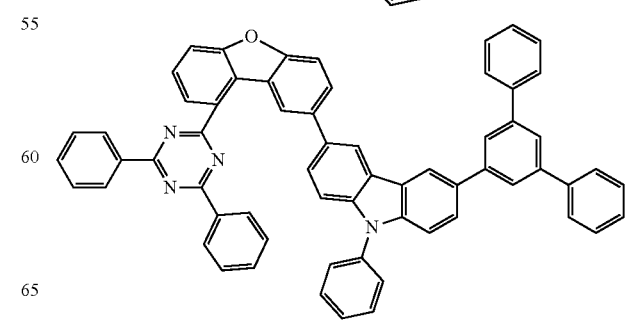

33
-continued
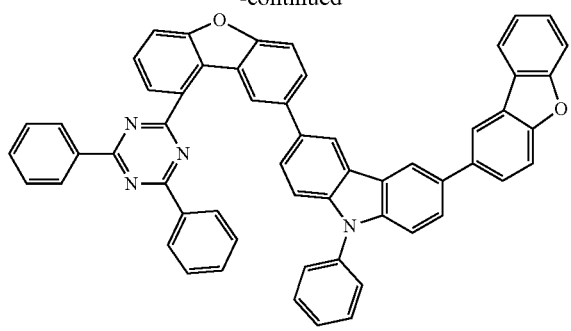
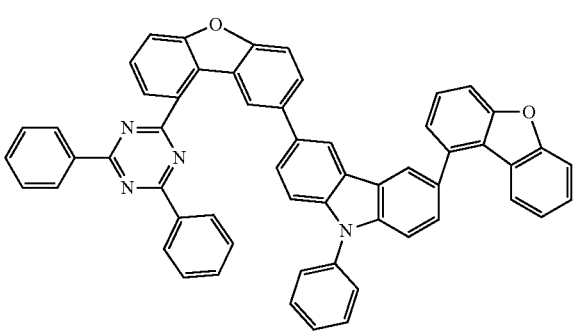
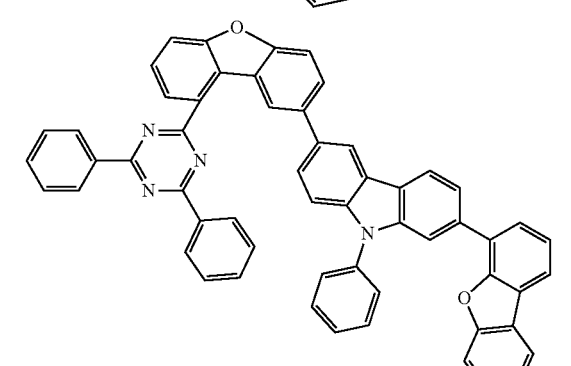
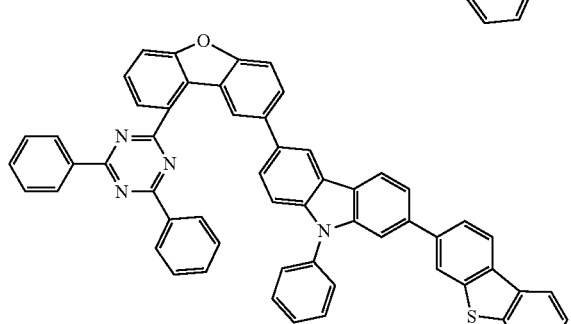
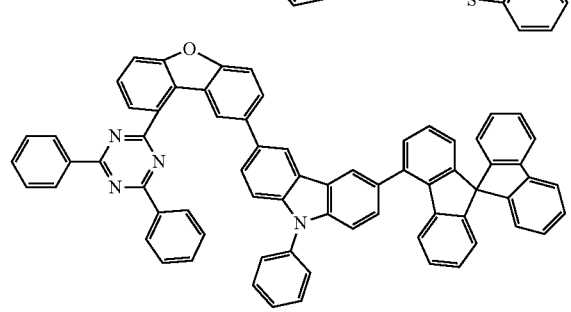
34
-continued
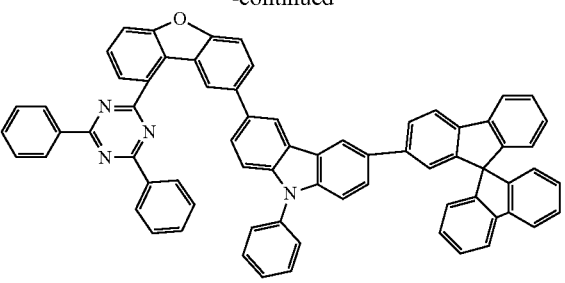
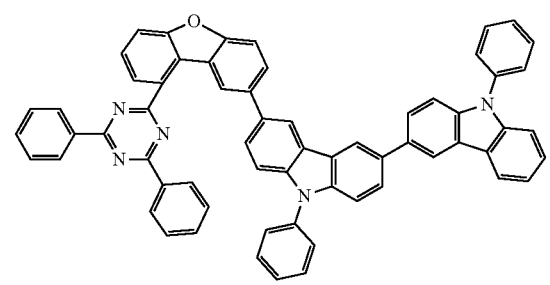
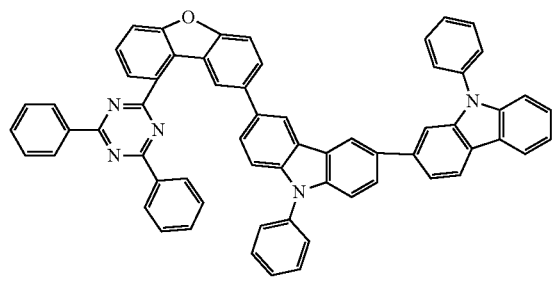
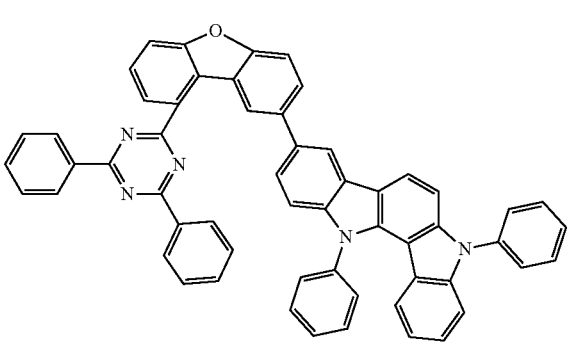
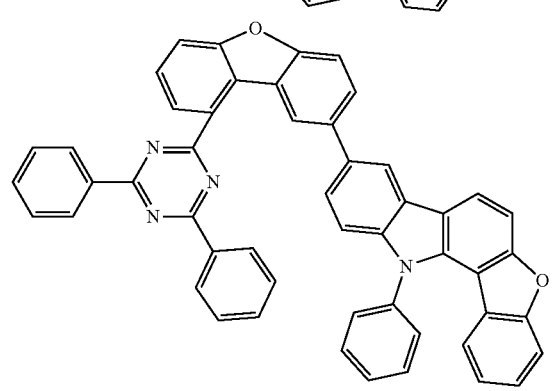

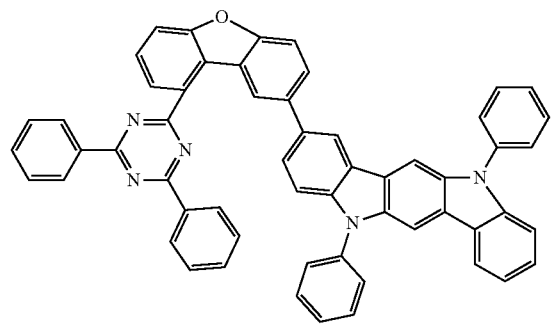
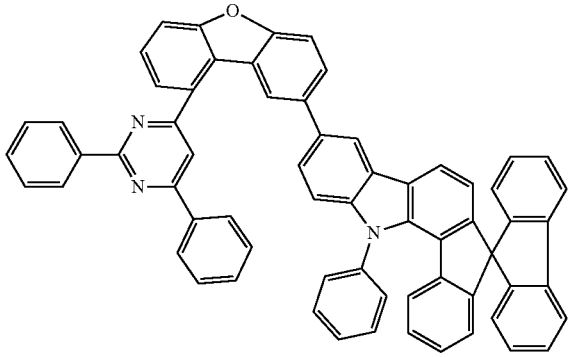
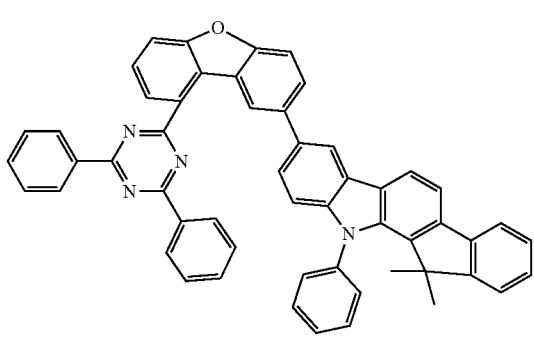
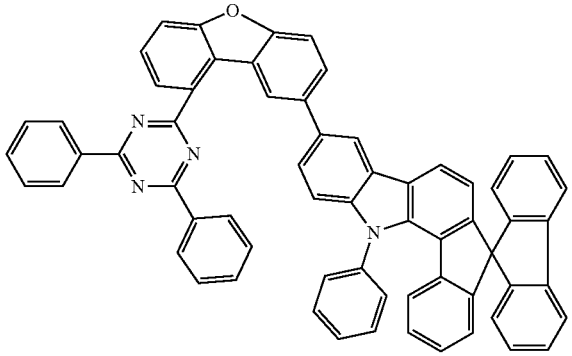
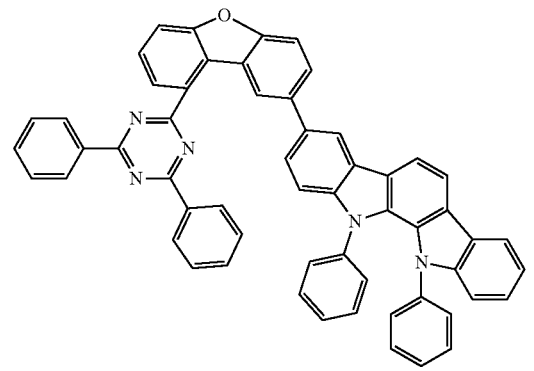
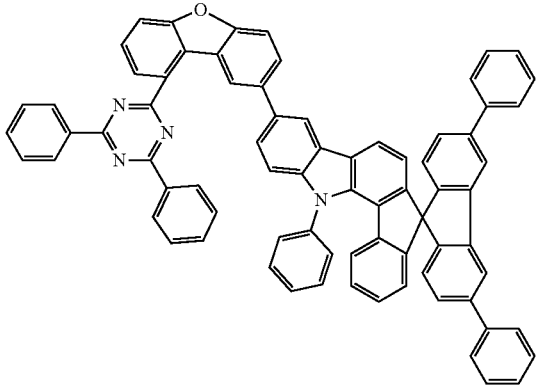
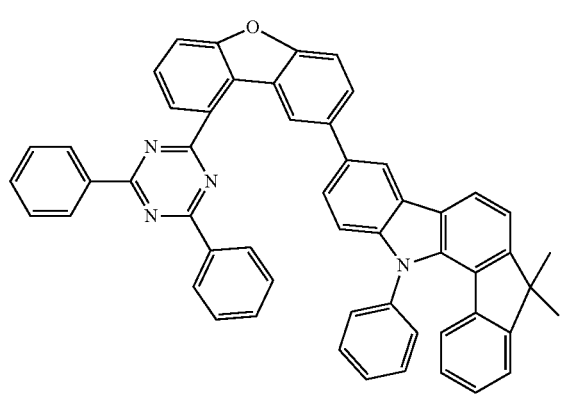

37
-continued
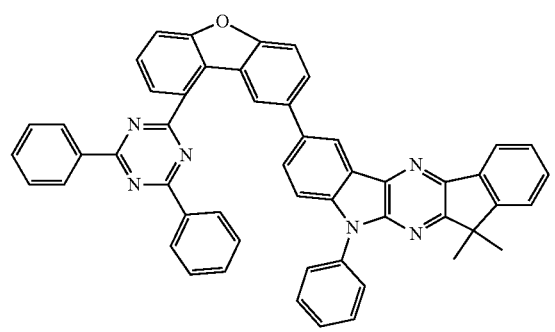
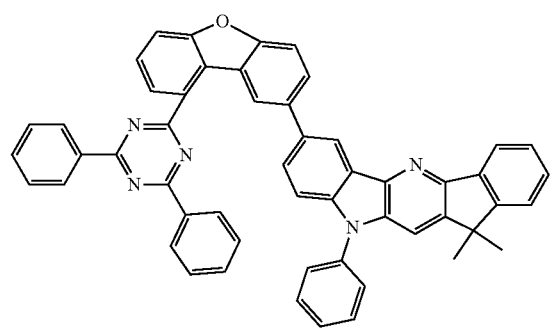
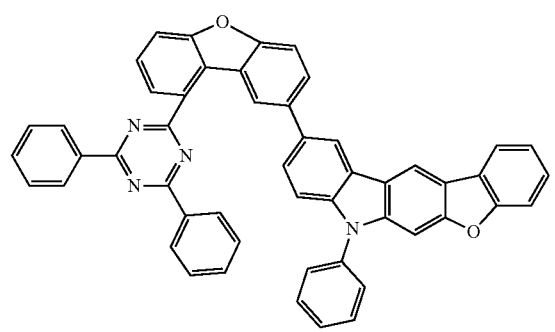
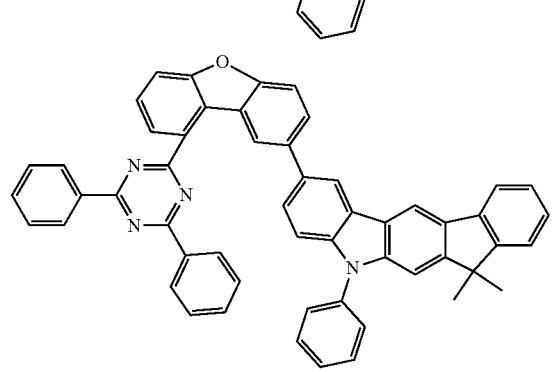
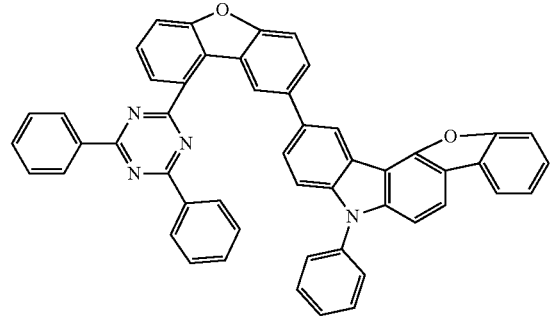
38
-continued
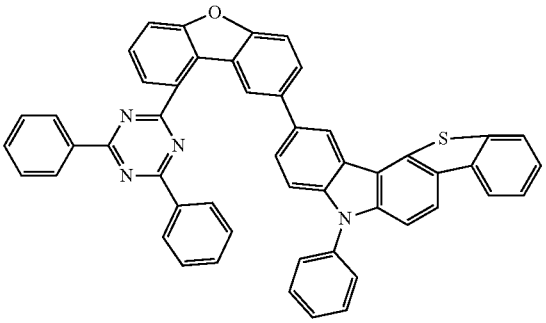
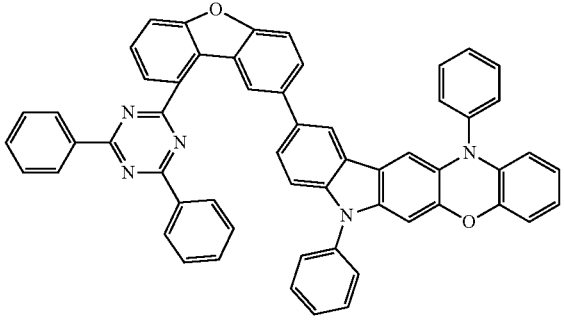
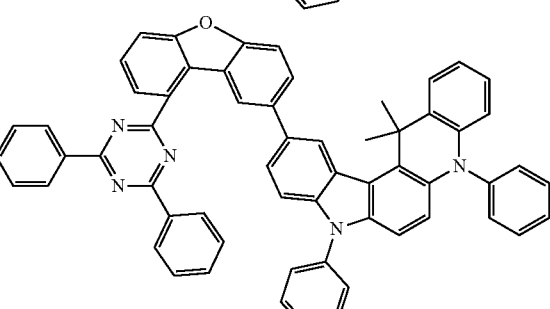
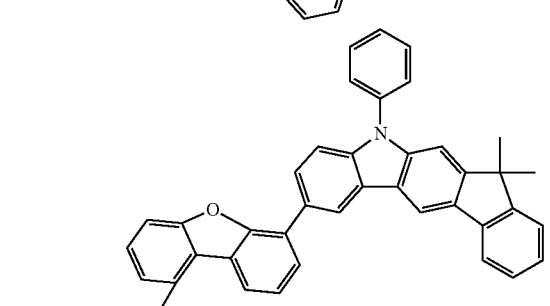
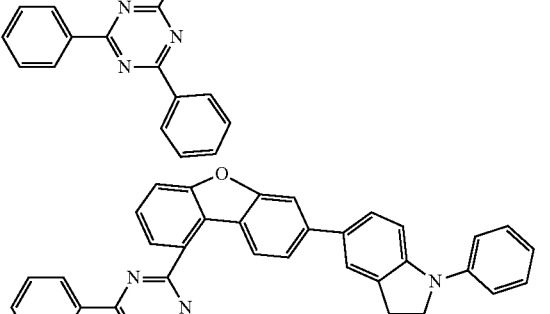
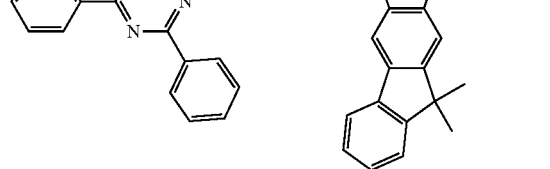

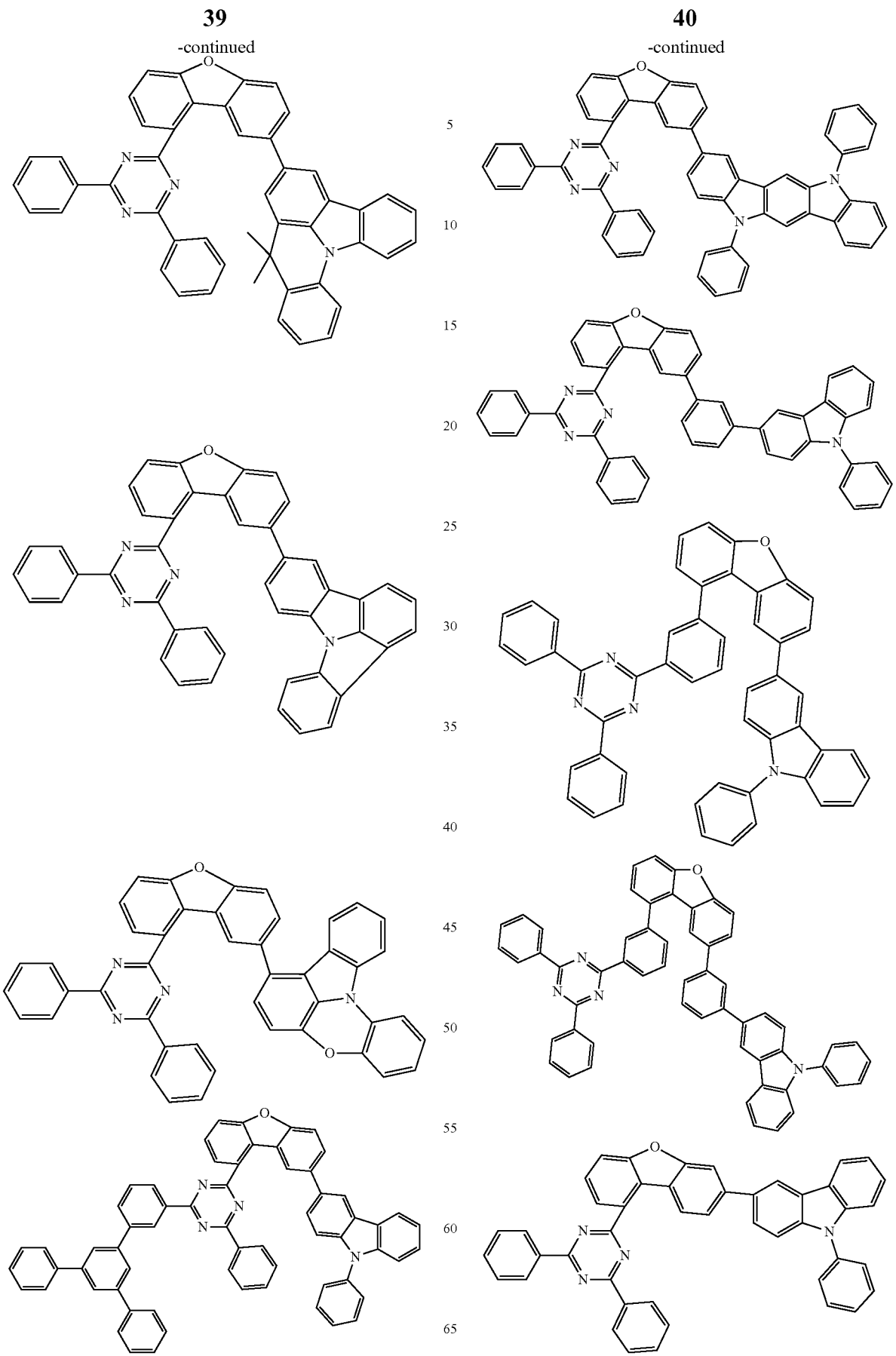

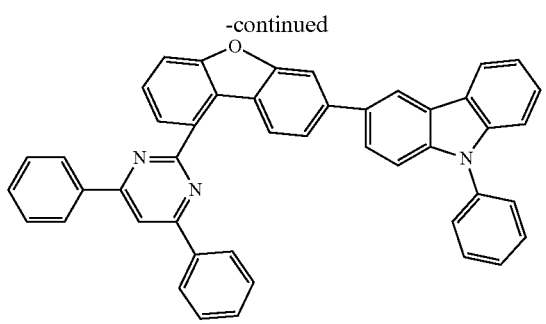
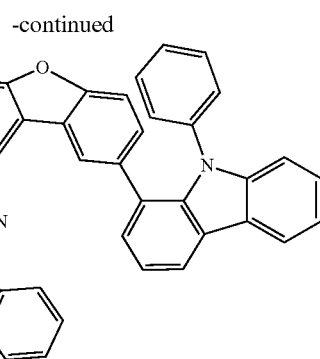
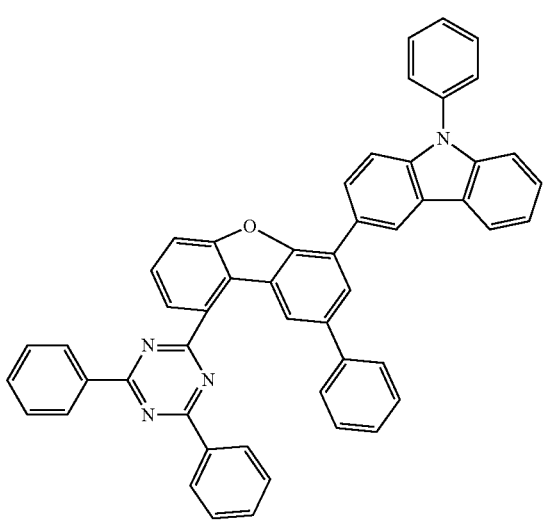
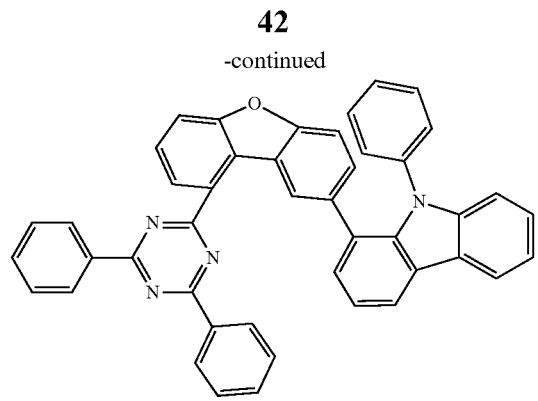
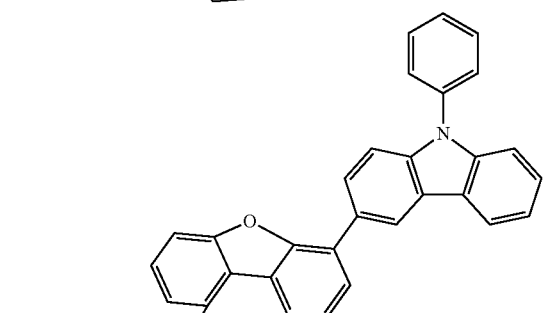
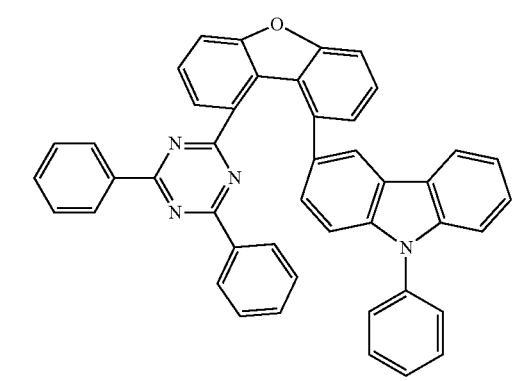
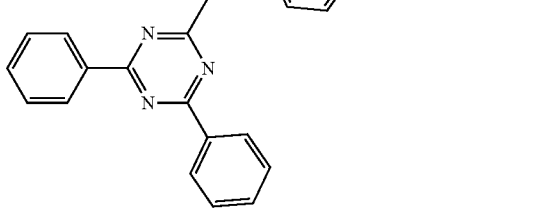
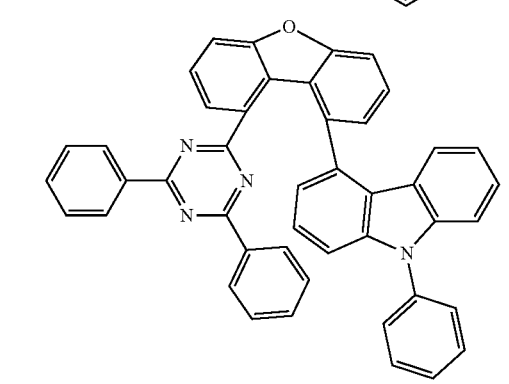
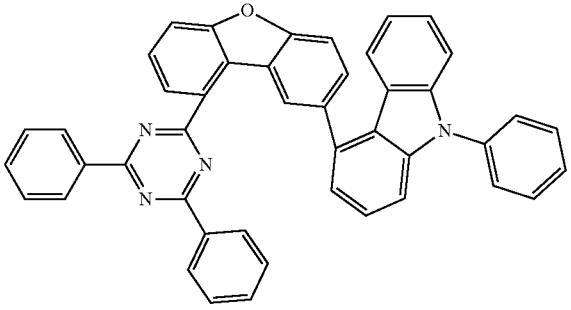
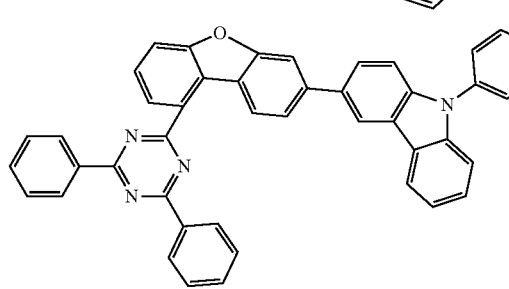
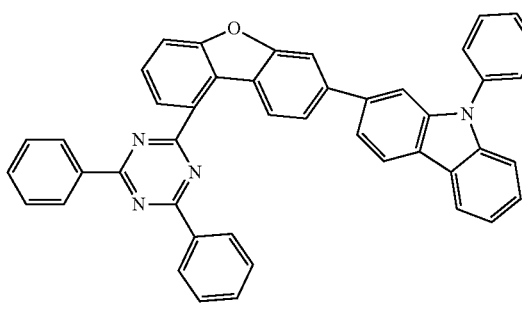

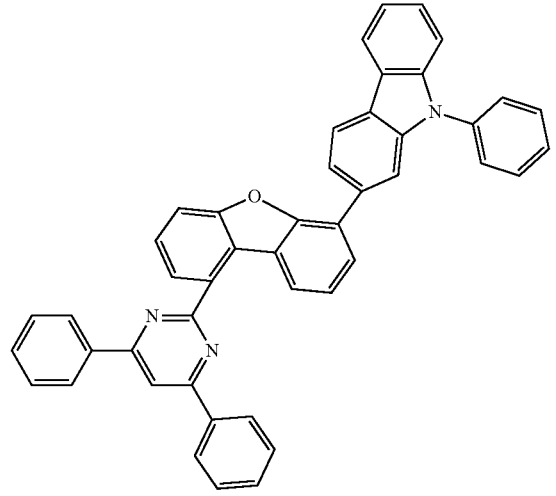
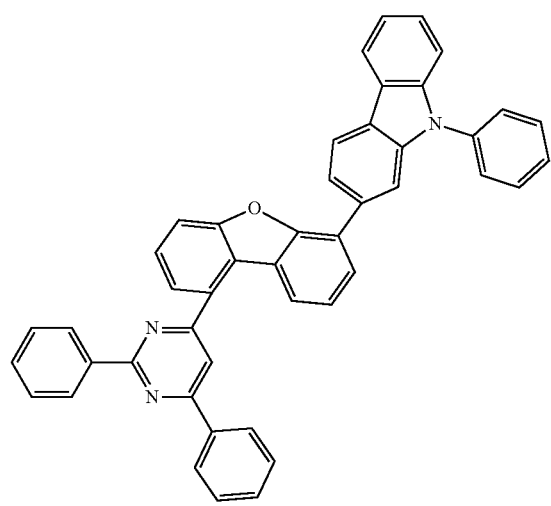
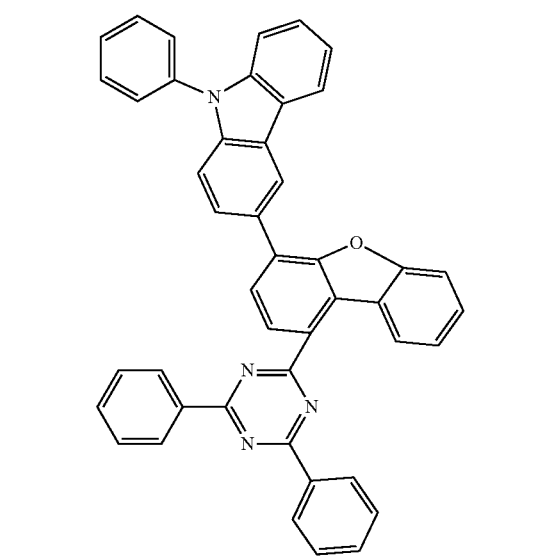
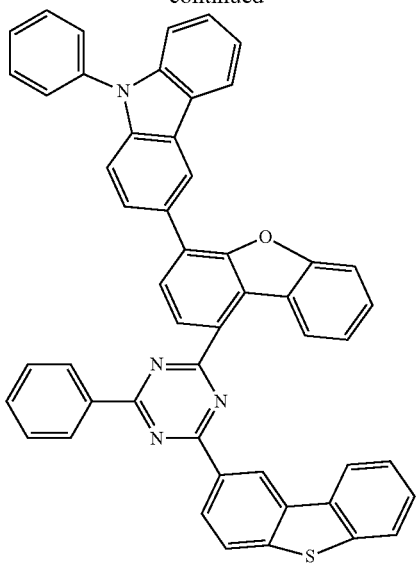
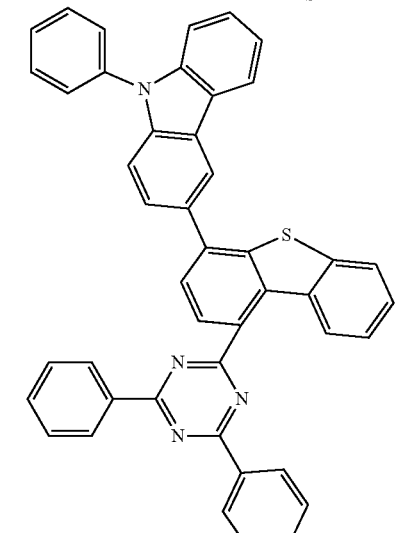
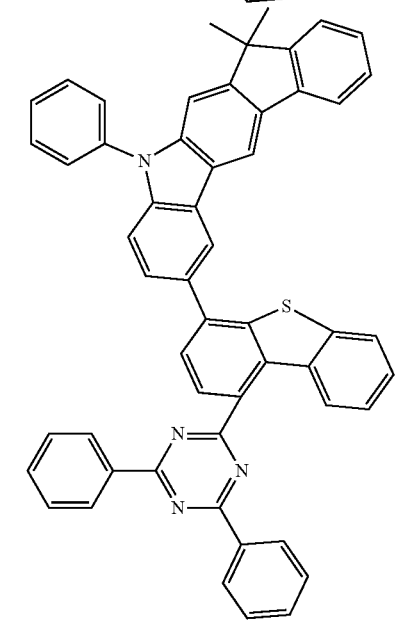

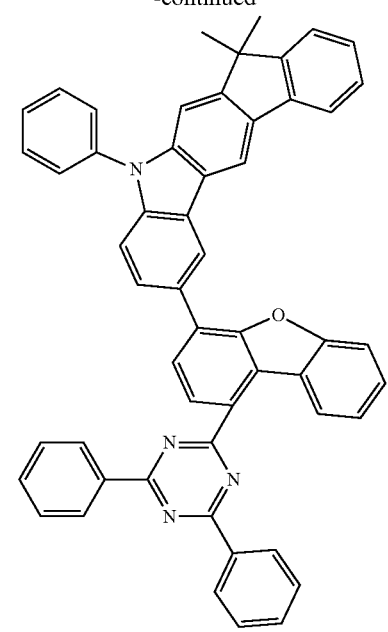
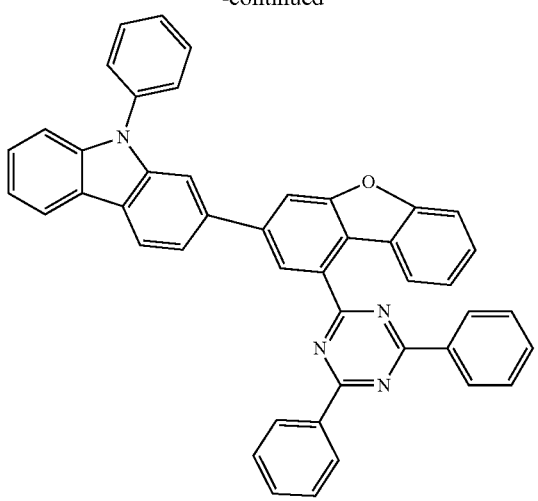
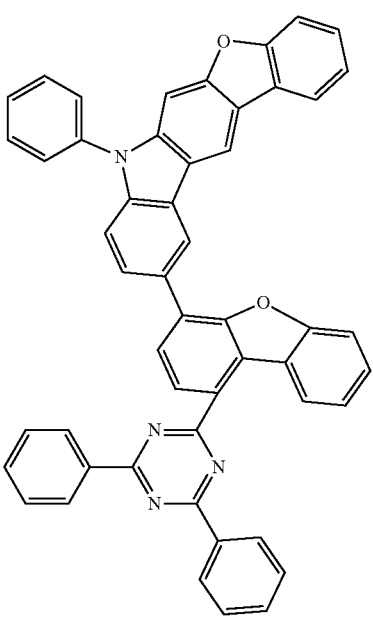
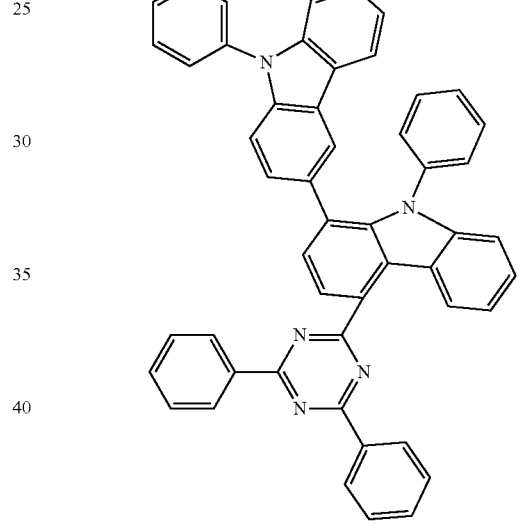
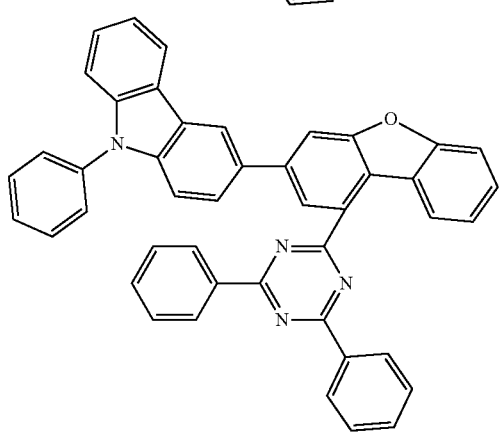
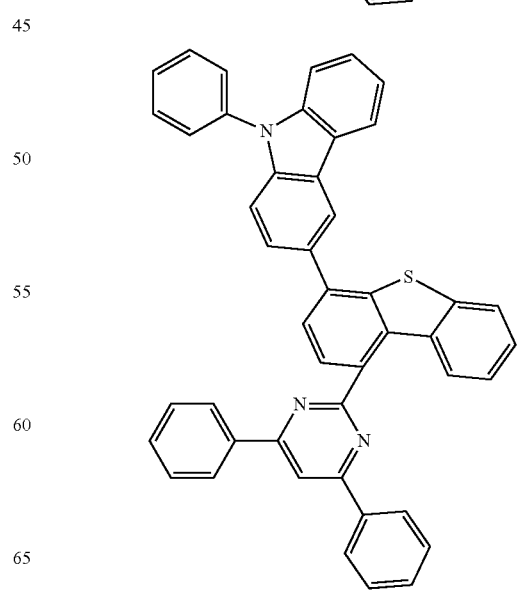

-continued
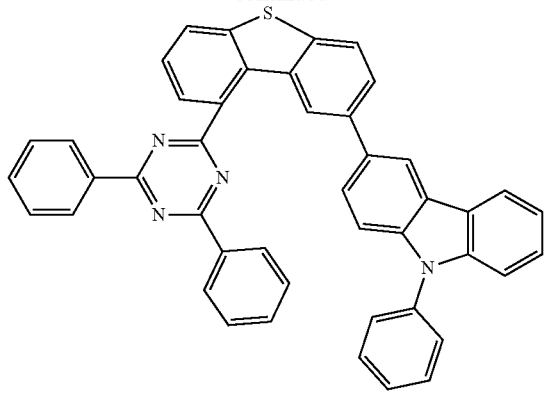
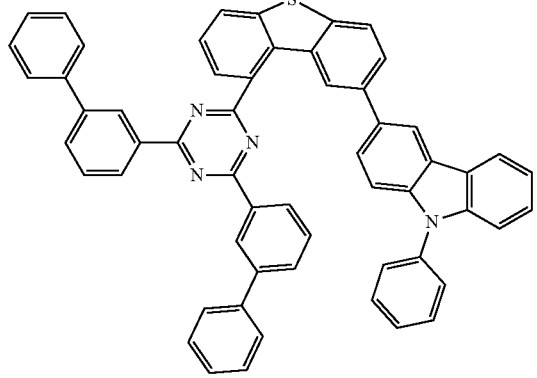
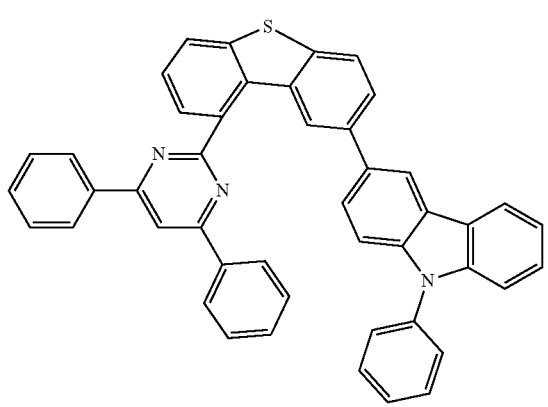
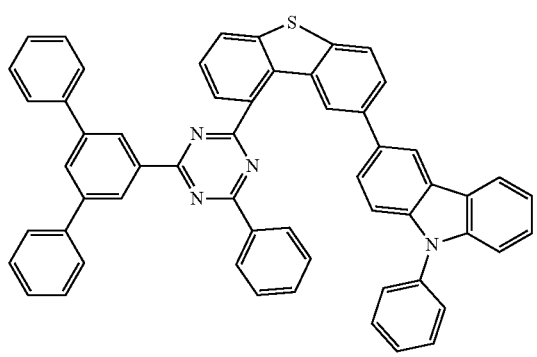
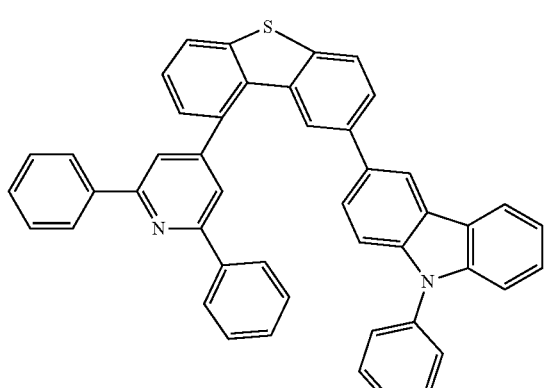
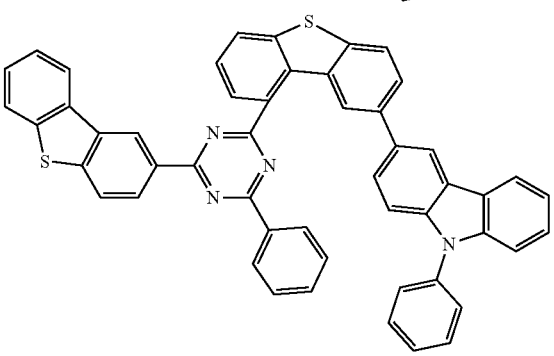
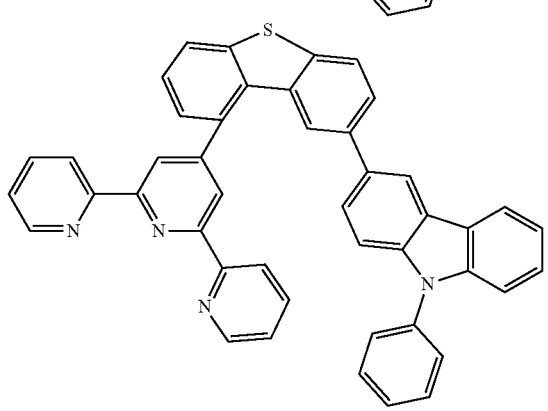
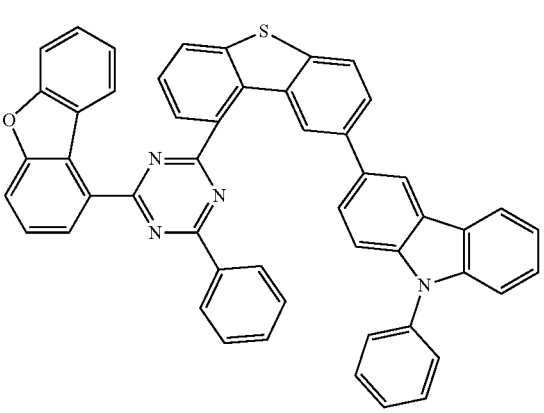

49
-continued
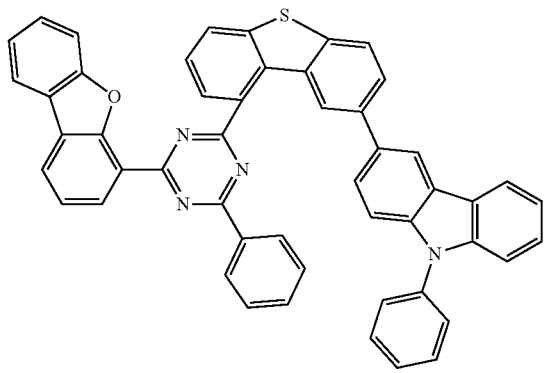
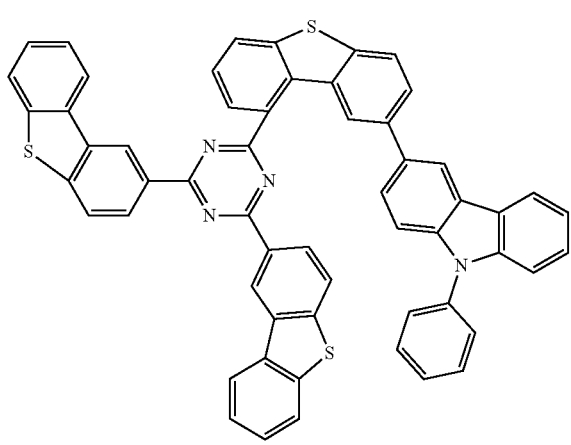
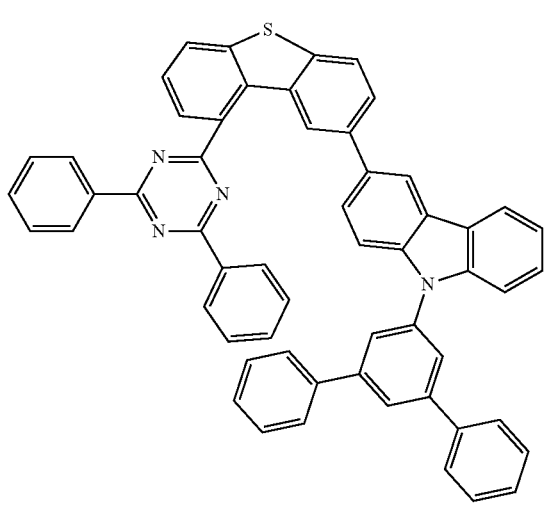
50
-continued
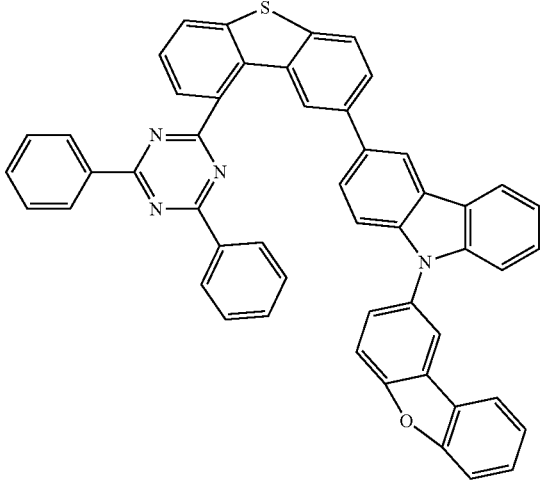
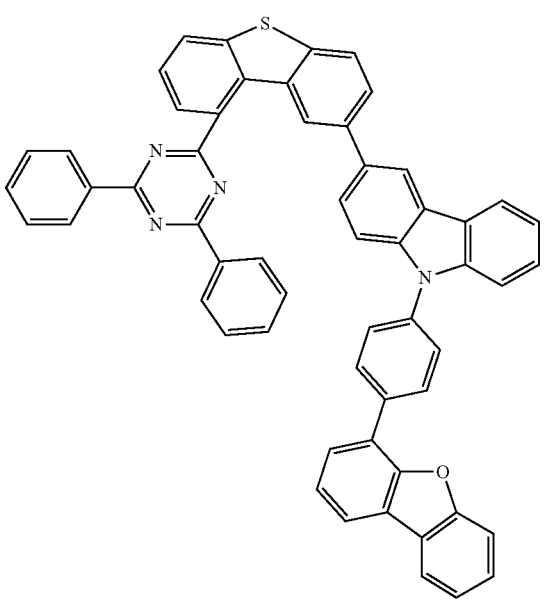

51
-continued
52
-continued
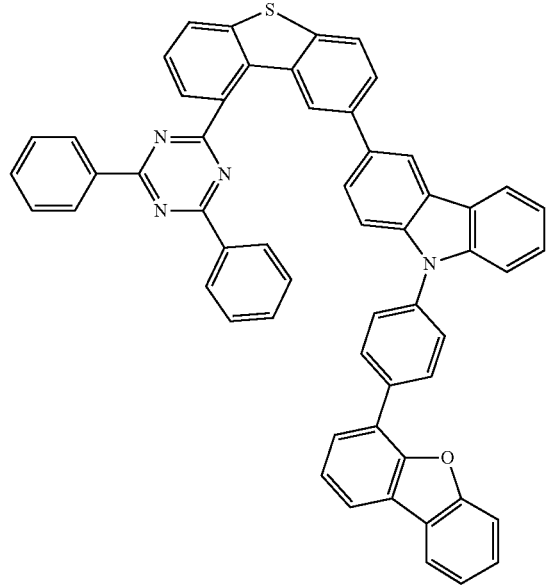
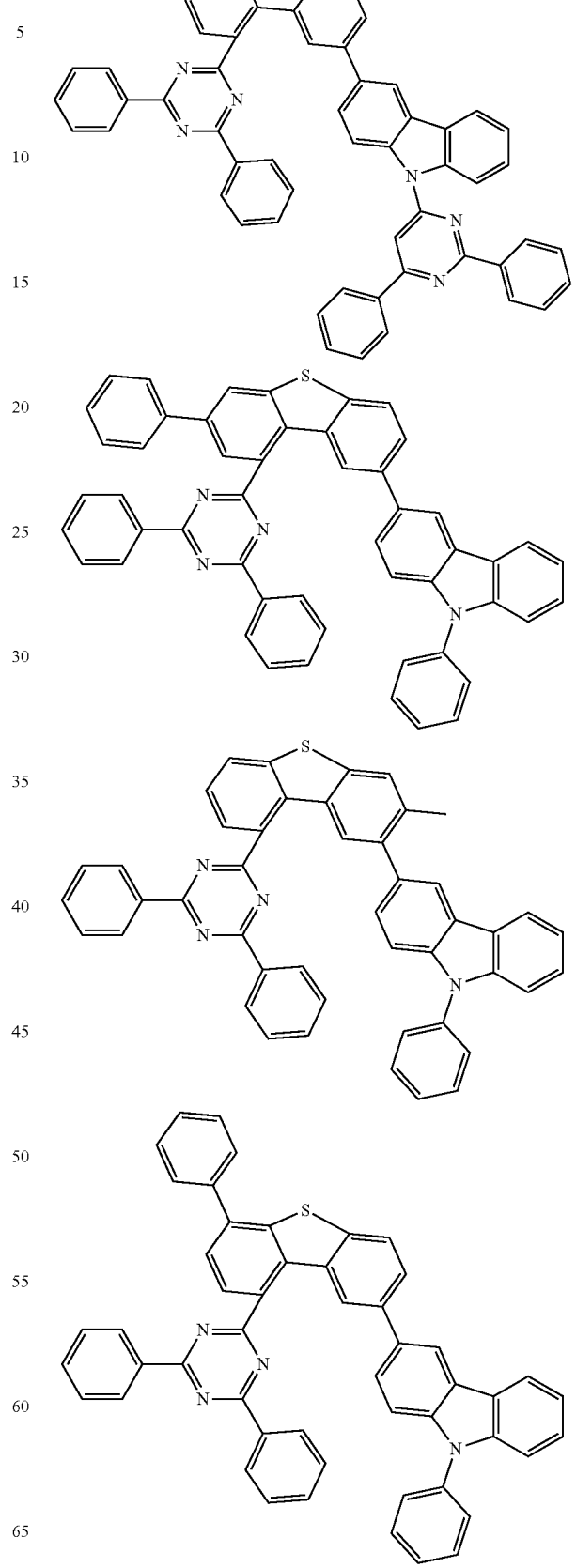

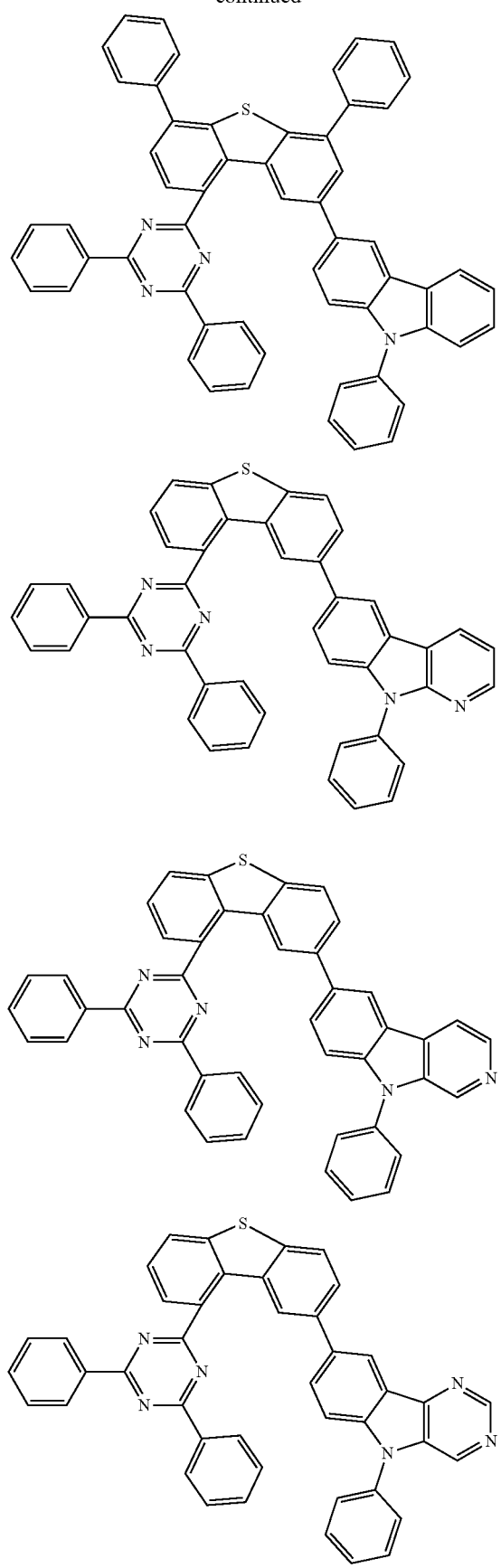
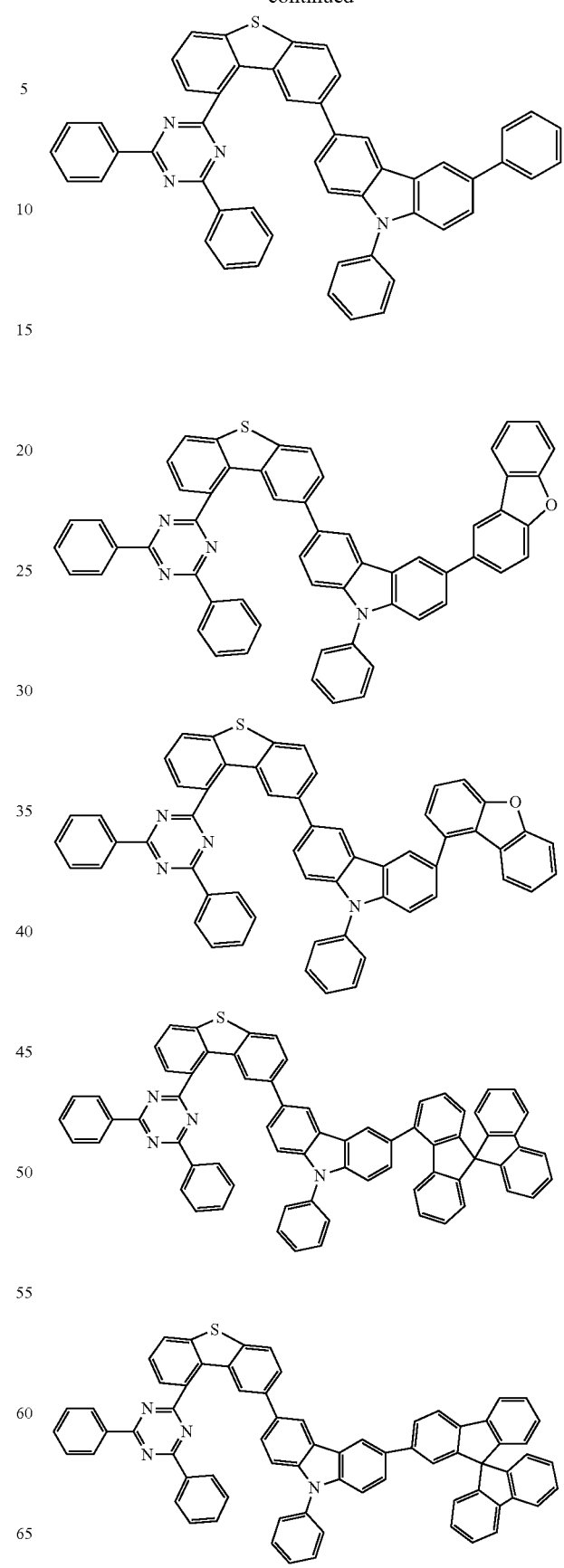

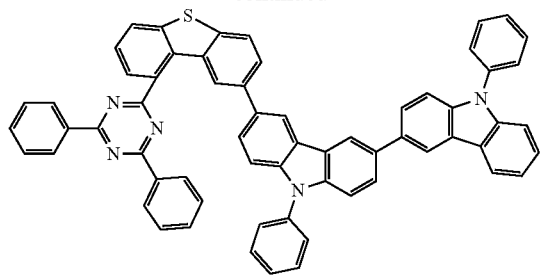
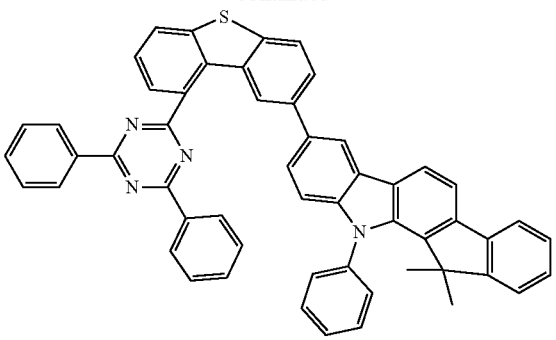
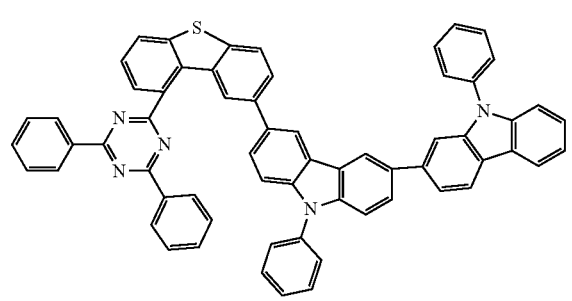
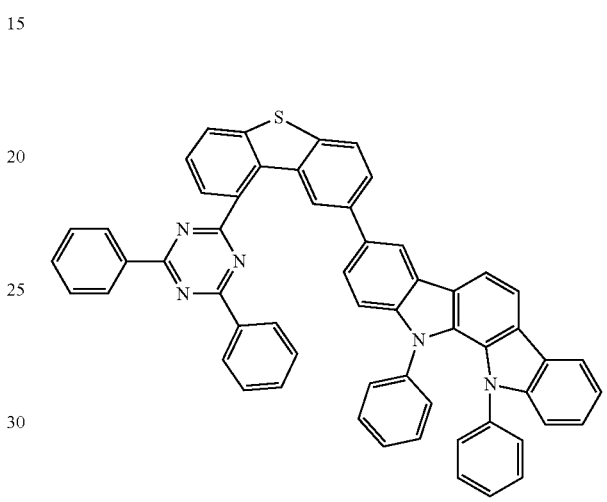
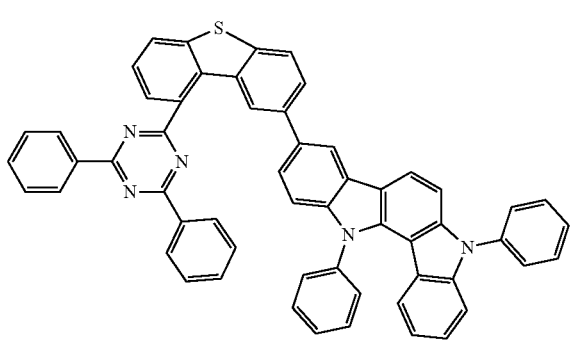
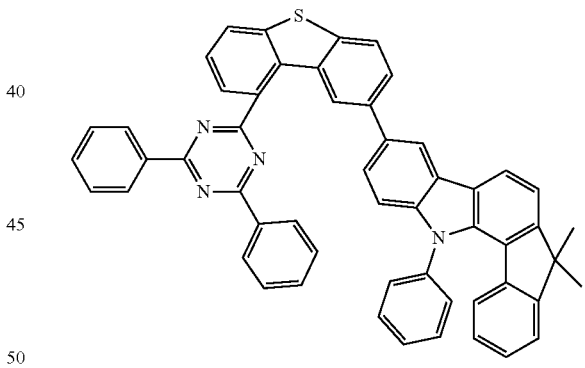
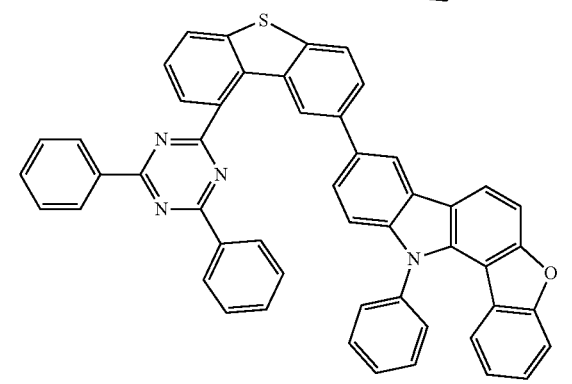
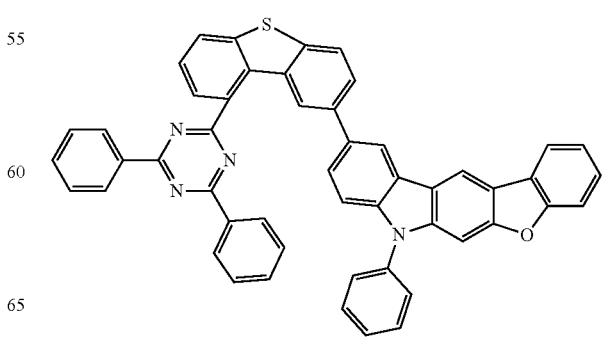

57
-continued
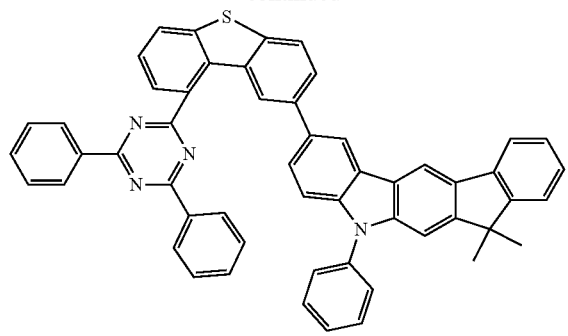
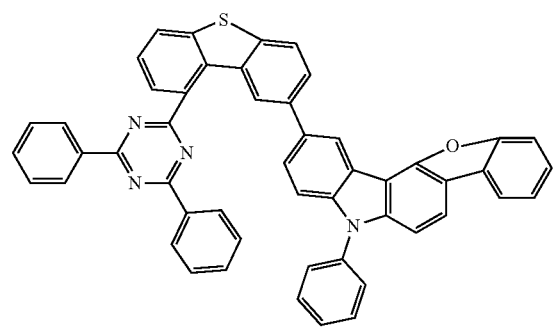
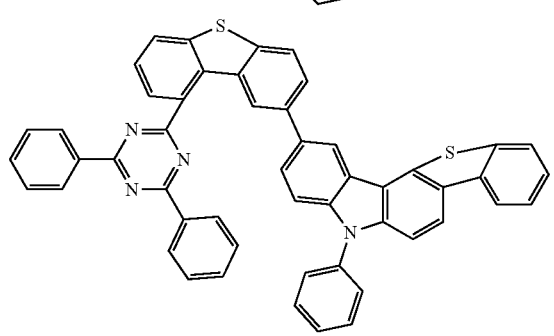
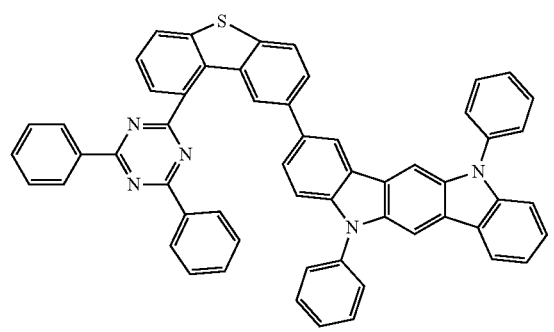
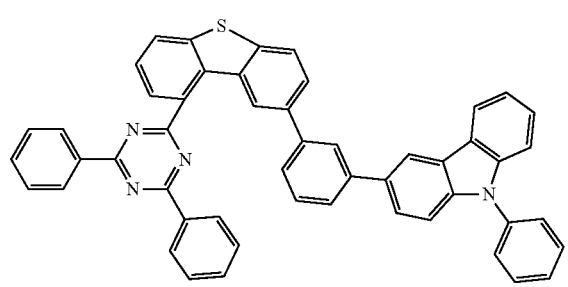
58
-continued
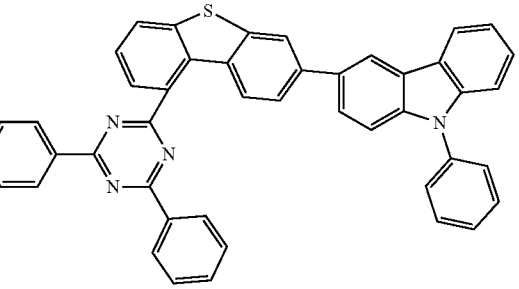
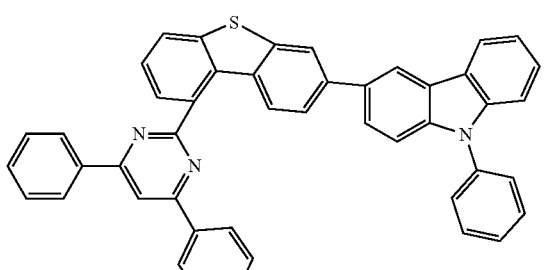
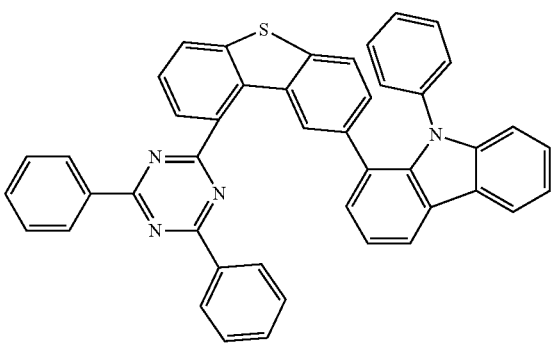
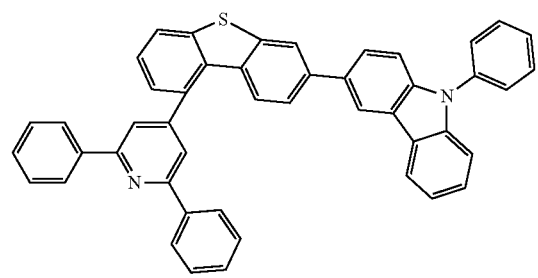

-continued

61
-continued
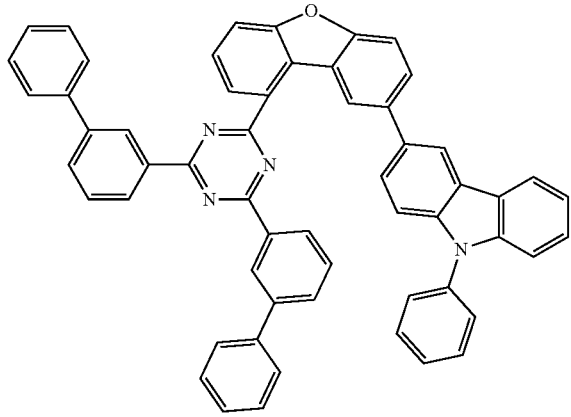
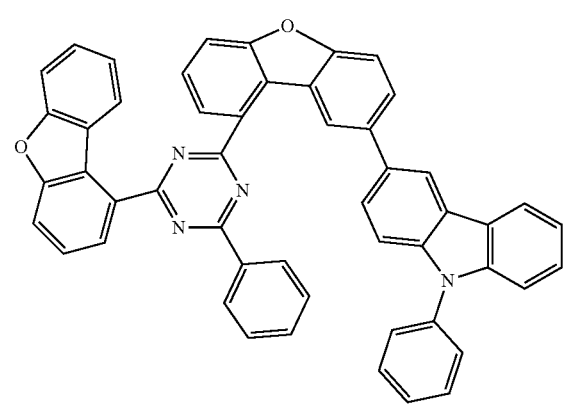
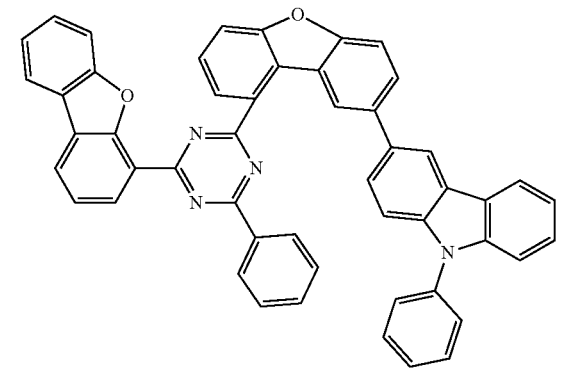
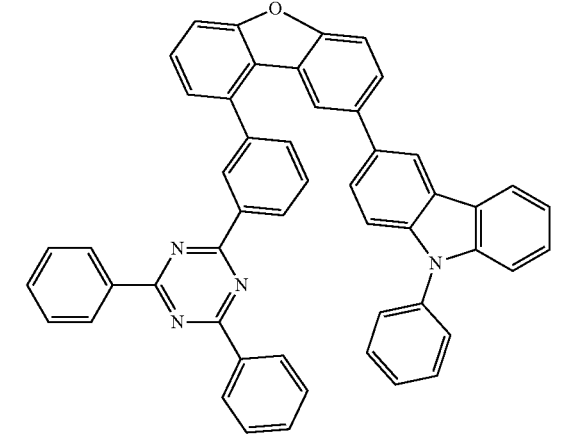
62
-continued
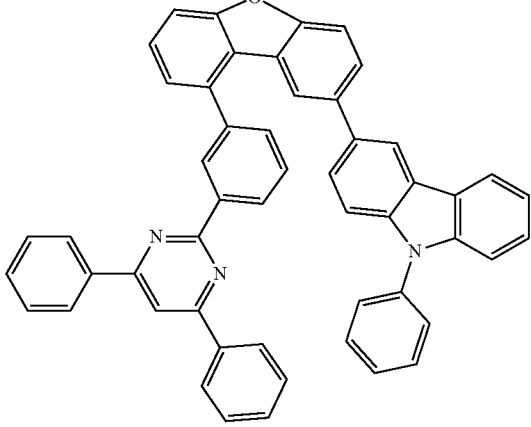
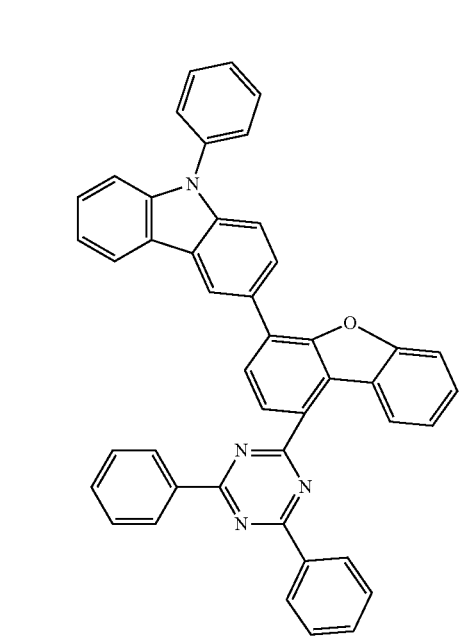
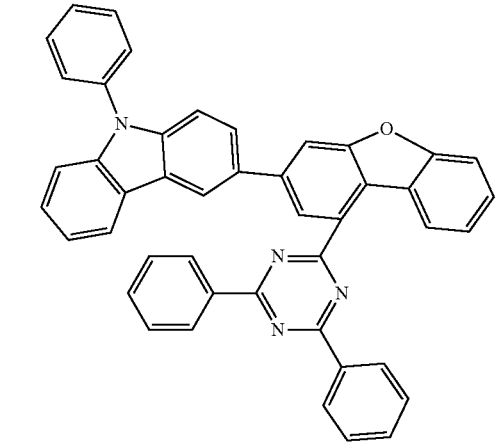

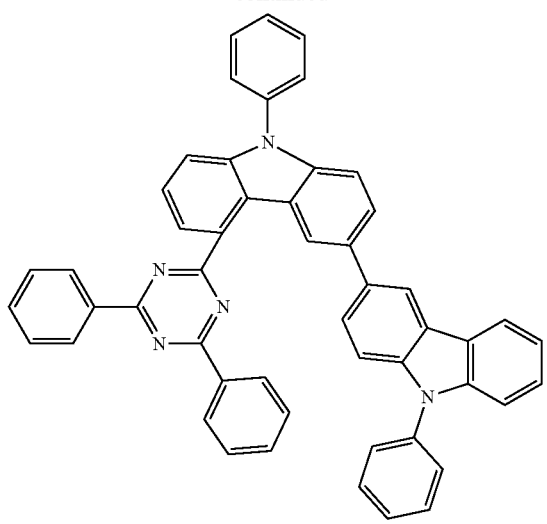
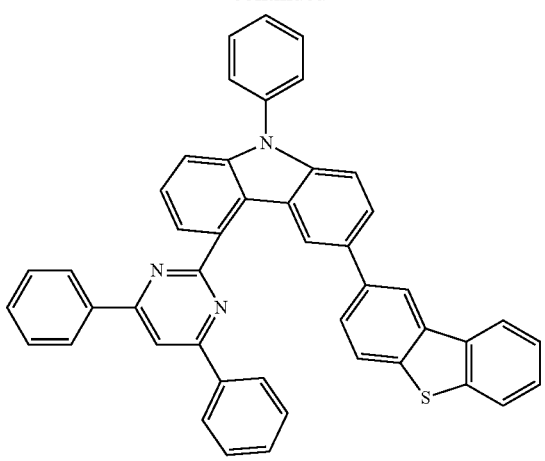
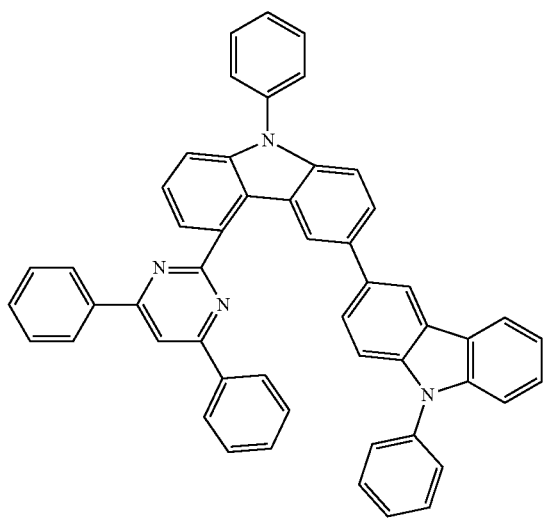
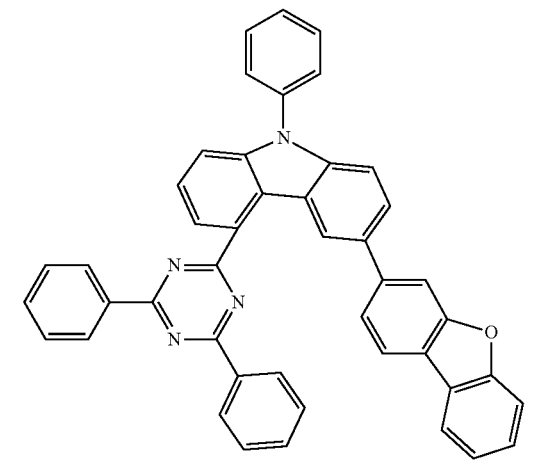
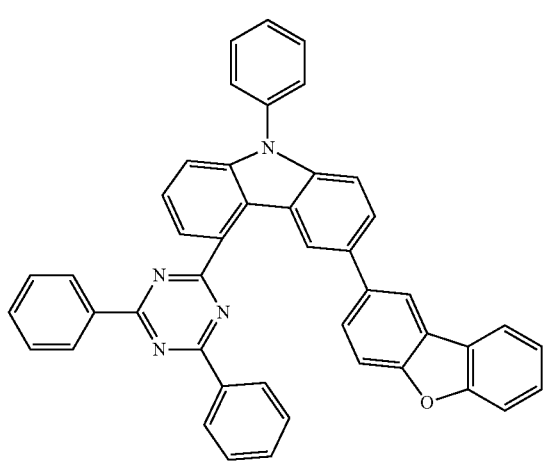
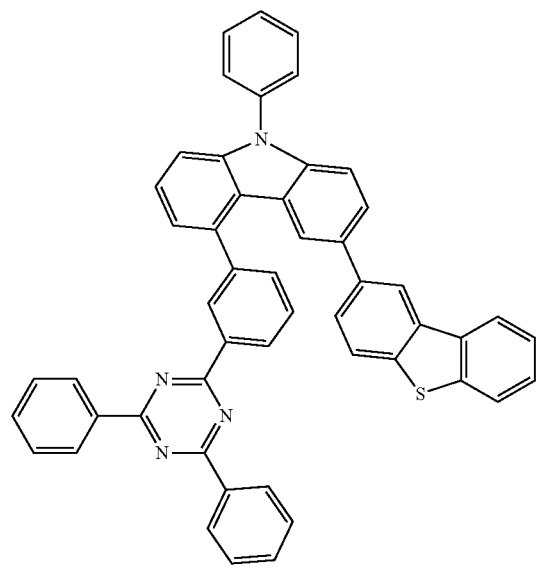

65
-continued
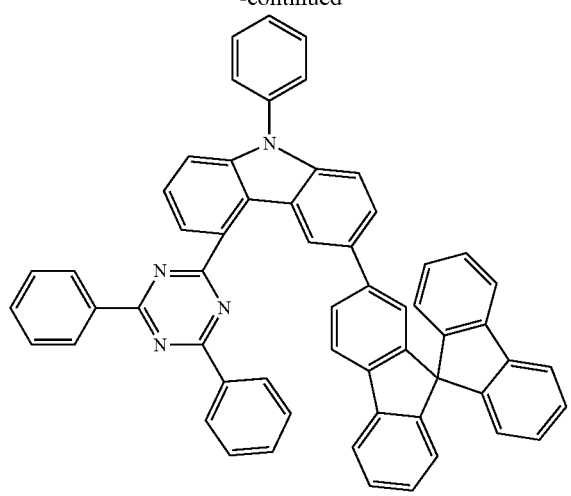
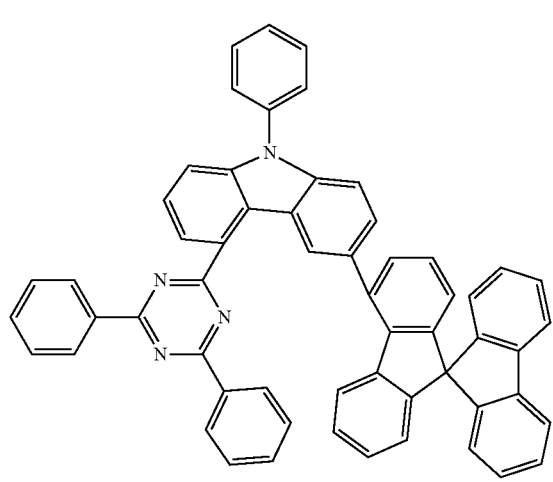
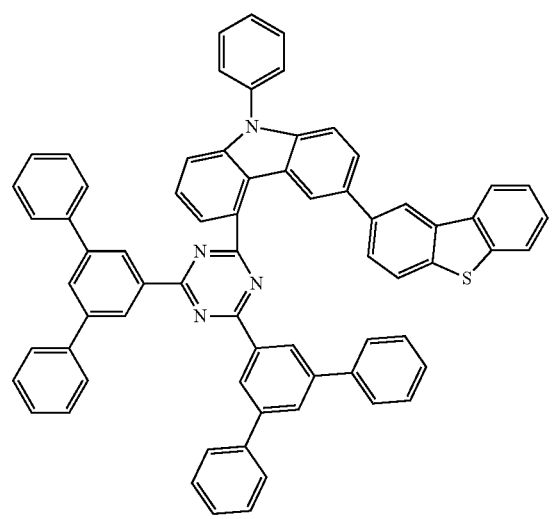
66
-continued
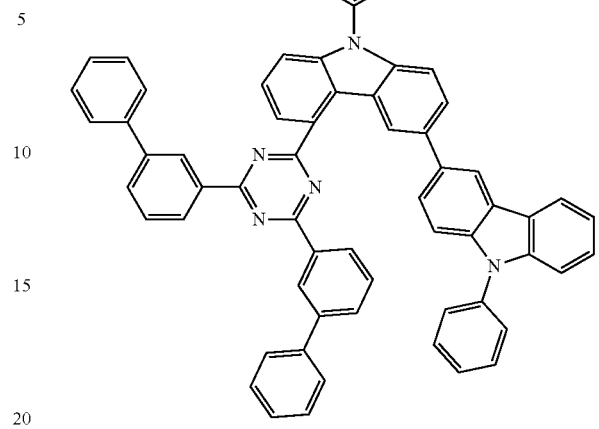
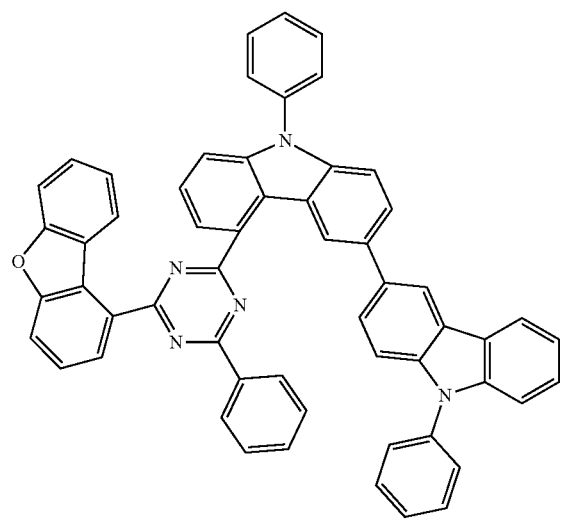
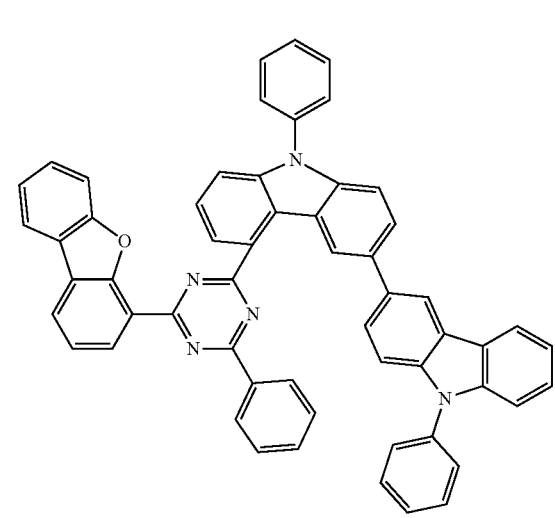

67
-continued
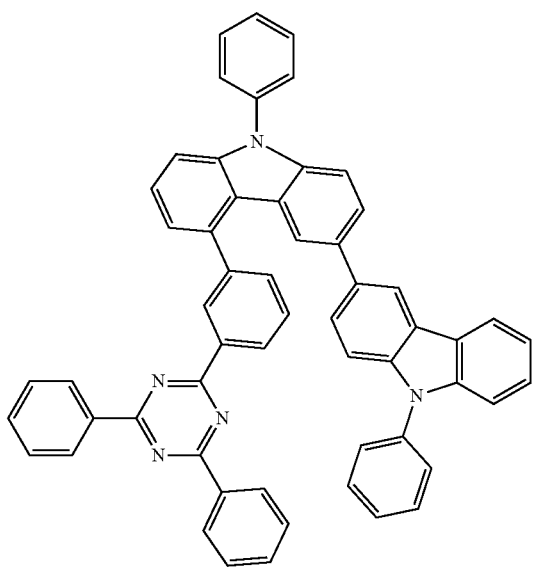
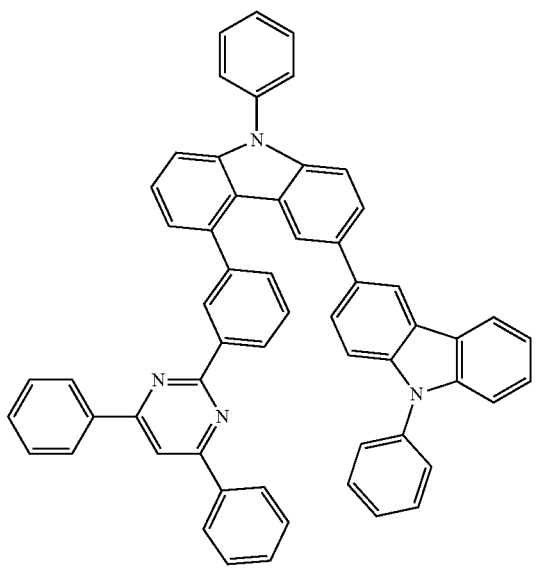
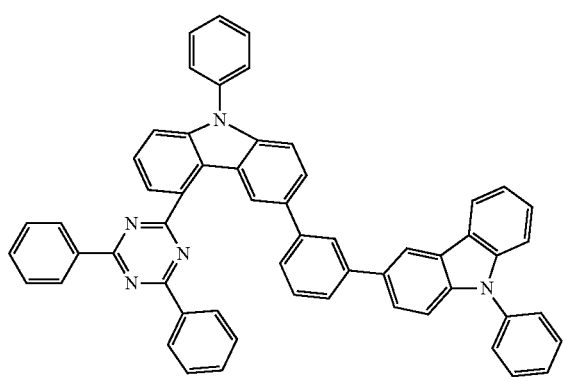
68
-continued
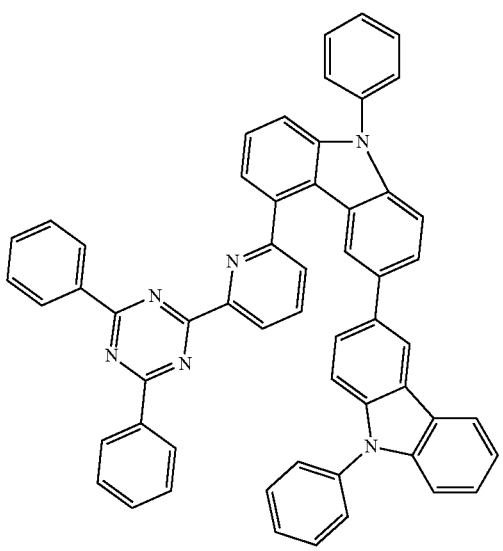
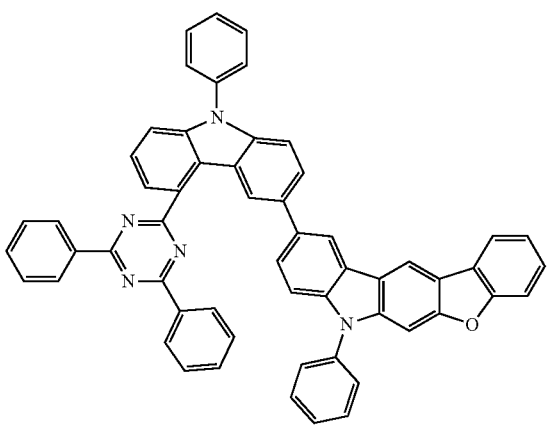
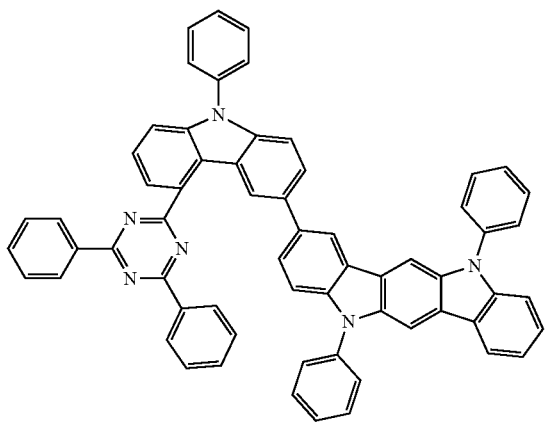

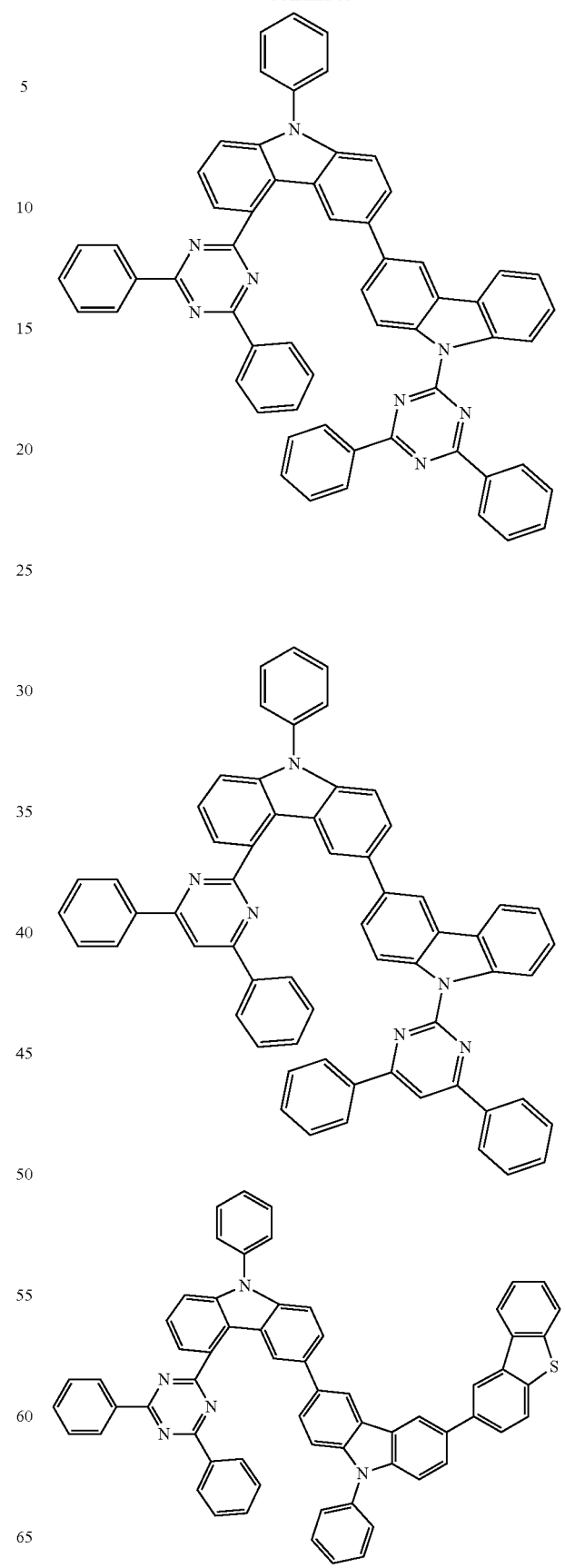

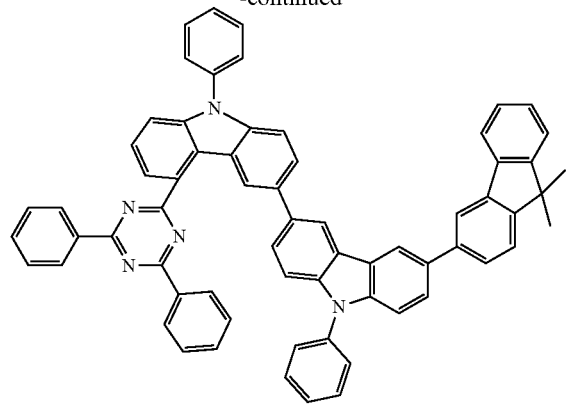
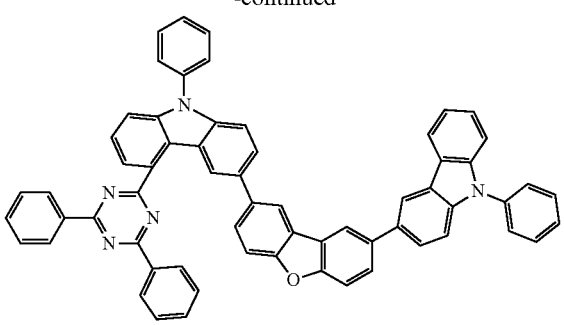
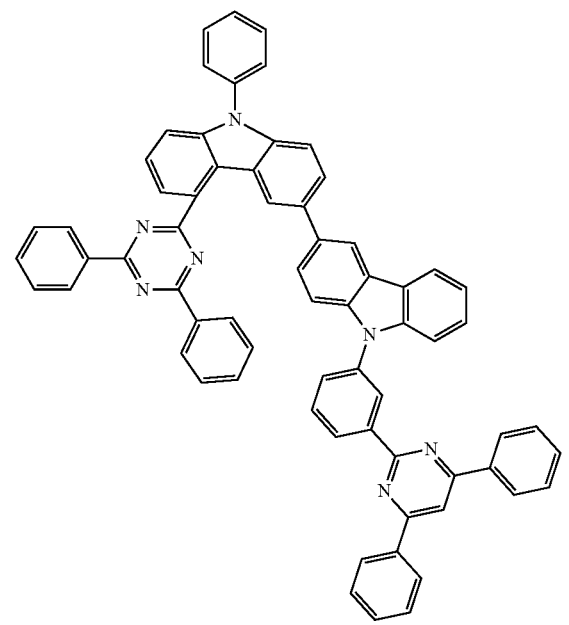
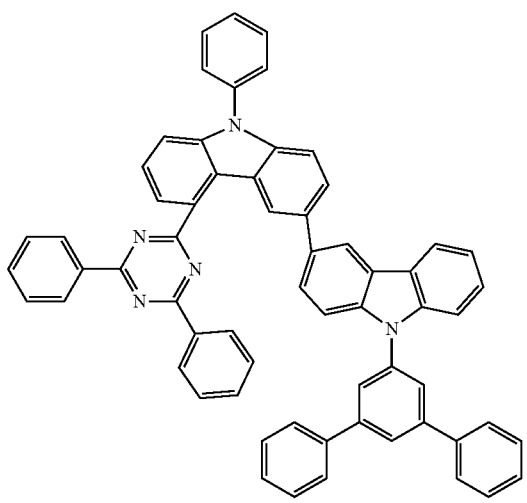
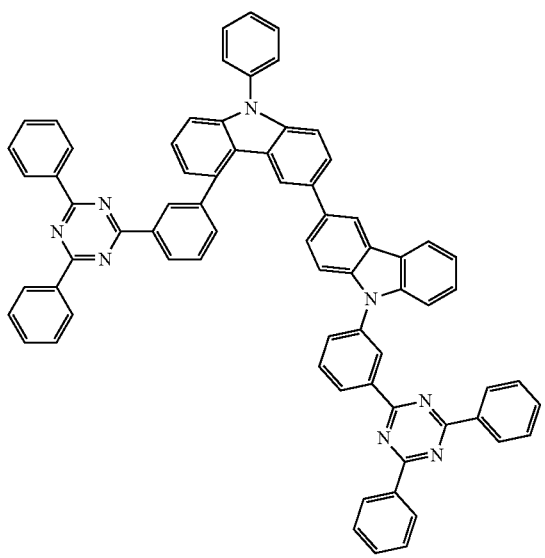
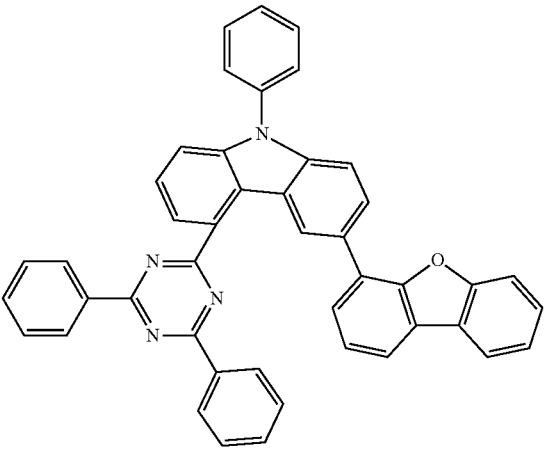

73
-continued
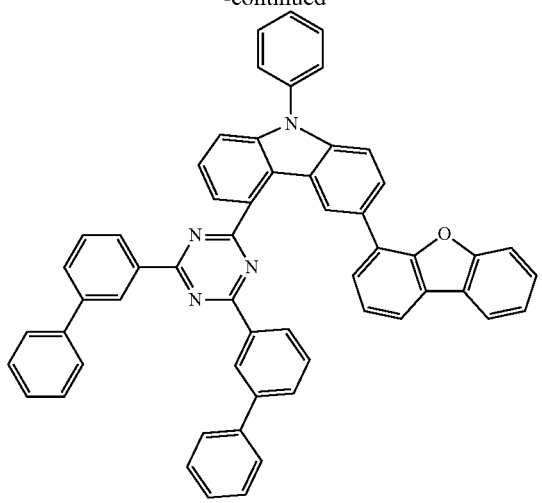
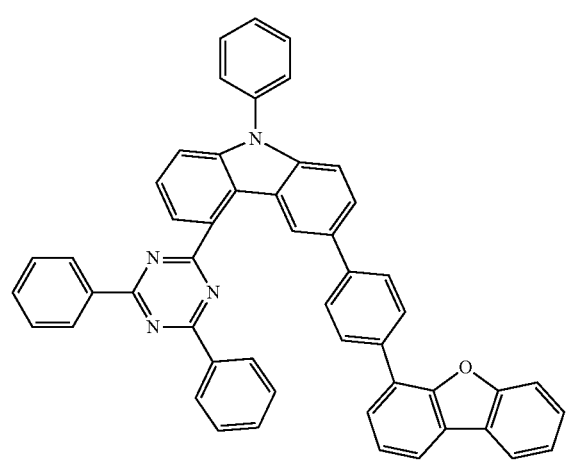
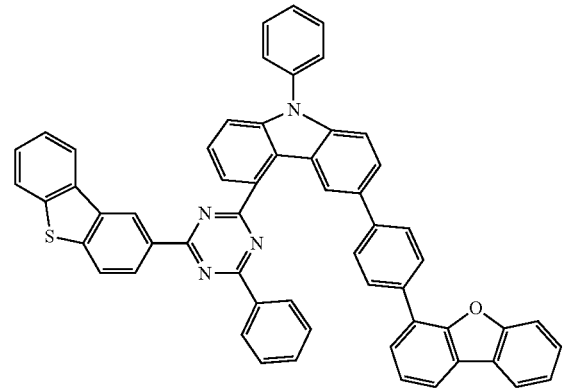
74
-continued
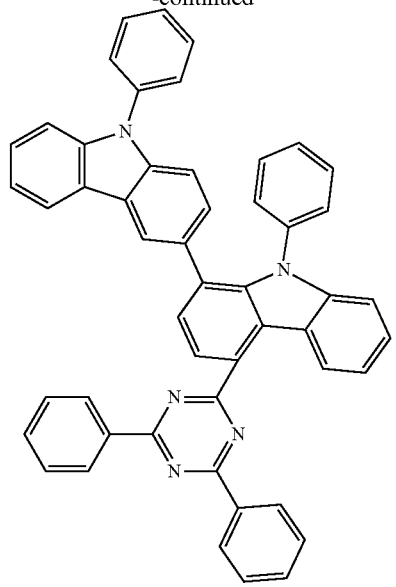
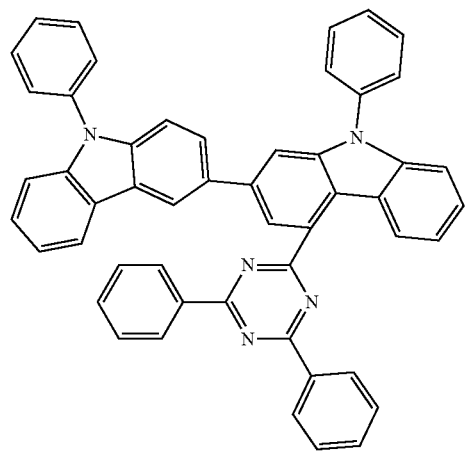
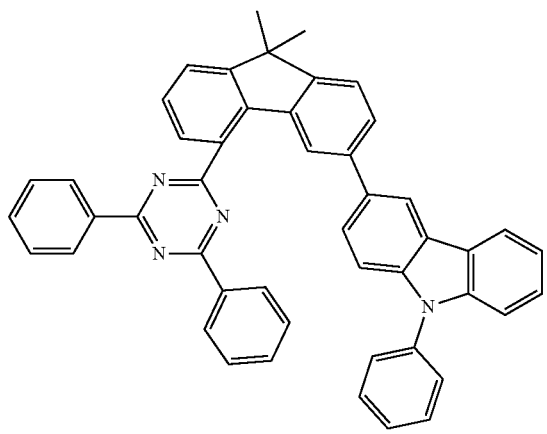

75
-continued
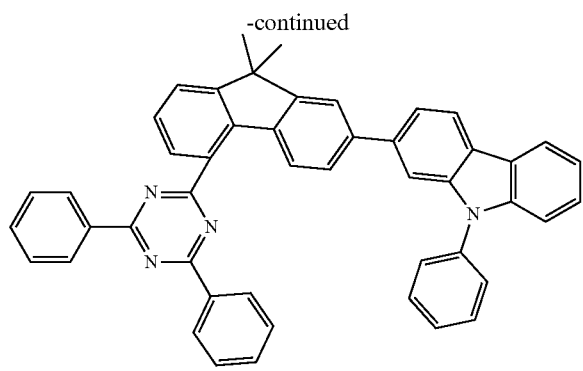
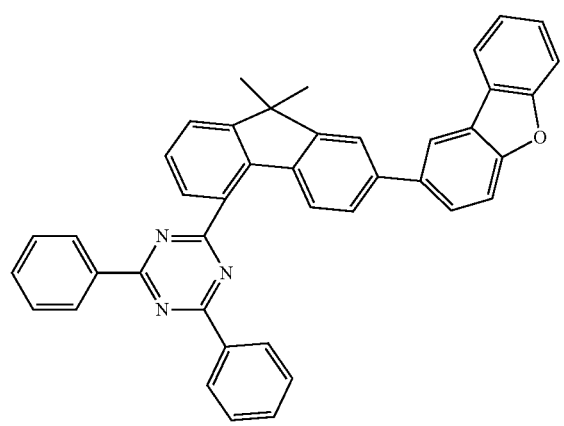
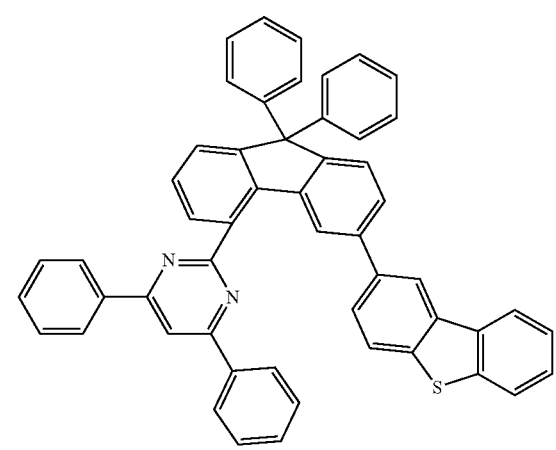
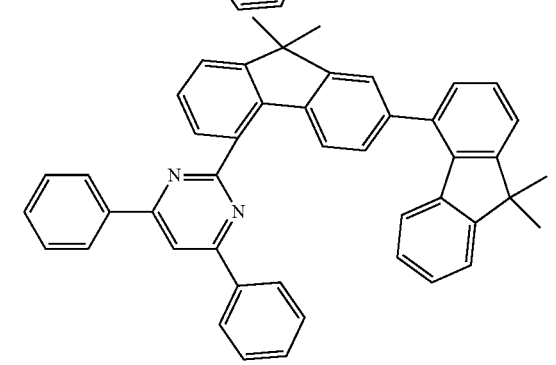
76
-continued
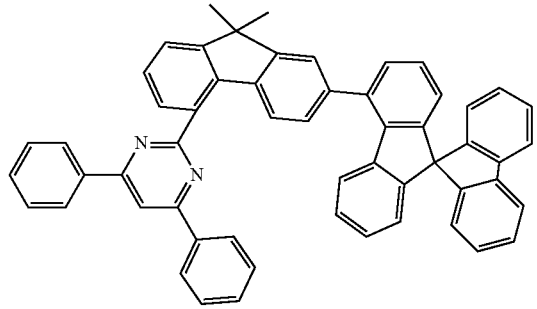
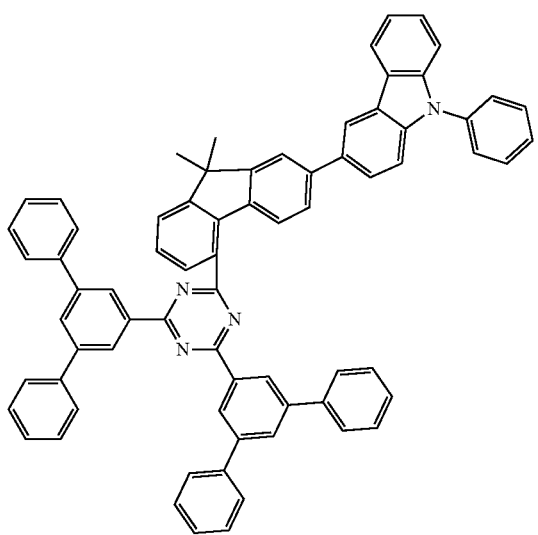
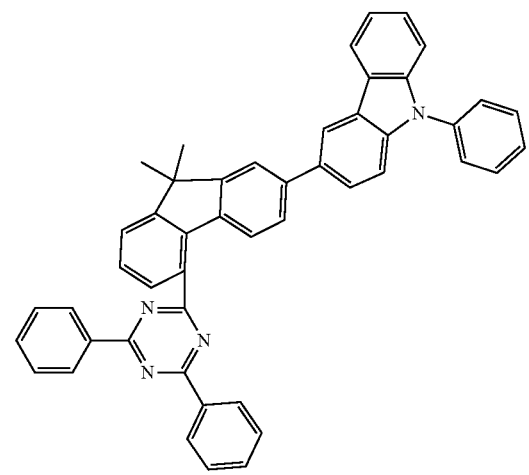
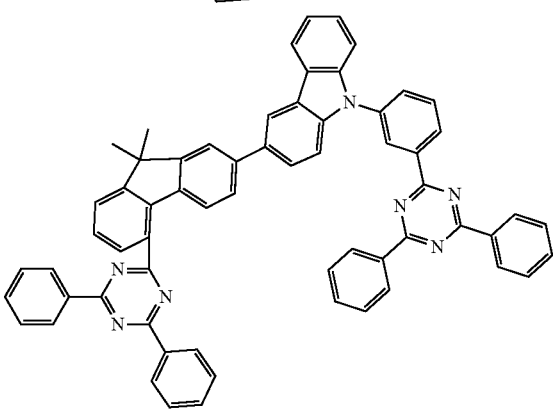

77
-continued
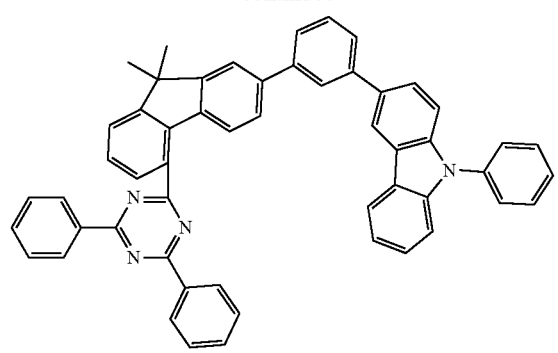
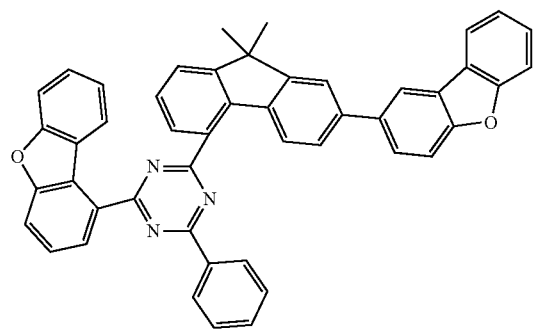
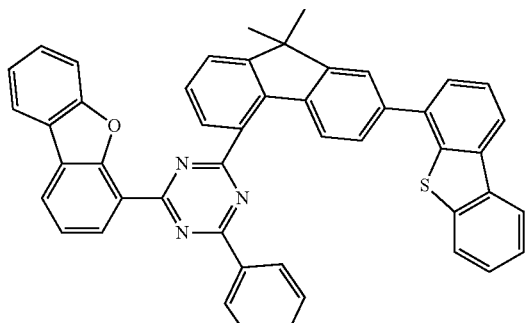
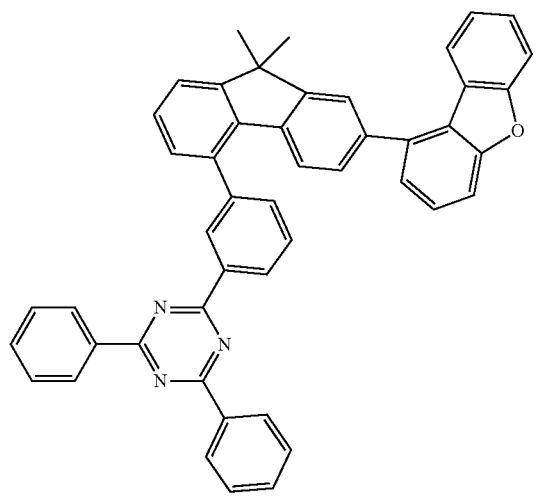
78
-continued
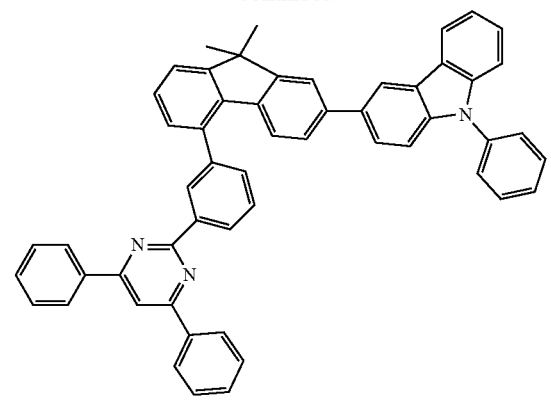
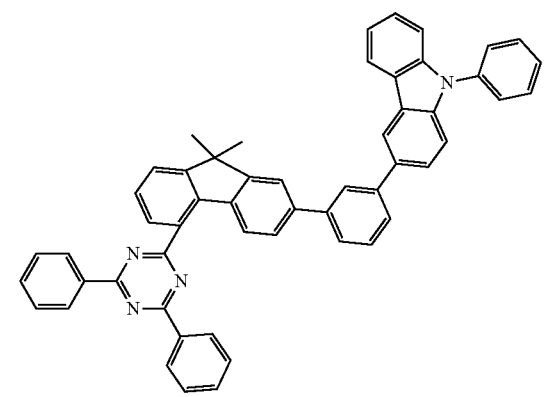
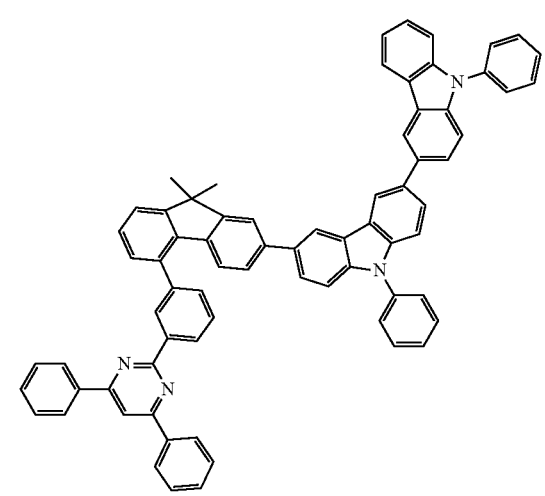

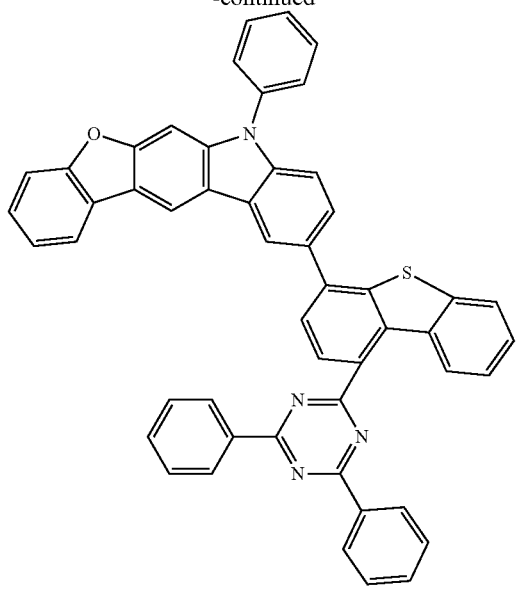
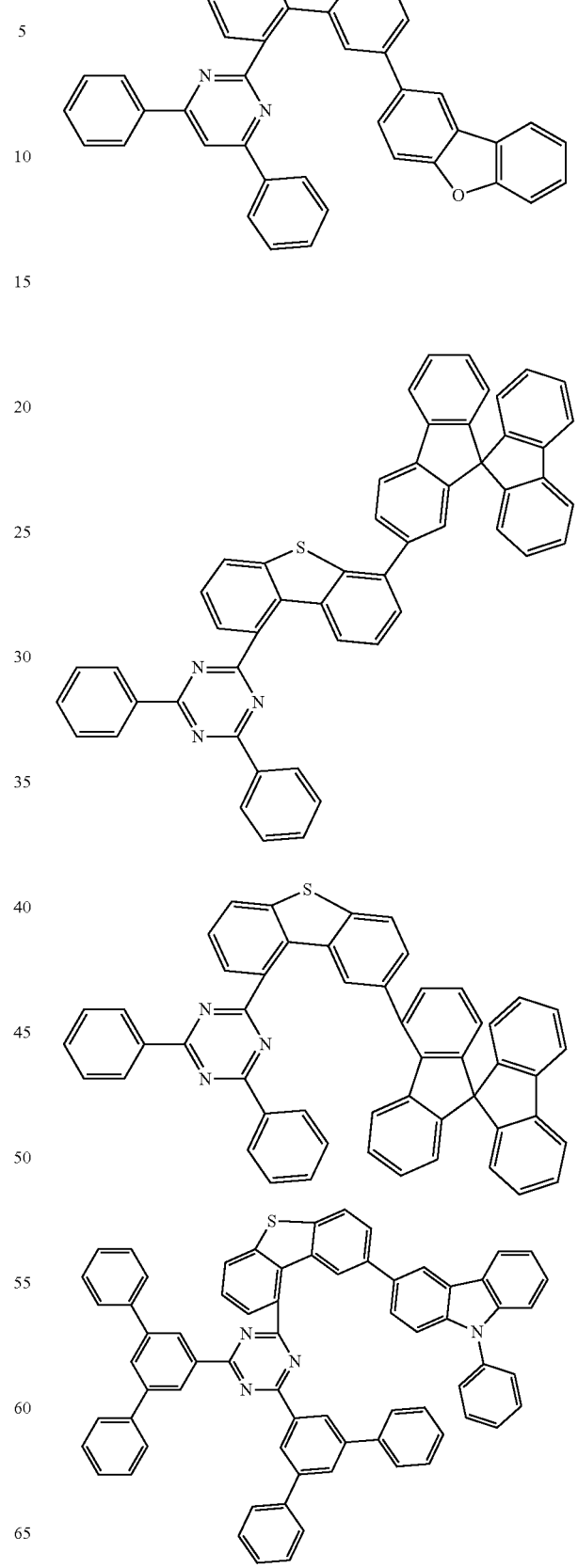

-continued
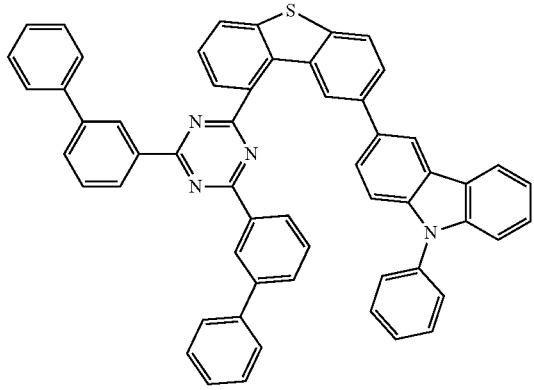
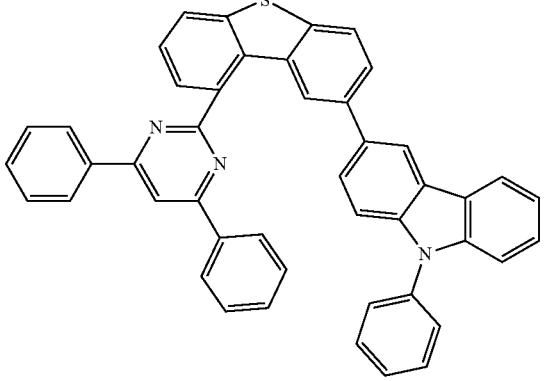
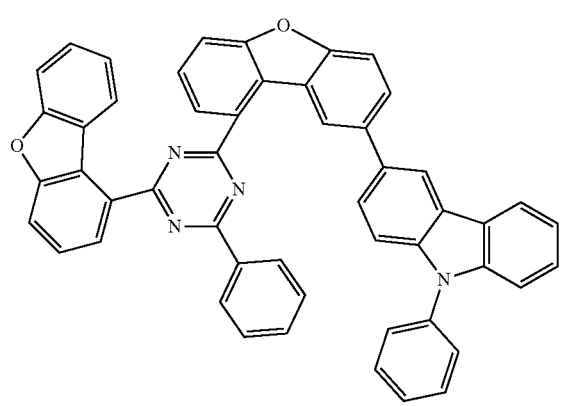
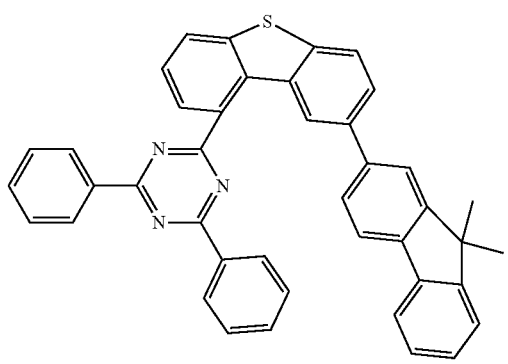
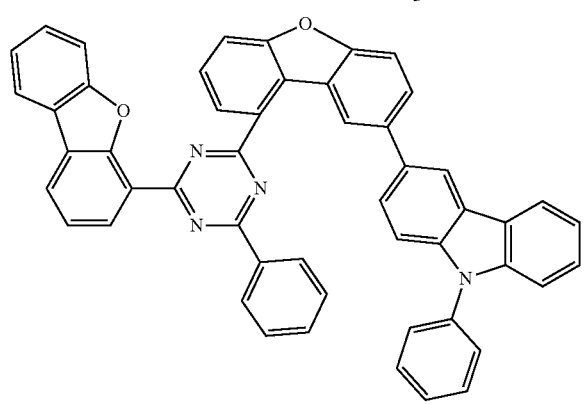
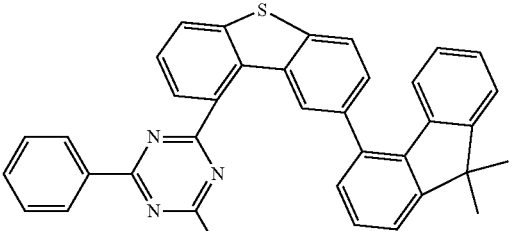
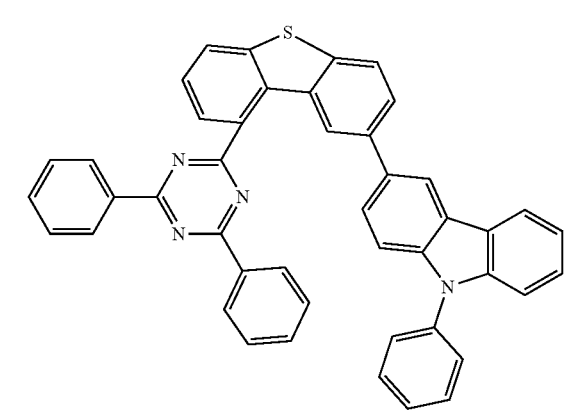
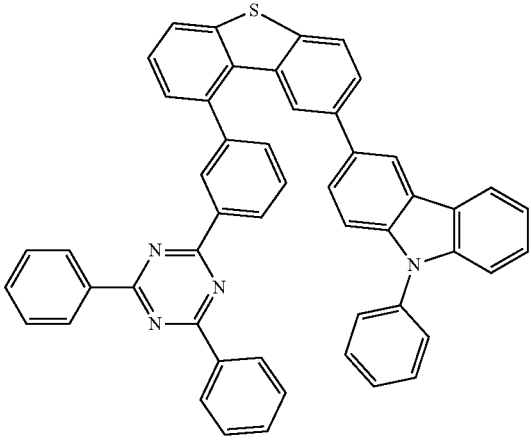

83
-continued
84
-continued
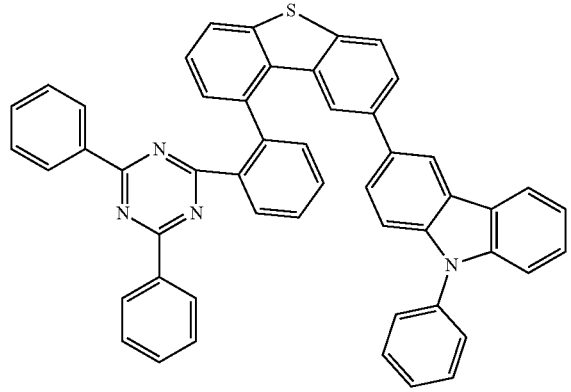
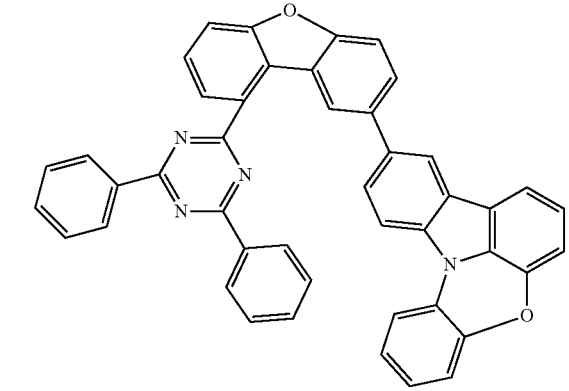
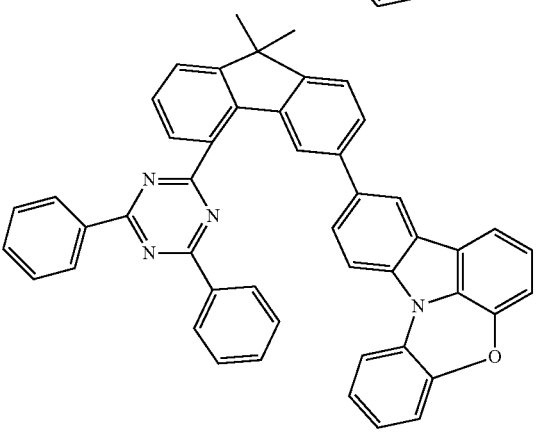
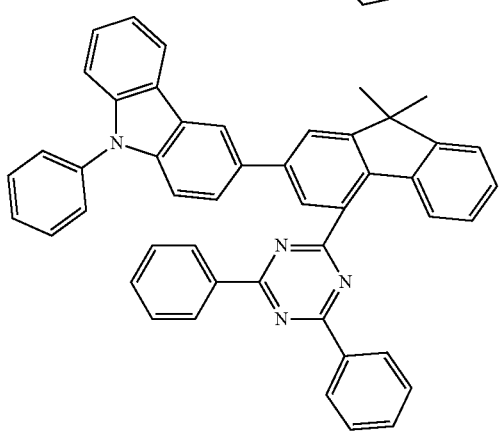
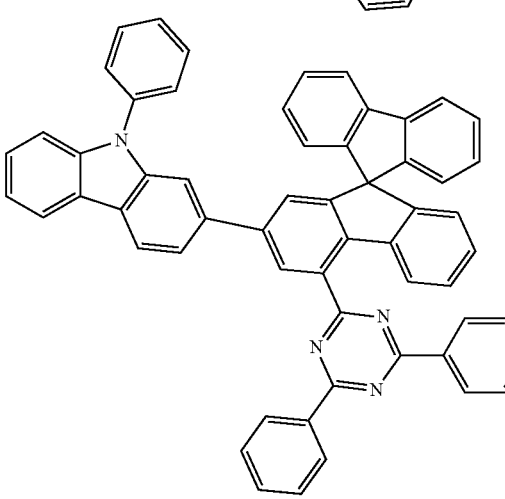

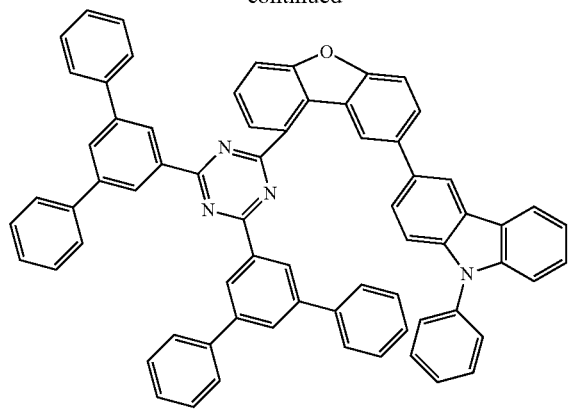
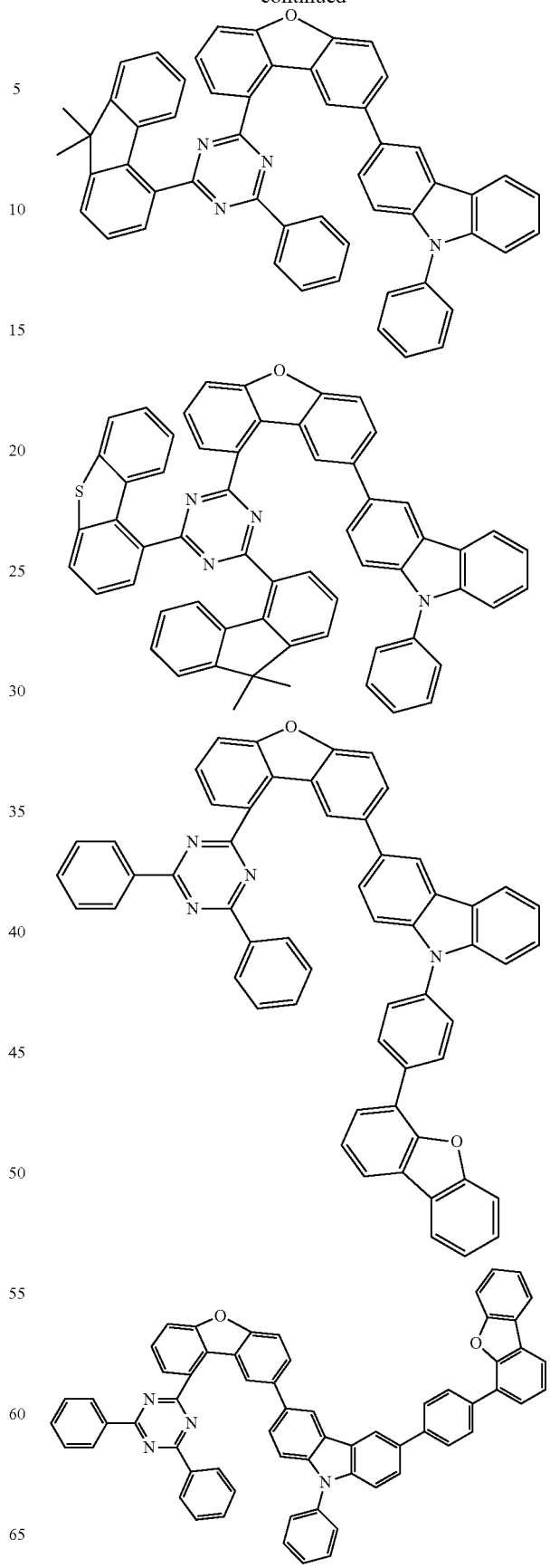

87
-continued
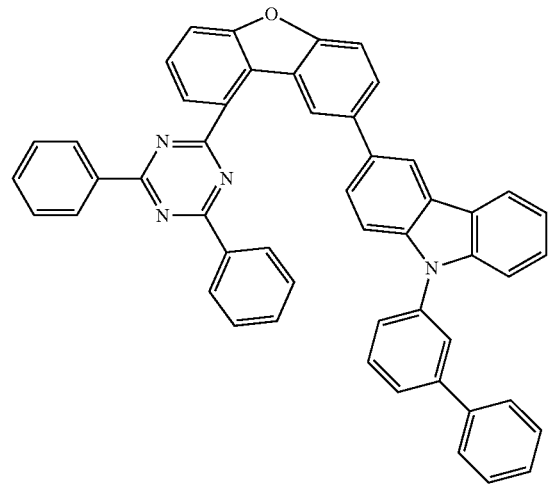
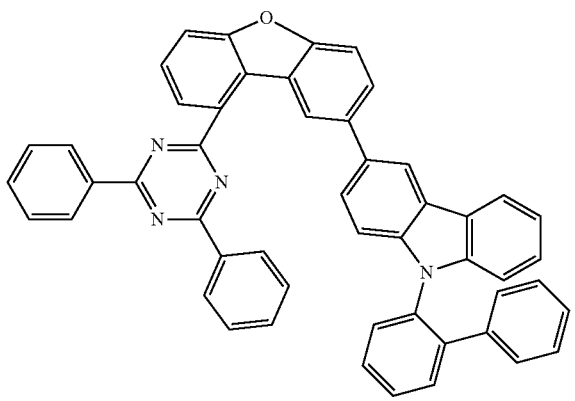
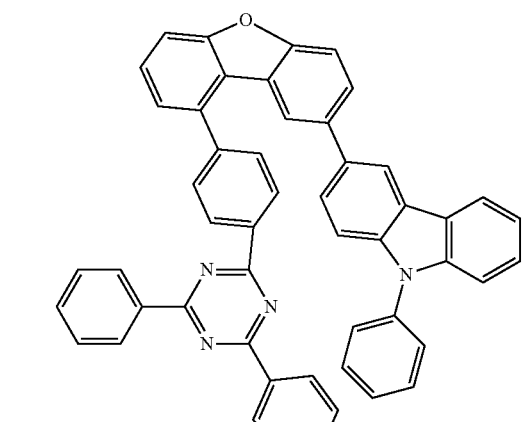
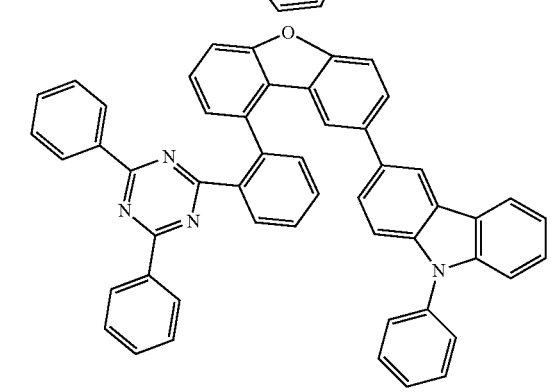
88
-continued
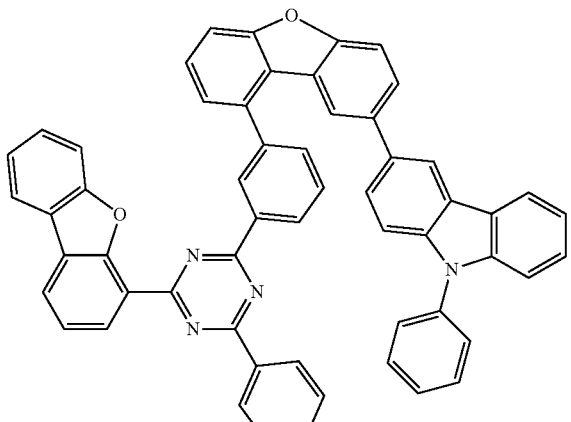
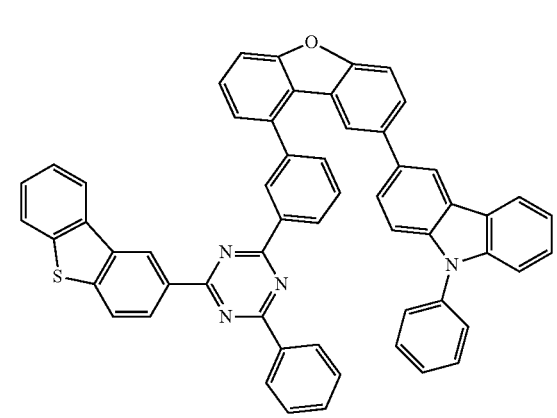
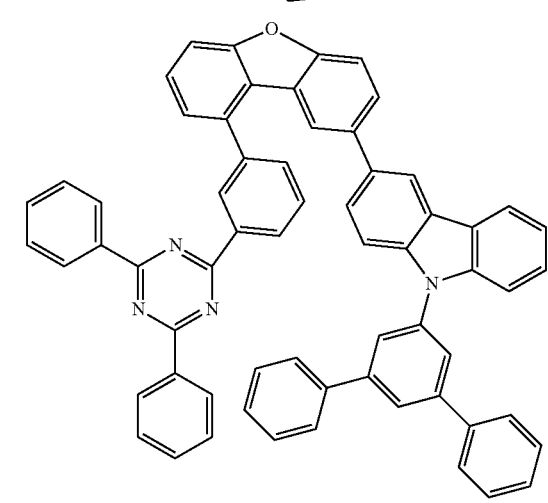
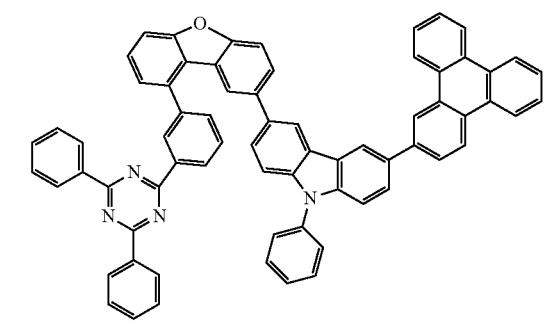

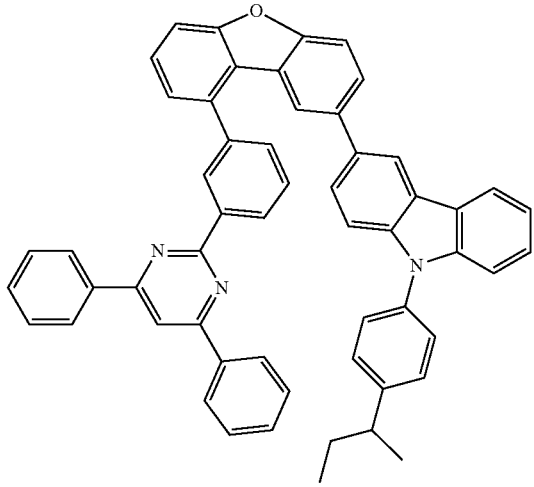
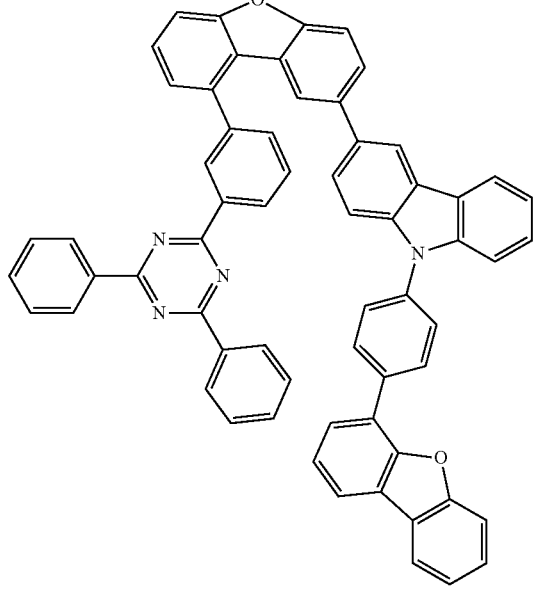
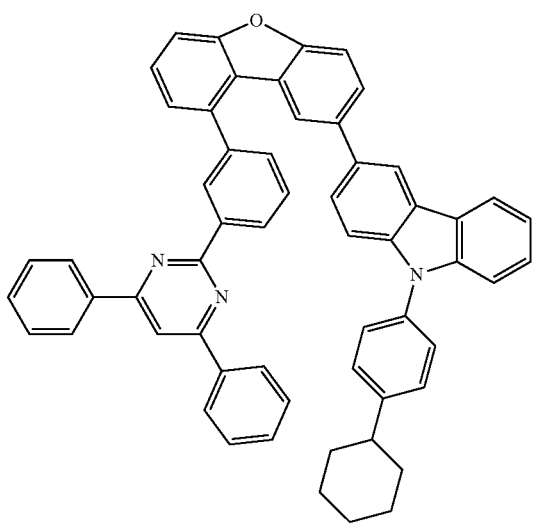
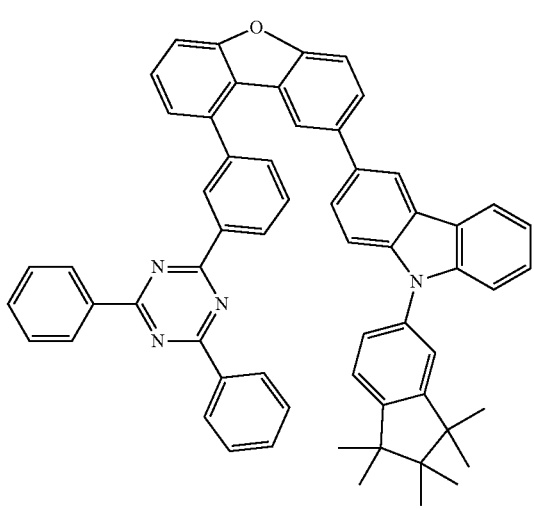
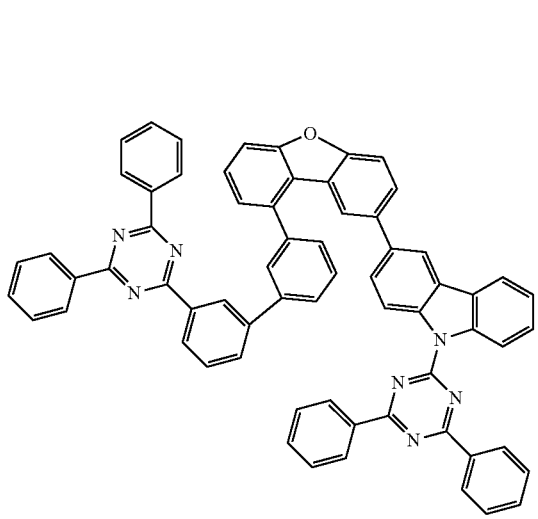

91
-continued
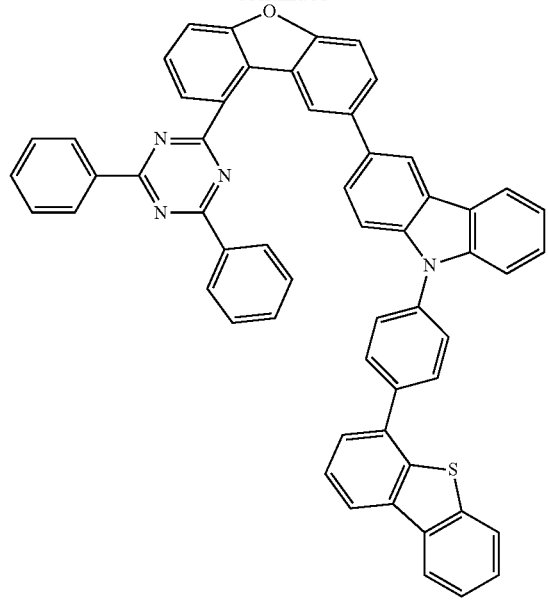
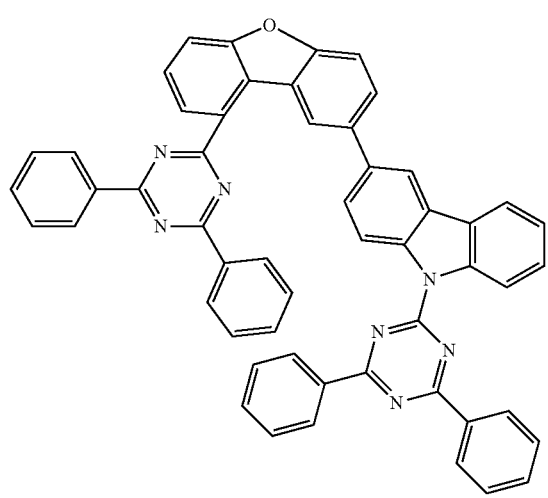
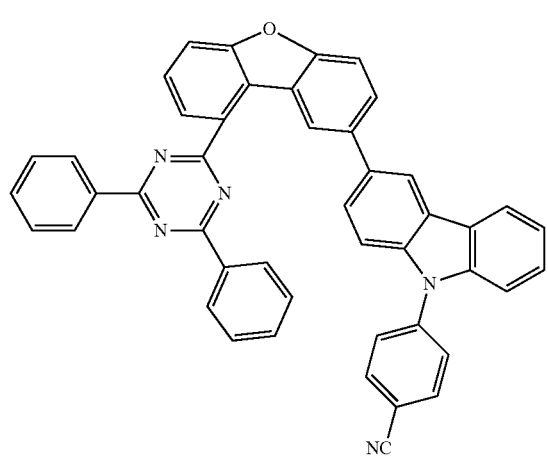
92
-continued
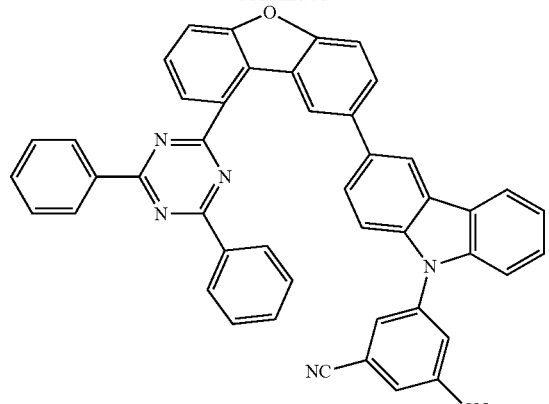
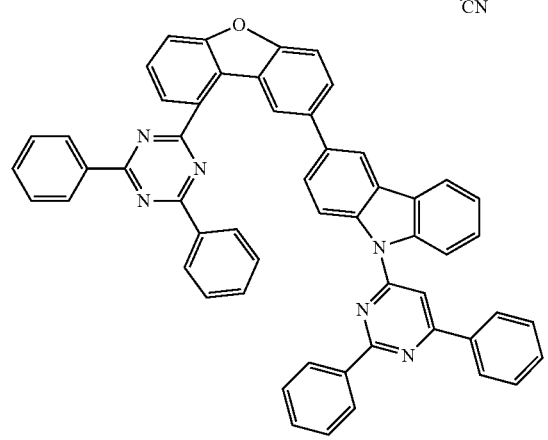
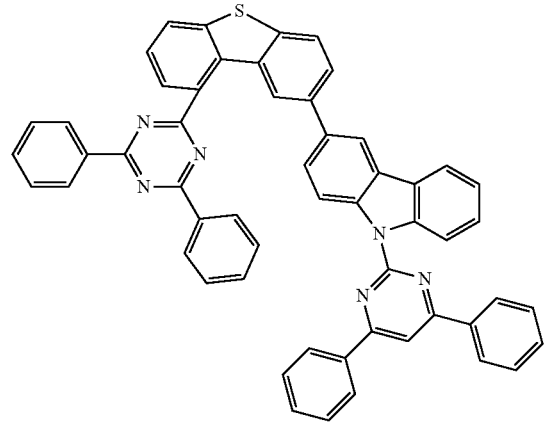
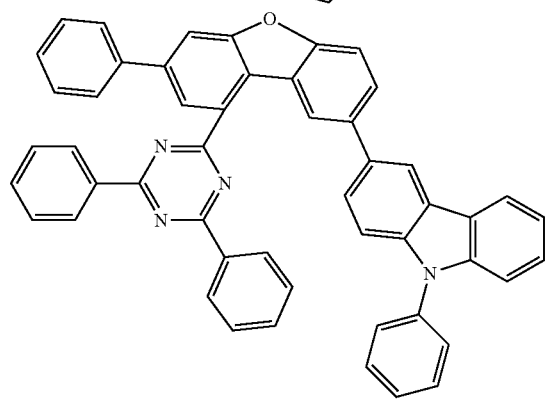

93
-continued
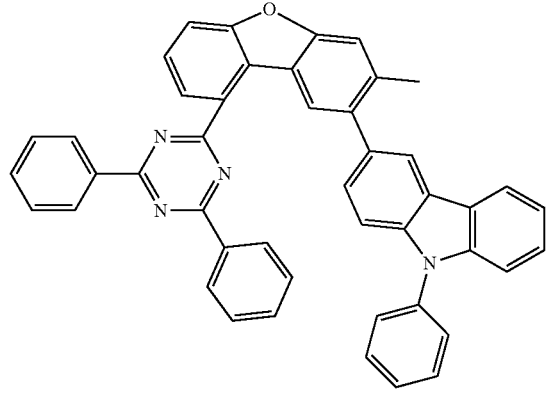
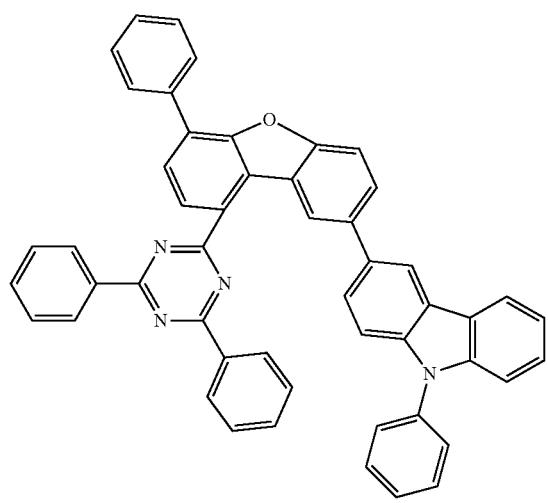
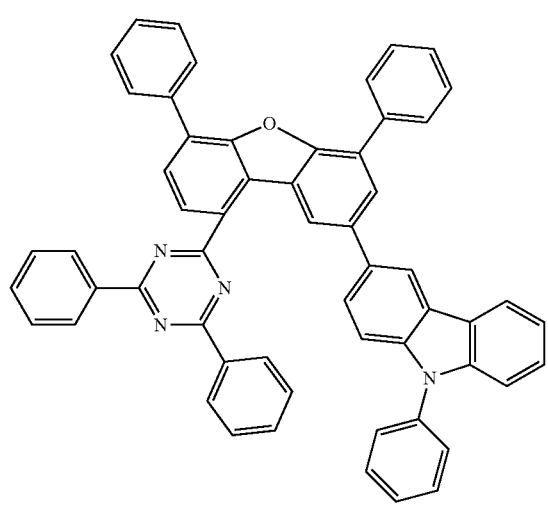
94
-continued
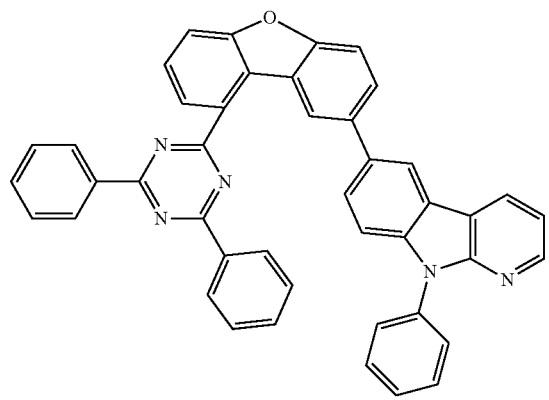
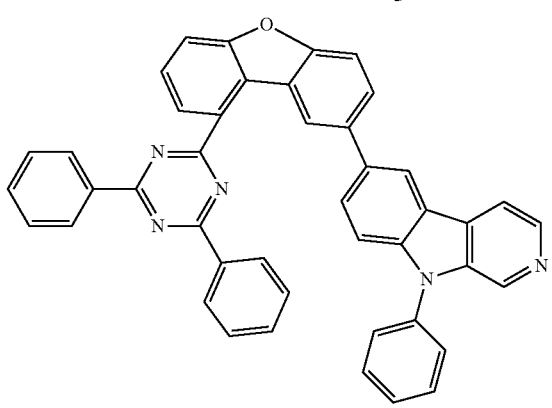
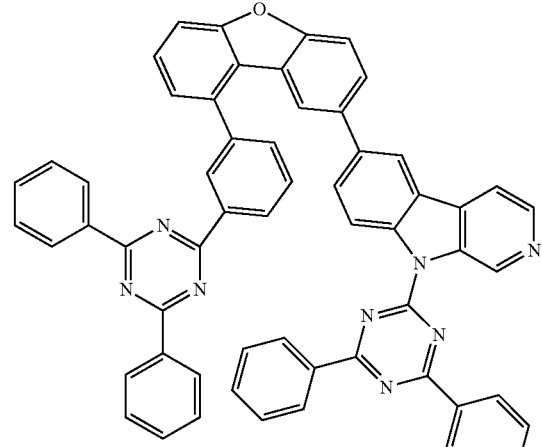
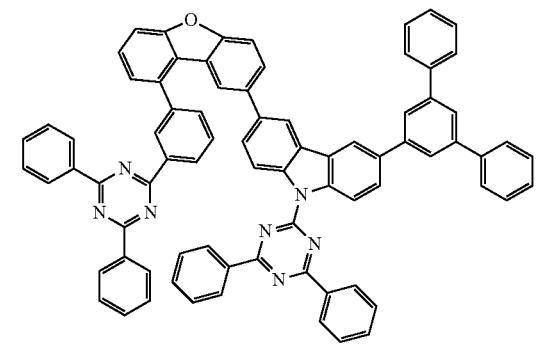

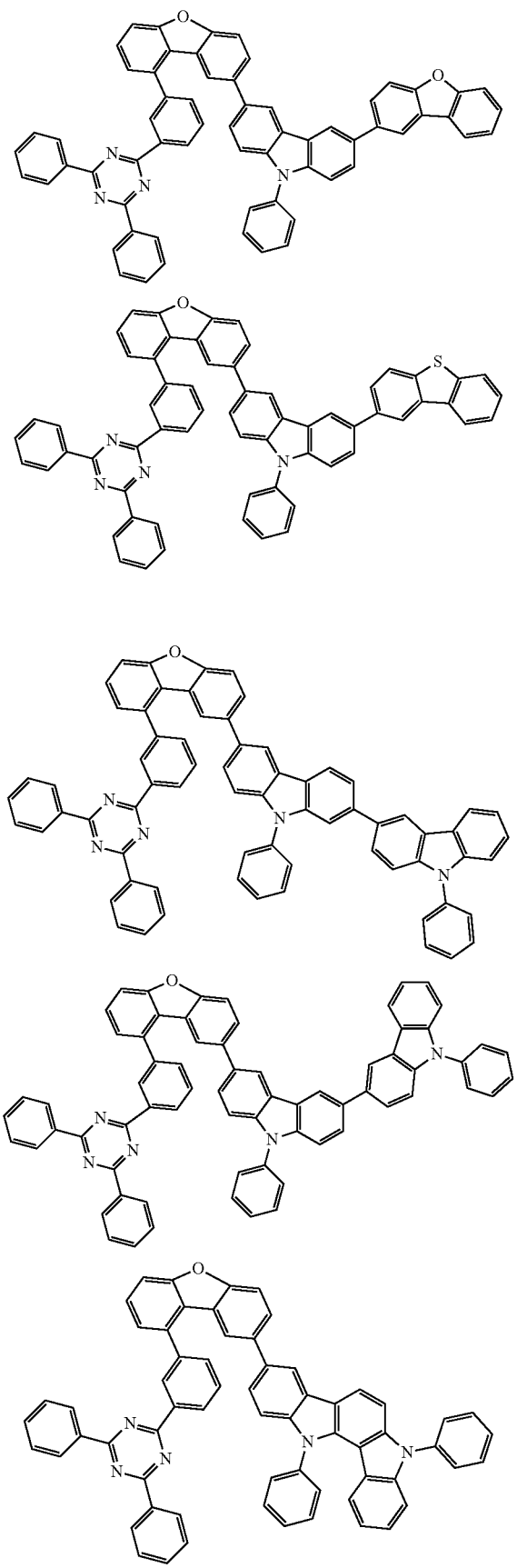
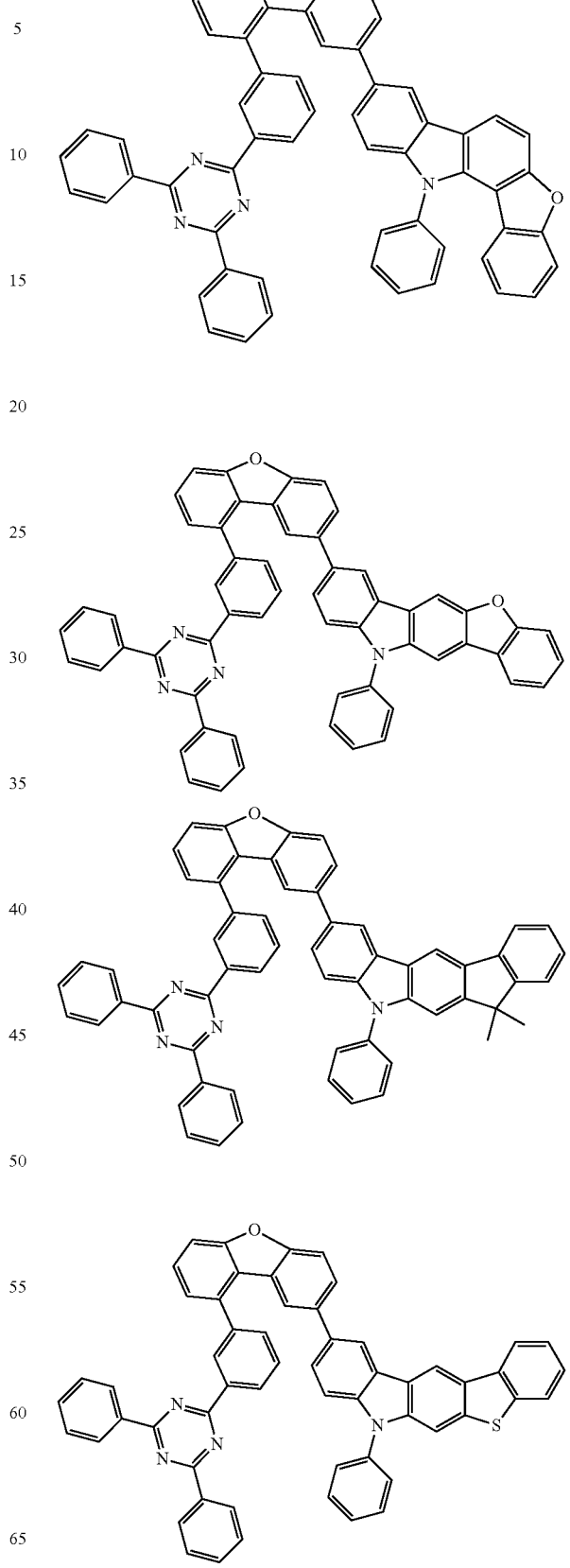

97
-continued
98
-continued
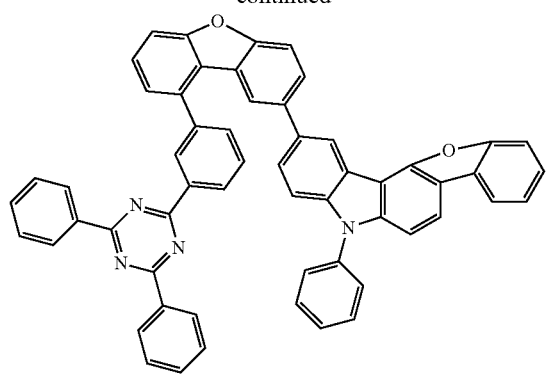
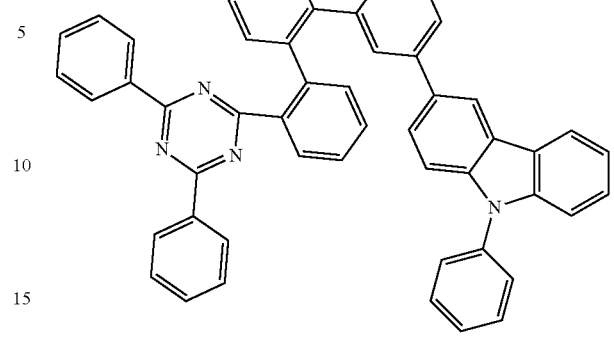
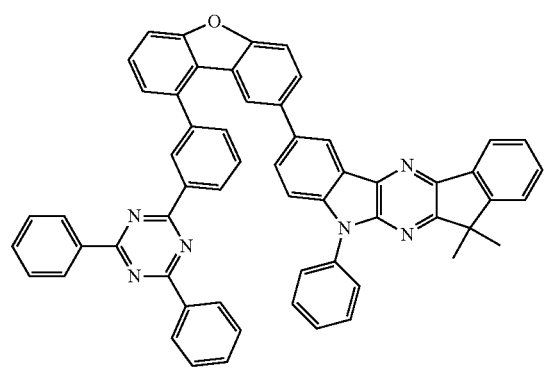
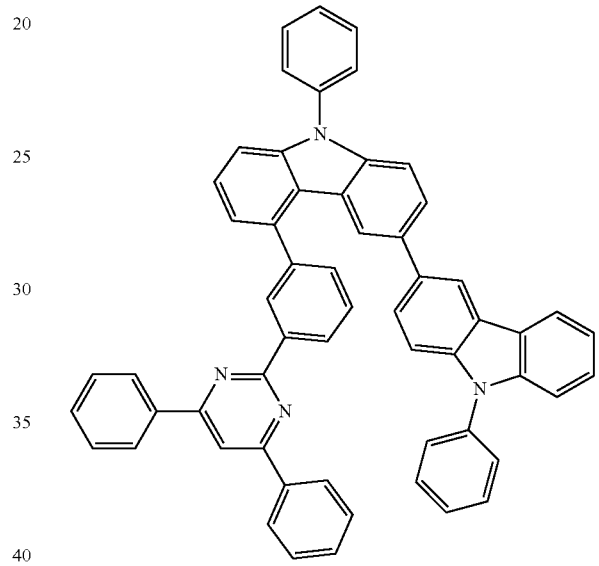
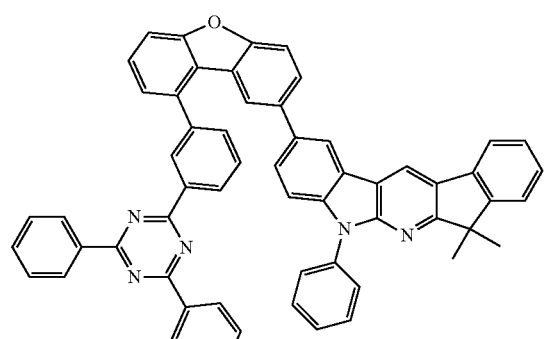
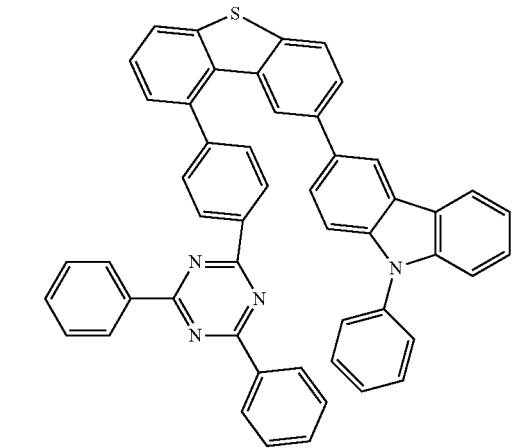
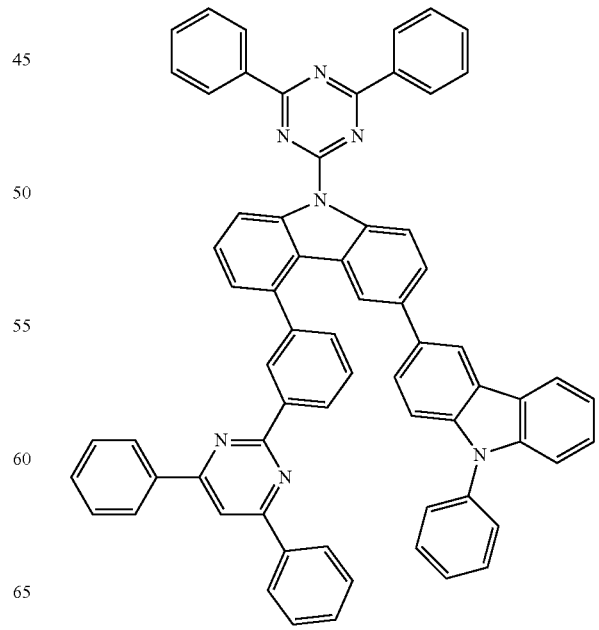

99
-continued
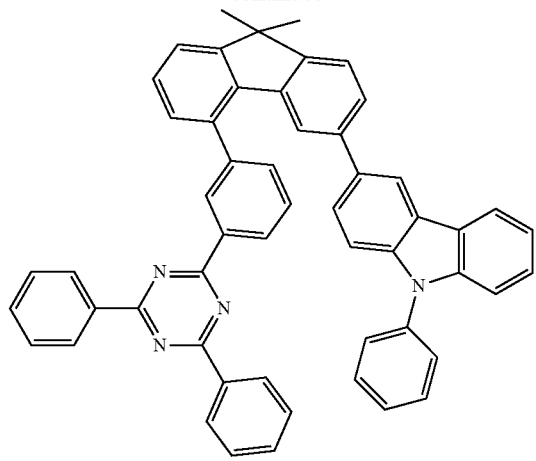
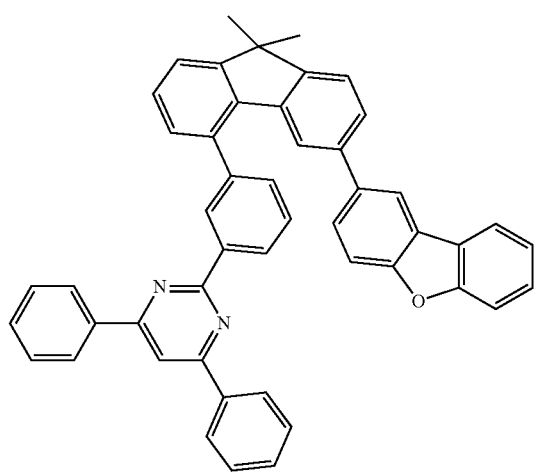
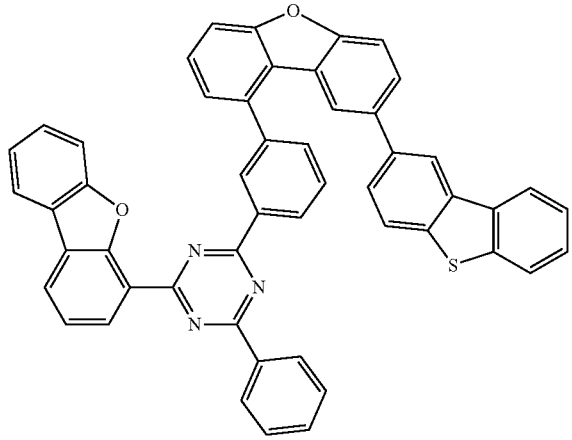
100
-continued
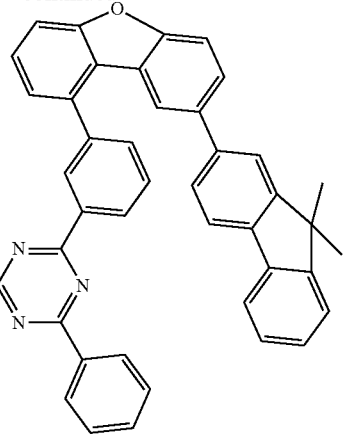
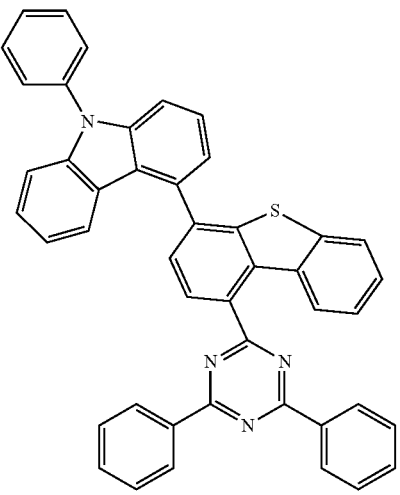
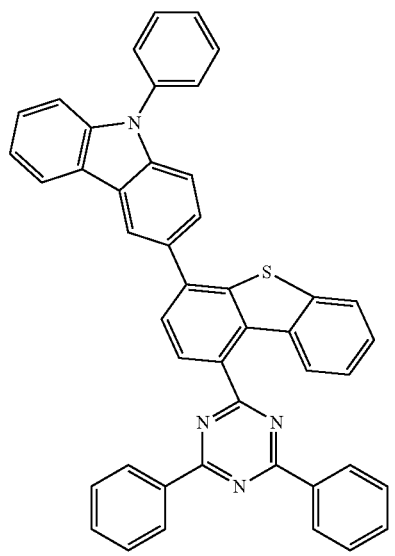

101
-continued
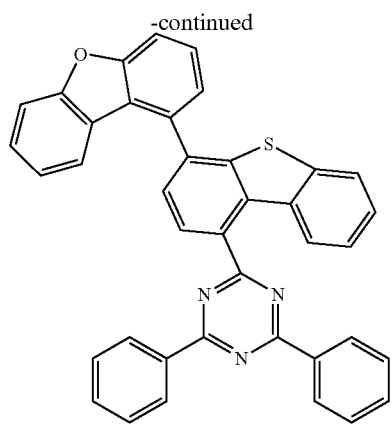
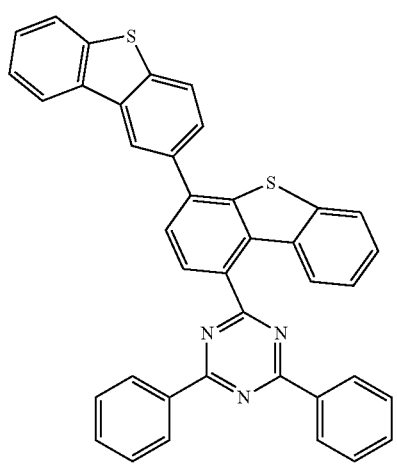
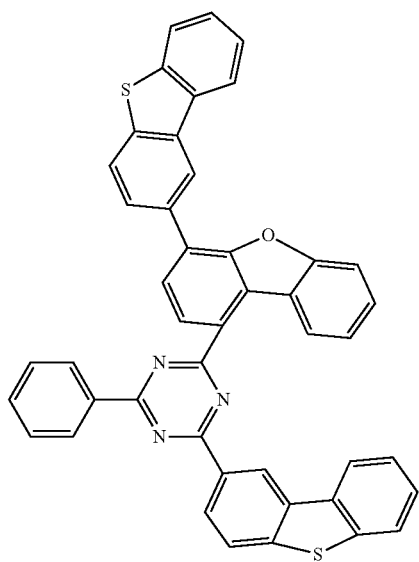
102
-continued
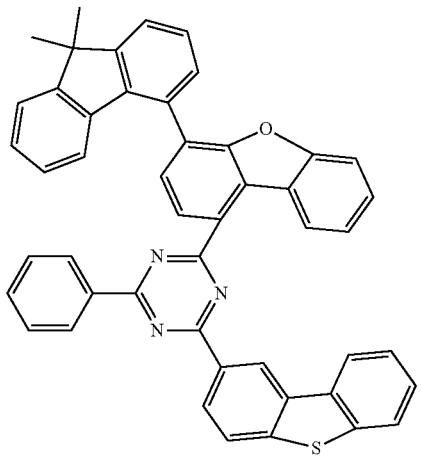
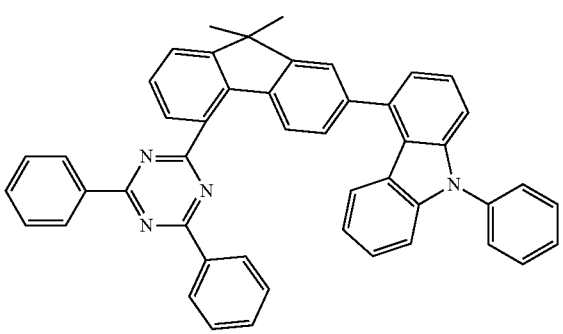
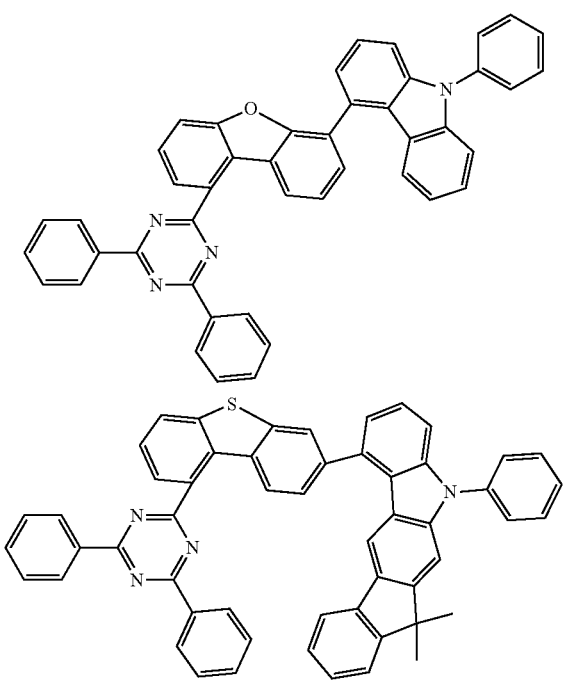

-continued
103
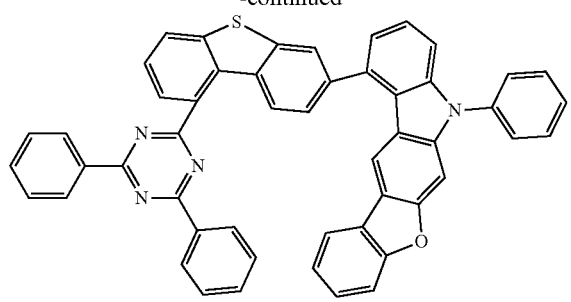
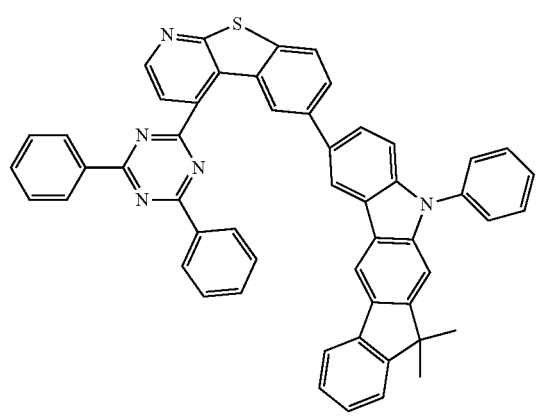
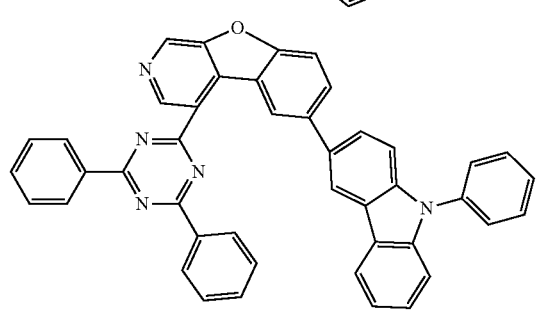
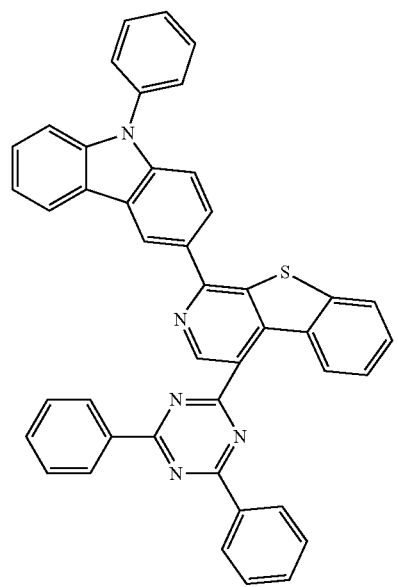
-continued
104
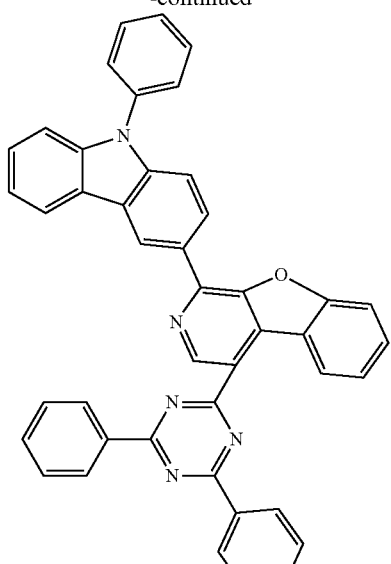
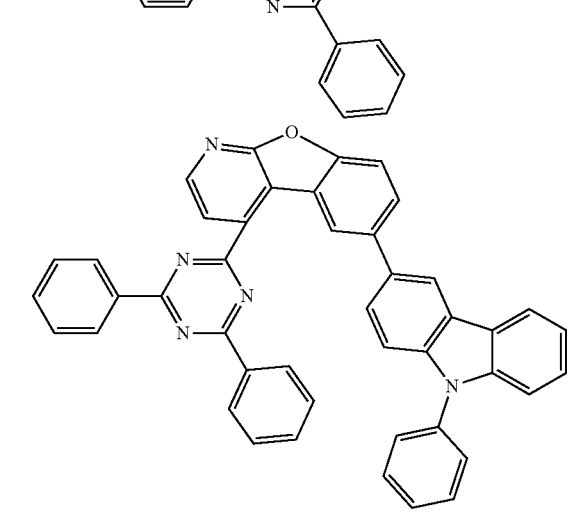
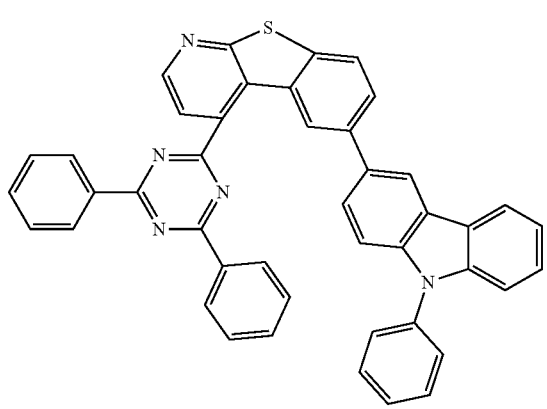
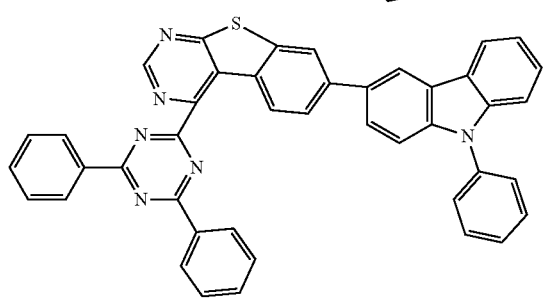

105
-continued
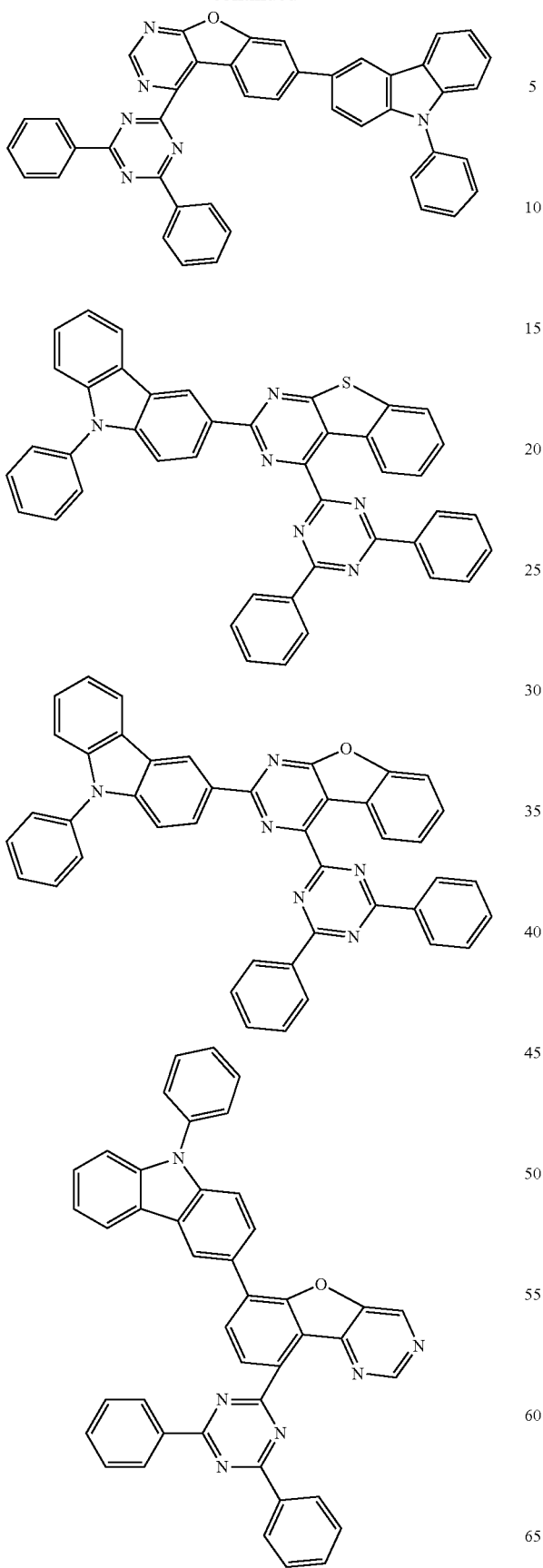
106
-continued

-continued
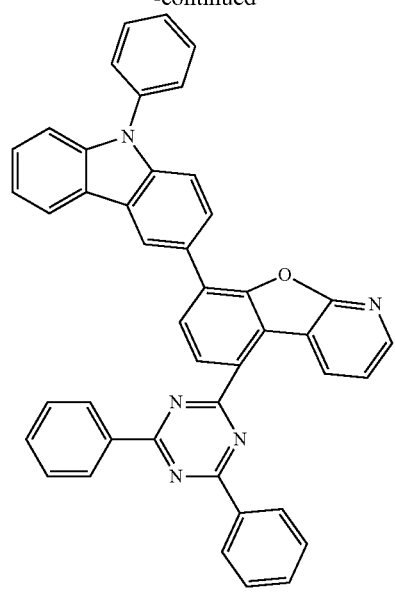
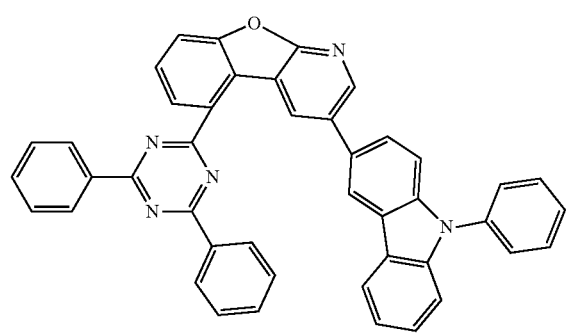
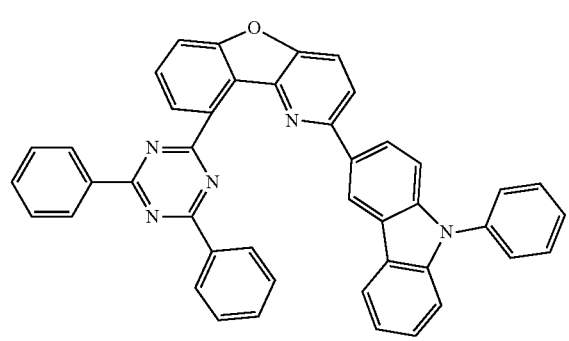
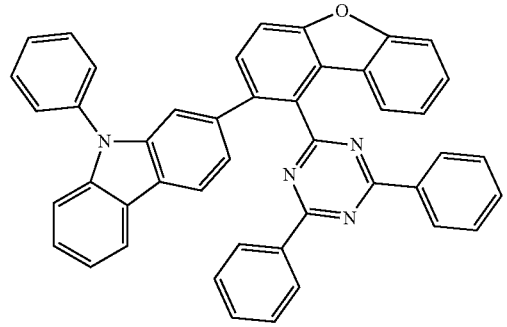
-continued
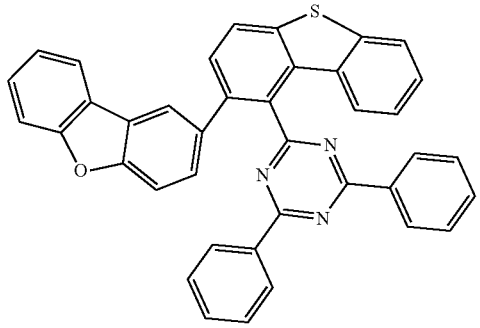
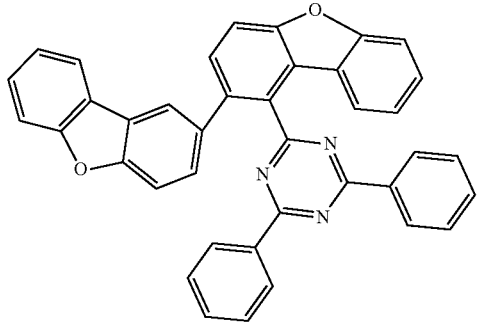
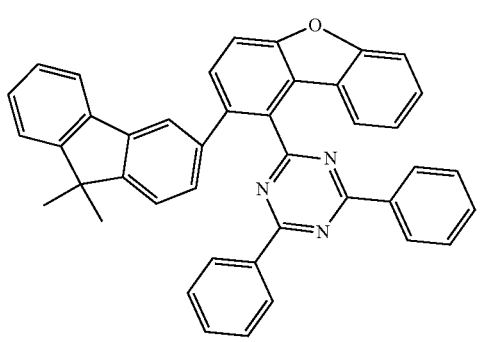
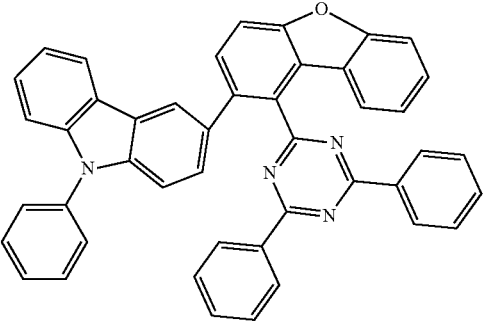
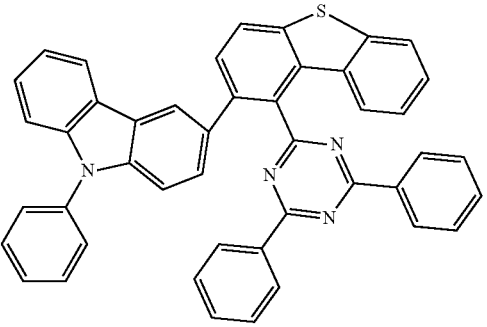

109
-continued
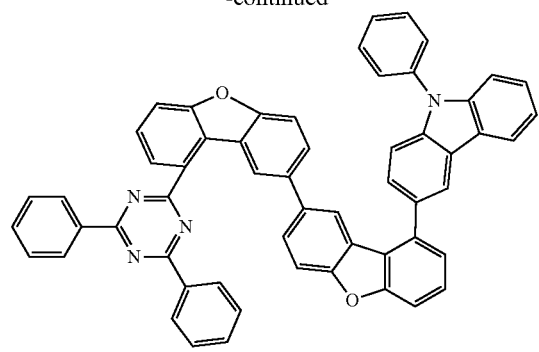
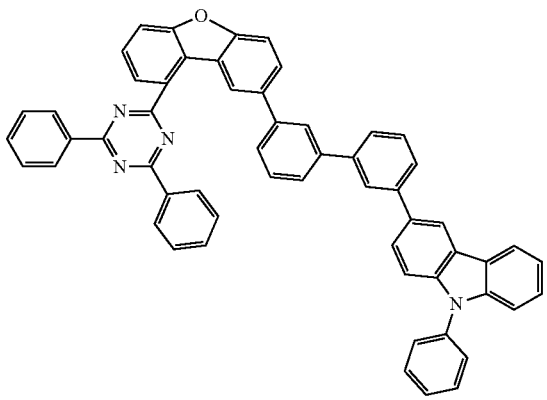
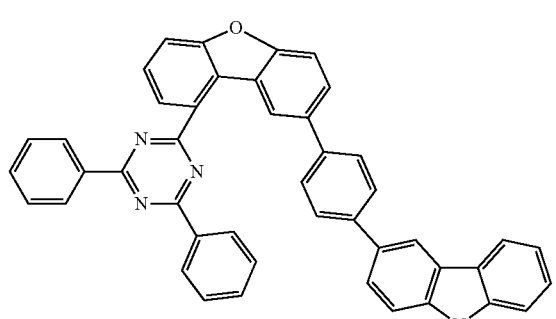
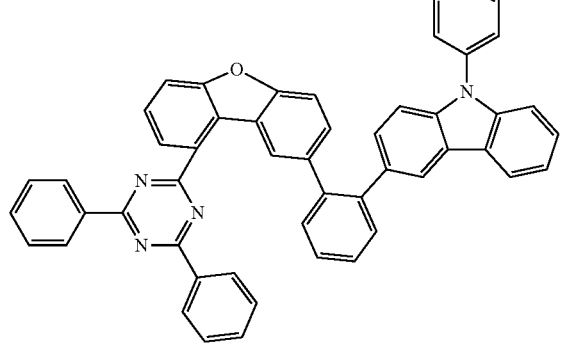
110
-continued
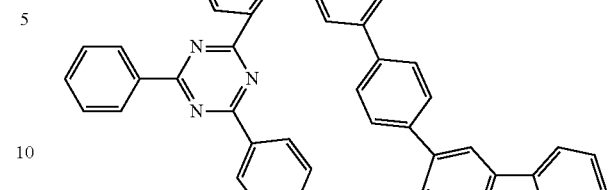
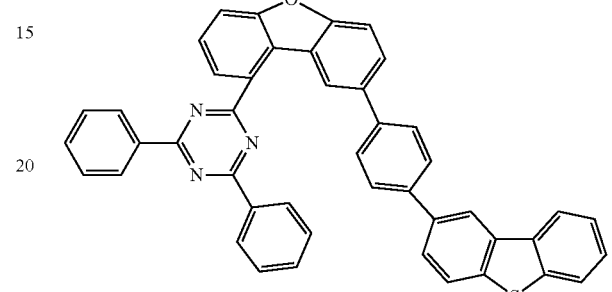
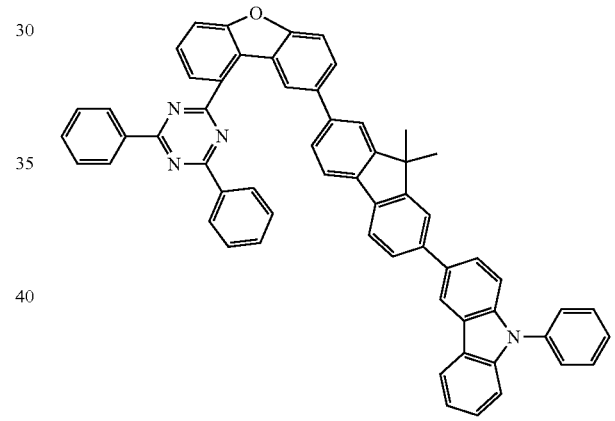
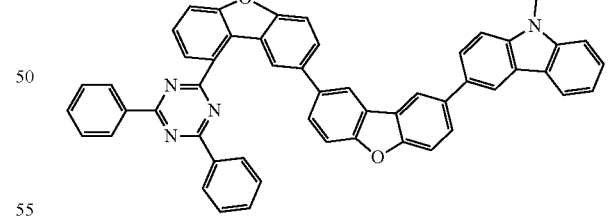
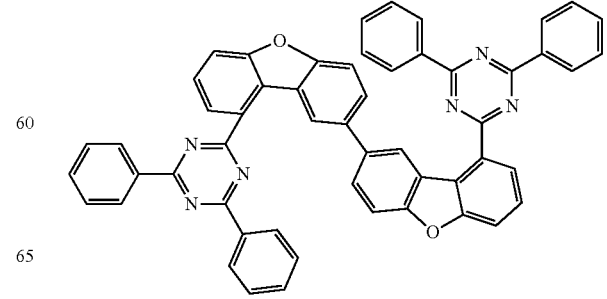

111
-continued
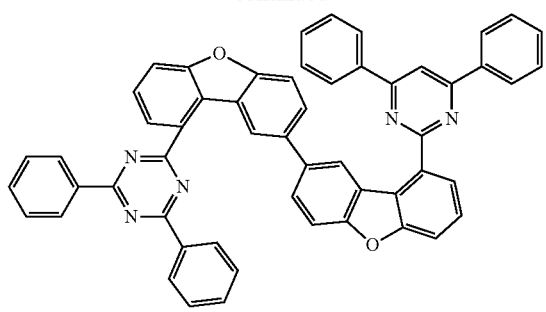
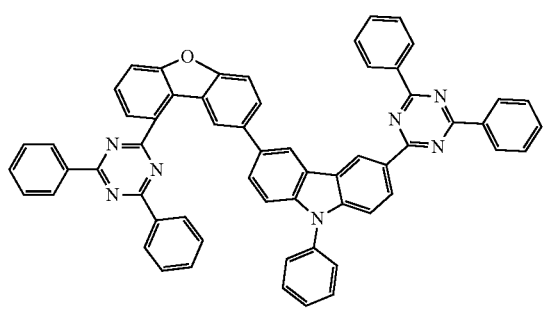
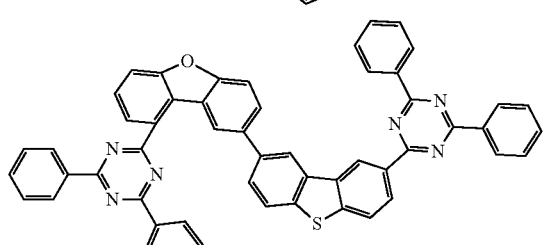
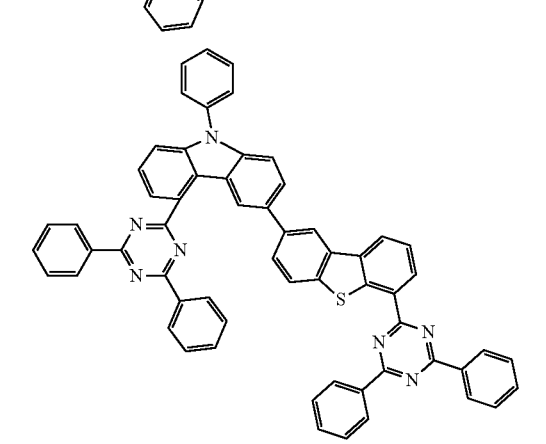
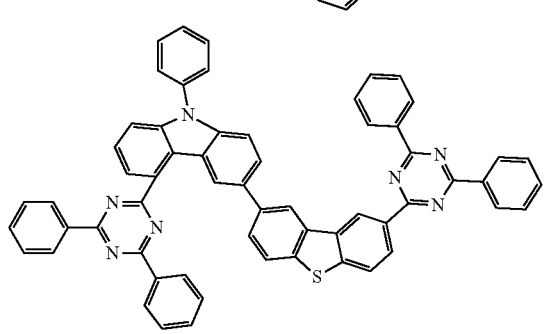
112
-continued
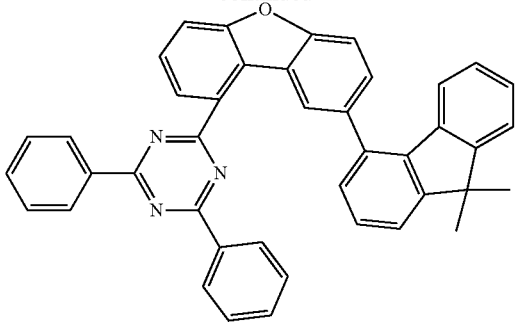
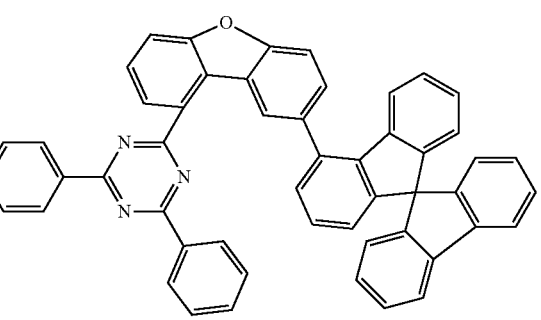
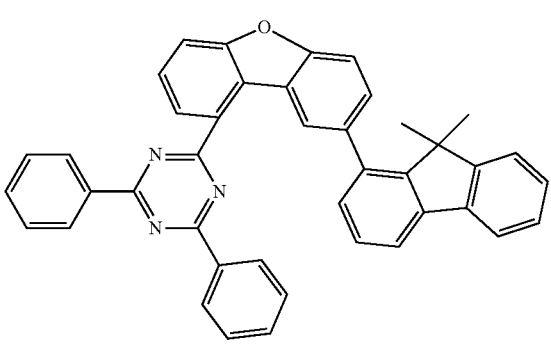
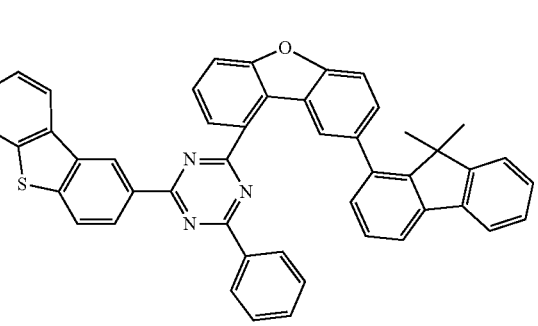

113
-continued
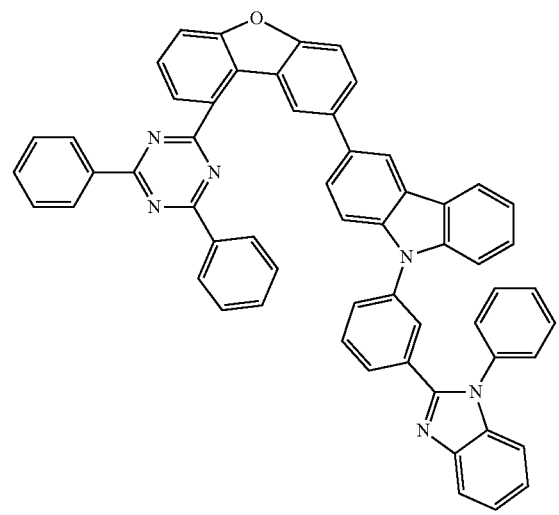
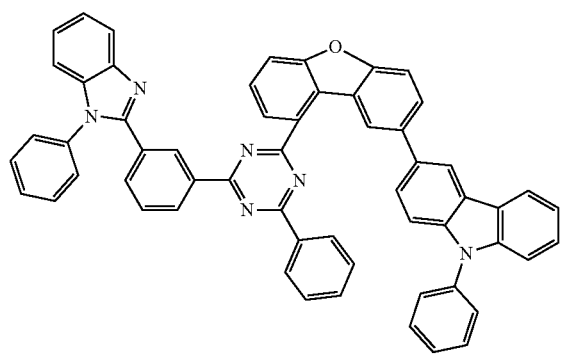
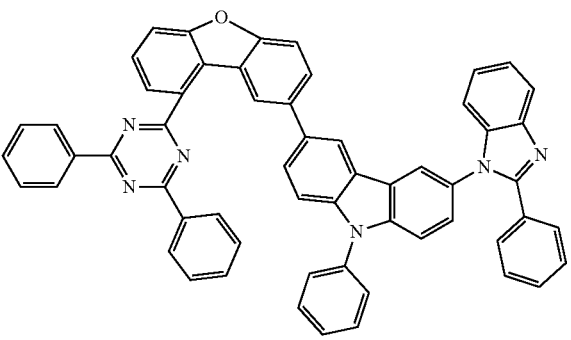
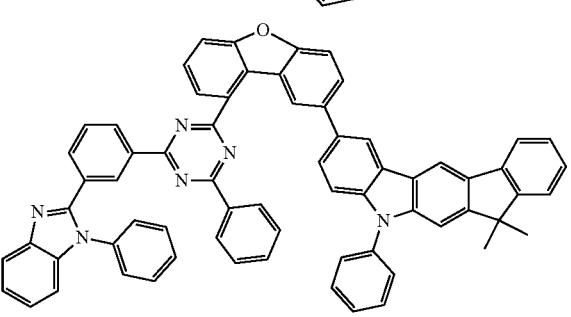
114
-continued
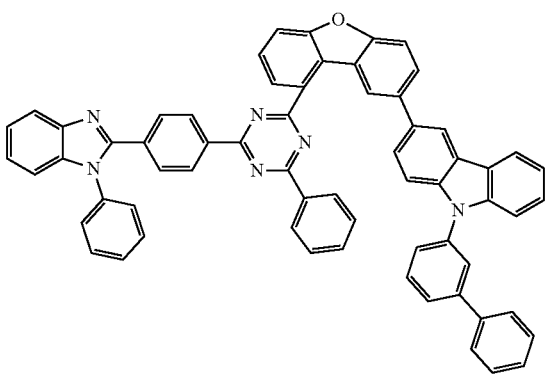
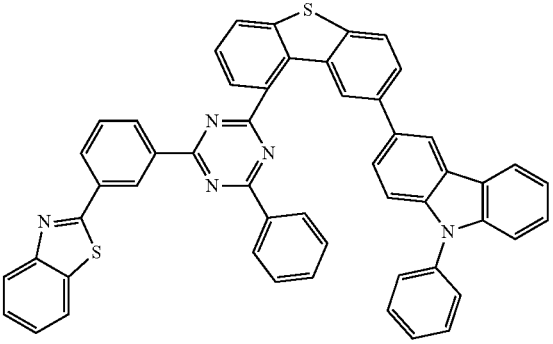
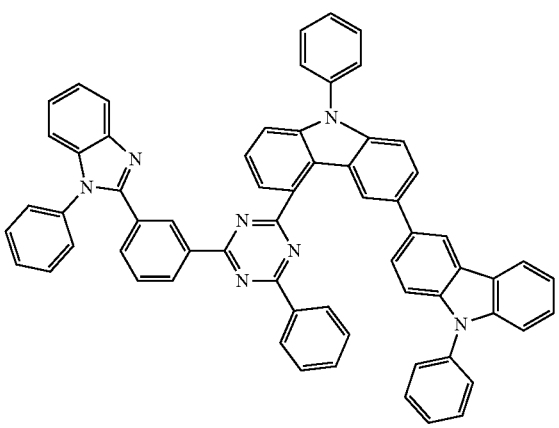

115
-continued
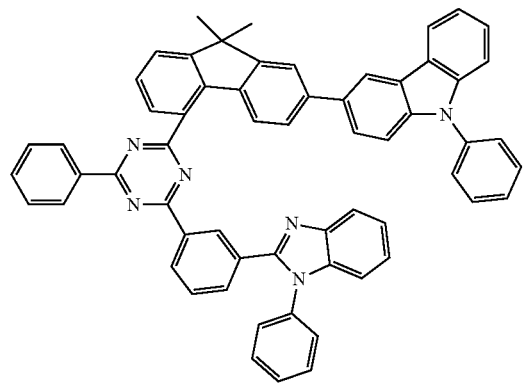
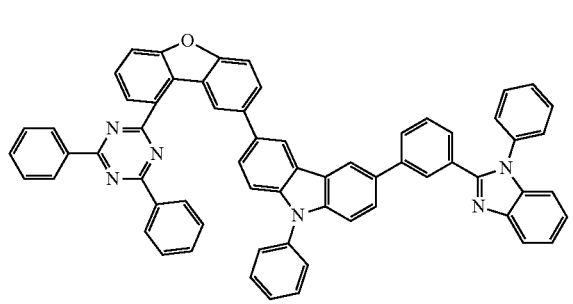
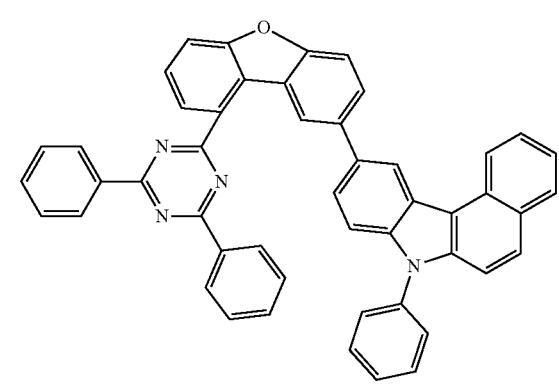
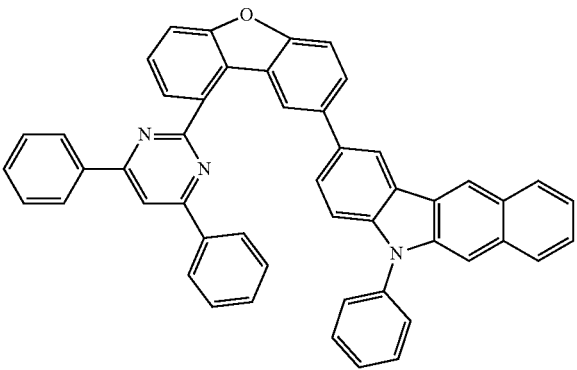
116
-continued
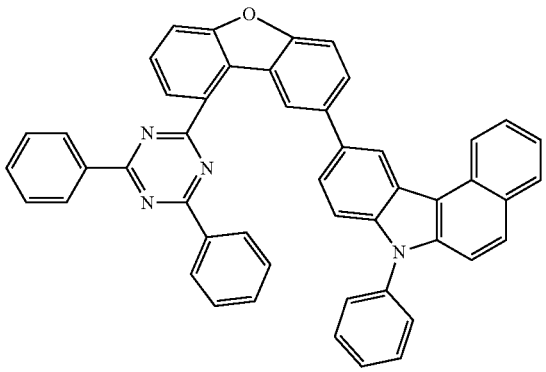
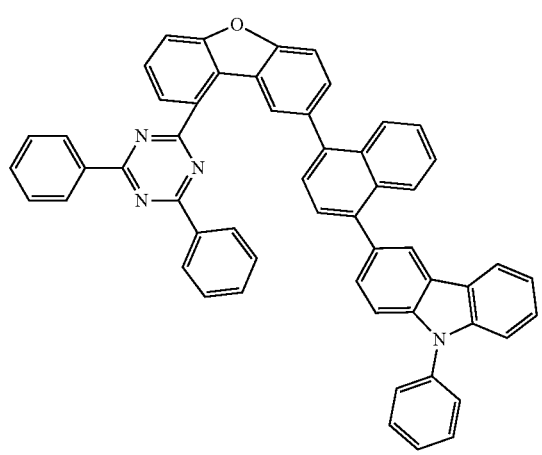
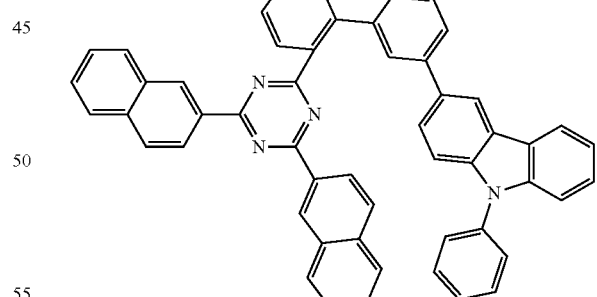
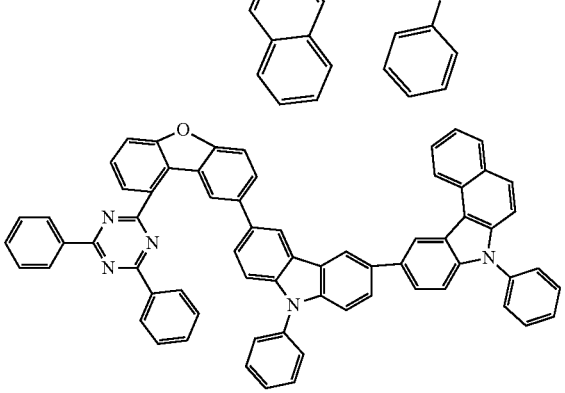

117
-continued
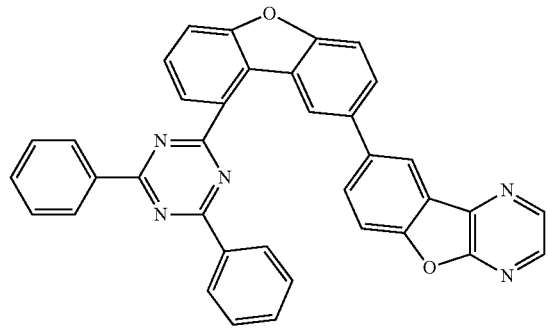
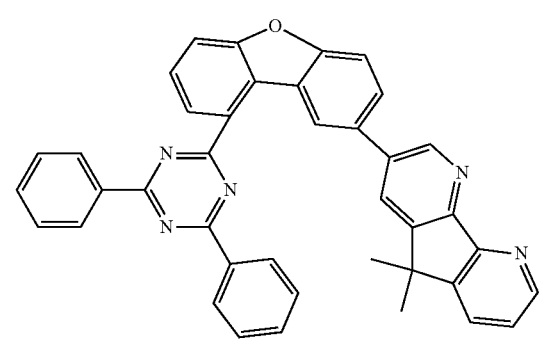
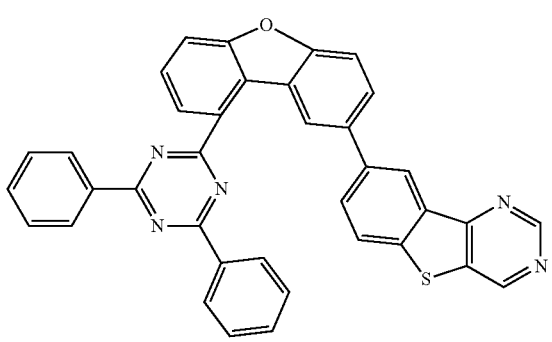

118
-continued
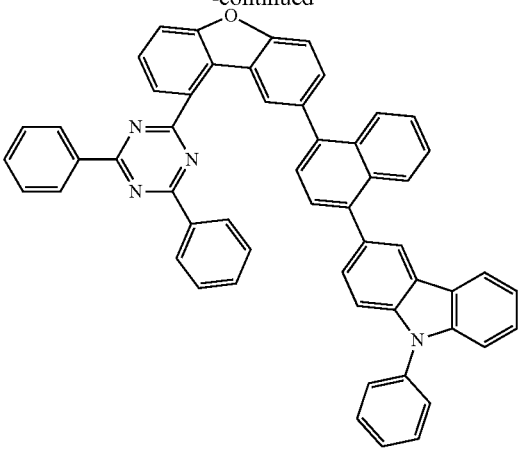
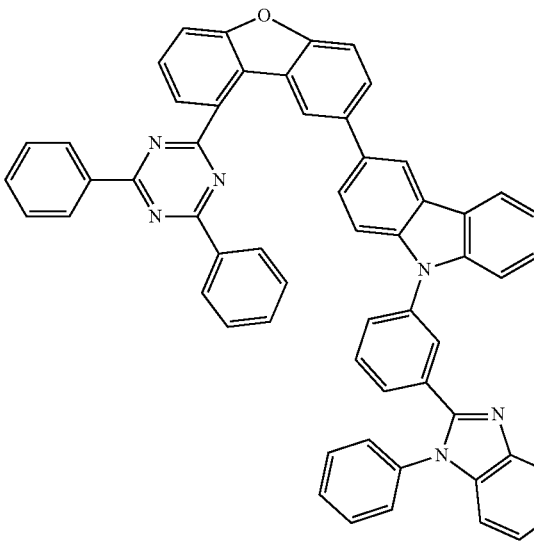
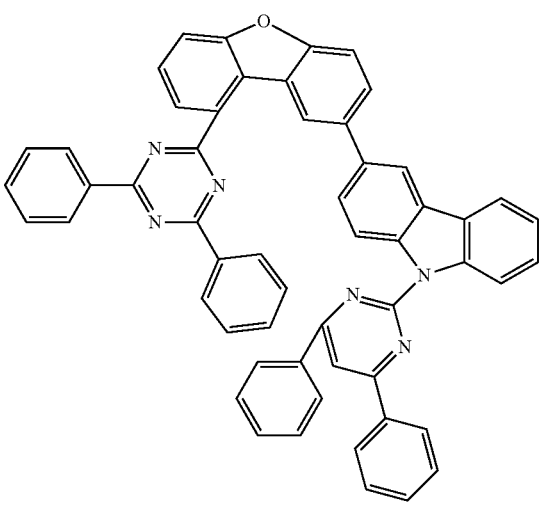

-continued
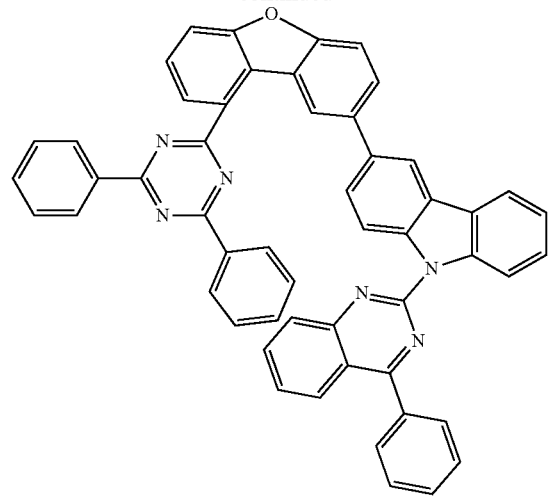
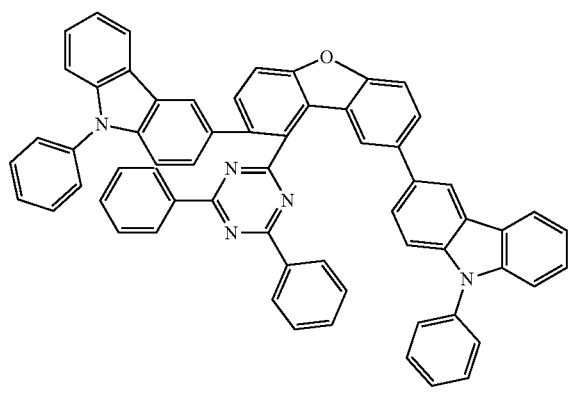
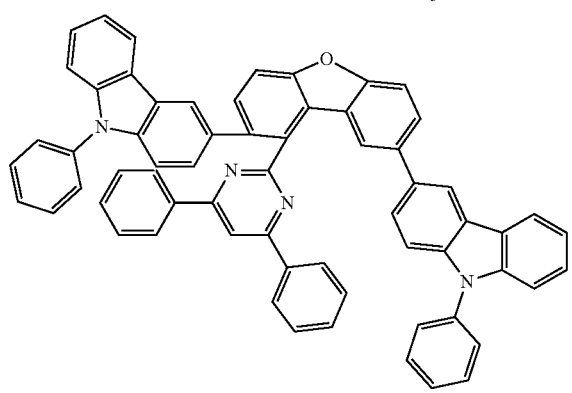
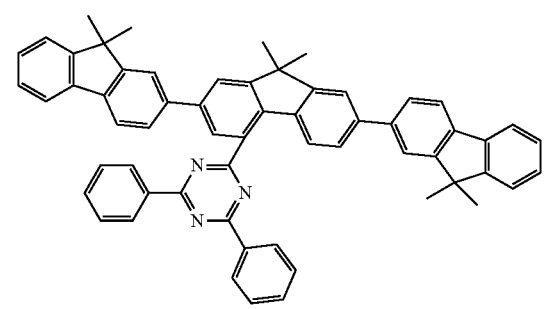
-continued
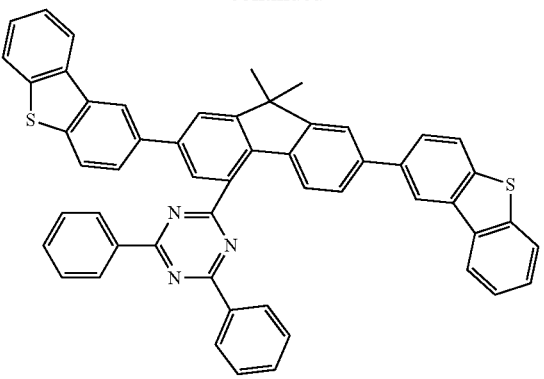
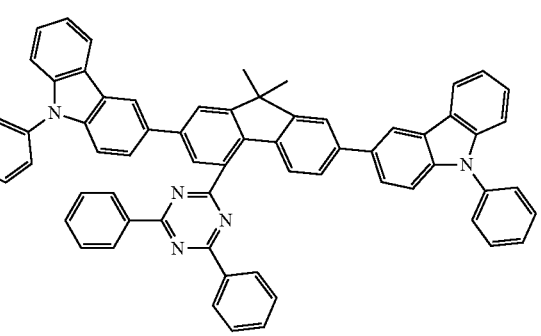
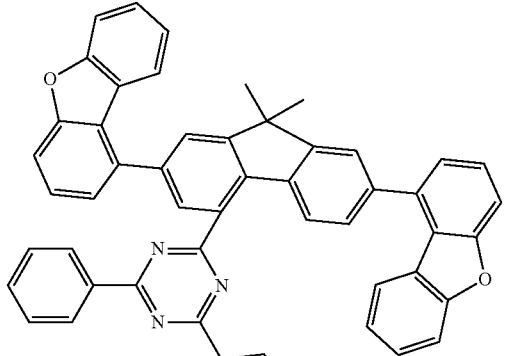
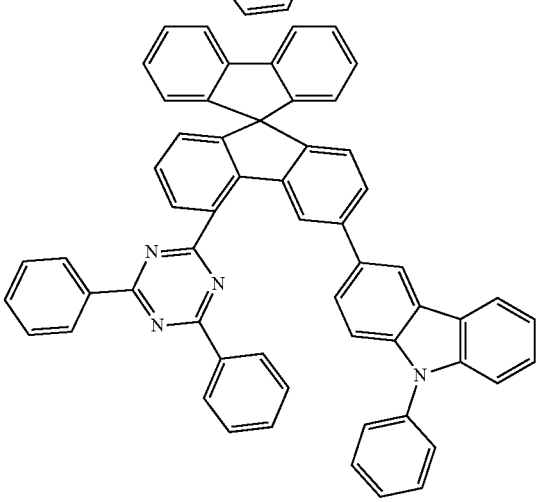

121
-continued
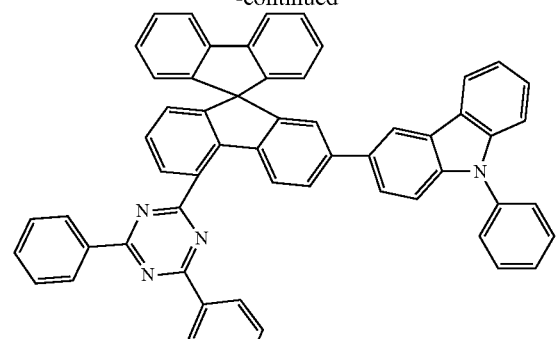
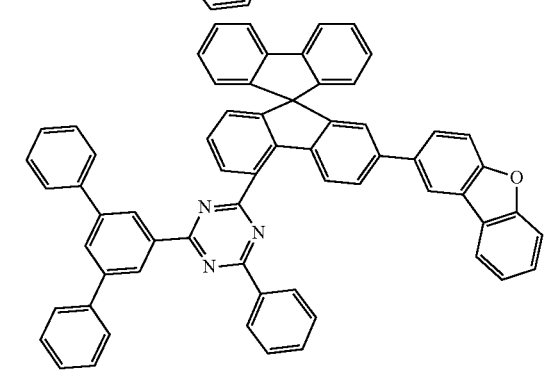
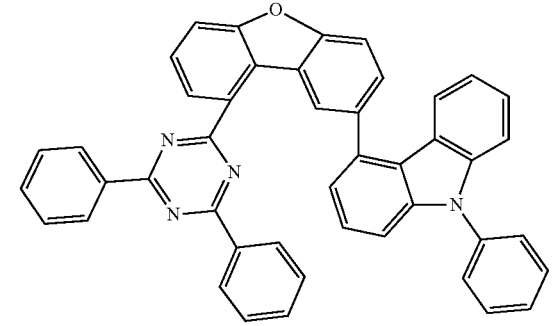
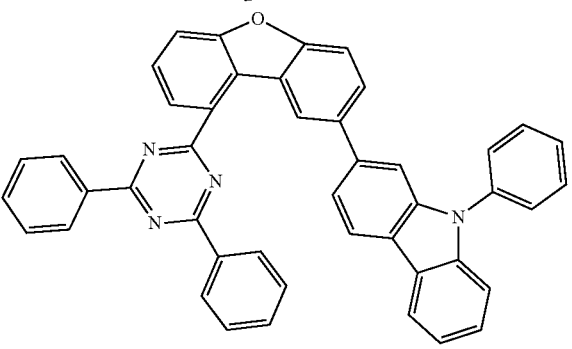
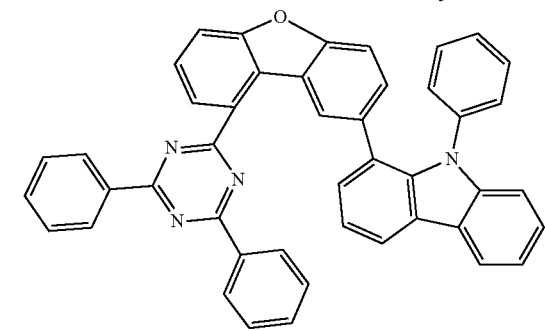
122
-continued
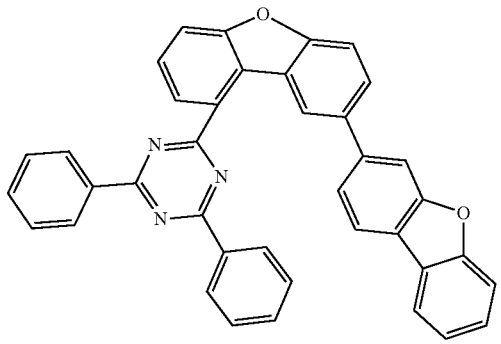
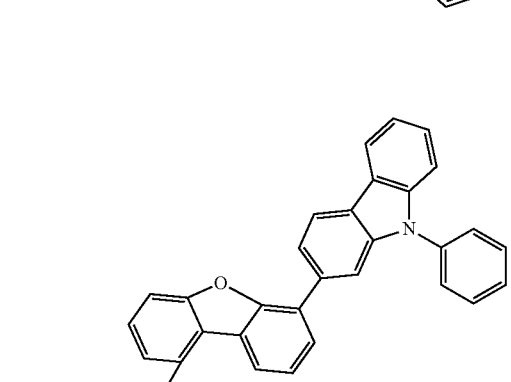
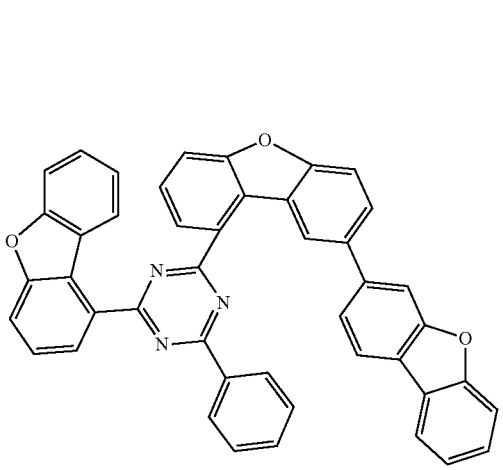
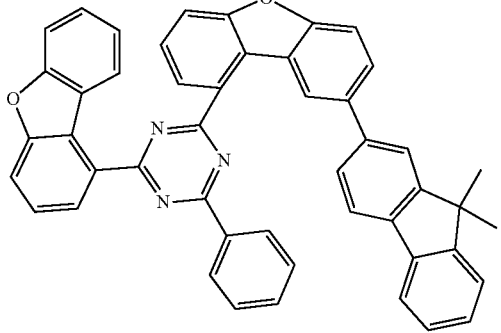

-continued
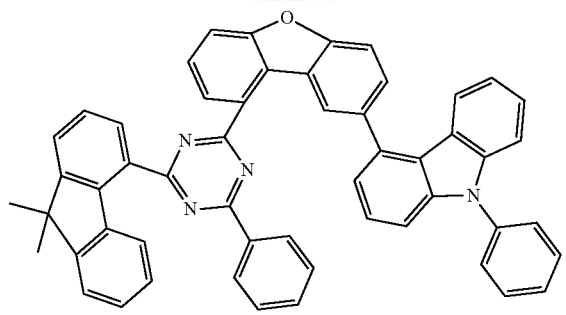
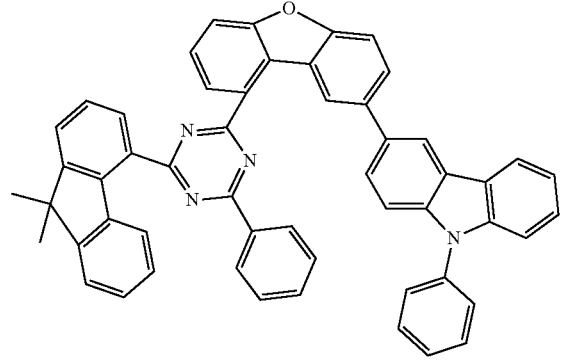
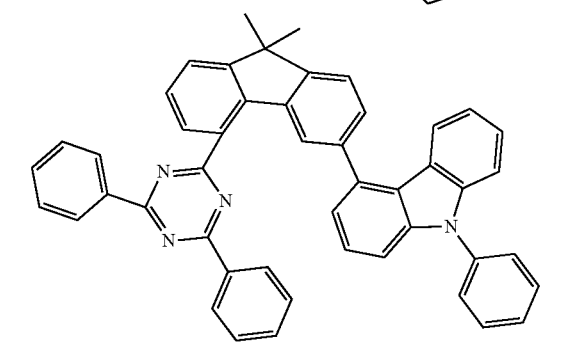
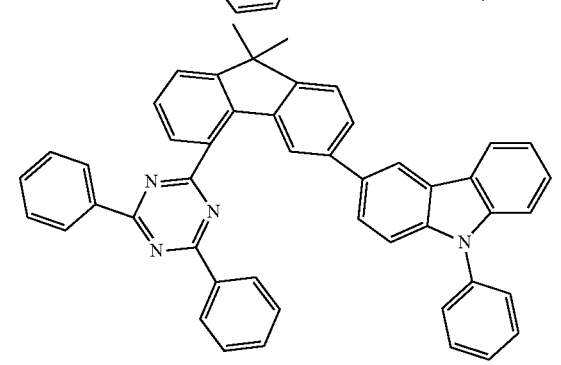
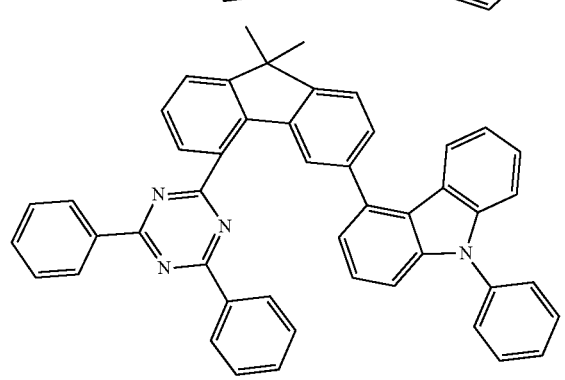
-continued
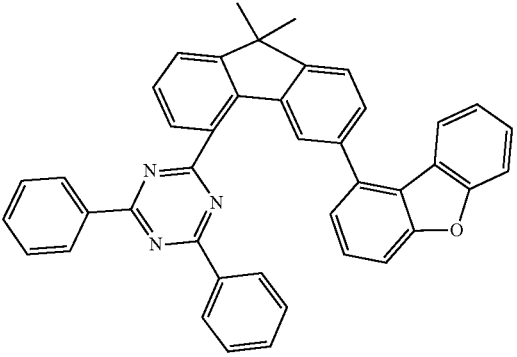
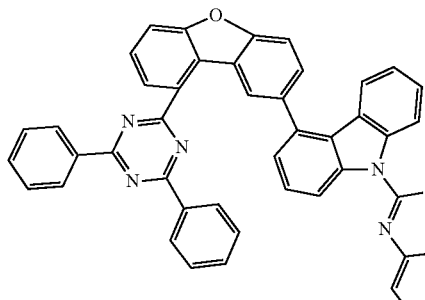
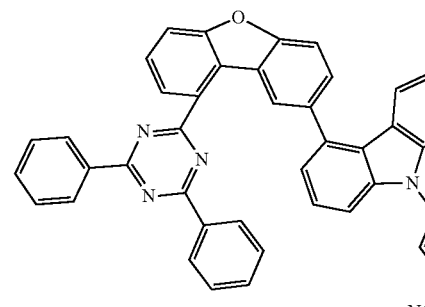
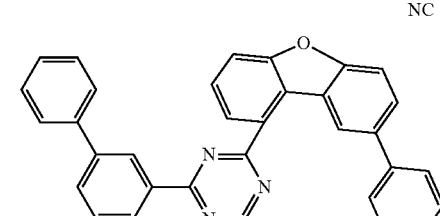
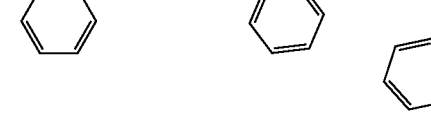

125
-continued
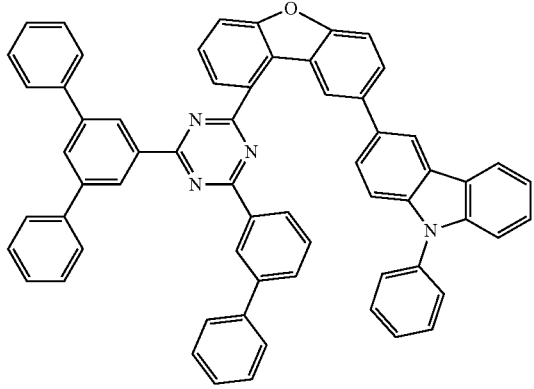
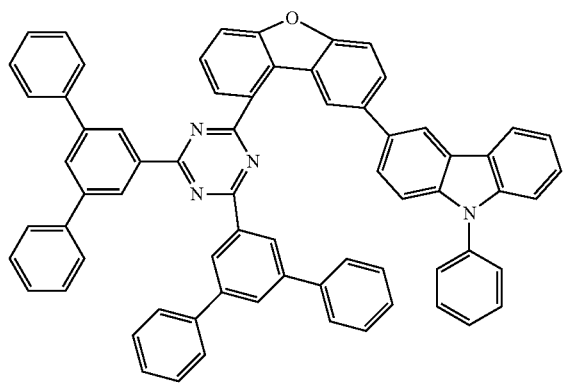
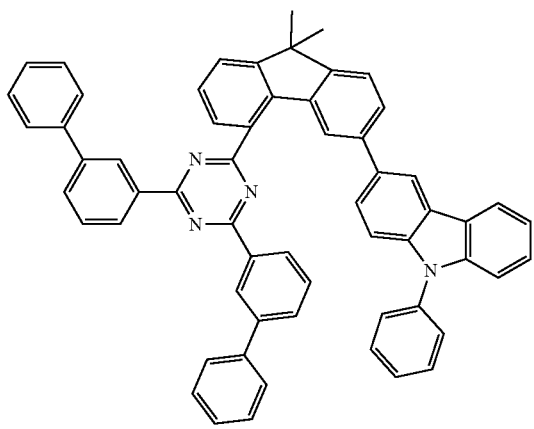
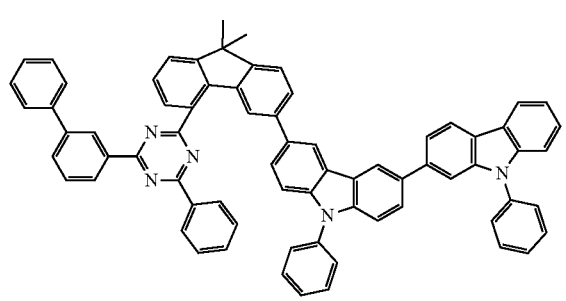
126
-continued
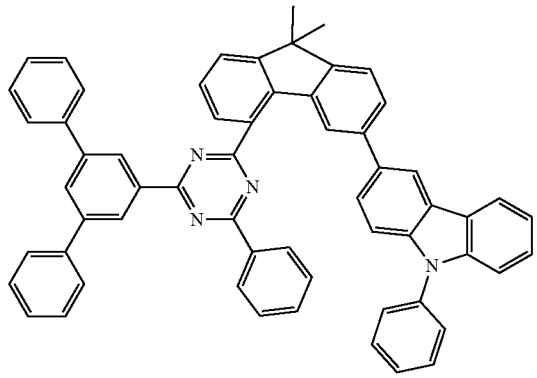
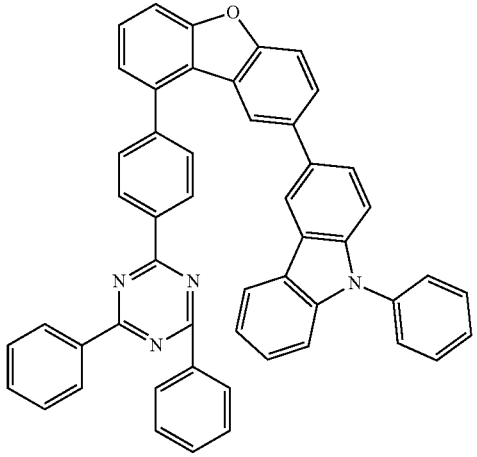
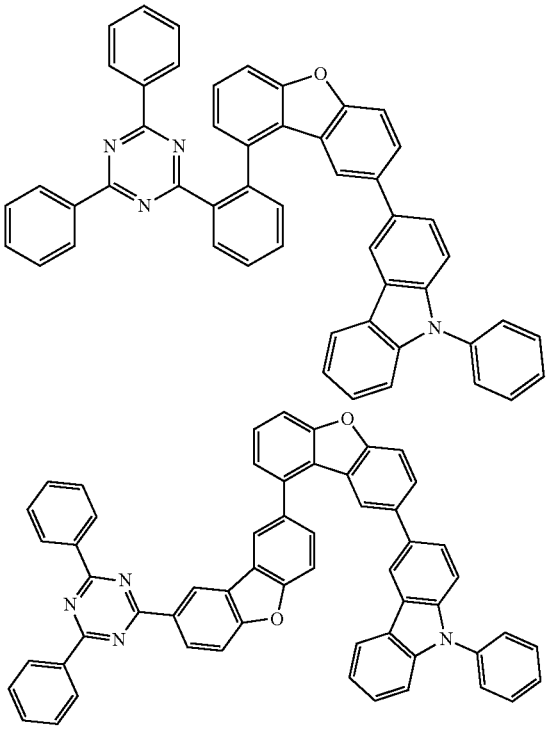

-continued
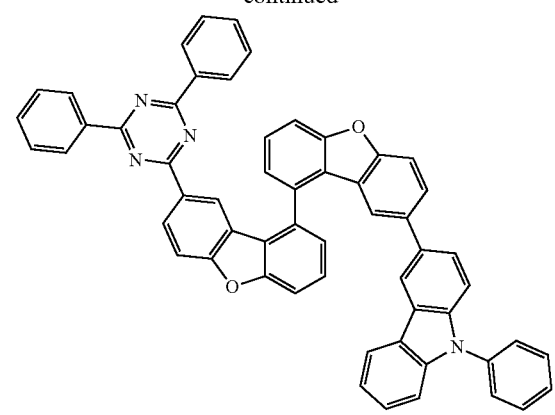
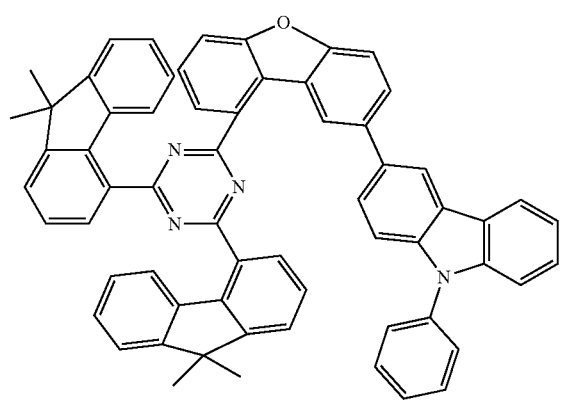
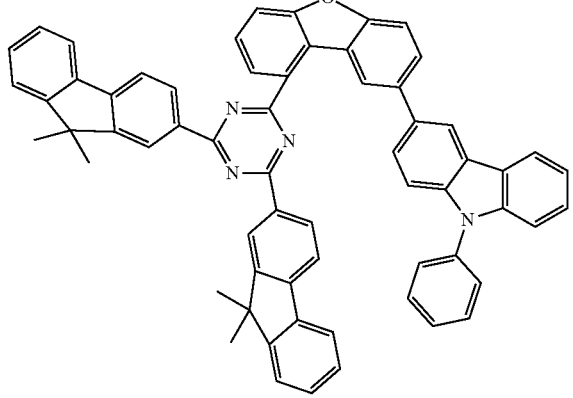
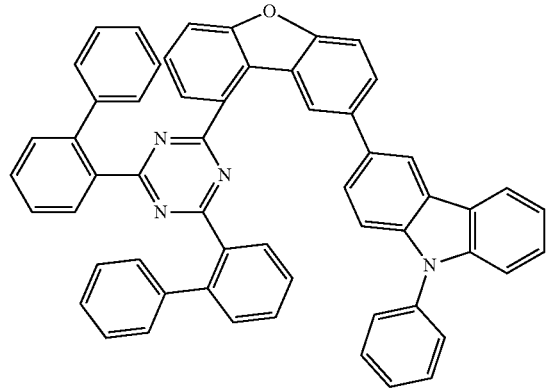
-continued
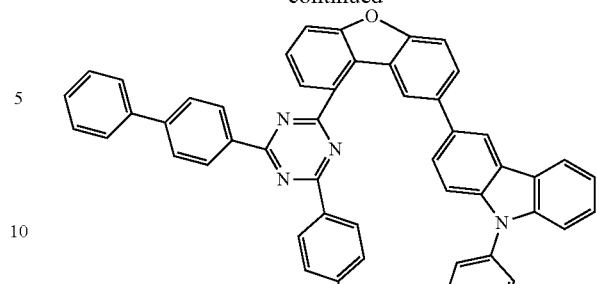
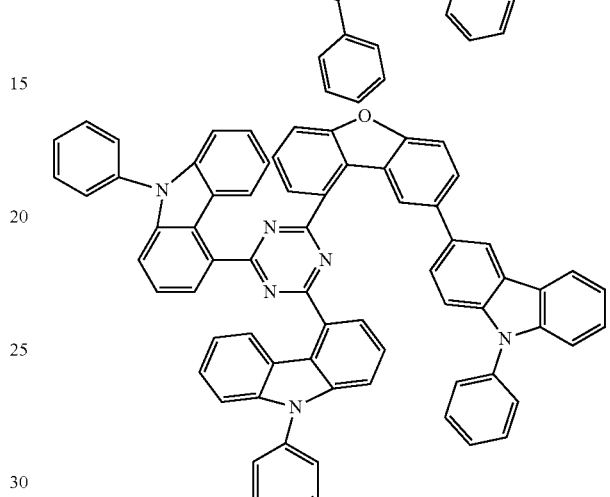
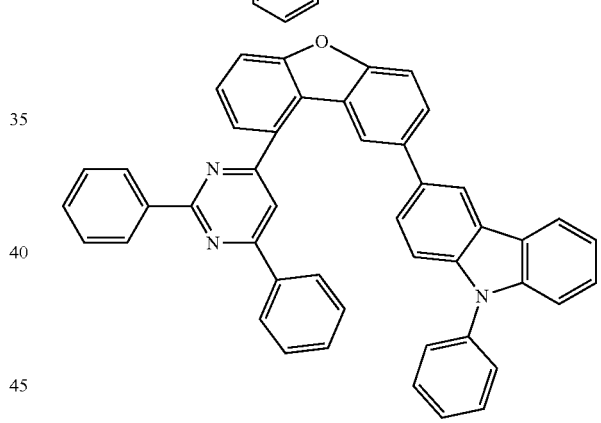
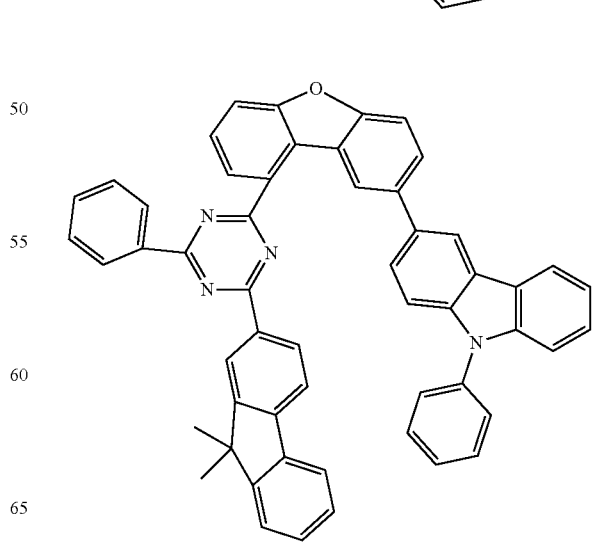

129
-continued
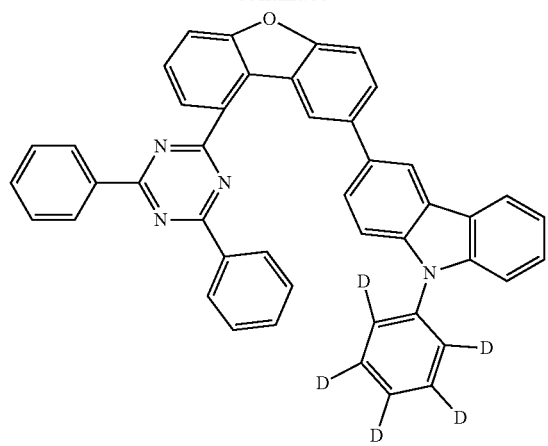
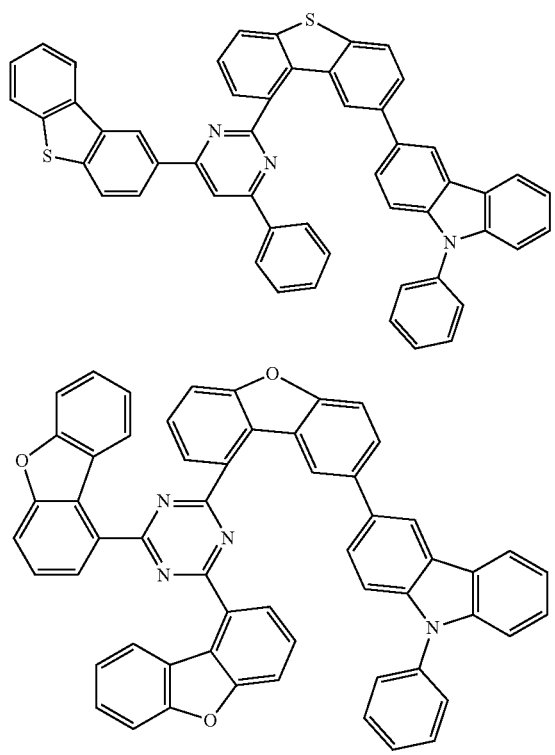
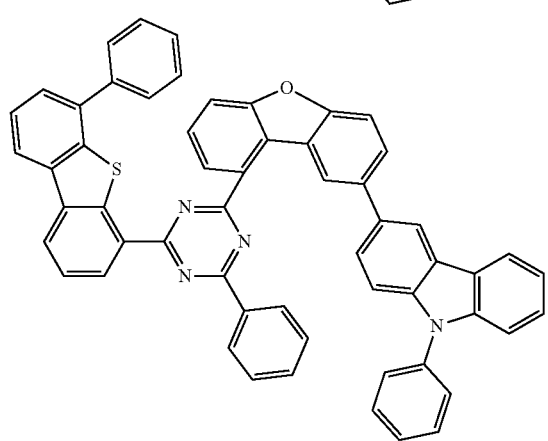
130
-continued
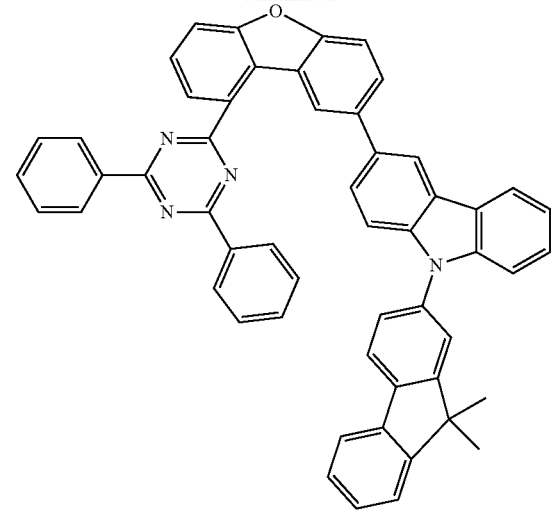
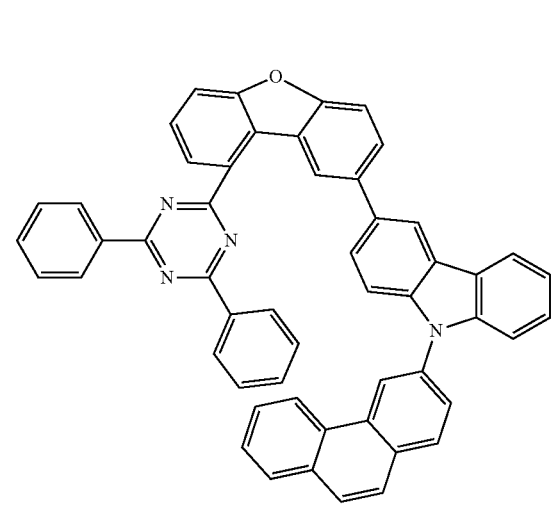
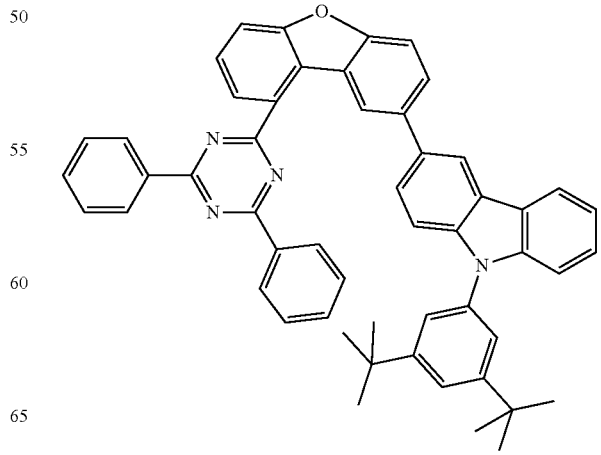

131
-continued
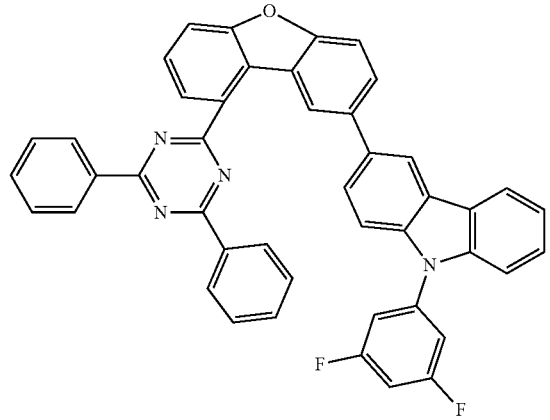
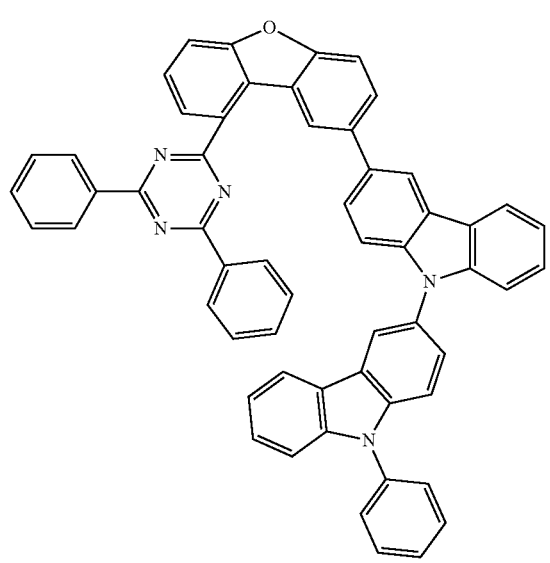
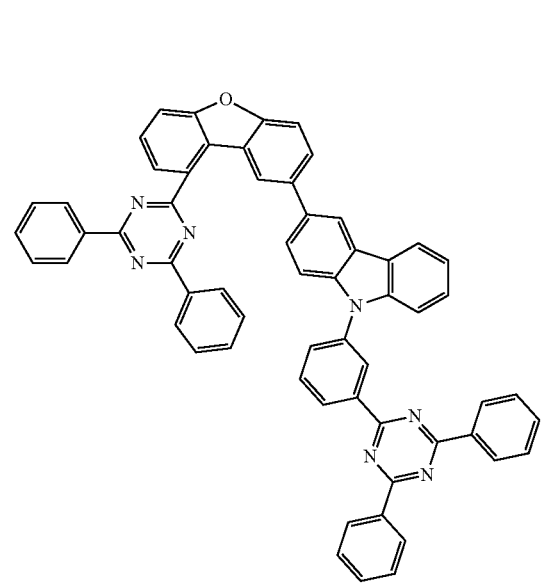
132
-continued
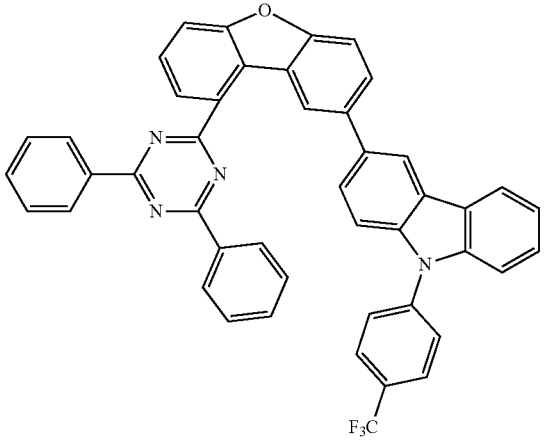
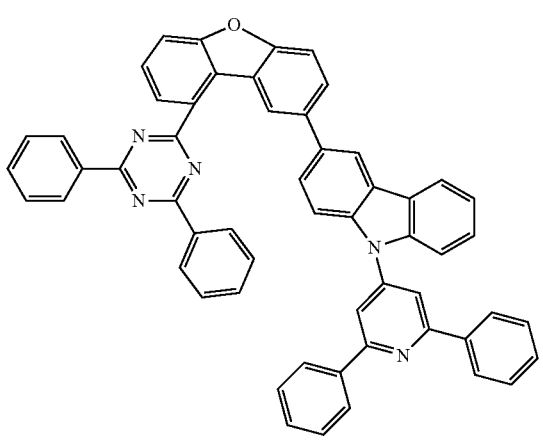
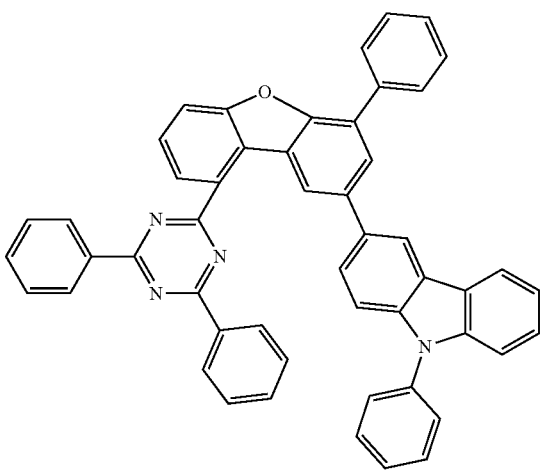

133
-continued
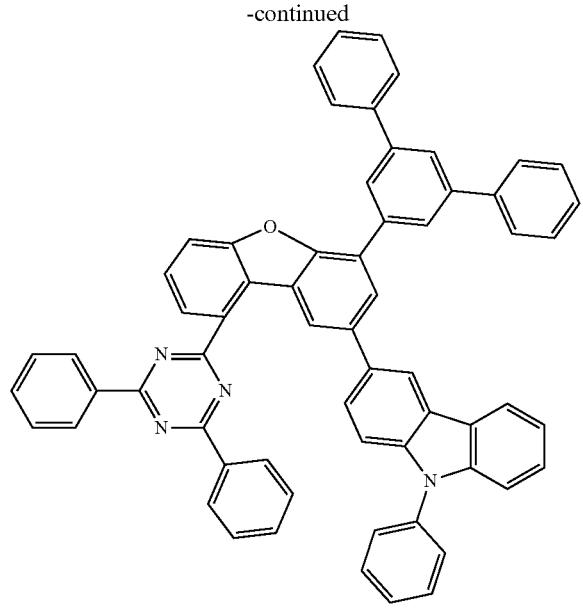
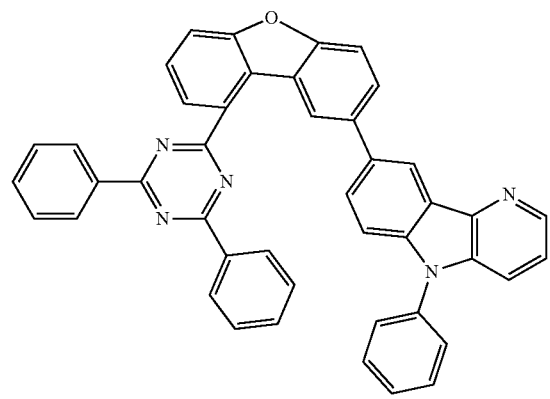
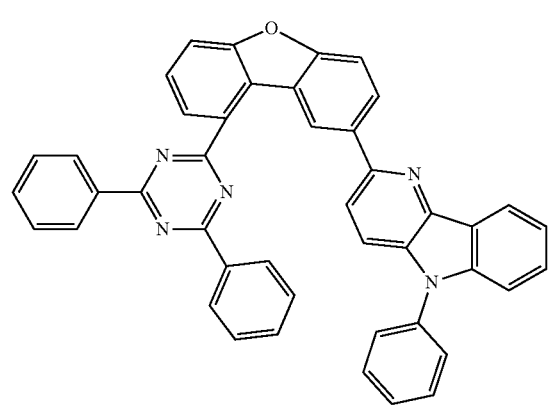
134
-continued
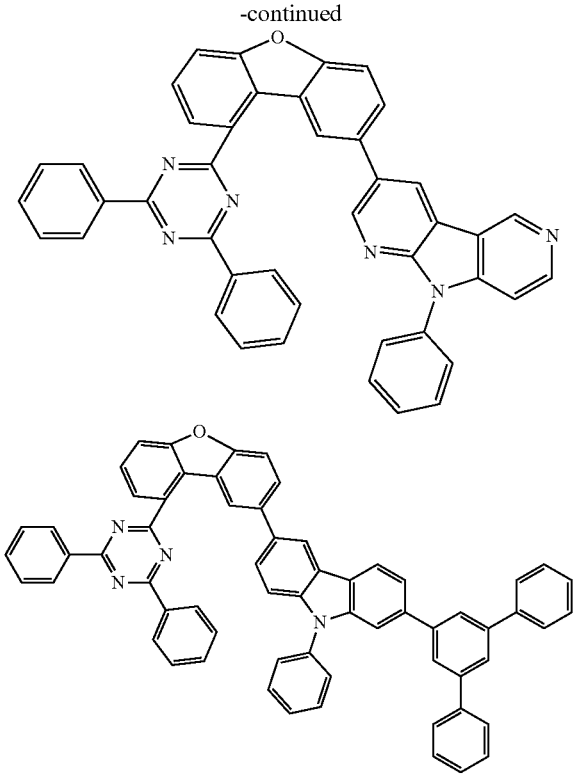
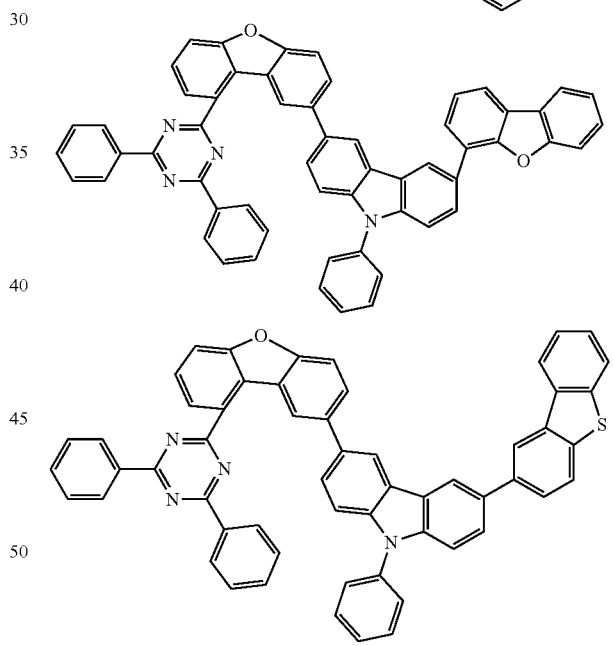
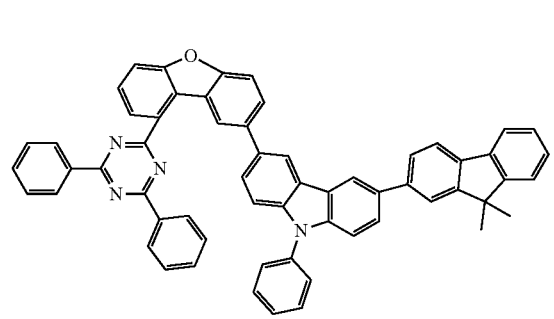

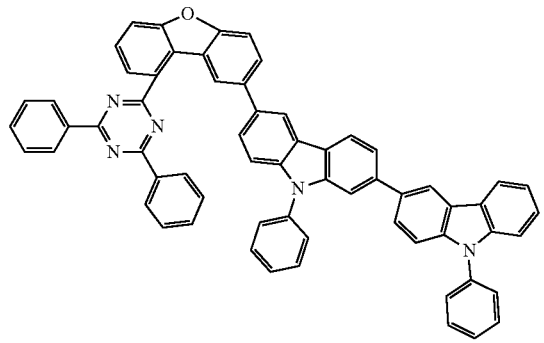
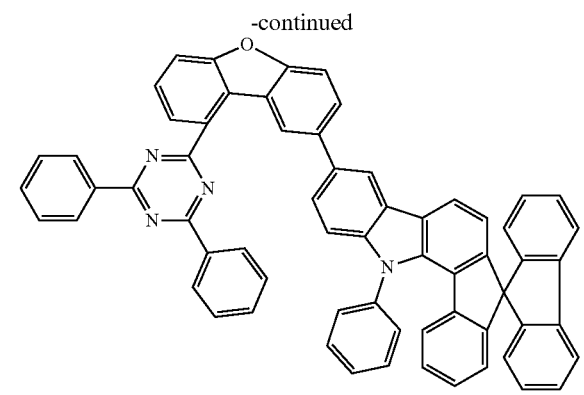
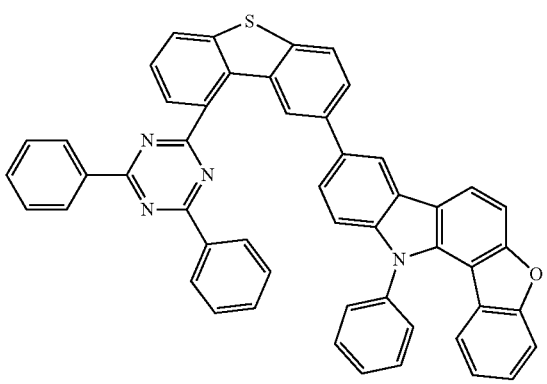
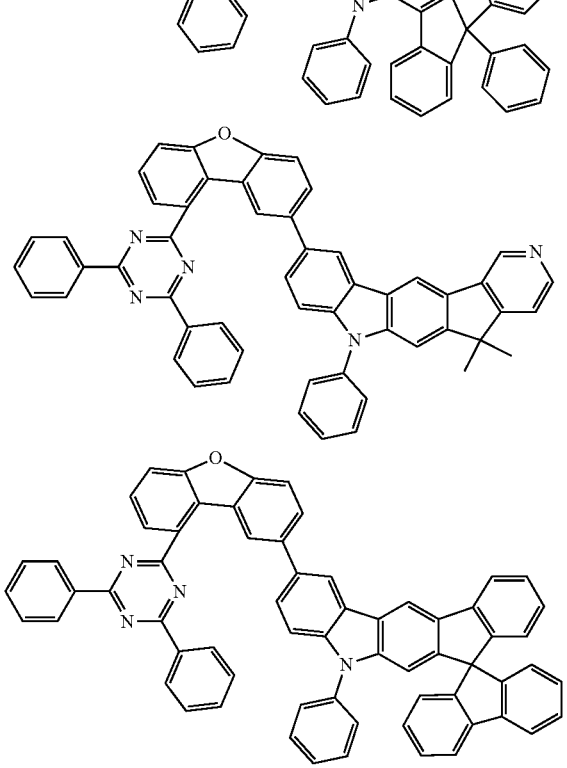
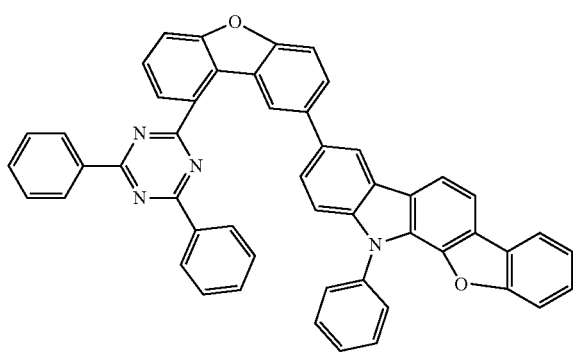
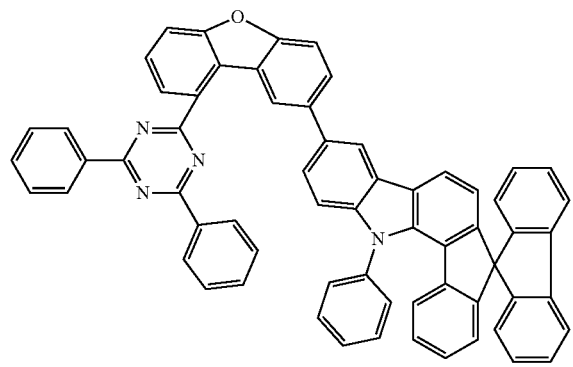
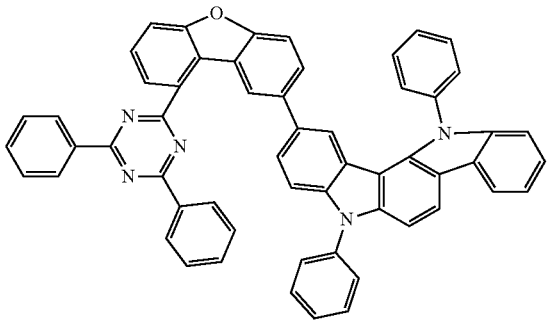

137
-continued
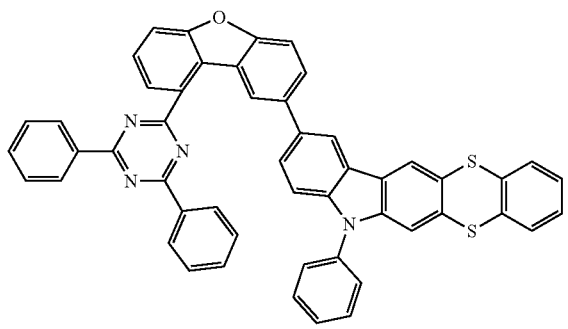
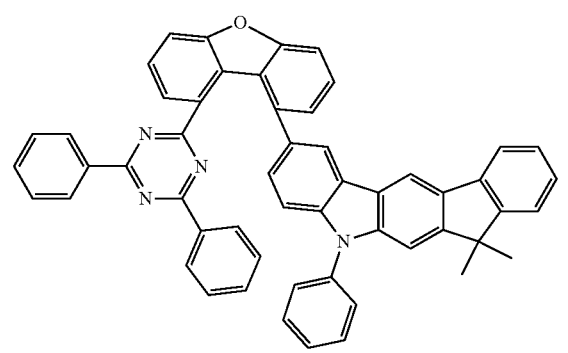
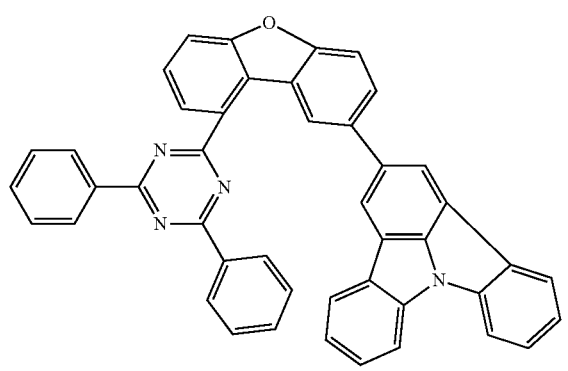
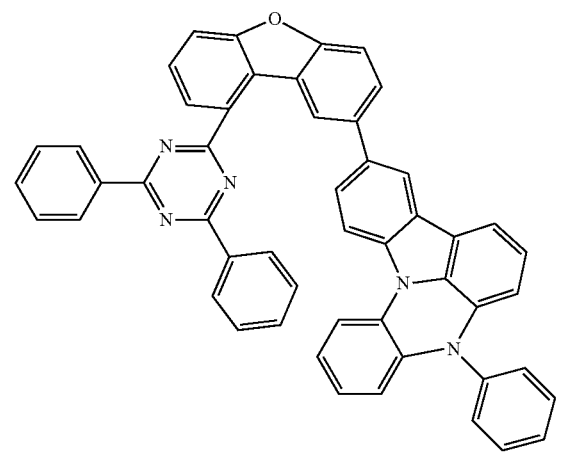
138
-continued
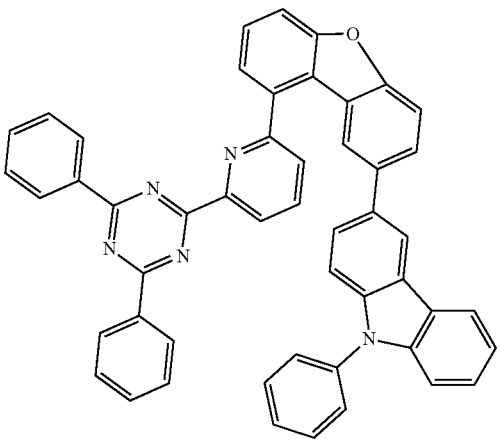
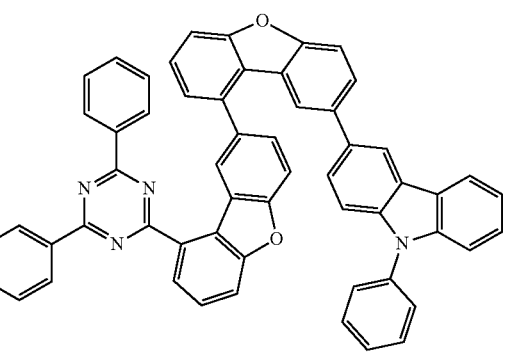
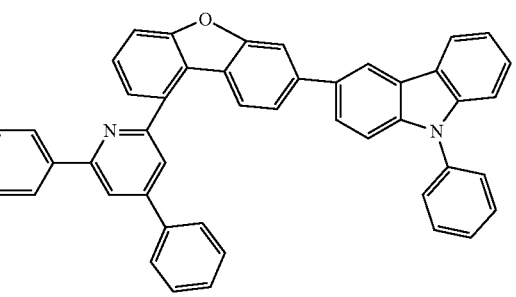
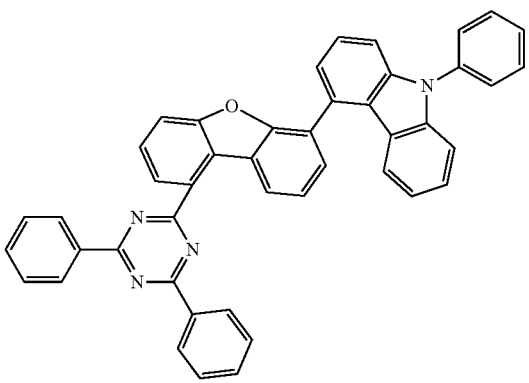

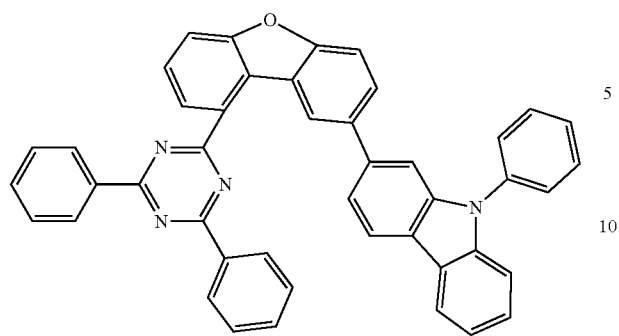
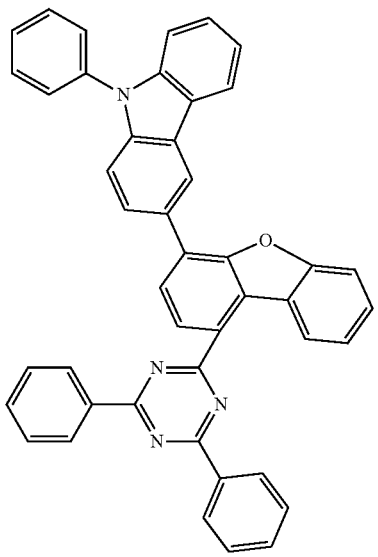
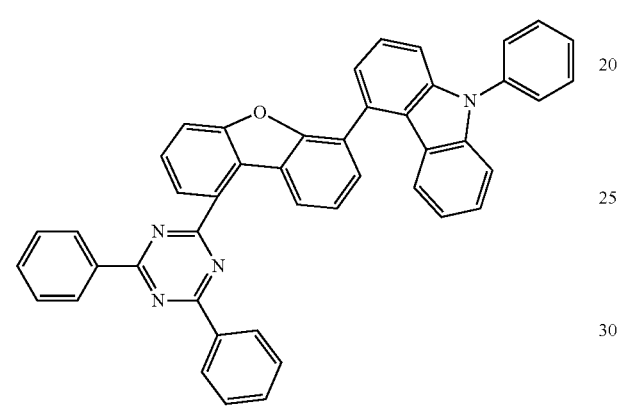
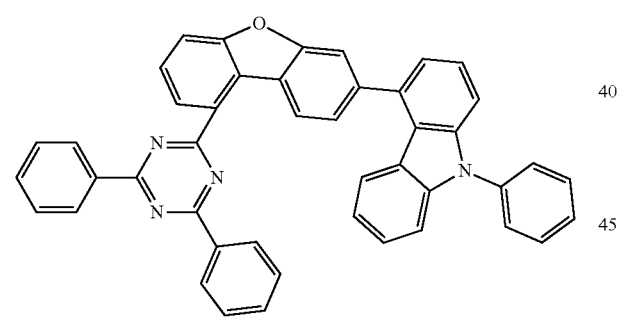
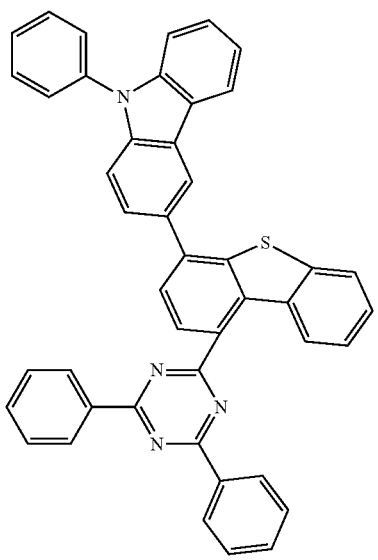
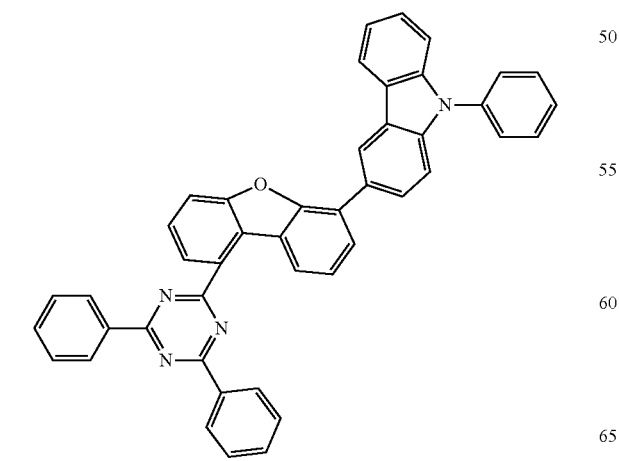

141
-continued
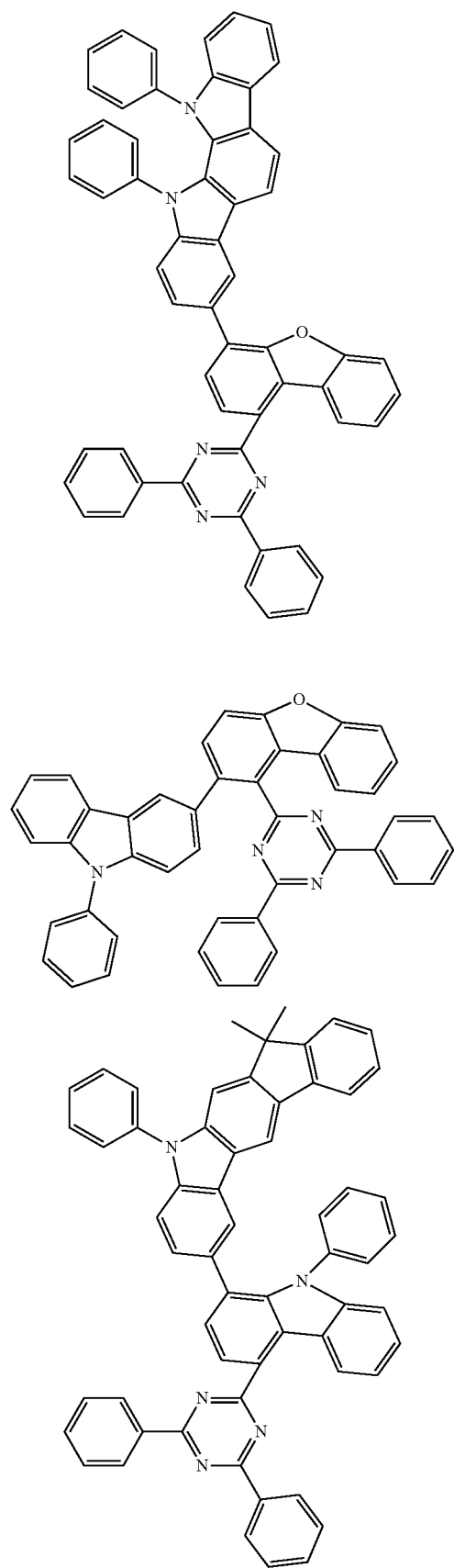
142
-continued
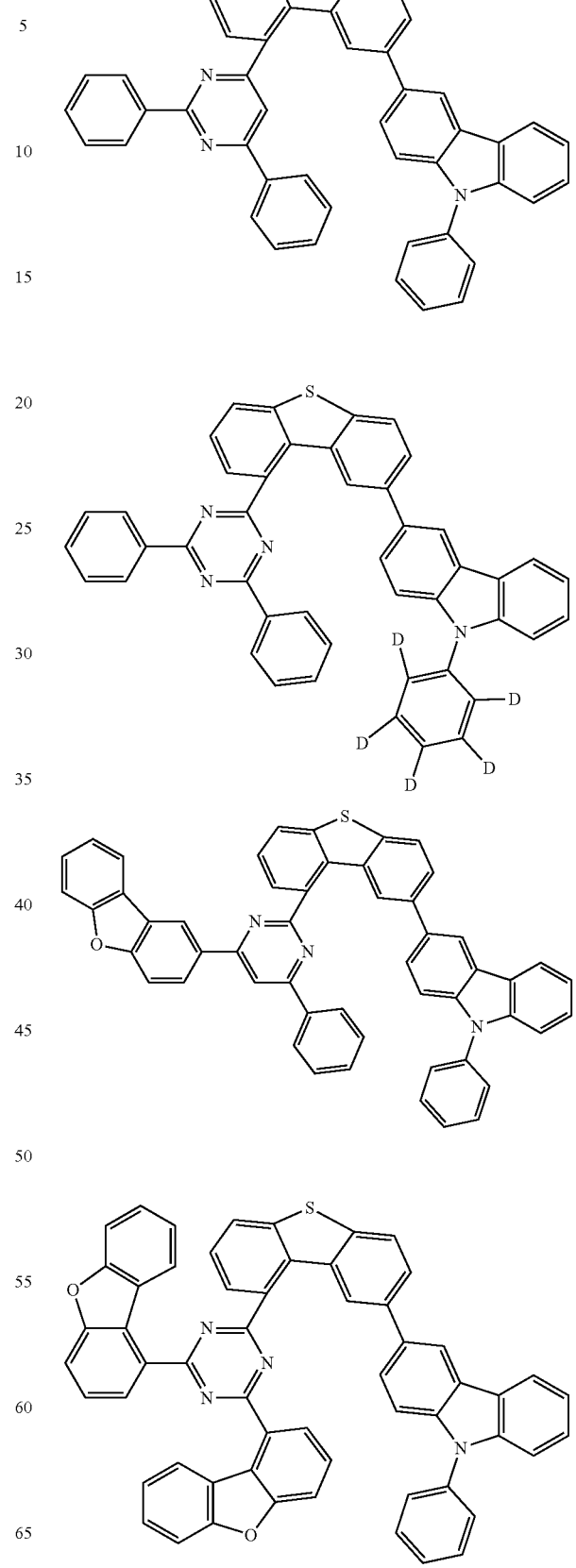

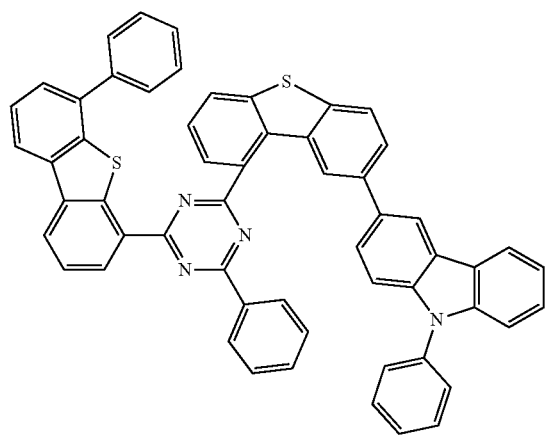
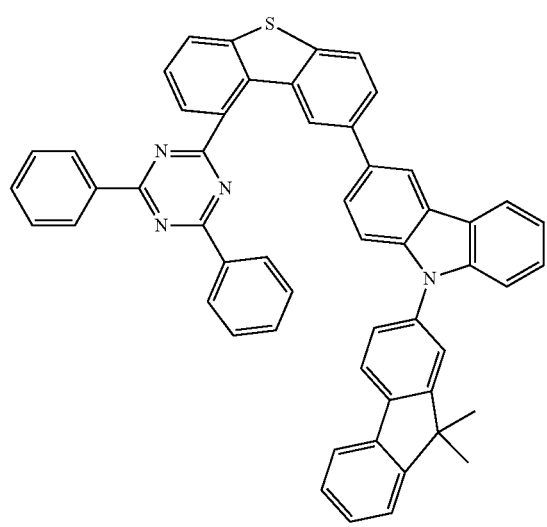
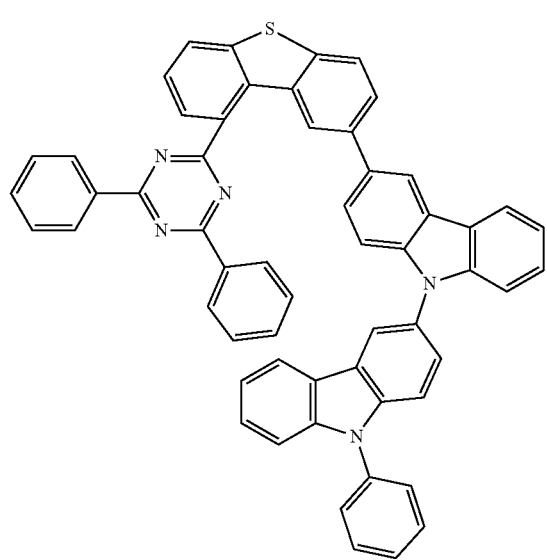
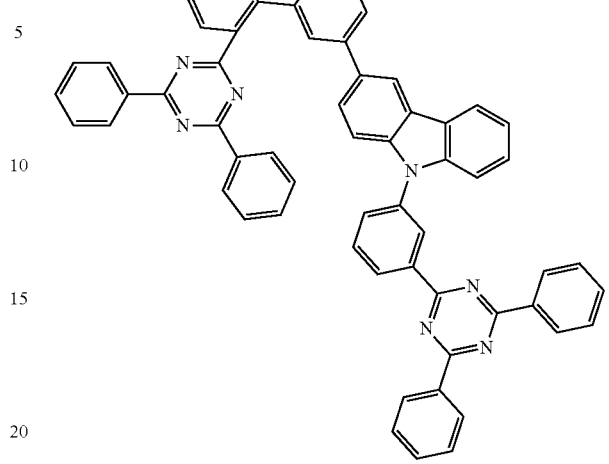
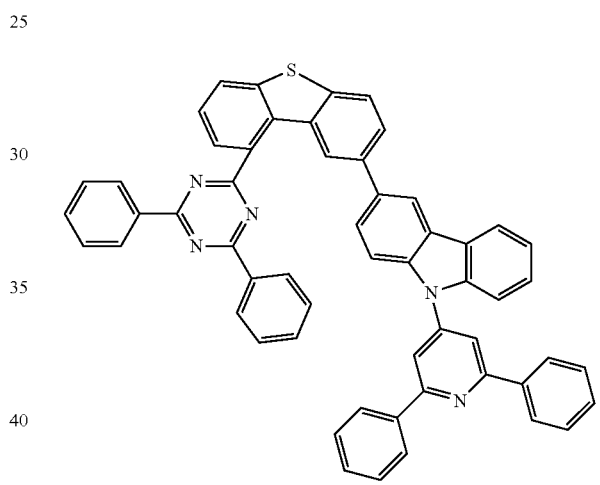
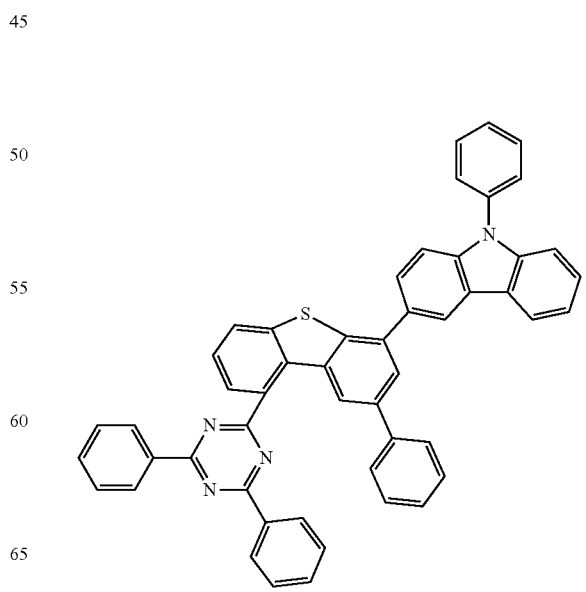

145
-continued
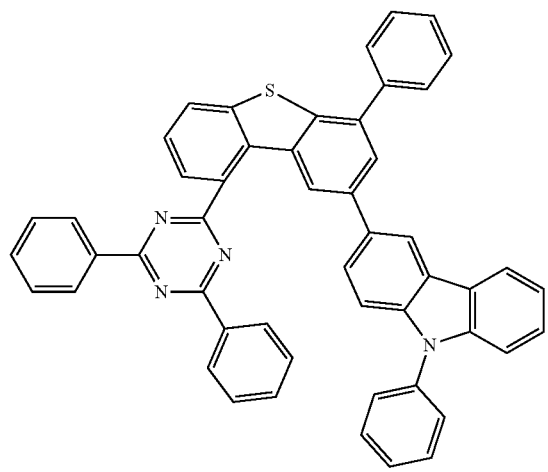
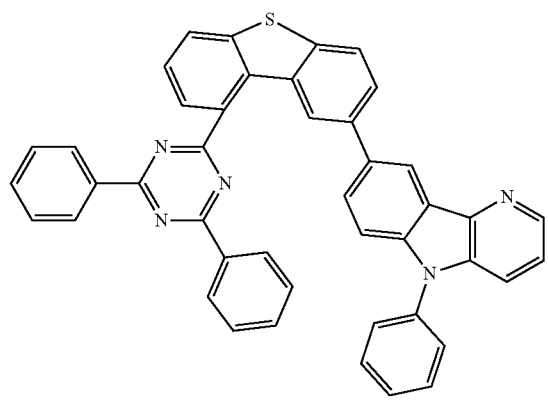
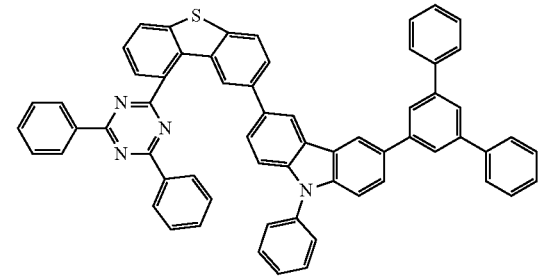
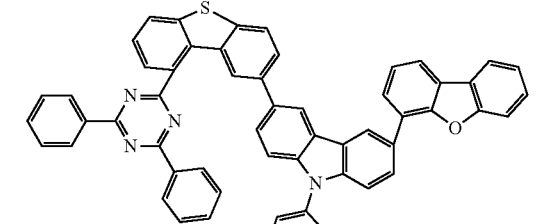
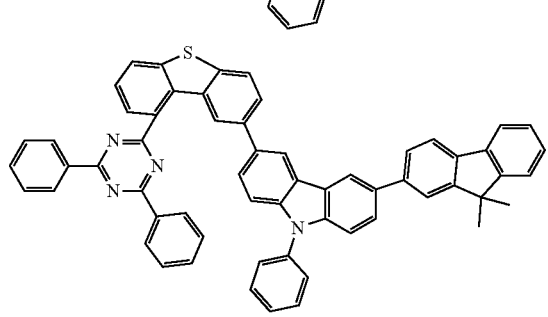
146
-continued
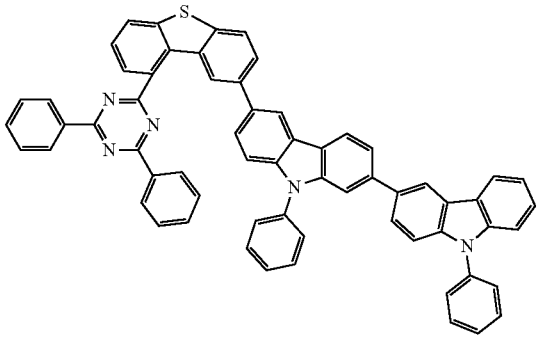
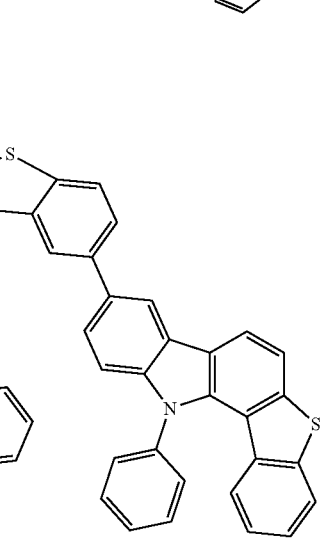
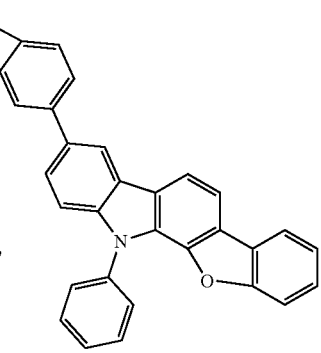
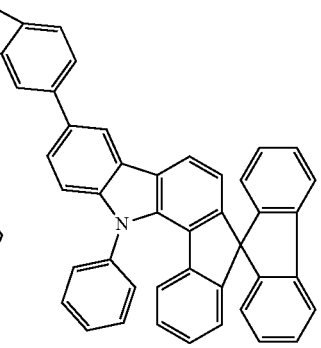

147
-continued
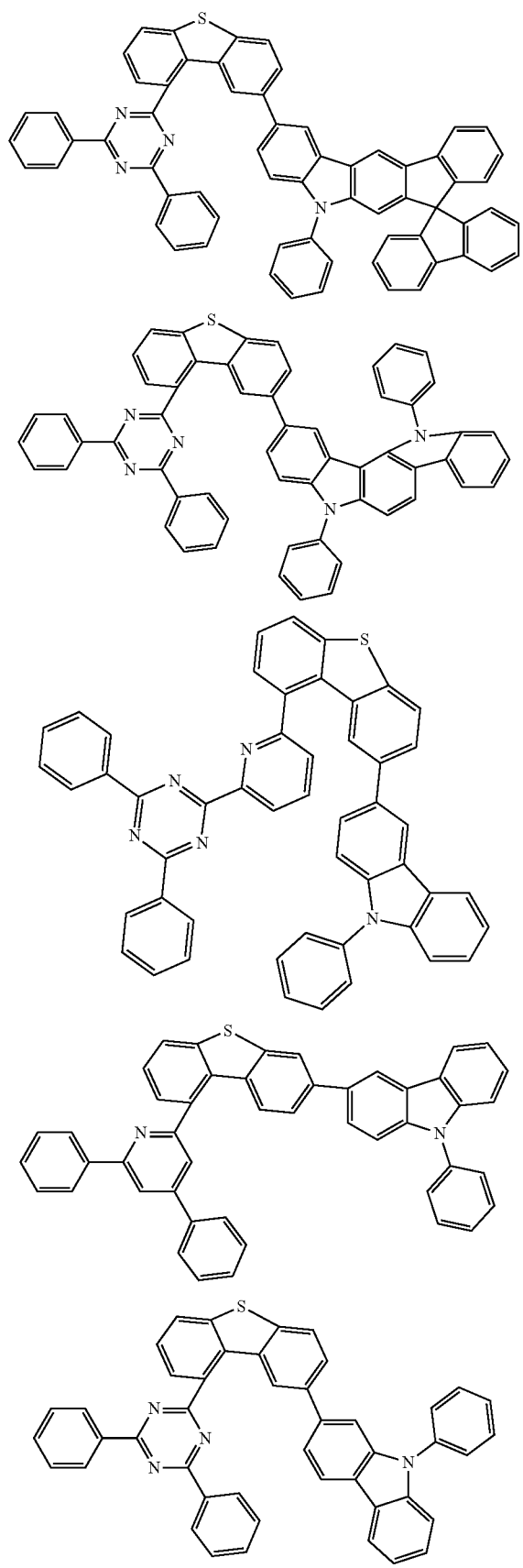
148
-continued
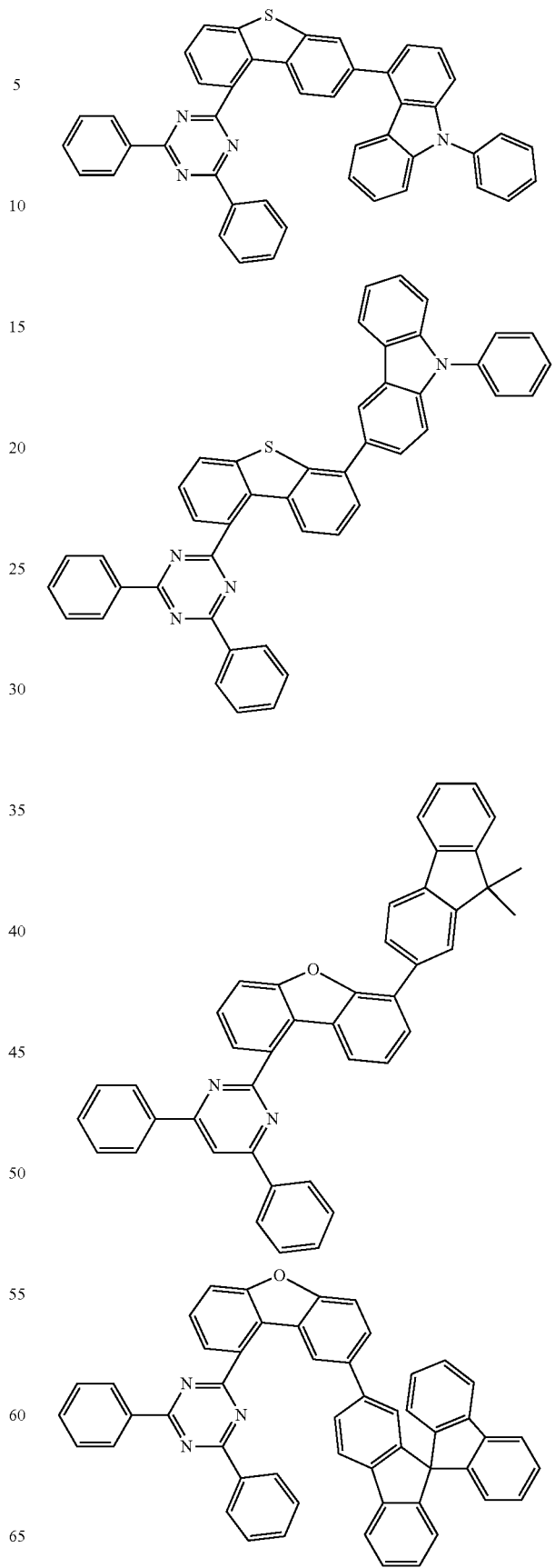

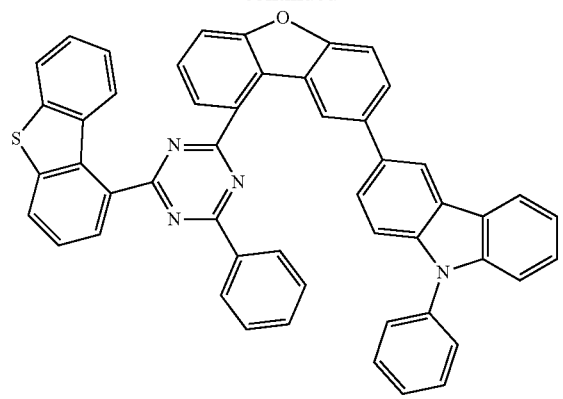
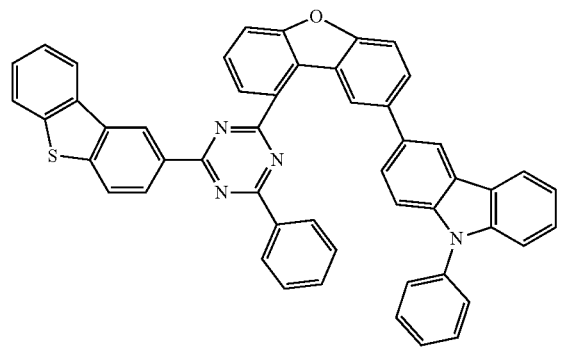
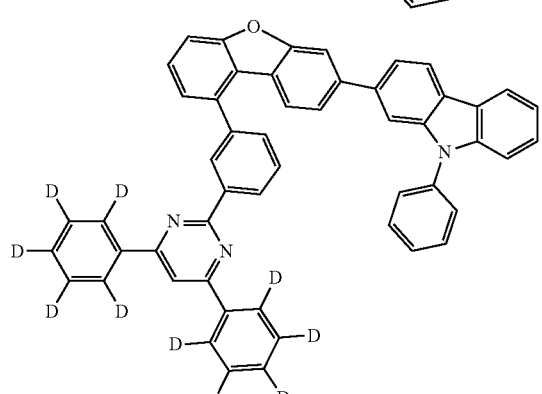
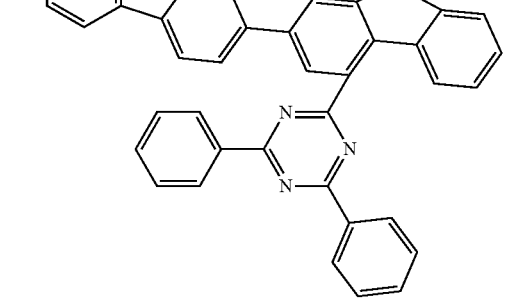
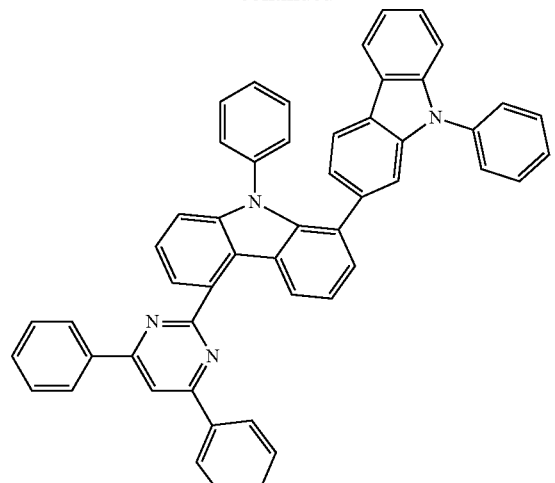
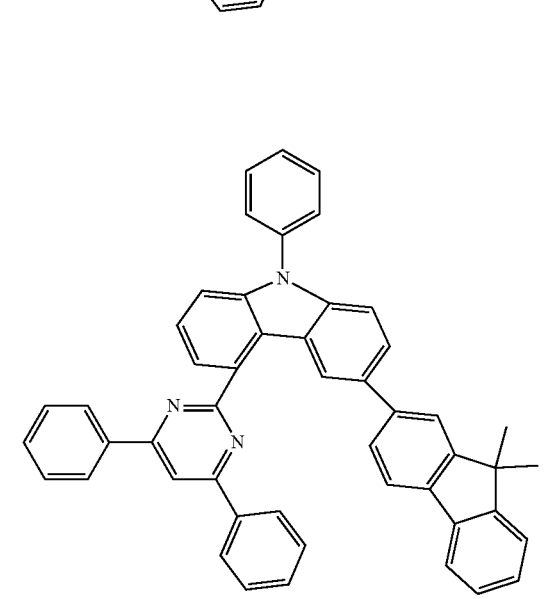

151
-continued
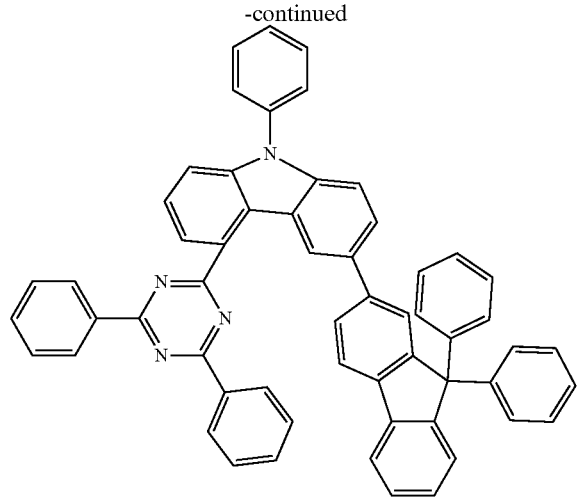
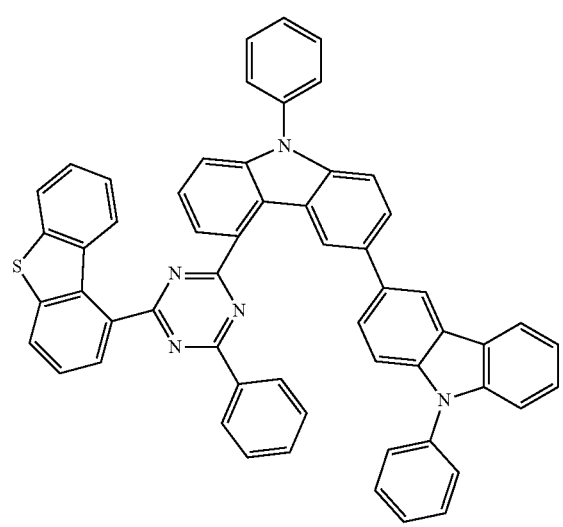
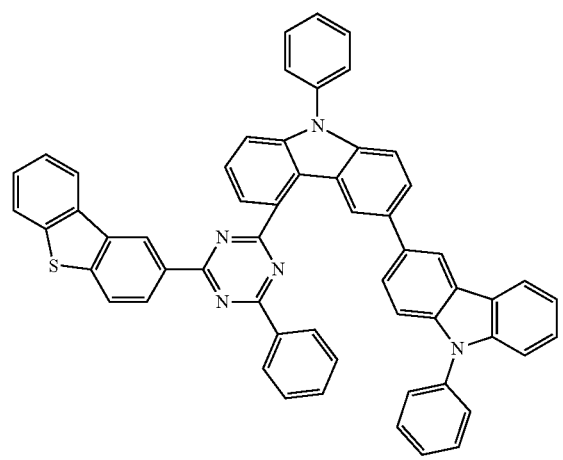
152
-continued
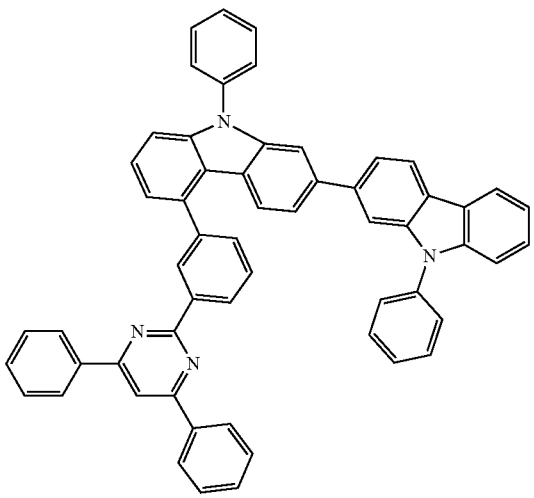
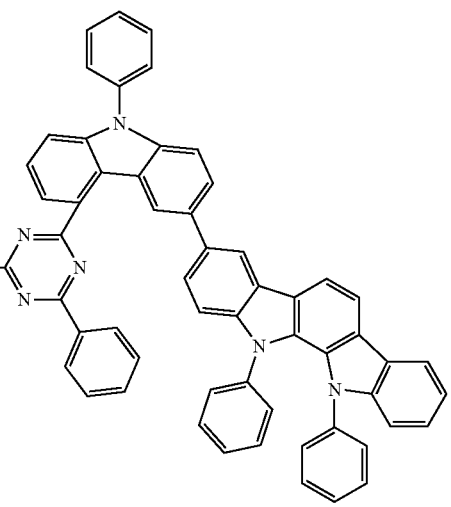

153
-continued
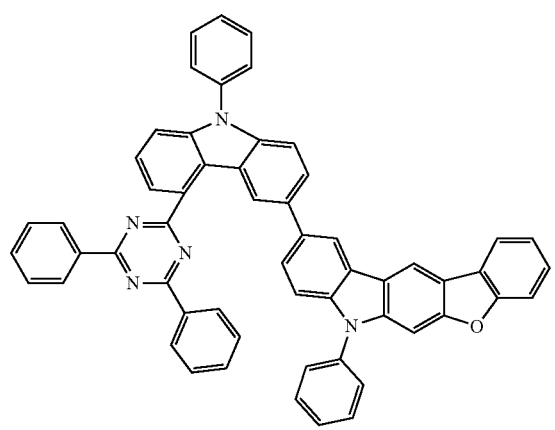
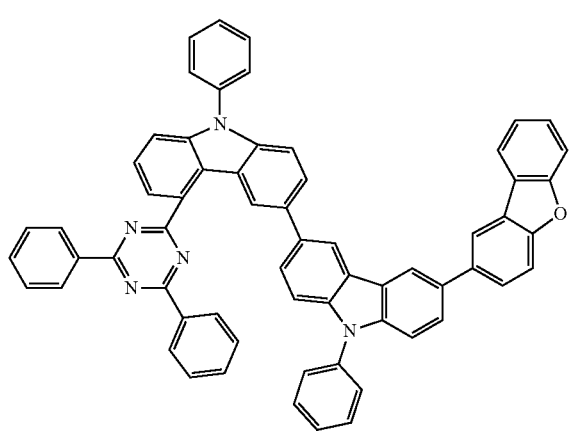
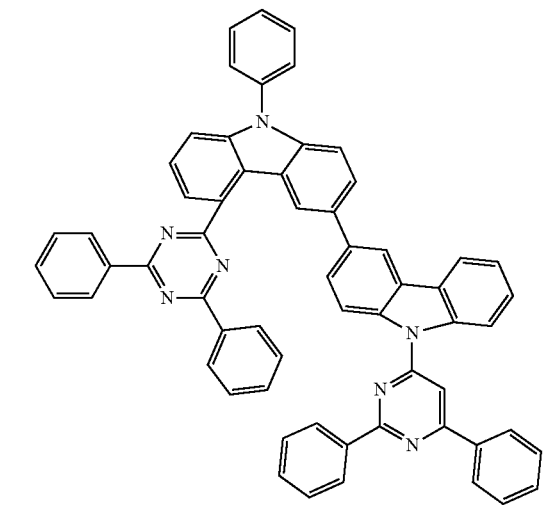
154
-continued
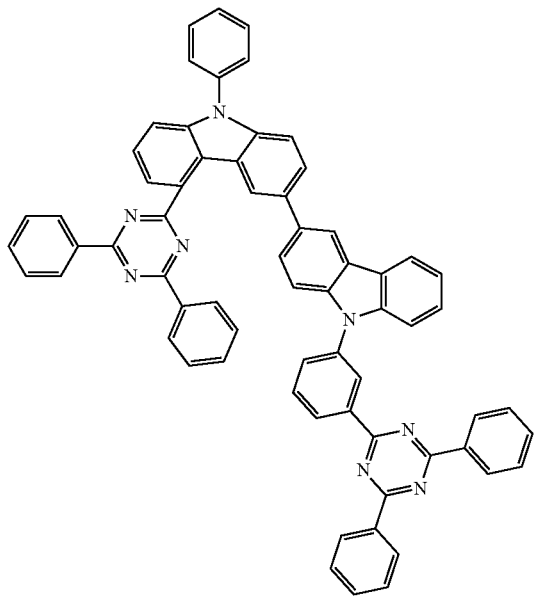
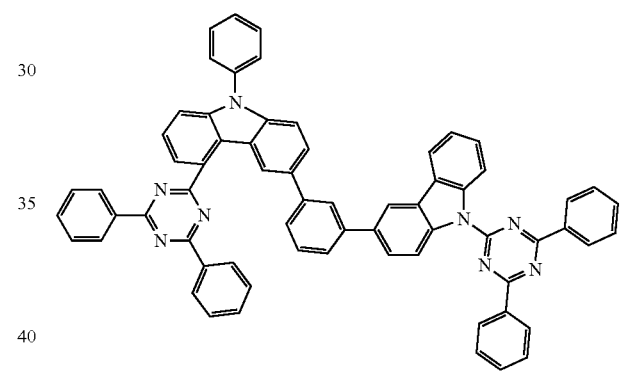
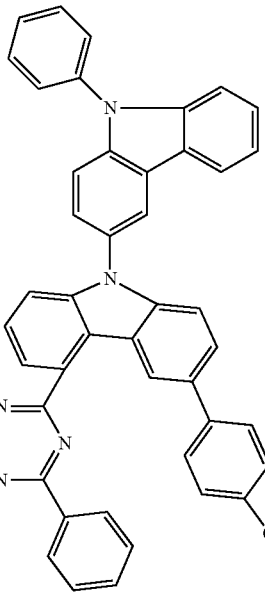

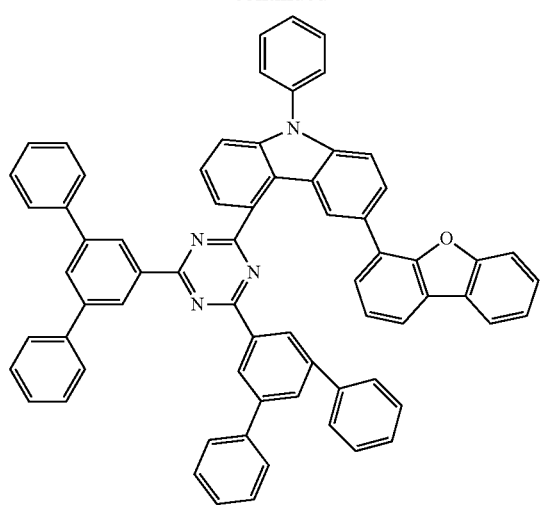
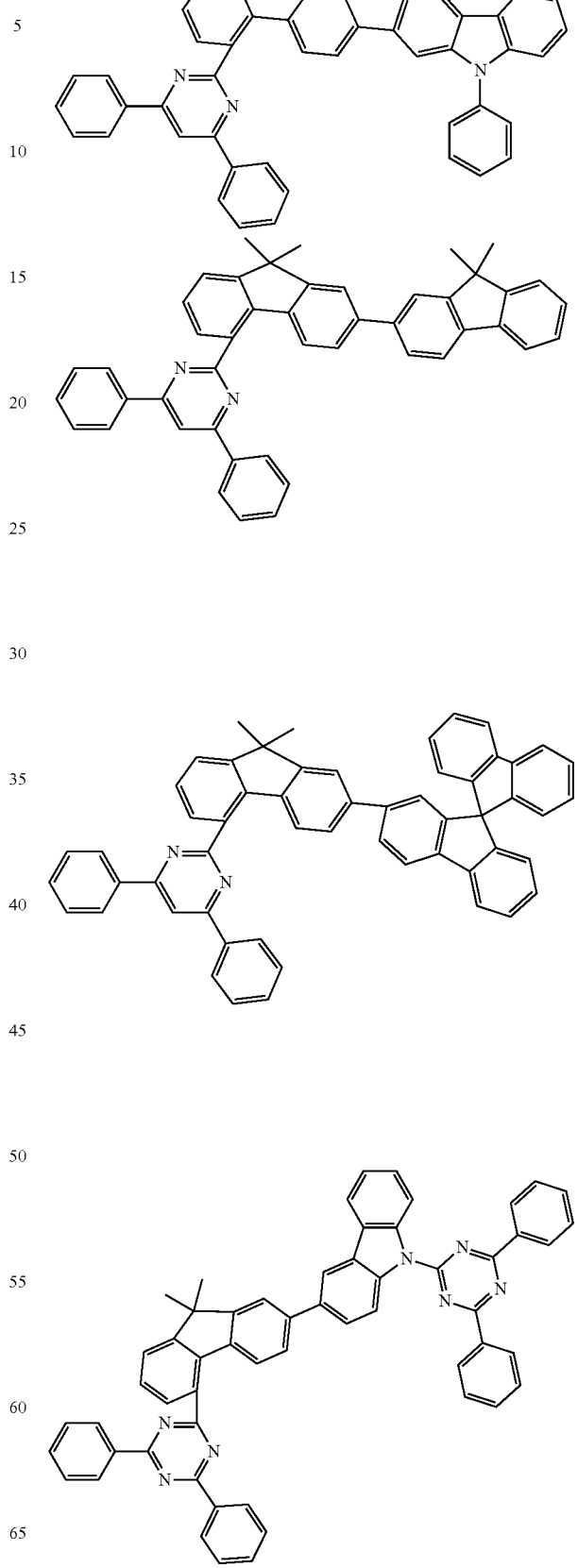

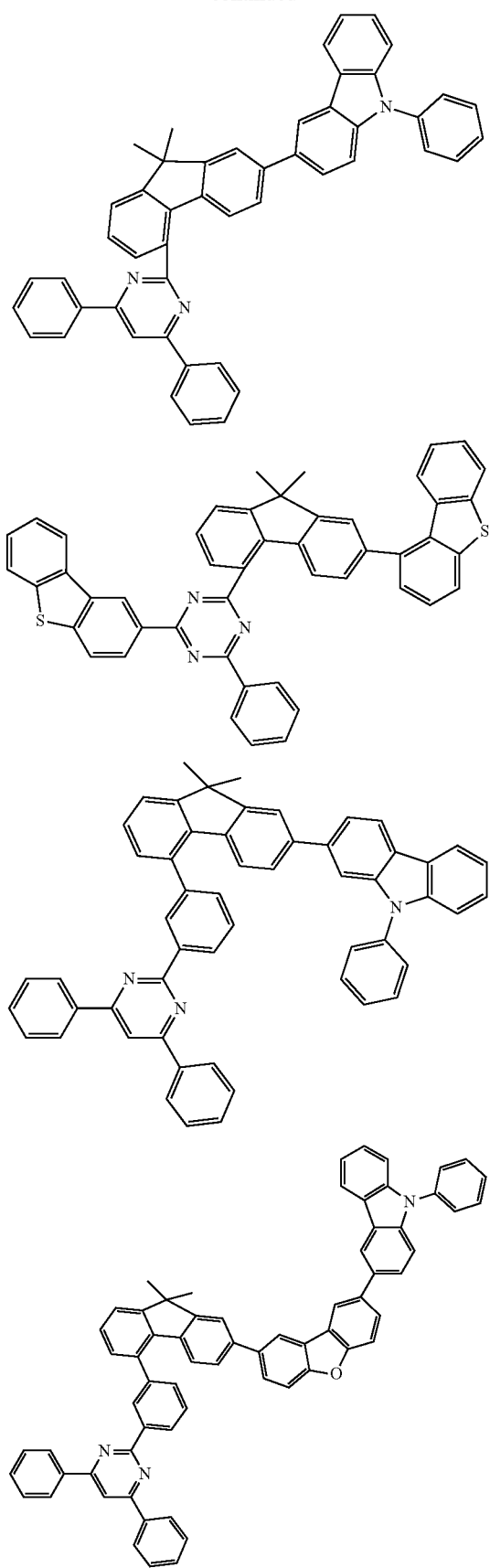
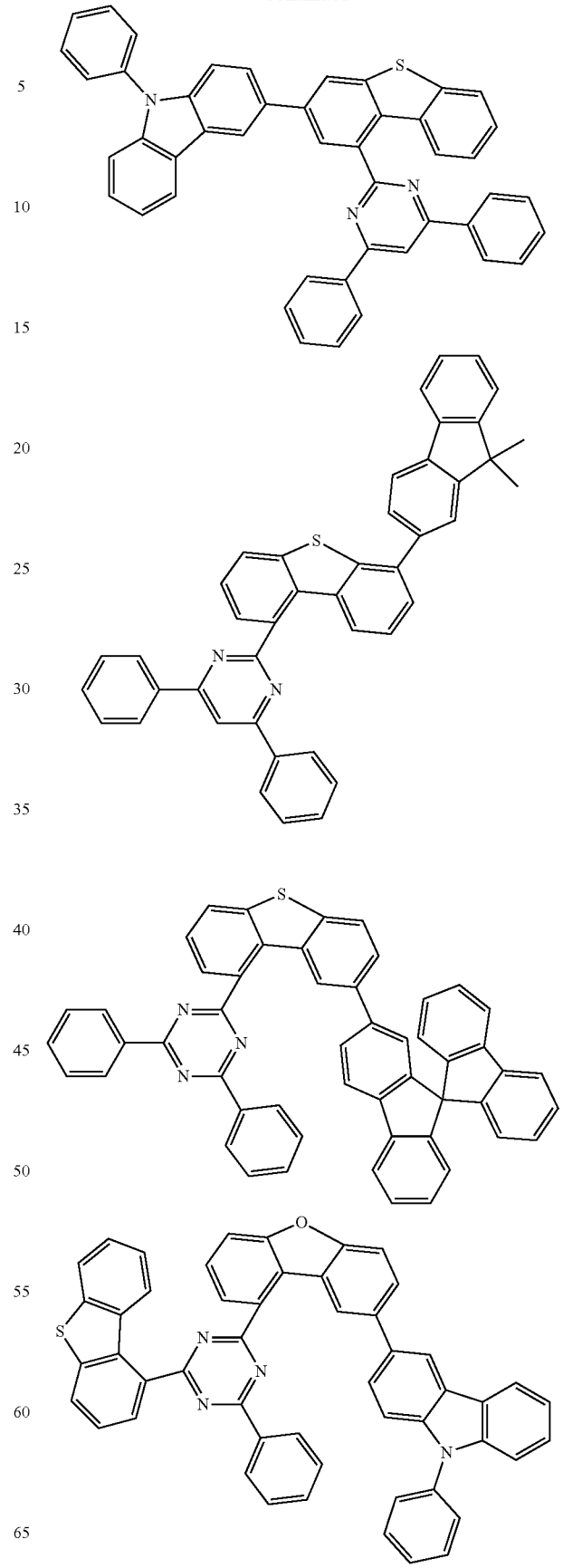

159
-continued
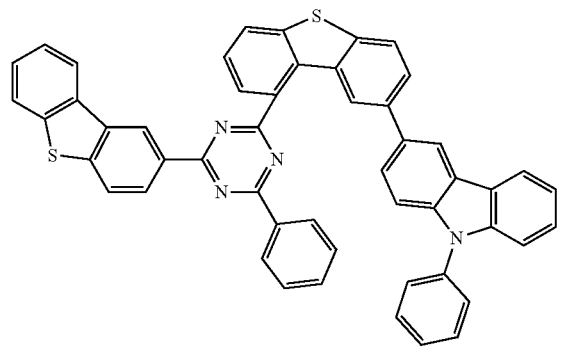
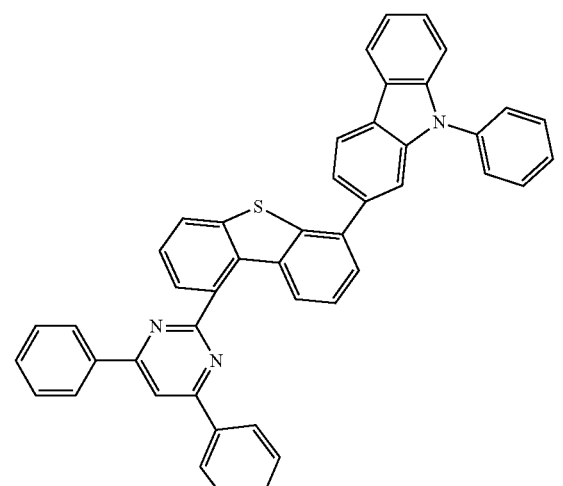
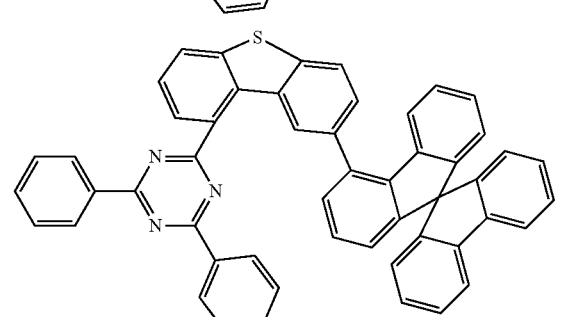
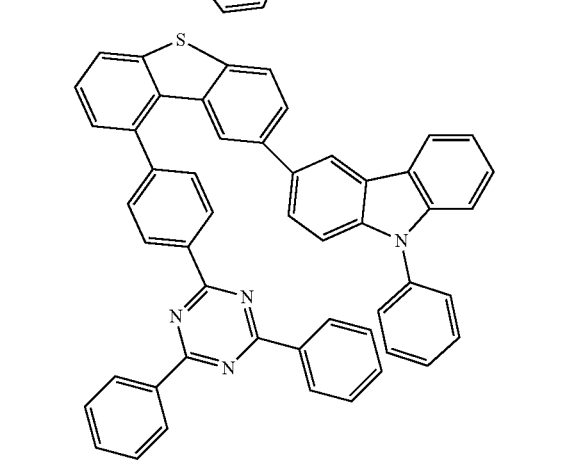
160
-continued
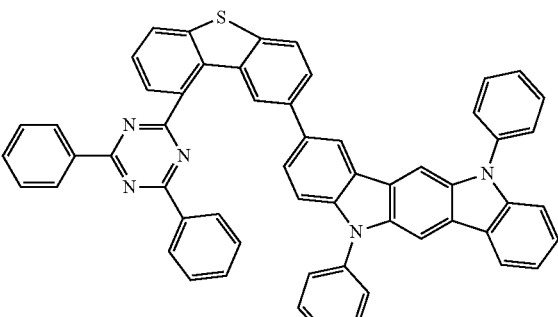
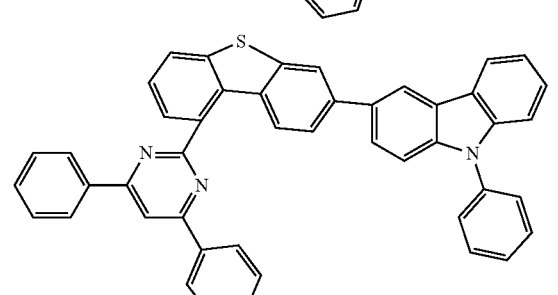
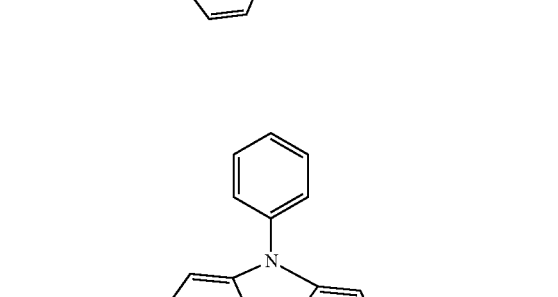
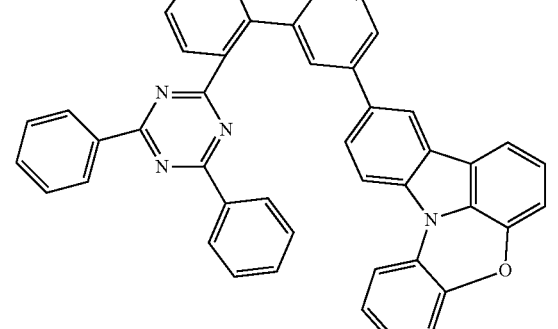
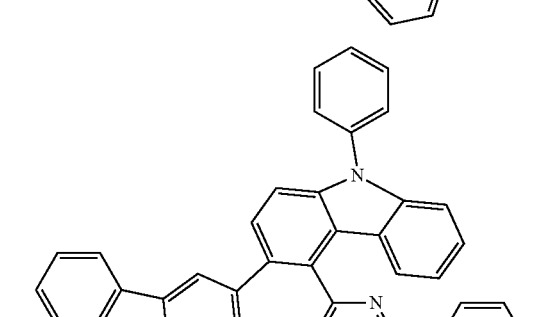
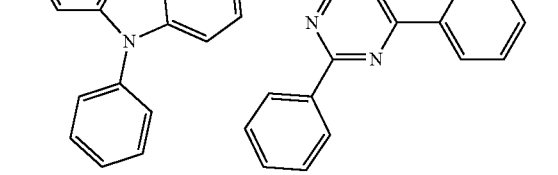

161
-continued
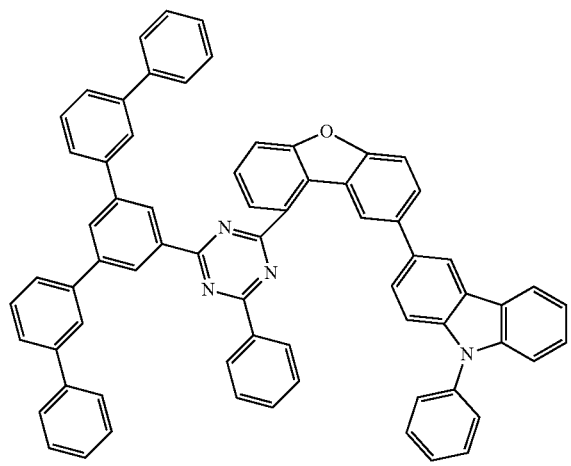
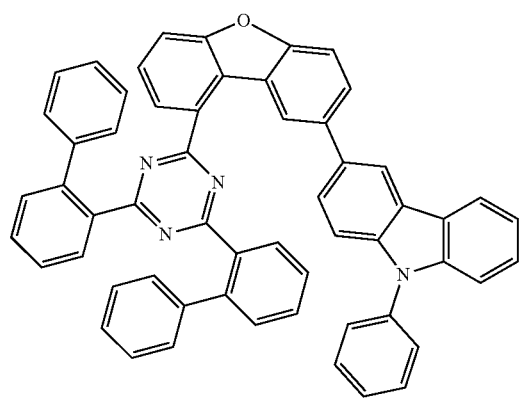
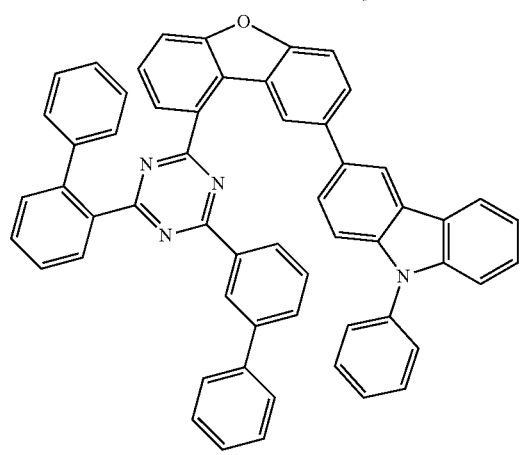
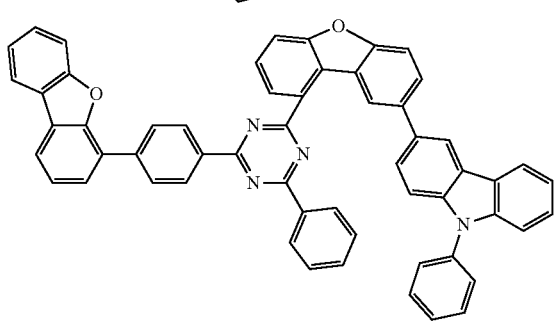
162
-continued
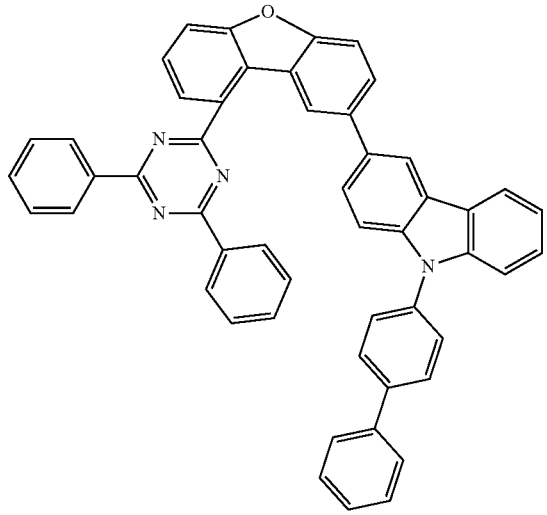
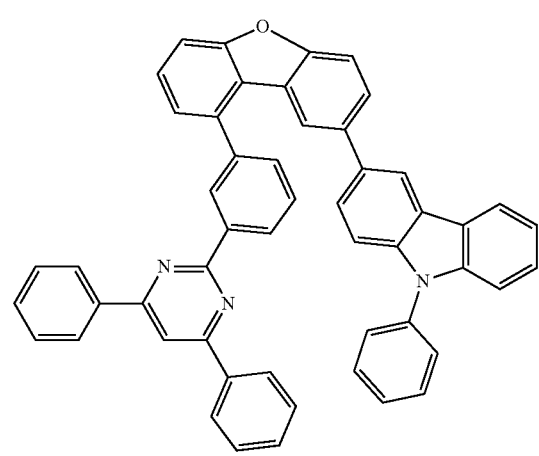
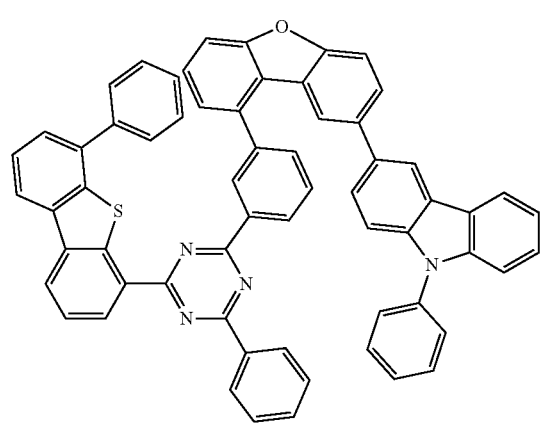

163
-continued
164
-continued
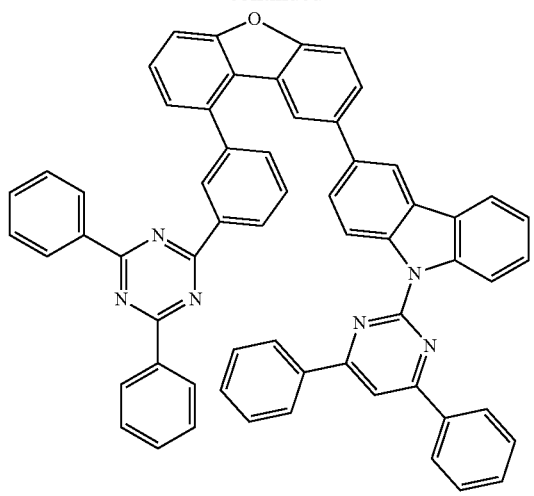
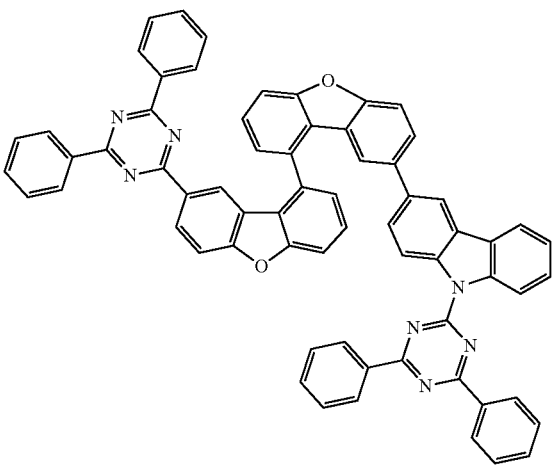
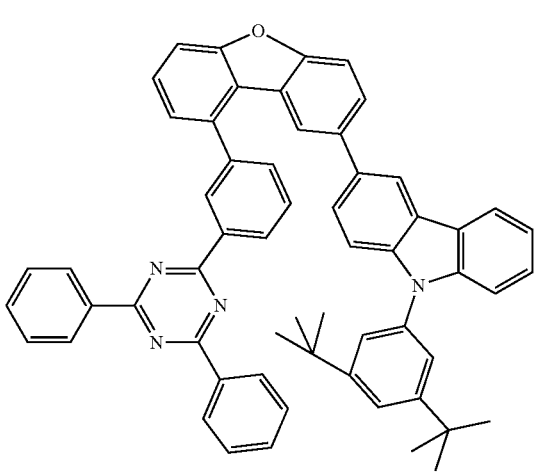
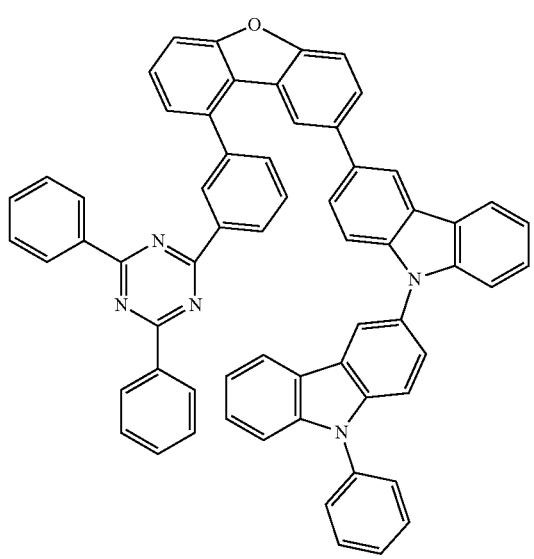

165
-continued
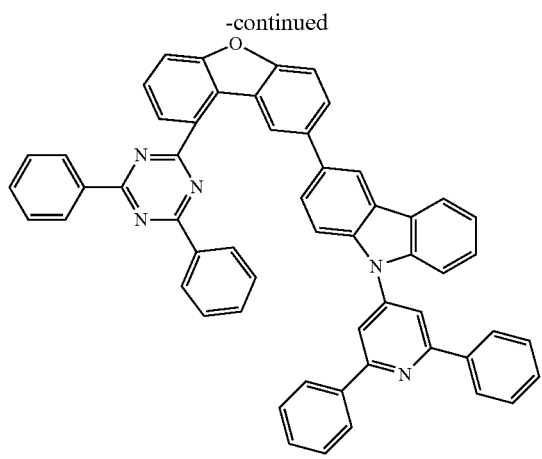
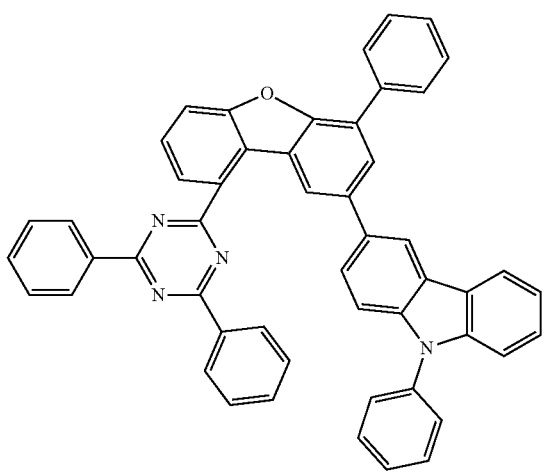
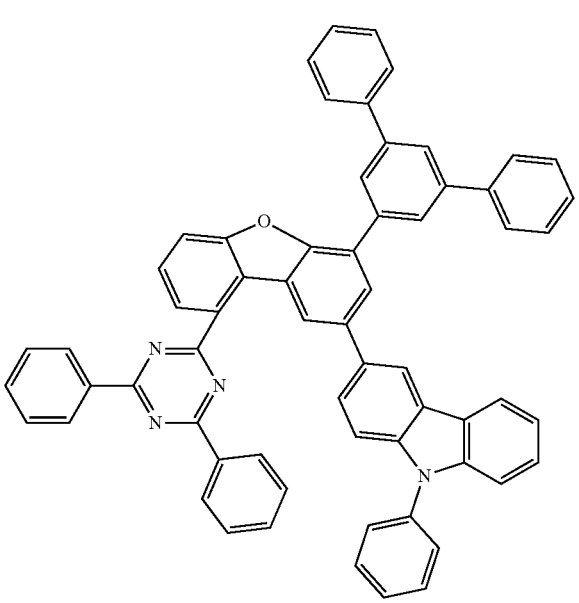
166
-continued
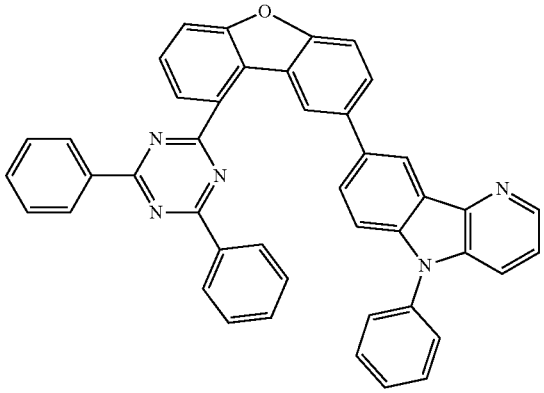
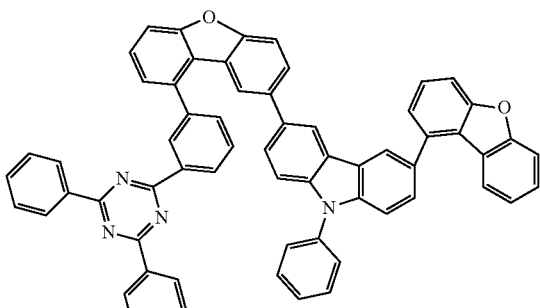
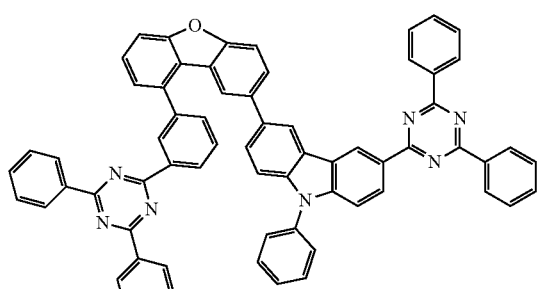
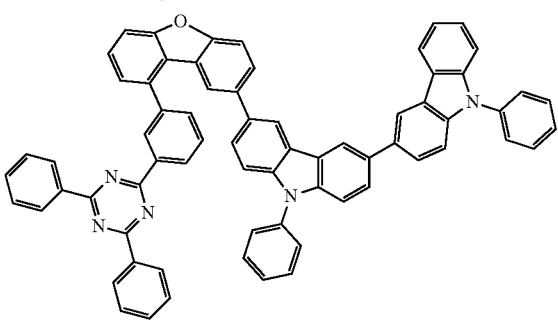
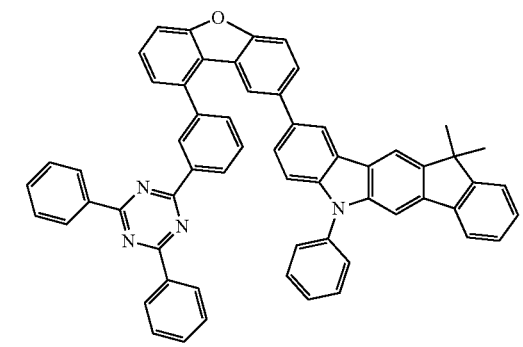

-continued
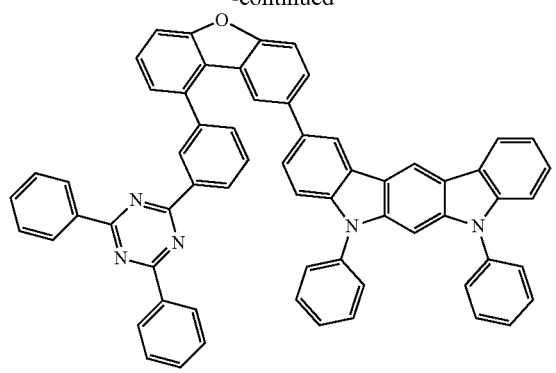
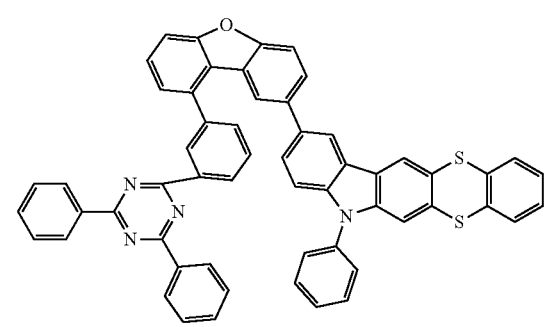
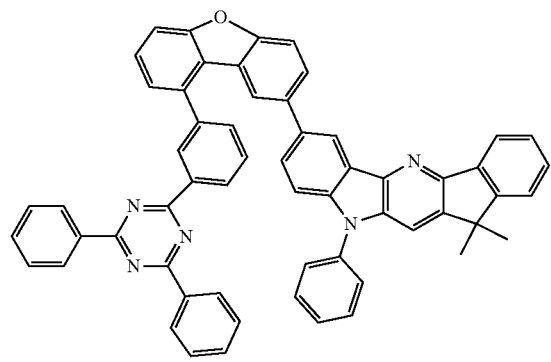
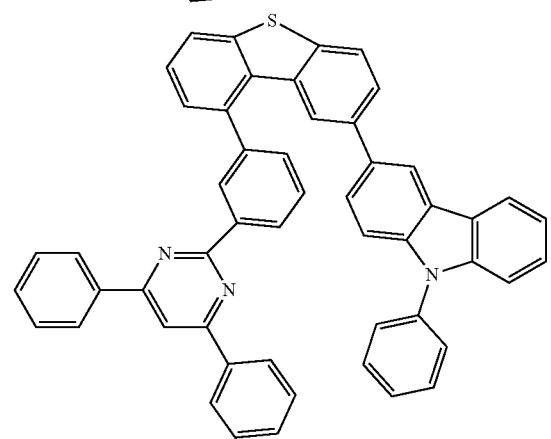
-continued
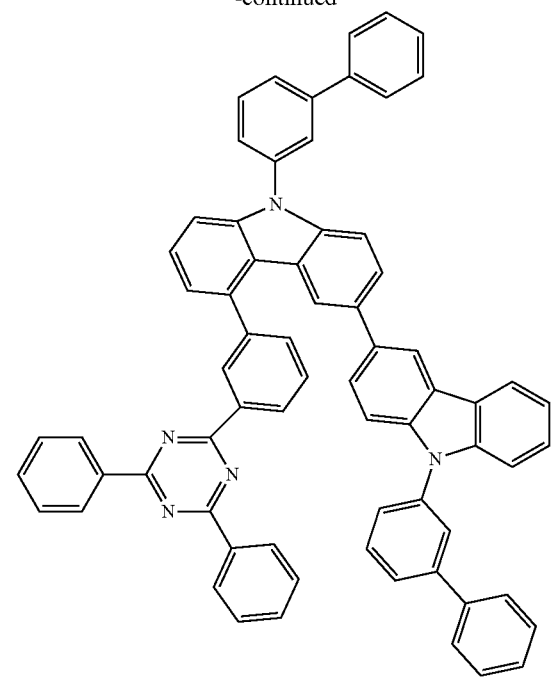
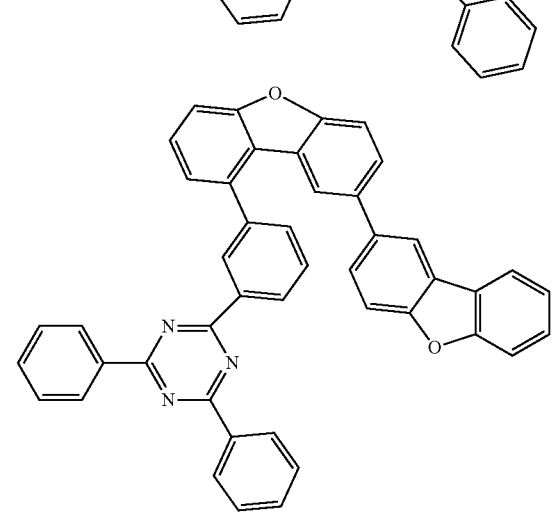
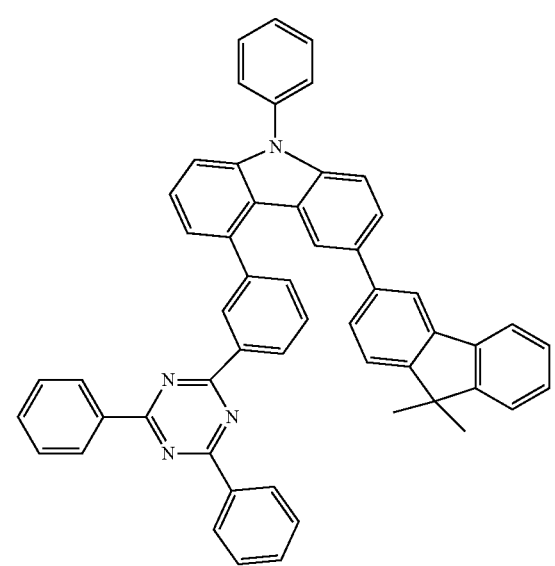

169
-continued
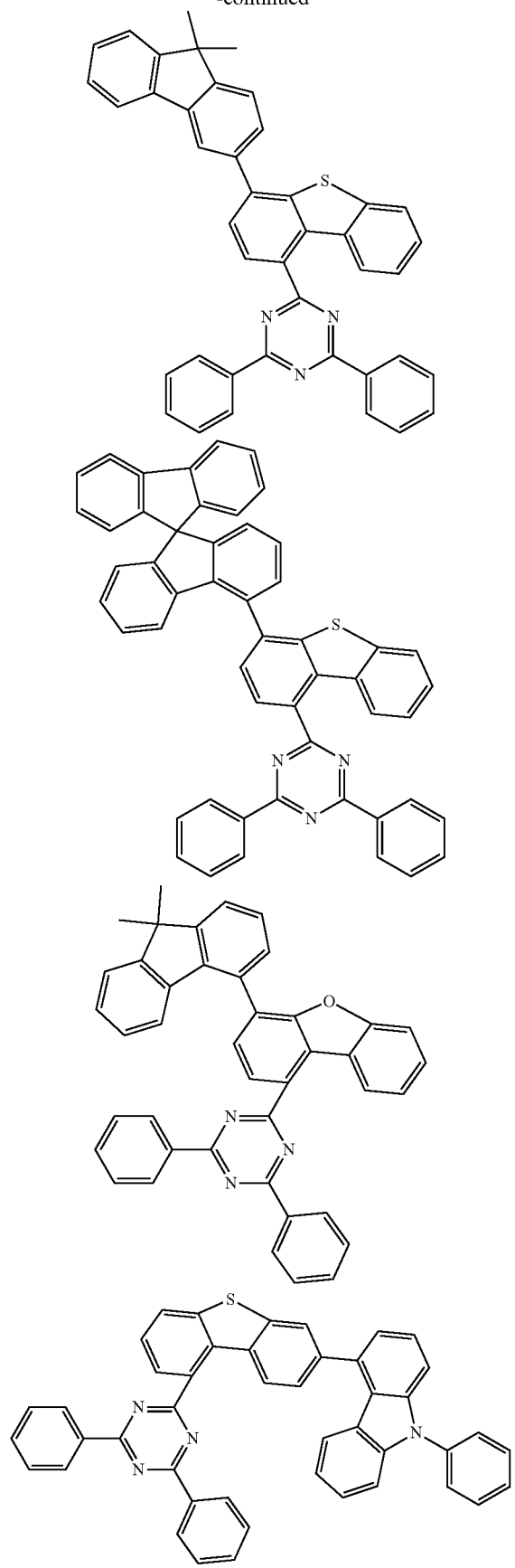
170
-continued
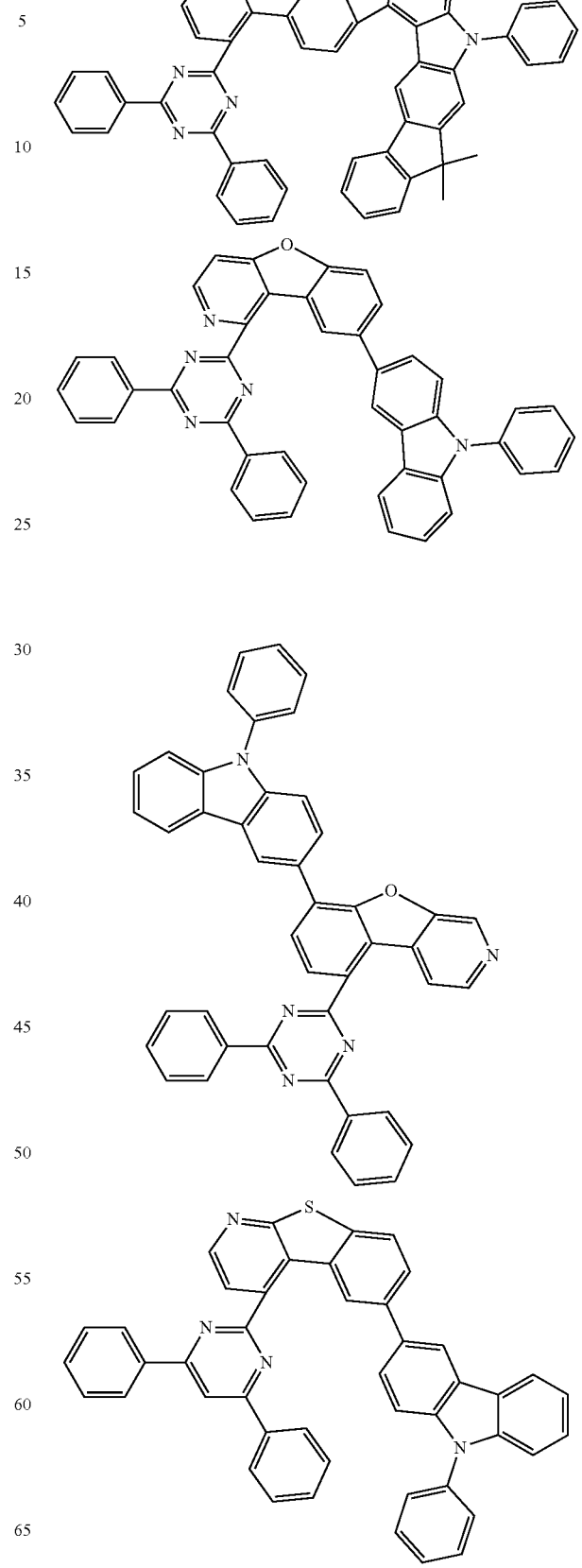

171
-continued
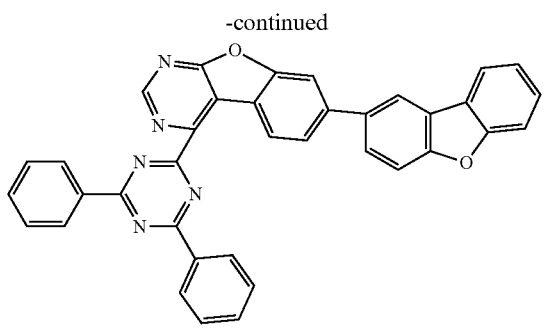
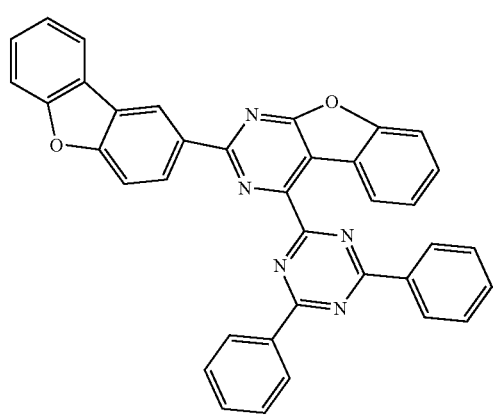
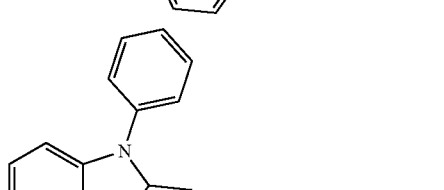
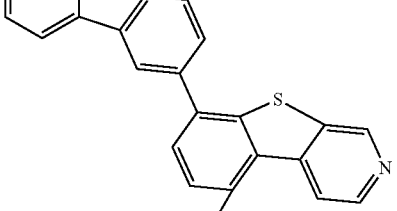
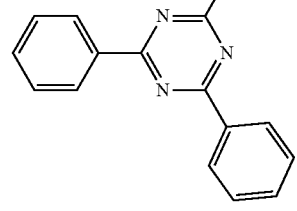
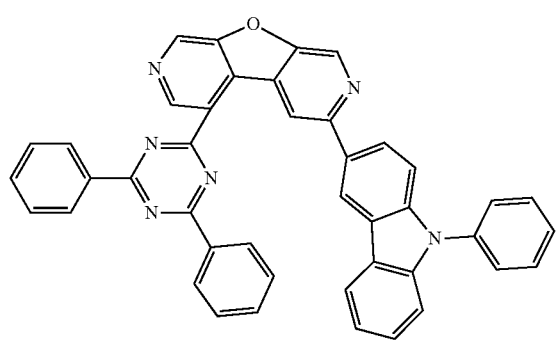
172
-continued
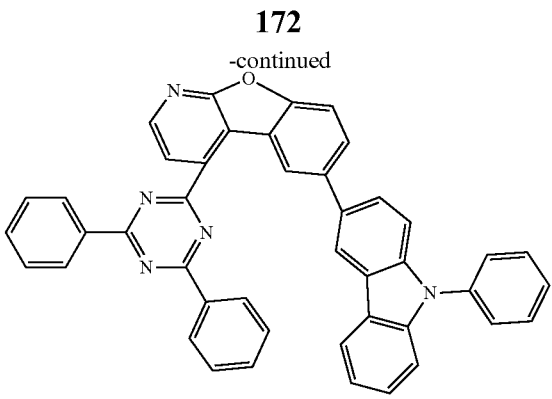
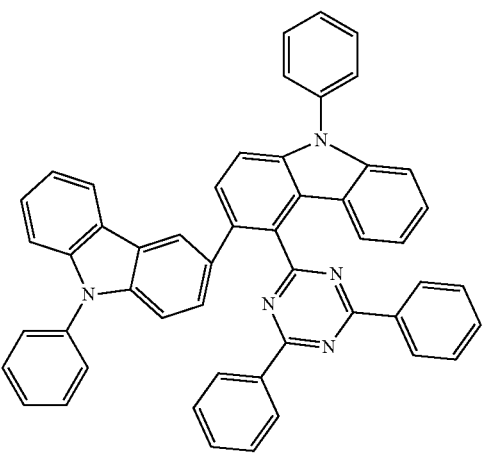
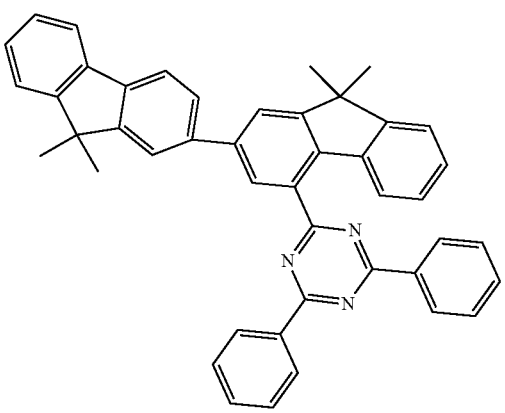
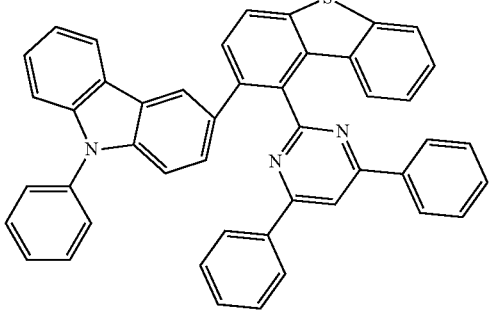

173
-continued
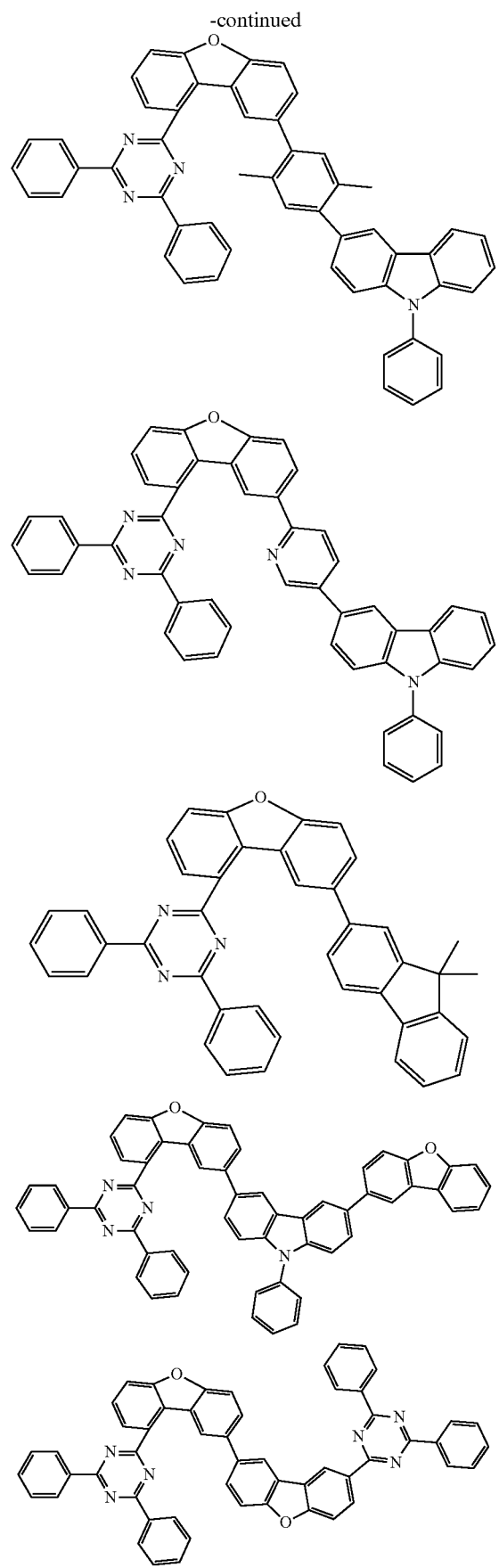
174
-continued
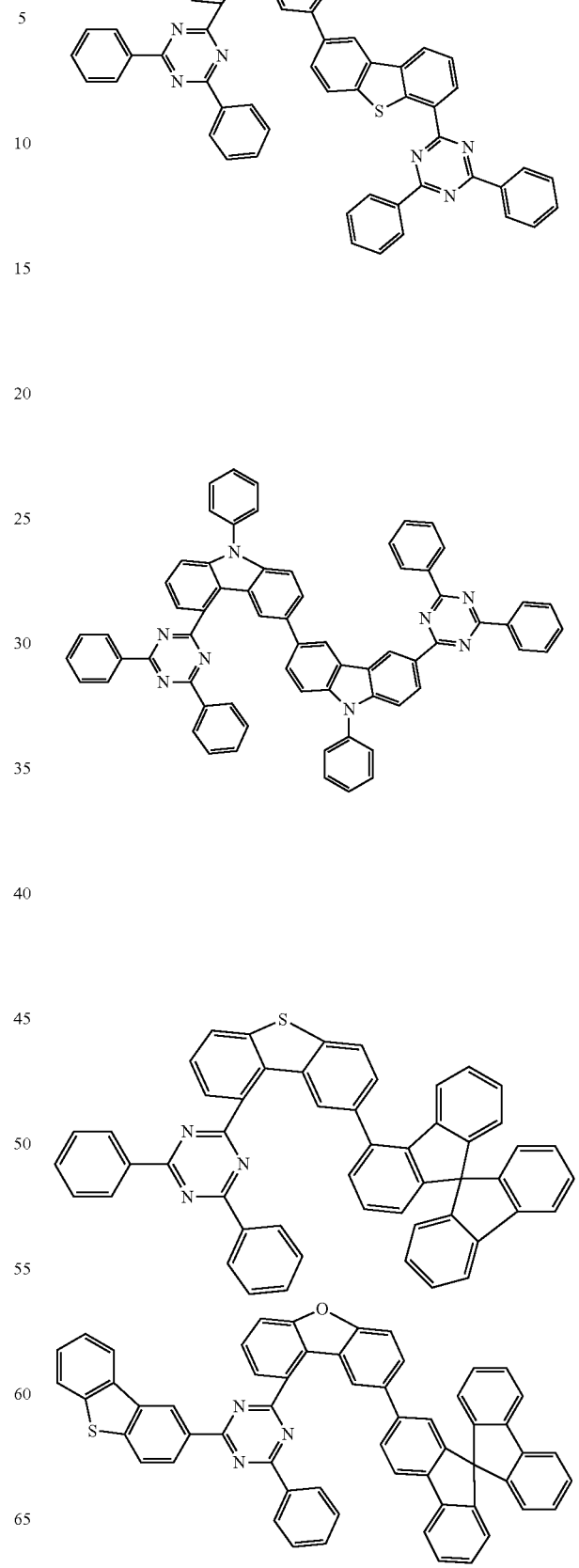

175
-continued
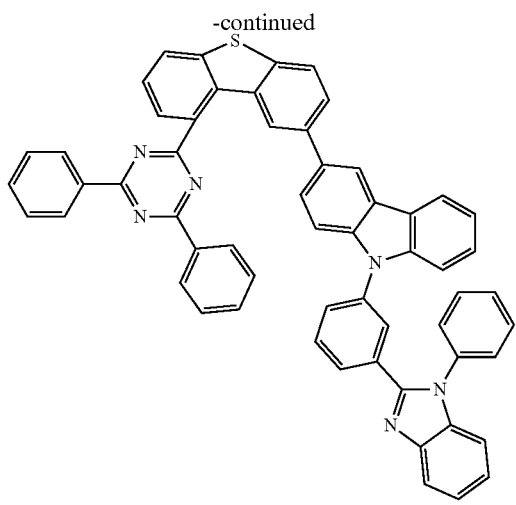
176
-continued
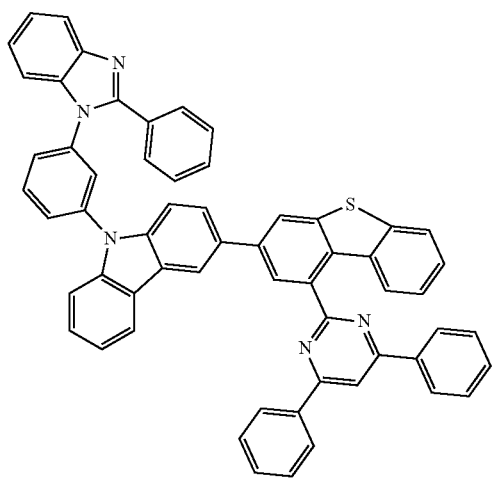
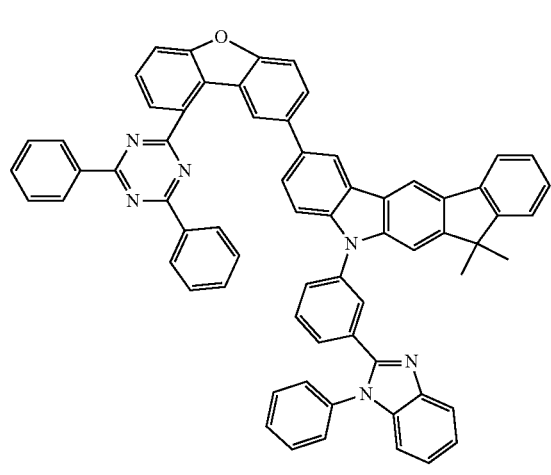
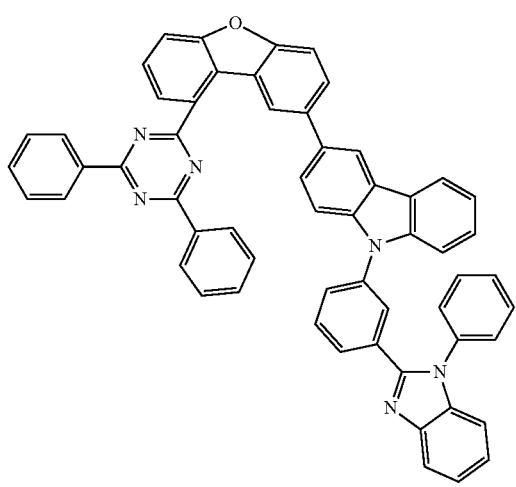
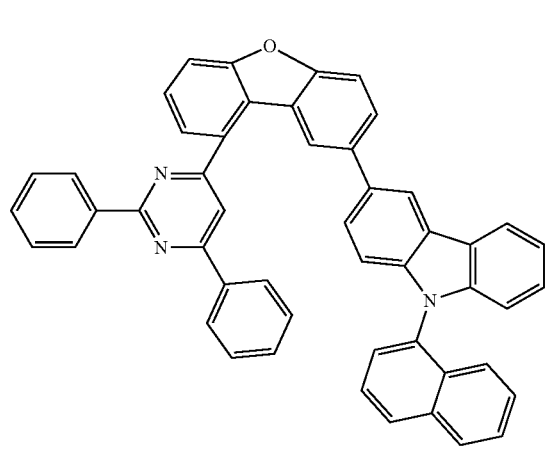

-continued
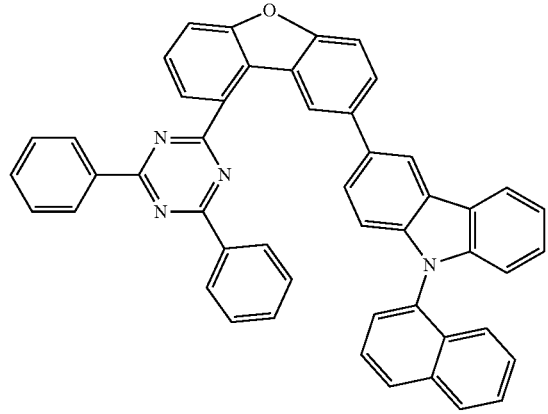
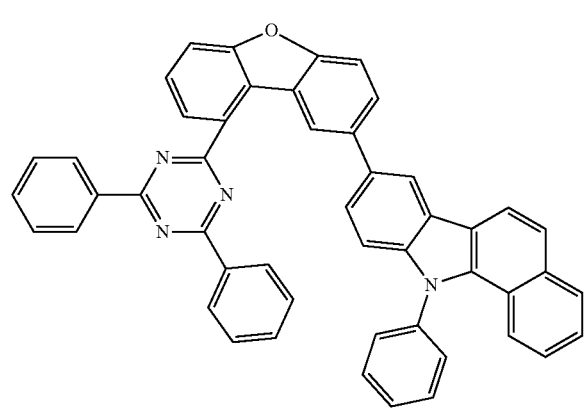
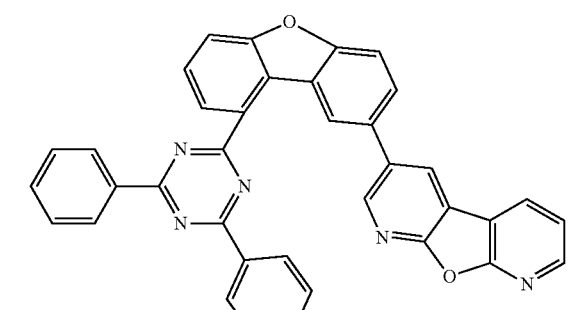
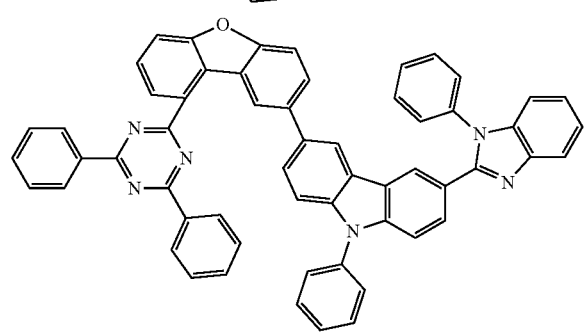
-continued
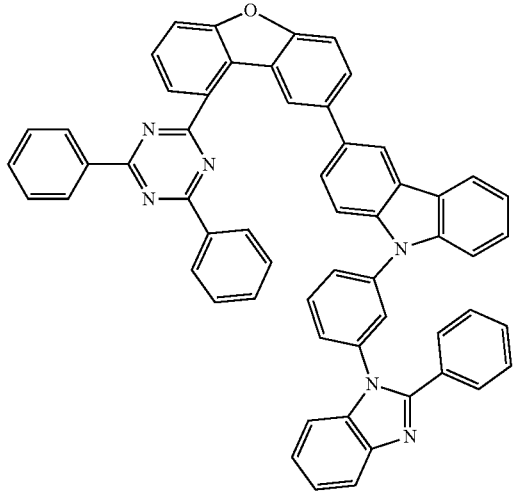
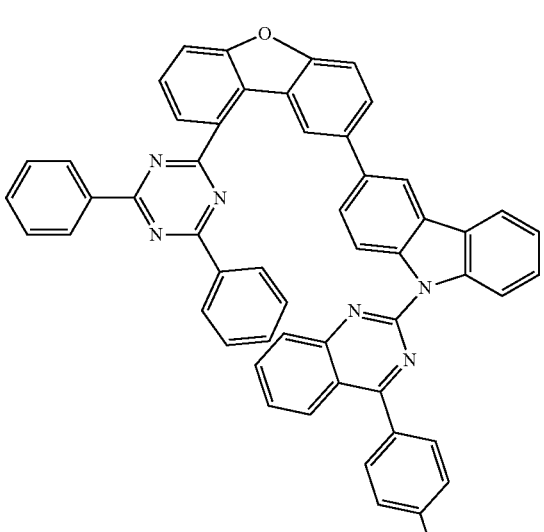
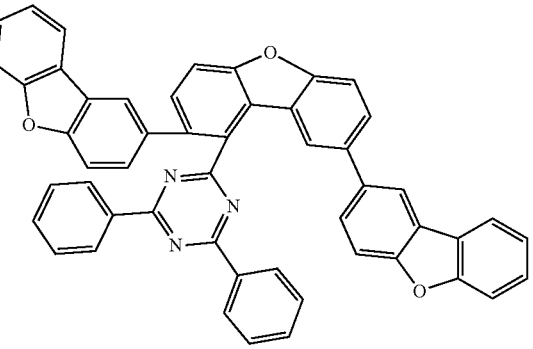

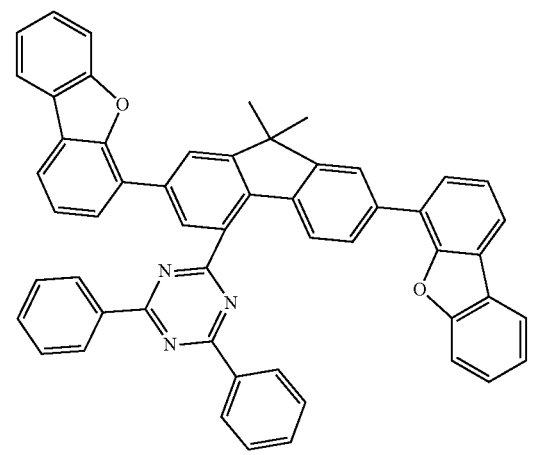
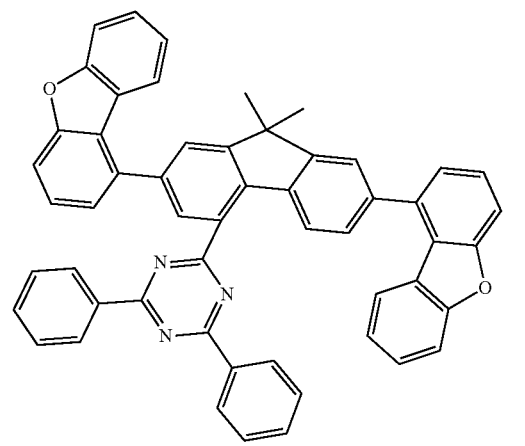
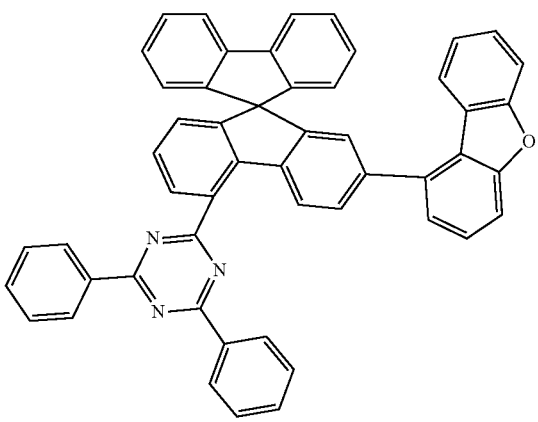
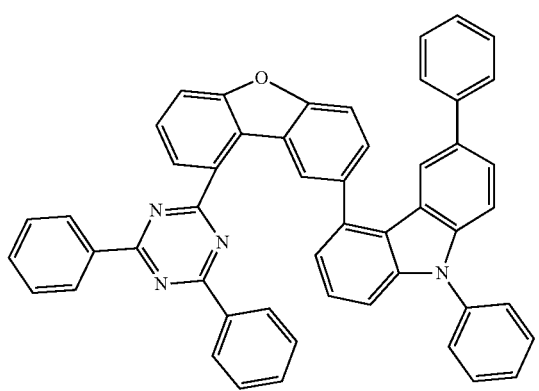
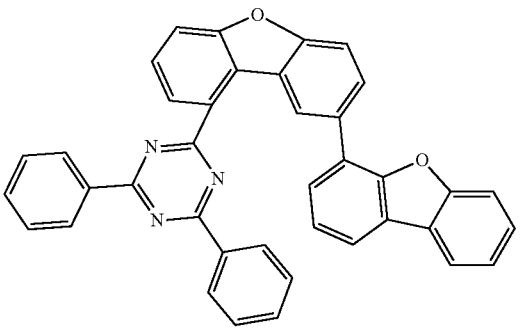
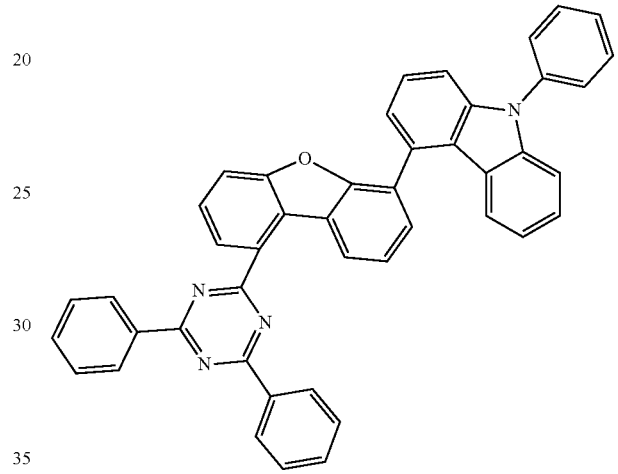
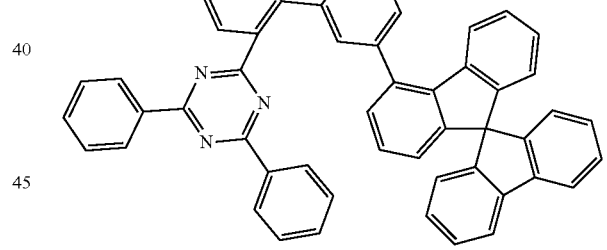
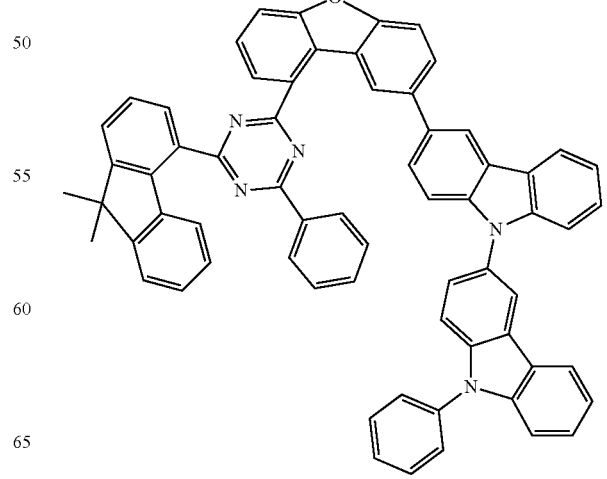

-continued
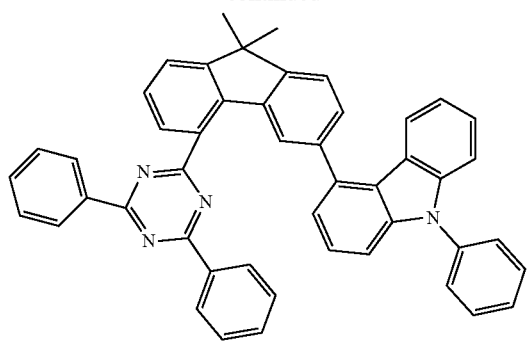
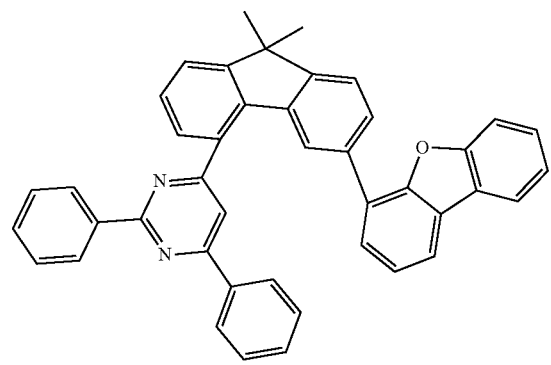
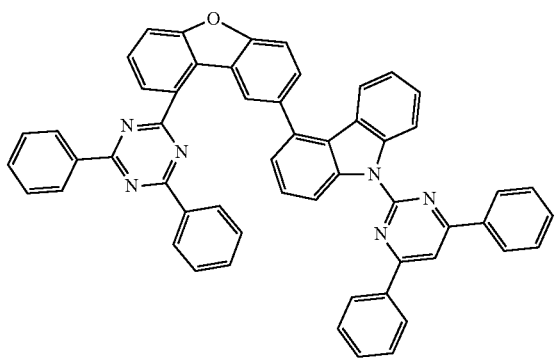
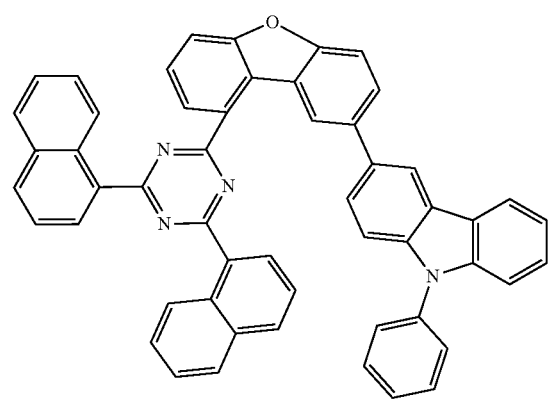
-continued
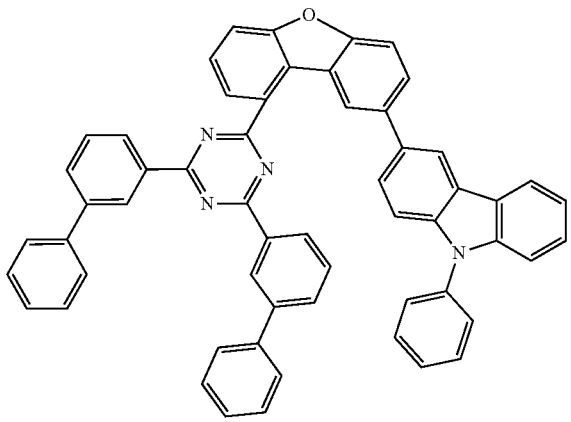
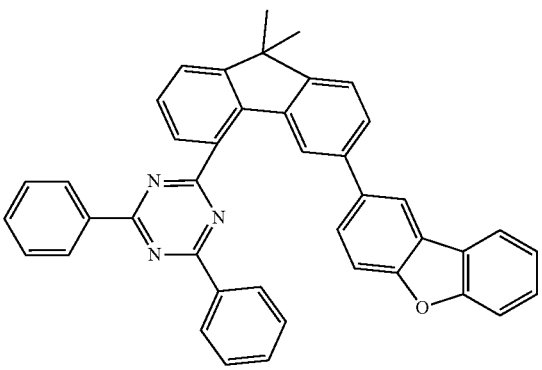
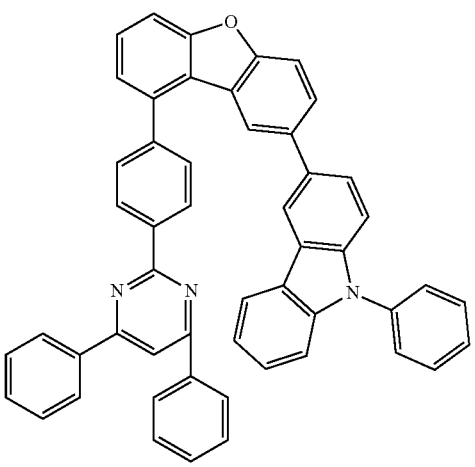
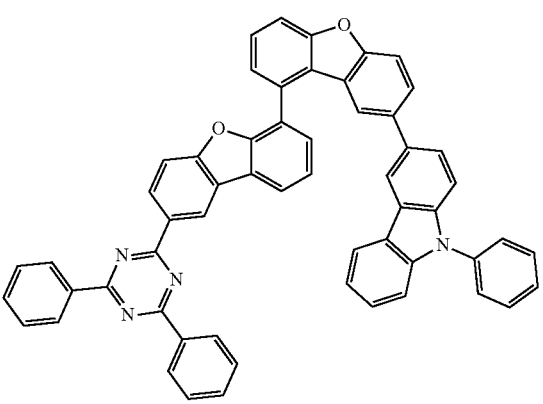

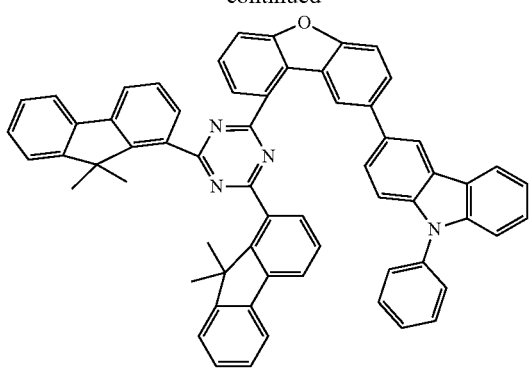
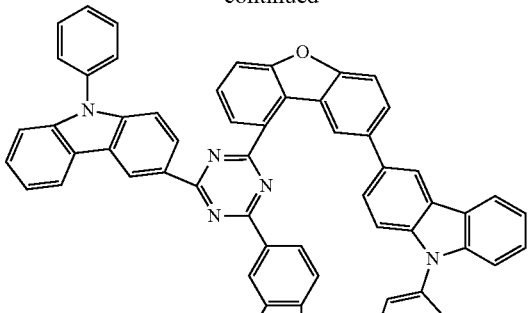
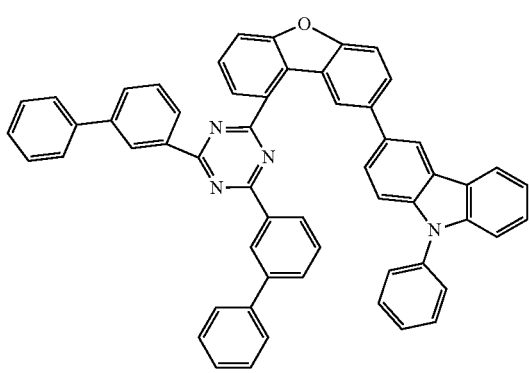
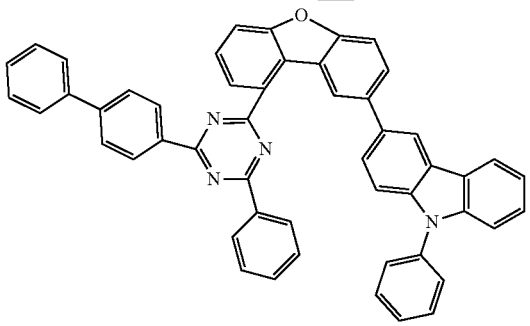 [SMILES: c1ccc(-c2ccc(-c3nc(-c4ccccc4)nc(-c4cccc5oc6ccc(-c7ccc8c(c7)c7ccccc7n8-c7ccccc7)cc6c45)n3)cc2)cc1]
The compounds according to the invention can be prepared by synthesis steps known to the person skilled in the art, such as, for example, bromination, Suzuki coupling, Ullmann coupling, Hartwig-Buchwald coupling, etc. A suitable synthetic process is depicted in general terms in Scheme 1 below.
Scheme 1
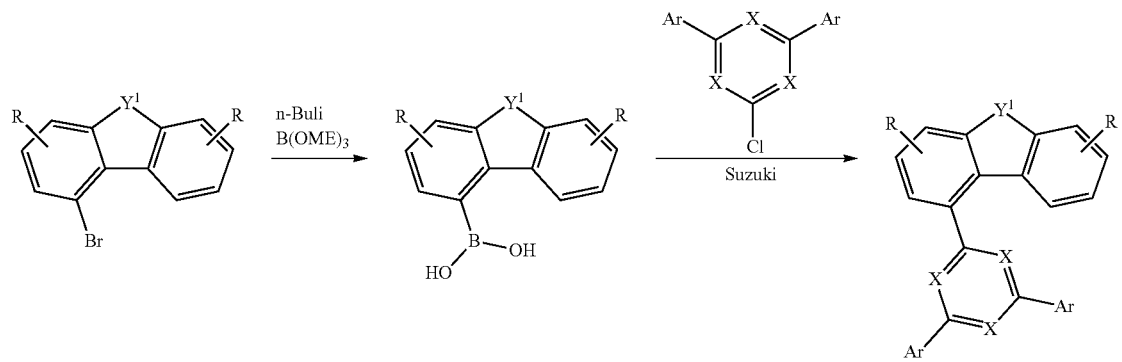

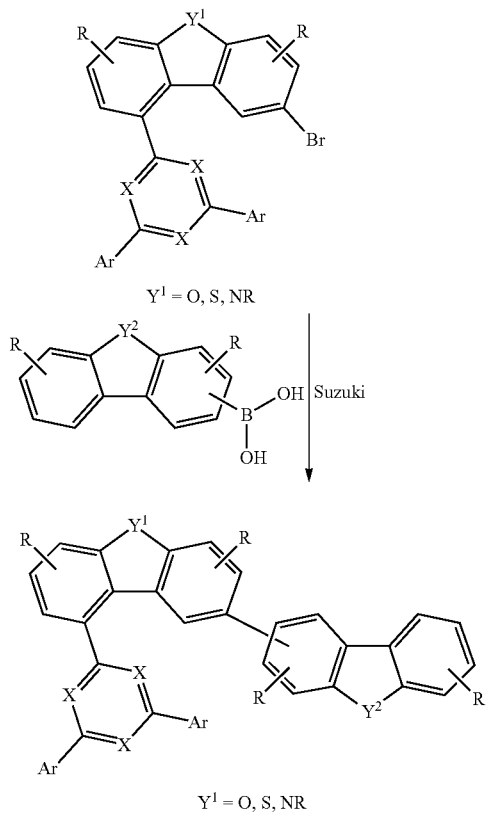

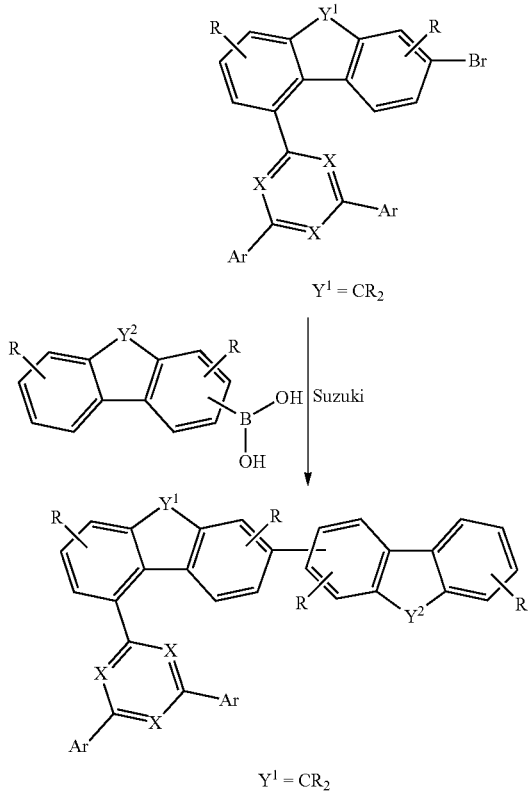

Processing of the compounds according to the invention from the liquid phase, for example by spin coating or by printing processes, requires formulations of the compounds according to the invention. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, □-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be \at least one further organic or inorganic compound which is likewise employed in the electronic device, for example an emitting compound, in particular a phosphorescent dopant, and/or a further matrix material. Suitable emitting compounds and further matrix materials are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another. A white-emitting electroluminescent device can be used, for example, for lighting applications, but also in combination with a coloured filter for full-colour displays.

The compound according to the invention in accordance with the embodiments indicated above can be employed in various layers, depending on the precise structure. Preference is given to an organic electroluminescent device comprising a compound of the formula (1) or formula (2) or in accordance with the preferred embodiments as matrix material for fluorescent or phosphorescent emitters, in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or formula (2) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or formula (2) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) or formula (2) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material. If the compounds are processed from solution, the corresponding amounts in % by weight are preferably used instead of the amounts indicated above in % by vol.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960 and the as yet unpublished applications EP 13004411.8, EP 14000345.0, EP 14000417.7 and EP 14002623.8. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

A further preferred embodiment of the present invention is the use of the compound of the formula (1) or formula (2) or the above-mentioned preferred embodiments as matrix material for a phosphorescent emitter in combination with a further matrix material. In a preferred embodiment of the invention, the further matrix material is a hole-transporting compound. In a further preferred embodiment of the invention, the further matrix material is an electron-transporting compound. In still a further preferred embodiment, the further matrix material is a compound having a large band gap which is not or not to a significant extent involved in the hole and electron transport in the layer.

Suitable matrix materials which can be employed in combination with the compounds of the formula (1) or formula (2) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, in particular monoamines, for example in accordance with WO 2014/015935, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, lactams, for example in accordance with WO 2011/116865, WO 2011/137951 or WO 2013/064206, or 4-spirocarbazole derivatives, for example in accordance with WO 2014/094963 or the as yet unpublished application EP 14002104.9. A further phosphorescent emitter which emits at shorter wavelength than the actual emitter may likewise be present in the mixture as co-host.

Preferred co-host materials are triarylamine derivatives, in particular monoamines, indenocarbazole derivatives, 4-spirocarbazole derivatives, lactams and carbazole derivatives.

Preferred triarylamine derivatives which are employed as co-host materials together with the compounds according to the invention are selected from the compounds of the following formula (11),

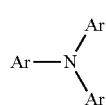

formula (11)

where Ar has, identically or differently on each occurrence, the meanings given above. The groups Ar are preferably selected, identically or differently on each occurrence, from groups Ar-1 to Ar-19 indicated above.

In a preferred embodiment of the compounds of the formula (11), at least one group Ar is selected from a biphenyl group, which can be an ortho-, meta- or para-biphenyl group. In a further preferred embodiment of the compounds of the formula (11), at least one group Ar is selected from a fluorene group or spirobifluorene group, where these groups may each be bonded to the nitrogen atom in the 1-, 2-, 3- or 4-position. In still a further preferred embodiment of the compounds of the formula (11), at least one group Ar is selected from a phenylene or biphenyl group, which is an ortho, meta- or para-linked group which is substituted by a dibenzofuran group, a dibenzothiophene group or a carbazole group, in particular a dibenzofuran group, where the dibenzofuran or dibenzothiophene group is linked to the phenylene or biphenyl group via the 1-, 2-, 3- or 4-position and where the carbazole group is linked to the phenylene or biphenyl group via the 1-, 2-, 3- or 4-position or via the nitrogen atom.

In a particularly preferred embodiment of the compounds of the formula (11), one group Ar is selected from a fluorene or spirobifluorene group, in particular a 4-fluorene or 4-spirobifluorene group, and one group Ar is selected from a biphenyl group, in particular a para-biphenyl group, or a fluorene group, in particular a 2-fluorene group, and the third group Ar is selected from a para-phenylene group or a para-biphenyl group, which is substituted by a dibenzofuran group, in particular a 4-dibenzofuran group, or a carbazole group, in particular an N-carbazole group or a 3-carbazole group.

Preferred indenocarbazole derivatives which are employed as co-host materials together with the compounds according to the invention are selected from the compounds of the following formula (12),

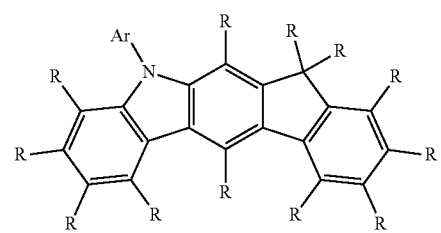

formula (12)

where Ar and R have the meanings given above. Preferred embodiments of the group Ar here are structures Ar-1 to Ar-19 indicated above.

A preferred embodiment of the compounds of the formula (12) are the compounds of the following formula (12a),

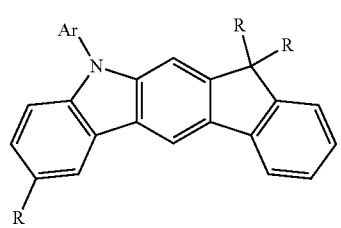

formula (12a)

where Ar and R have the meanings given above. The two groups R which are bonded to the indeno carbon atom preferably stand, identically or differently, for an alkyl group having 1 to 4 C atoms, in particular for methyl groups, or for an aromatic ring system having 6 to 12 C atoms, in particular for phenyl groups. Particularly preferably, the two groups R which are bonded to the indeno carbon atom stand for methyl groups. Furthermore preferably, the substituent R which is bonded to the indenocarbazole skeleton in formula (12a) stands for H or for a carbazole group, which can be bonded to the indenocarbazole skeleton via the 1-, 2-, 3- or 4-position or via the N atom, in particular via the 3-position.

Preferred 4-spirocarbazole derivatives which are employed as co-host materials together with the compounds according to the invention are selected from the compounds of the following formula (13), formula (13)

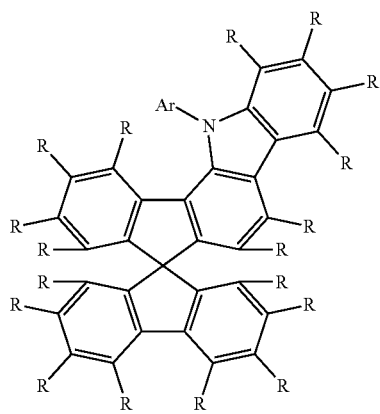

where Ar and R have the meanings given above. Preferred embodiments of the group Ar here are structures Ar-1 to Ar-19 indicated above.

A preferred embodiment of the compounds of the formula (13) are the compounds of the following formula (13a), formula (13a)

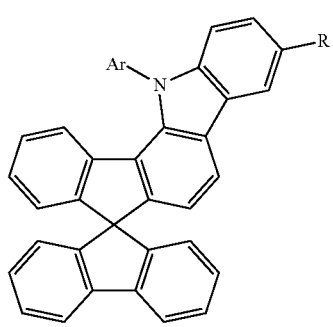

where Ar and R have the meanings given above.

Preferred lactams which are employed as co-host materials together with the compounds according to the invention are selected from the compounds of the following formula (14), formula (14)

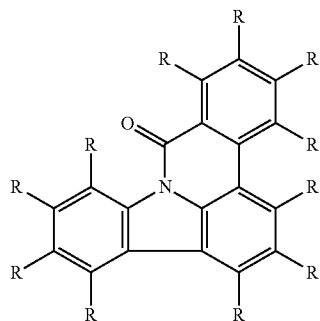

where R has the meanings given above.

A preferred embodiment of the compounds of the formula (14) are the compounds of the following formula (14a), formula (14a)

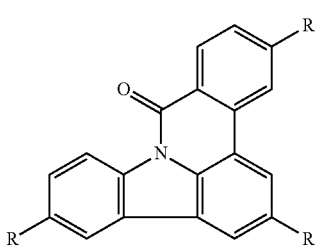

where R has the meanings given above. R here preferably stands, identically or differently on each occurrence, for H or an aromatic or heteroaromatic ring system having 5 to 40 aromatic ring atoms, which may be substituted by one or more radicals $R^1$. The substituents R are very particularly preferably selected from the group consisting of H or an aromatic or heteroaromatic ring system having 6 to 18 aromatic ring atoms, preferably having 6 to 13 aromatic ring atoms, which may in each case be substituted by one or more non-aromatic radicals $R^1$, but is preferably unsubstituted. Examples of suitable substituents R are selected from the group consisting of phenyl, ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals $R^1$, but is preferably unsubstituted. Suitable structures R here are the same structures as depicted above for Ar-1 to Ar-19, where these structures are substituted by $R^1$ instead of R.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in a hole-blocking or electron-transport layer. This applies, in particular, to compounds according to the invention which do not contain a carbazole structure. These may preferably also be substituted by one or more further electron-transporting groups, for example benzimidazole groups.

In the further layers of the organic electroluminescent device according to the invention, all materials as are usually employed in accordance with the prior art can be used. The person skilled in the art will therefore be able to employ, without inventive step, all materials known for organic electroluminescent devices in combination with the compounds of the formula (1) or formula (2) according to the invention or in accordance with the preferred embodiments.

Preference is furthermore given to an organic electroluminescent device, characterised in that one or more layers are applied by means of a sublimation process, in which the materials are applied by vapour deposition in vacuum sublimation units at an initial pressure of less than 10-5 mbar, preferably less than 10-6 mbar. However, it is also possible for the initial pressure to be even lower or higher, for example less than 10-7 mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between 10-5 mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. Thus, for example, it is possible to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention generally have very good properties on use in organic electroluminescent devices. In particular, the lifetime on use of the compounds according to the invention in organic electroluminescent devices is significantly better compared with similar compounds in accordance with the prior art. The other properties of the organic electroluminescent device, in particular the efficiency and the voltage, are likewise better or at least comparable.

The invention is now explained in greater detail by the following examples, without wishing to restrict it thereby.

EXAMPLES

The following syntheses are carried out, unless indicated otherwise, in dried solvents under a protective-gas atmosphere. The solvents and reagents can be purchased, for example, from Sigma-ALDRICH or ABCR. The corresponding CAS numbers are in each case also indicated for the compounds that are known from the literature.

Synthesis Examples a) Triazine synthesis:
2,4-Bisbiphenyl-3-yl-6-chloro-1,3,5-triazine

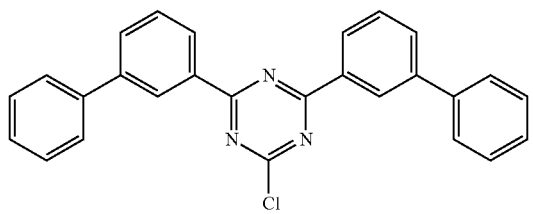 [SMILES: Clc1nc(-c2cccc(-c3ccccc3)c2)nc(-c2cccc(-c3ccccc3)c2)n1]

5.2 g of magnesium (0.215 mol) are initially introduced in a 500 ml four-necked flask, and a solution of 50 g of bromobiphenyl (214 mmol) in 200 ml of THF is slowly added dropwise. The reaction mixture is heated at the boil for 1.5 h and subsequently cooled to room temperature. Cyanogen chloride (17.2 g, 93 mmol) in 150 ml of THF is initially introduced in a second flask and cooled to 0° C. The cooled Grignard reagent is added dropwise at this temperature, and the mixture is stirred at room temperature for 12 h. After this time, 150 ml of HCl are added to the reaction mixture, and the aqueous phase is extracted three times with dichloromethane. The combined organic phases are washed with water, dried over $Na_2SO_4$ and evaporated. The residue is recrystallised from EtOH. The yield is 32.8 g (78 mmol, 84%).

b) 4-Bromo-9-methyl-9-phenyl-9H-fluorene

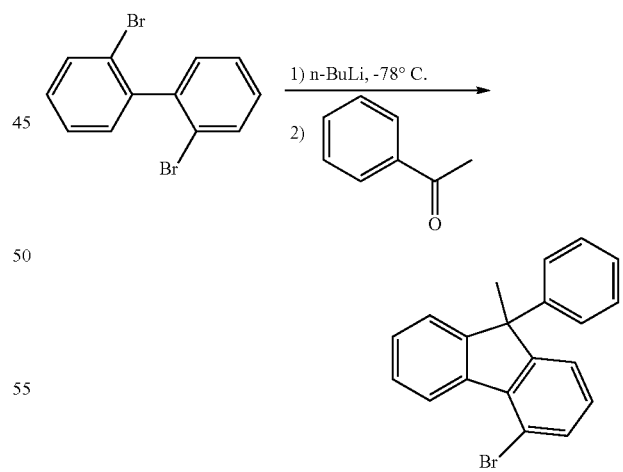

30 g (94 mmol) of 2,2'-dibromobiphenyl are dissolved in 200 ml of dried THF in a flask which has been dried by heating. The reaction mixture is cooled to −78° C. At this temperature, 37.7 ml of a 2.5 M solution of n-butyllithium in hexane (94 mmol) are slowly added dropwise (duration: about 1 h). The batch is stirred at −70° C. for a further 1 h. 11.1 ml of acetophenone (94 mmol) are subsequently dissolved in 100 ml of THF and added dropwise at −70° C.

When the addition is complete, the reaction mixture is slowly warmed to room temperature, quenched with NH₄Cl and subsequently concentrated in a rotary evaporator. 300 ml of acetic acid are carefully added to the concentrated solution, and 50 ml of fuming HCl are subsequently added. The batch is heated at 75° C. for 6 h, during which a white solid precipitates out. The batch is cooled to room temperature, and the solid which has precipitated out is filtered off with suction and rinsed with methanol. The residue is dried at 40° C. in vacuo. The yield is 25.3 g (75 mmol) (80% of theory).

c) 4-Bromo-9,9-diphenyl-9H-fluorene

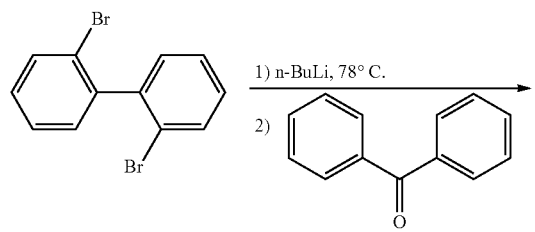

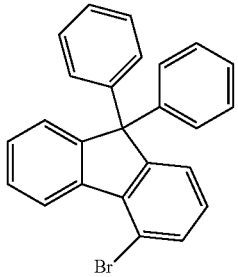

37 g (152 mmol) of 2,2'-dibromobiphenyl are dissolved in 300 ml of dried THF in a flask which has been dried by heating. The reaction mixture is cooled to −78° C. At this temperature, 75 ml of a 15% solution of n-butyllithium in hexane (119 mmol) are slowly added dropwise (duration: about 1 h). The batch is stirred at −70° C. for a further 1 h. 21.8 g of benzophenone (119 mmol) are subsequently dissolved in 100 ml of THF and added dropwise at −70° C. When the addition is complete, the reaction mixture is slowly warmed to room temperature, quenched with NH₄C₁ and subsequently concentrated in a rotary evaporator. 510 ml of acetic acid are carefully added to the concentrated solution, and 100 ml of fuming HCl are subsequently added. The batch is heated at 75° C. for 4 h, during which a white solid precipitates out. The batch is then cooled to room temperature, and the solid which has precipitated out is filtered off with suction and rinsed with methanol. The residue is dried at 40° C. in vacuo. The yield is 33.2 g (83 mmol) (70% of theory).

The following brominated compounds are prepared analogously:

| | Starting material 1 | Starting material 2 | Product | Yield |
|---|---|---|---|---|
| c1 | | | | 78% |
| c2 | | | | 70% |

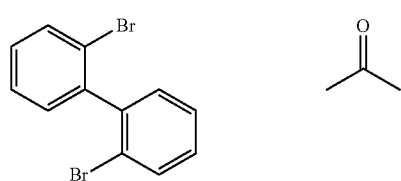

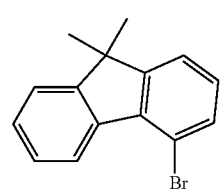 [SMILES: CC1(C)c2ccccc2-c2c(Br)cccc21]

| | Starting material 1 | Starting material 2 | Product | Yield |
|---|---|---|---|---|
| c3 | 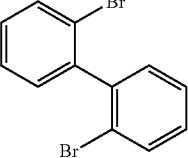 | 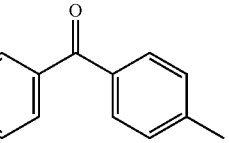 | 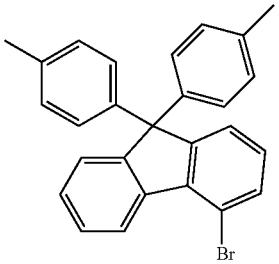 | 82% | d) 6-Bromo-2-fluoro-2'-methoxybiphenyl

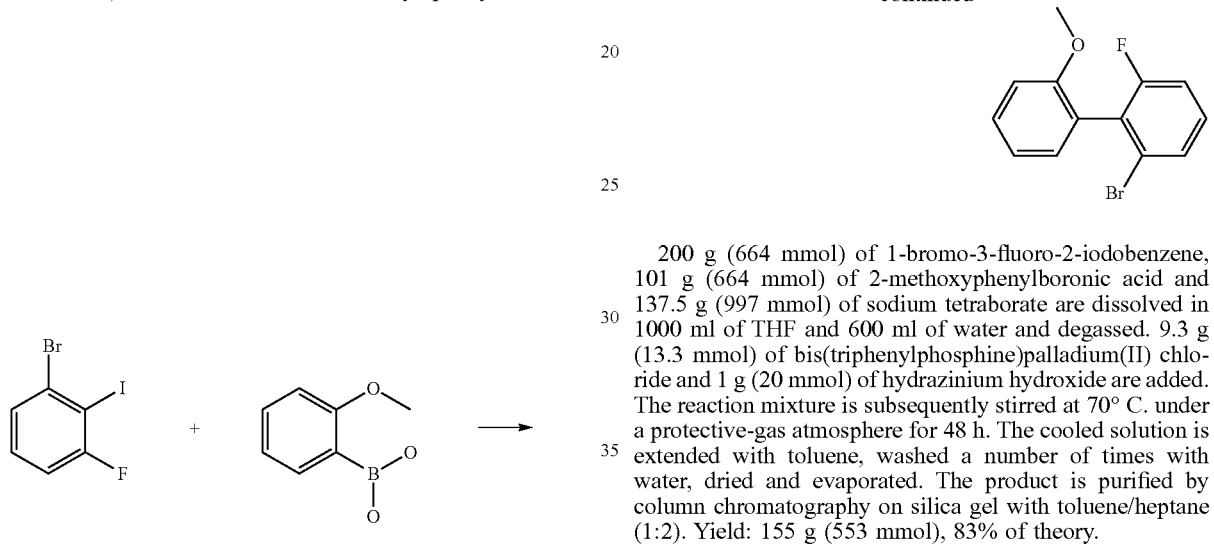

200 g (664 mmol) of 1-bromo-3-fluoro-2-iodobenzene, 101 g (664 mmol) of 2-methoxyphenylboronic acid and 137.5 g (997 mmol) of sodium tetraborate are dissolved in 1000 ml of THF and 600 ml of water and degassed. 9.3 g (13.3 mmol) of bis(triphenylphosphine)palladium(II) chloride and 1 g (20 mmol) of hydrazinium hydroxide are added. The reaction mixture is subsequently stirred at 70° C. under a protective-gas atmosphere for 48 h. The cooled solution is extended with toluene, washed a number of times with water, dried and evaporated. The product is purified by column chromatography on silica gel with toluene/heptane (1:2). Yield: 155 g (553 mmol), 83% of theory.

The following compounds are prepared analogously:

| | Starting material 1 | Starting material 2 | Product | Yield |
|---|---|---|---|---|
| d1 | 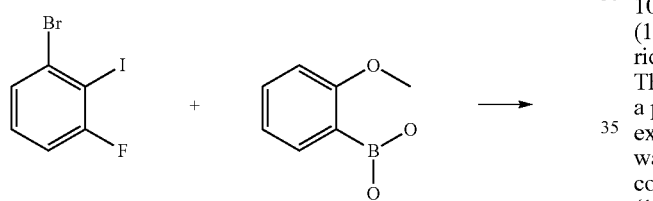[1000576-09-9] | 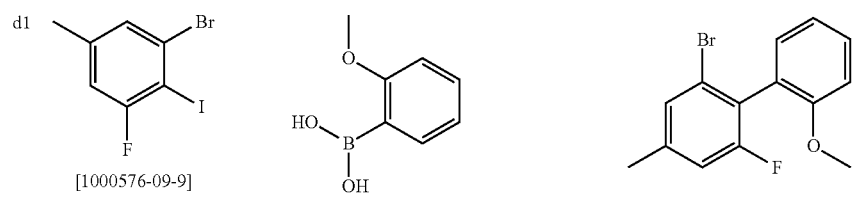 | 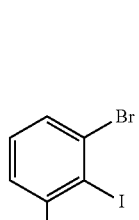 | 77% |
| d2 | 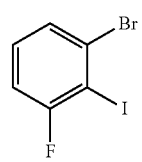 | 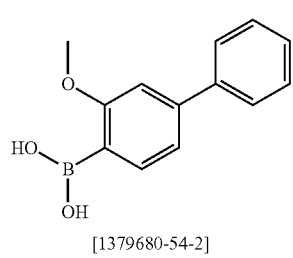 [SMILES: COc1cc(-c2ccccc2)ccc1B(O)O][1379680-54-2] | 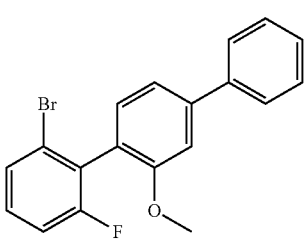 [SMILES: COc1cc(-c2ccccc2)ccc1-c1c(F)cccc1Br] | 74% |

| | Starting material 1 | Starting material 2 | Product | Yield |
|---|---|---|---|---|
| d3 | 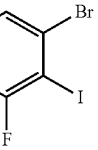 | 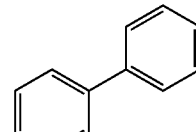[1199350-14-5] | 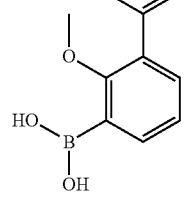 | 76% |
| d4 | 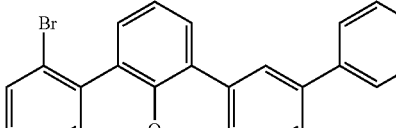 | 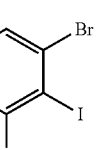[1114496-44-4] | 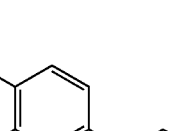 | 71% | e) 6'-Bromo-2'-fluorobiphenyl-2-ol

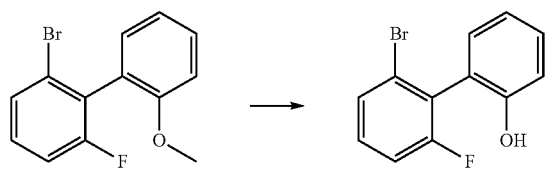 [SMILES: COc1ccccc1-c1c(F)cccc1Br ; Oc1ccccc1-c1c(F)cccc1Br]

112 g (418 mmol) of 6-bromo-2-fluoro-2'-methoxybiphenyl are dissolved in 2 l of dichloromethane and cooled to 5° C. 41.01 ml (431 mmol) of boron tri bromide are added dropwise to this solution over the course of 90 min., and stirring is continued overnight. Water is subsequently slowly added to the mixture, and the organic phase is washed three times with water, dried over $Na_2SO_4$, evaporated in a rotary evaporator and purified by chromatography. Yield: 104 g (397 mmol), 98% of theory.

The following compounds are prepared analogously:

| | Starting material 1 | Product | Yield |
|---|---|---|---|
| e1 | 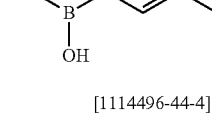 | 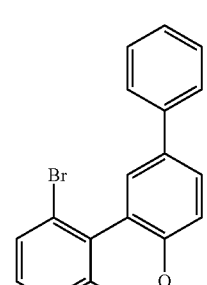 | 92% |
| e2 | | | 90% |

-continued

| | Starting material 1 | Product | Yield |
|---|---|---|---|
| e3 | | | 93% |
| e4 | | | 94% | f) 1-Bromodibenzofuran

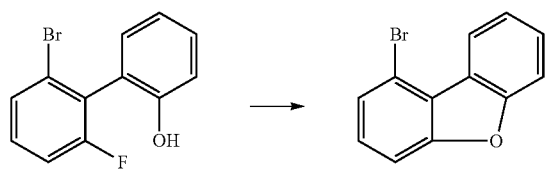 [SMILES: Oc1ccccc1-c1c(F)cccc1Br ; Brc1cccc2oc3ccccc3c12]

111 g (416 mmol) of 6'-bromo-2'-fluorobiphenyl-2-ol are dissolved in 2 l of SeccoSolv® DMF (max. 0.003% of $H_2O$) and cooled to 5° C. 20 g (449 mmol) of sodium hydride (60% suspension in paraffin oil) are added to this solution in portions, and the mixture is stirred for a further 20 min. after the addition is complete and then heated at 100° C. for 45 min. After cooling, 500 ml of ethanol are slowly added to the mixture, which is then evaporated in a rotary evaporator and then purified by chromatography. Yield: 90 g (367 mmol), 88.5% of theory.

The following compounds are prepared analogously:

| | Starting material 1 | Product | Yield |
|---|---|---|---|
| f1 | | | 81% |
| f2 | | | 78% |
| f3 | | | 73% |

| Starting material 1 | Product | Yield |
|---|---|---|
| f4 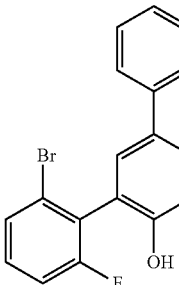 | | 79% | g) Dibenzofuran-1-boronic acid and boronic acid esters

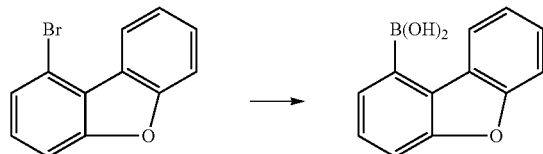

180 g (728 mmol) of 1-bromodibenzofuran are dissolved in 1500 ml of dry THF and cooled to −78° C. At this temperature, 305 ml (764 mmol/2.5 M in hexane) of n-butyl-lithium are added over the course of about 5 min., and the mixture is subsequently stirred at −78° C. for a further 2.5 h. At this temperature, 151 g (1456 mmol) of trimethyl borate are added as rapidly as possible, and the reaction is allowed to come slowly to room temperature (about 18 h). The reaction solution is washed with water, the solid which has precipitated out is filtered off and the organic phase are dried azeotropically with toluene. The crude product is washed by stirring with toluene/methylene chloride at about 40° C. and filtered off with suction. Yield: 146 g (690 mmol), 95% of theory.

The following compounds are prepared analogously:

| Starting material 1 | Product | Yield |
|---|---|---|
| g1 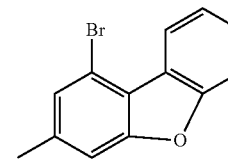 | 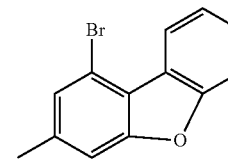 | 81% |
| g2 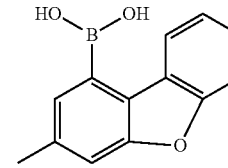 | 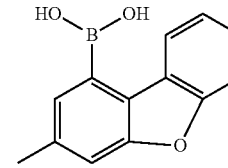 | 78% |
| g3 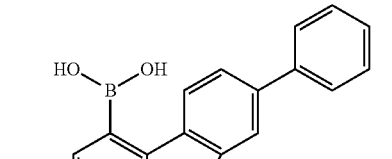 | 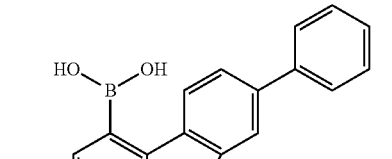 | 73% |

-continued
| Starting material 1 | Product | Yield |
|---|---|---|
| g4 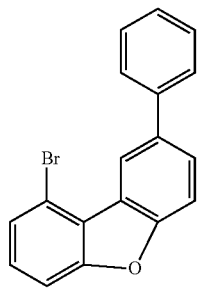 [SMILES: Brc1cccc2oc3ccc(-c4ccccc4)cc3c12] | 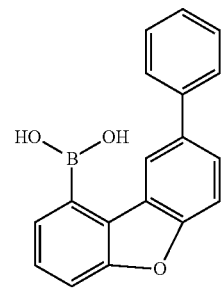 [SMILES: OB(O)c1cccc2oc3ccc(-c4ccccc4)cc3c12] | 79% |
| g5 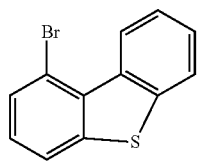 [65642-94-6] | 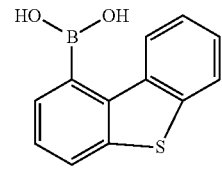 | 73% |
| g6 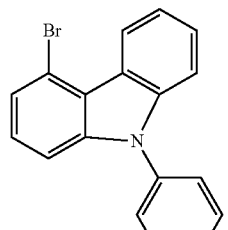 [1097884-37-1] | 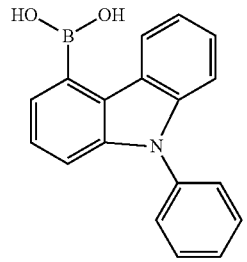 [SMILES: OB(O)c1cccc2c1c1ccccc1n2-c1ccccc1] | 70% |
| g7 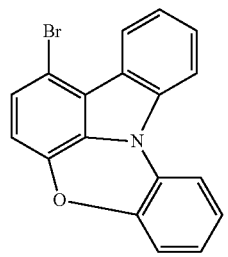 [1415901-44-8] | 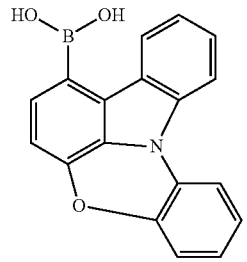 [SMILES: OB(O)c1ccc2c3c1c1ccccc1n3-c1ccccc1O2] | 70% |
| g8 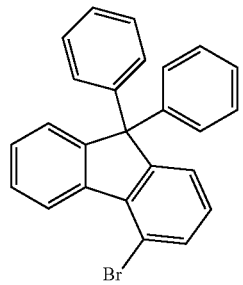 [SMILES: Brc1cccc2c1-c1ccccc1C2(c1ccccc1)c1ccccc1] | 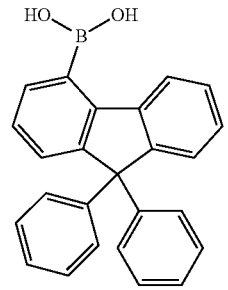 [SMILES: OB(O)c1cccc2c1-c1ccccc1C2(c1ccccc1)c1ccccc1] | 78% |

-continued
| | Starting material 1 | Product | Yield |
|---|---|---|---|
| g9 | 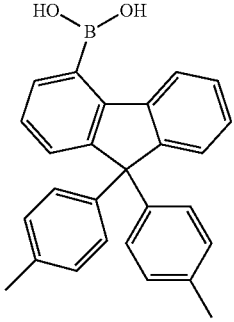 [SMILES: Cc1ccc(C2(c3ccc(C)cc3)c3ccccc3-c3c(B(O)O)cccc32)cc1] | 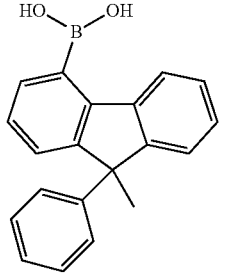 [SMILES: CC1(c2ccccc2)c2ccccc2-c2c(B(O)O)cccc21] | 81% |
| g10 | | | 86% |
| g11 | 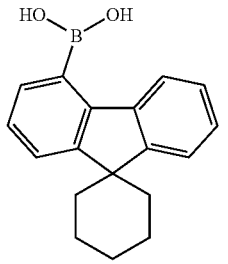 [SMILES: OB(O)c1cccc2c1-c1ccccc1C21CCCCC1] | | 83% |
| g12 | | 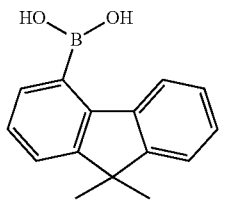 [SMILES: CC1(C)c2ccccc2-c2c(B(O)O)cccc21] | 85% |
| g13 | 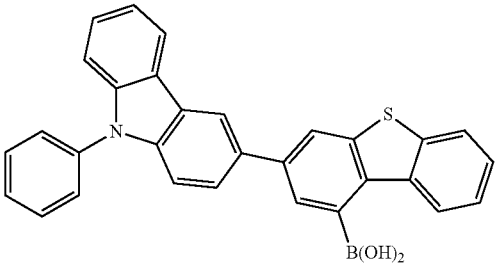 [SMILES: OB(O)c1cc(-c2ccc3c(c2)c2ccccc2n3-c2ccccc2)cc2sc3ccccc3c12] K) | | 82% |

-continued
| | Starting material 1 | Product | Yield |
|---|---|---|---|
| g14 | 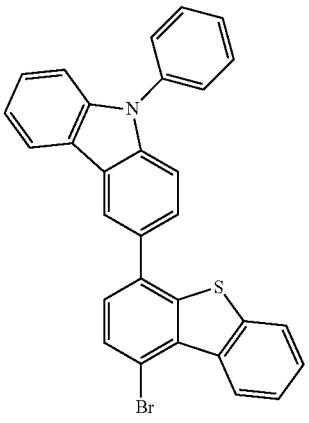 K1 | 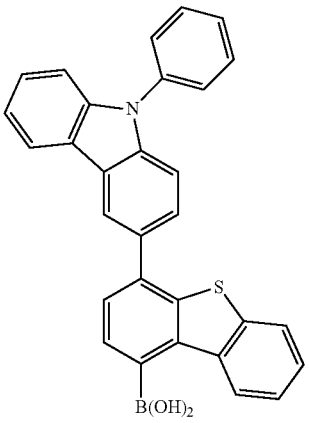 [SMILES: OB(O)c1ccc(-c2ccc3c(c2)c2ccccc2n3-c2ccccc2)c2sc3ccccc3c12] | 80% |
| g15 | 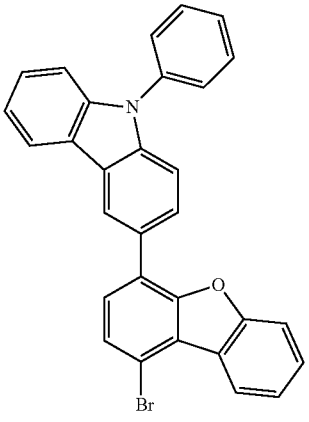 K2 | 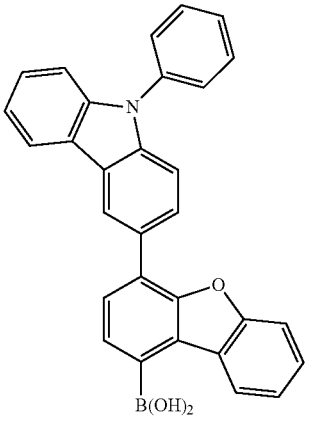 [SMILES: OB(O)c1ccc(-c2ccc3c(c2)c2ccccc2n3-c2ccccc2)c2oc3ccccc3c12] | 83% |
| g16 | 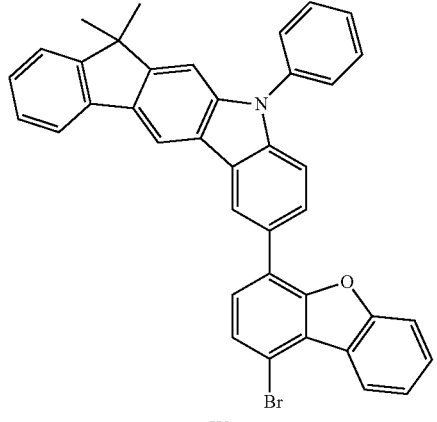 K3 | 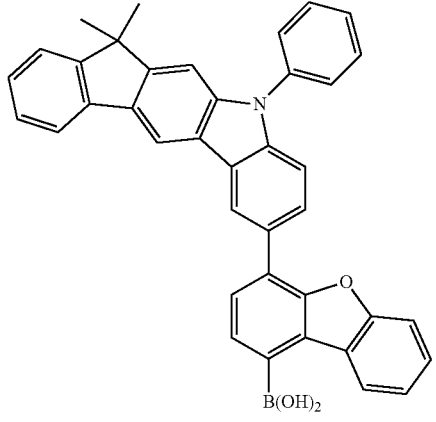 [SMILES: CC1(C)c2ccccc2-c2cc3c4cc(-c5ccc(B(O)O)c6c5oc5ccccc56)ccc4n(-c4ccccc4)c3cc21] | 82% |
| g17 | 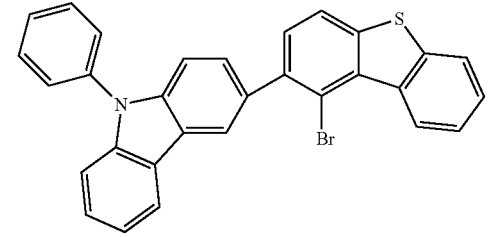 K4 | 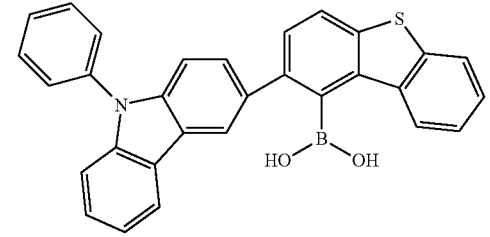 [SMILES: OB(O)c1c(-c2ccc3c(c2)c2ccccc2n3-c2ccccc2)ccc2sc3ccccc3c12] | 81% |

-continued

| Starting material 1 | Product | Yield |
|---|---|---| g18

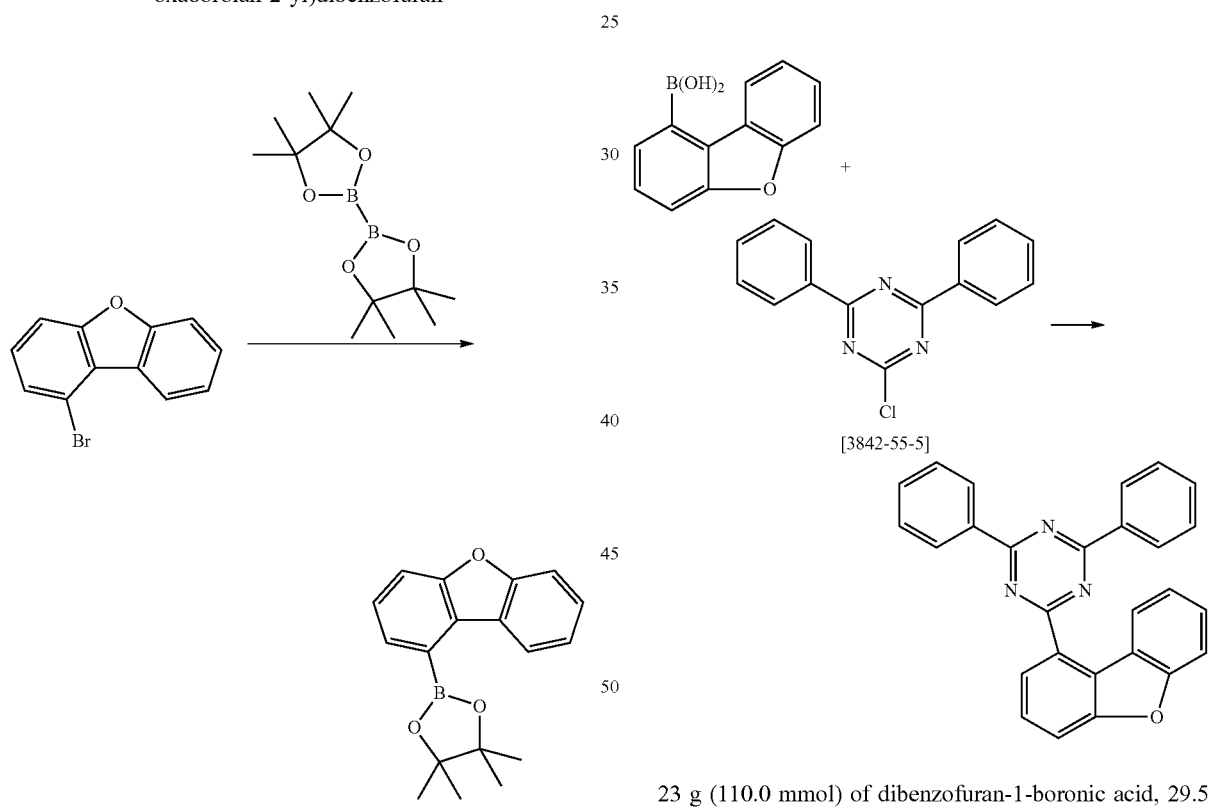

84% k5 g19) Synthesis of 1-(4,4,5,5-tetramethyl-1,3,2-dioxaborolan-2-yl)dibenzofuran 101 g (410 mmol) of 1-bromodibenzofuran are dissolved in 1500 ml of dry DMF together with 273 g (1055 mmol) of bis(pinacolato)diborane (CAS 73183-34-3) under protective gas in a 500 ml flask and degassed for 30 minutes. 121 g (1229 mmol) of potassium acetate and 8.4 g (37 mmol) of palladium acetate are subsequently added, and the batch is heated overnight at 80° C. When the reaction is complete, the mixture is diluted with 300 ml of toluene and extracted with water. The solvent is removed in a rotary evaporator, and the product is recrystallised from heptane. Yield: 118 g (401 mmol), 98% of theory.

h) 2-Dibenzofuran-1-yl-4,6-diphenyl-1,3,5-triazine

[3842-55-5]

23 g (110.0 mmol) of dibenzofuran-1-boronic acid, 29.5 g (110.0 mmol) of 2-chloro-4,6-diphenyl-1,3,5-triazine and 21 g (210.0 mmol) of sodium carbonate are suspended in 500 ml of ethylene glycol diamine ether and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/heptane. The yield is 37 g (94 mmol), corresponding to 87% of theory.

The following compounds are prepared analogously:

| | Starting material 1 | Starting material 2 | Product | Yield |
|---|---|---|---|---|
| h1 | (dibenzofuran-methyl-boronic acid) | 4-bromo-2,6-diphenylpyrimidine [40734-24-5] | | 73% |
| h2 | dibenzofuran-1-boronic acid | 2-([1,1'-biphenyl]-3-yl)-4-chloro-6-phenyl-1,3,5-triazine | | 82% |
| h3 | 8-phenyldibenzofuran-1-boronic acid | 4-chloro-2,6-diphenylpyrimidine [3842-55-5] | | 73% |

| | Starting material 1 | Starting material 2 | Product | Yield |
|---|---|---|---|---|
| h4 | | 40734-4-5 | | 72% |
| h5 | | | | 65% |
| h6 | | | | 63% |

-continued

| | Starting material 1 | Starting material 2 | Product | Yield |
|---|---|---|---|---|
| h7 | | | | 72% |
| h8 | | | | 75% |

| | Starting material 1 | Starting material 2 | Product | Yield |
|---|---|---|---|---|
| h9 | 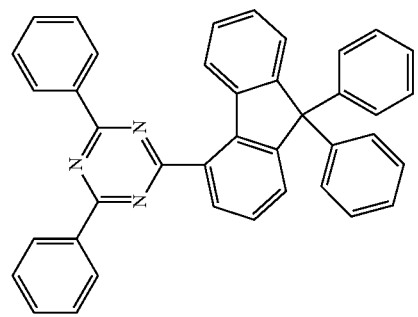 | 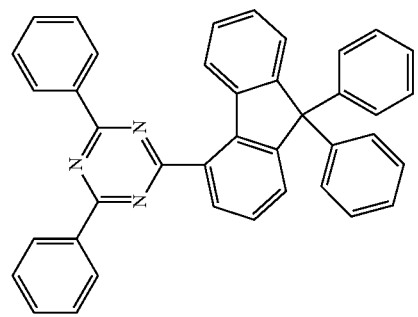 | 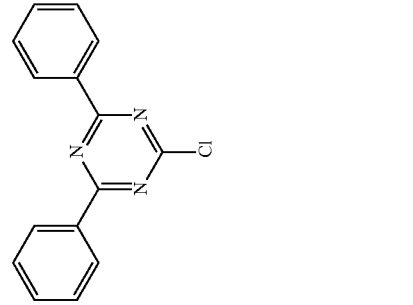 | 79% |
| h10 | | | | 81% |

-continued

| | Starting material 1 | Starting material 2 | Product | Yield |
|---|---|---|---|---|
| h11 | (9-methyl-9-phenylfluoren-1-yl)boronic acid | 4-chloro-2,6-diphenylpyrimidine | 4-(9-methyl-9-phenylfluoren-1-yl)-2,6-diphenylpyrimidine | 85% |
| h12 | (9,9-spiro-cyclohexyl-fluoren-1-yl)boronic acid | 4-chloro-2,6-diphenylpyrimidine | 4-(9,9-spiro-cyclohexyl-fluoren-1-yl)-2,6-diphenylpyrimidine | 80% |

| | Starting material 1 | Starting material 2 | Product | Yield |
|---|---|---|---|---|
| h13 | 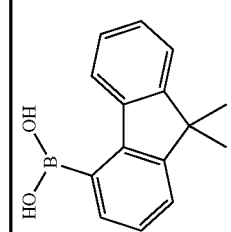 | 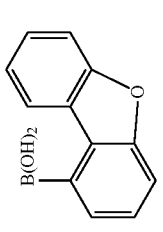 | 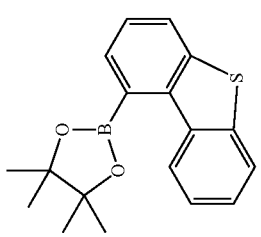 | 79% |
| h14 | 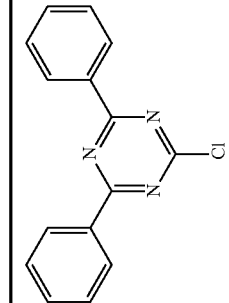 | 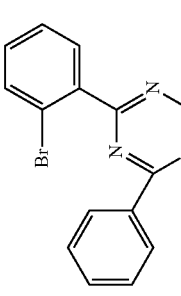<br>77989-15-2 | 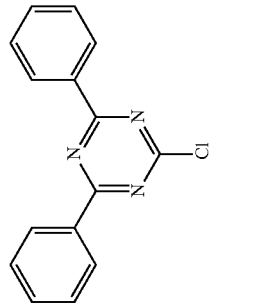 | 77% |
| h15 | 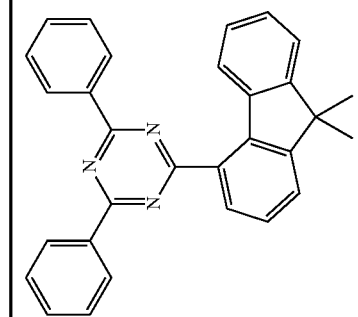<br>[1434286-69-7] | 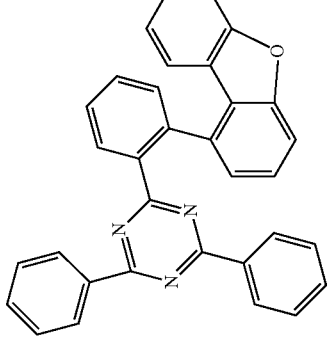 | 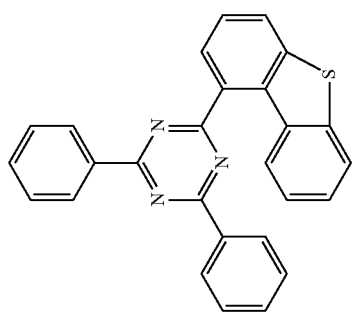 | 76% |

-continued
| Starting material 1 | Starting material 2 | Product | Yield |
|---|---|---|---|
| h16 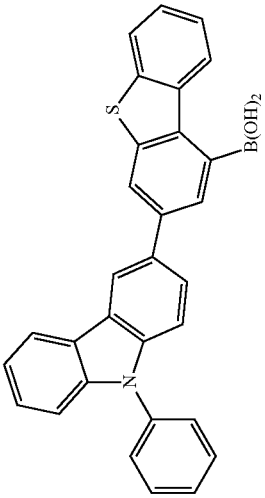 | 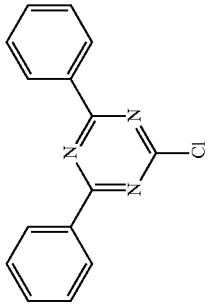 | 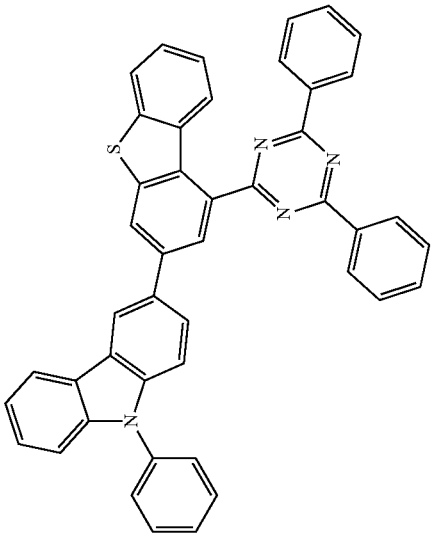 | 71% |
| h17 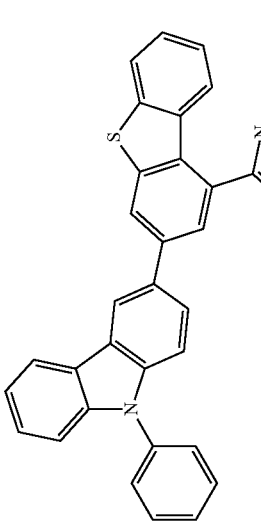 | 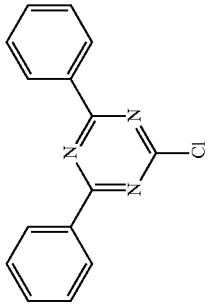 | 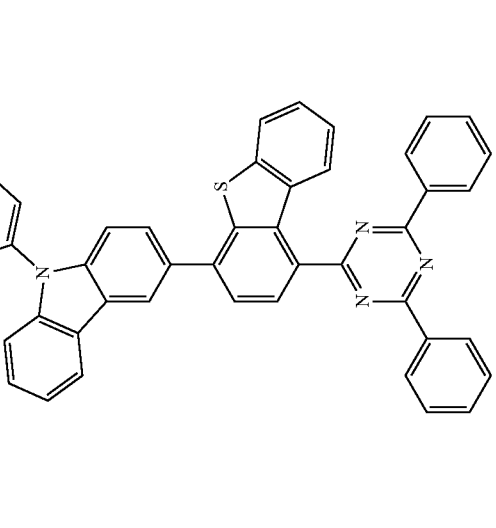 | 75% |

-continued

| Starting material 1 | Starting material 2 | Product | Yield |
|---|---|---|---|
| h18 | | | 76% |

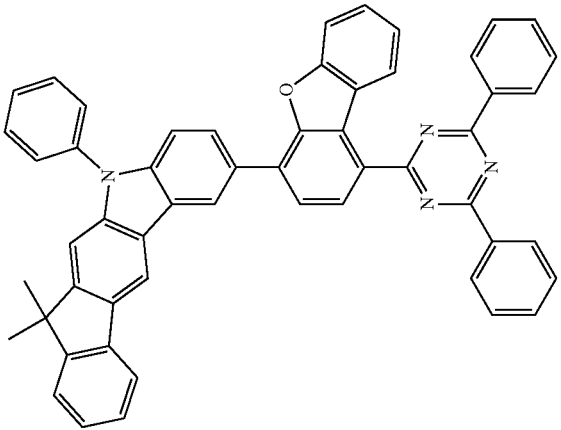

-continued
| | Starting material 1 | Starting material 2 | Product | Yield |
|---|---|---|---|---|
| h20 | 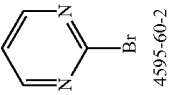 | 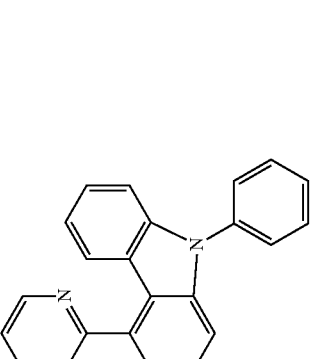 | 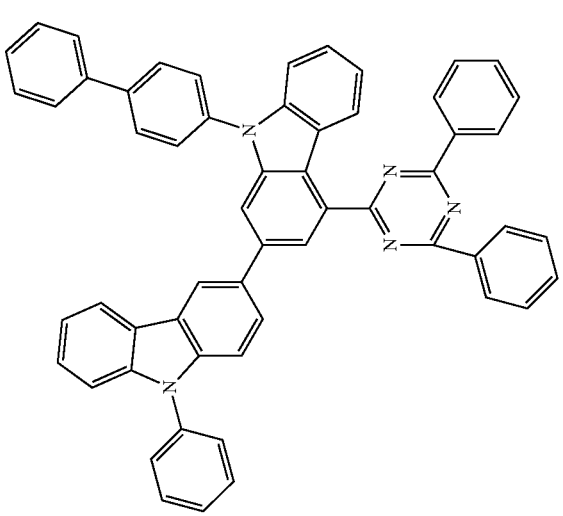 | 79% |
| h21 | 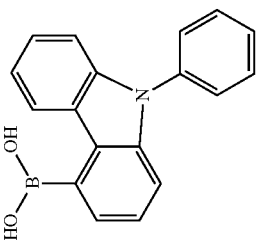 | 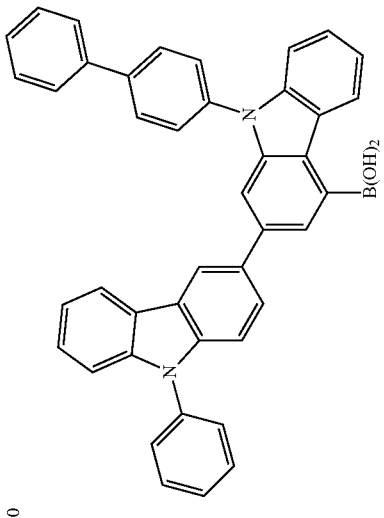
4595-60-2 | 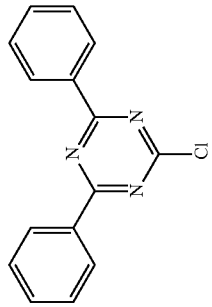 | 82% |

233 i) 2-(8-Bromodibenzofuran-1-yl)-4,6-diphenyl-1,3,5-triazine

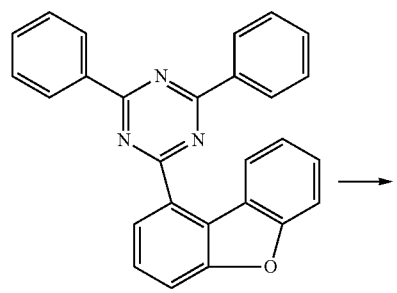

→

234

-continued

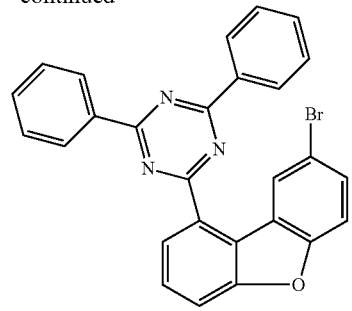

70 g (190.0 mmol) of 2-dibenzofuran-1-yl-4,6-diphenyl-1,3,5-triazine are suspended in 2000 ml of acetic acid (100%) and 2000 ml of sulfuric acid (95-98%). 34 g (190 mmol) of NBS are added to this suspension in portions, and the mixture is stirred in the dark for 2 h. Water/ice are then added, and the solid is separated off and rinsed with ethanol. The residue is recrystallised from toluene. The yield is 80 g (167 mmol), corresponding to 87% of theory.

The following compounds are prepared analogously:

| | Starting material 1 | Product | Yield |
|---|---|---|---|
| i1 | | | 80% |
| i2 | 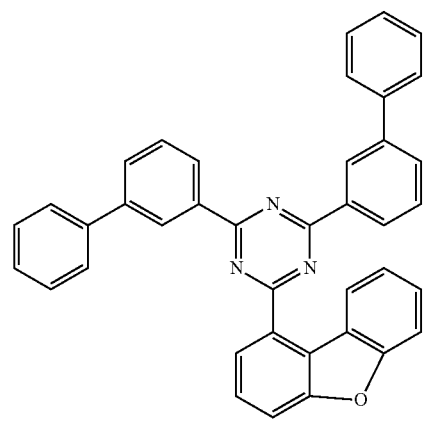 [SMILES: c1ccc(-c2cccc(-c3nc(-c4cccc(-c5ccccc5)c4)nc(-c4cccc5oc6ccccc6c45)n3)c2)cc1] | 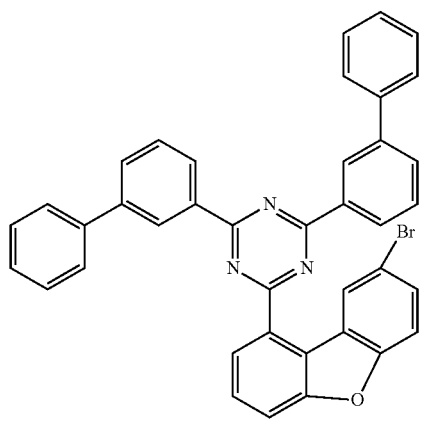 [SMILES: Brc1ccc2oc3cccc(-c4nc(-c5cccc(-c6ccccc6)c5)nc(-c5cccc(-c6ccccc6)c5)n4)c3c2c1] | 41% |

-continued

| | Starting material 1 | Product | Yield |
|---|---|---|---|
| i3 | | | 52% |
| i4 | | | 64% |
| i5 | | | 33% |
| i6 | | | 73% |

|  | Starting material 1 | Product | Yield |
|---|---|---|---|
| i7 | 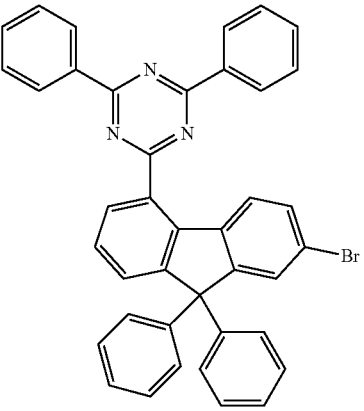 [SMILES: Brc1ccc2c(c1)C(c1ccccc1)(c1ccccc1)c1cccc(-c3nc(-c4ccccc4)nc(-c4ccccc4)n3)c1-2] | | 78% |
| i8 | | | 80% |
| i9 | 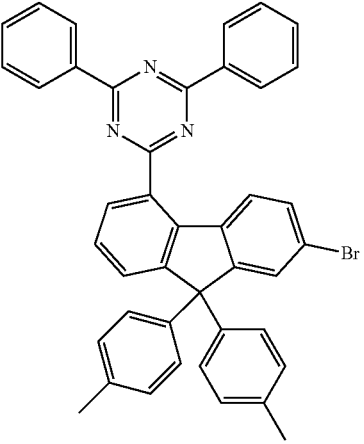 [SMILES: Cc1ccc(C2(c3ccc(C)cc3)c3cc(Br)ccc3-c3c(-c4nc(-c5ccccc5)nc(-c5ccccc5)n4)cccc32)cc1] | 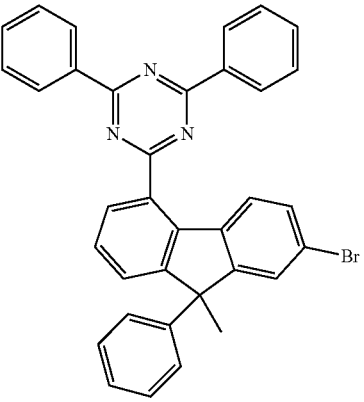 [SMILES: CC1(c2ccccc2)c2cc(Br)ccc2-c2c(-c3nc(-c4ccccc4)nc(-c4ccccc4)n3)cccc21] | 70% |

-continued
| | Starting material 1 | Product | Yield |
|---|---|---|---|
| i10 | 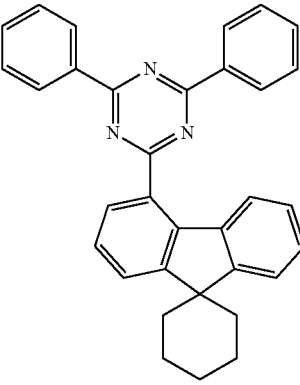 | 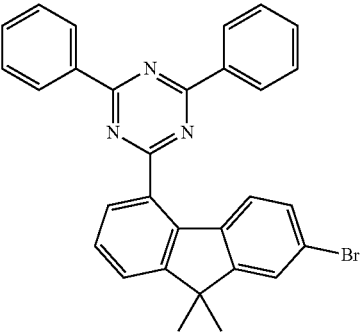 [SMILES: CC1(C)c2cc(Br)ccc2-c2c(-c3nc(-c4ccccc4)nc(-c4ccccc4)n3)cccc21] | 86% |
| i11 | | | 88% |
| i12 | | | 41% |
| i13 | 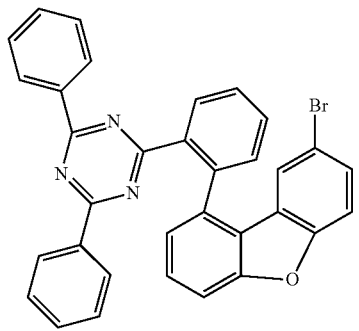 [SMILES: Brc1ccc2oc3cccc(-c4ccccc4-c4nc(-c5ccccc5)nc(-c5ccccc5)n4)c3c2c1] | 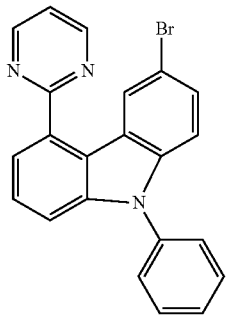 [SMILES: Brc1ccc2c(c1)c1c(-c3ncccn3)cccc1n2-c1ccccc1] | 73% |

In the case of the dibenzothiophene derivatives, nitrobenzene is employed instead of sulfuric acid and elemental bromine is employed instead of NBS:

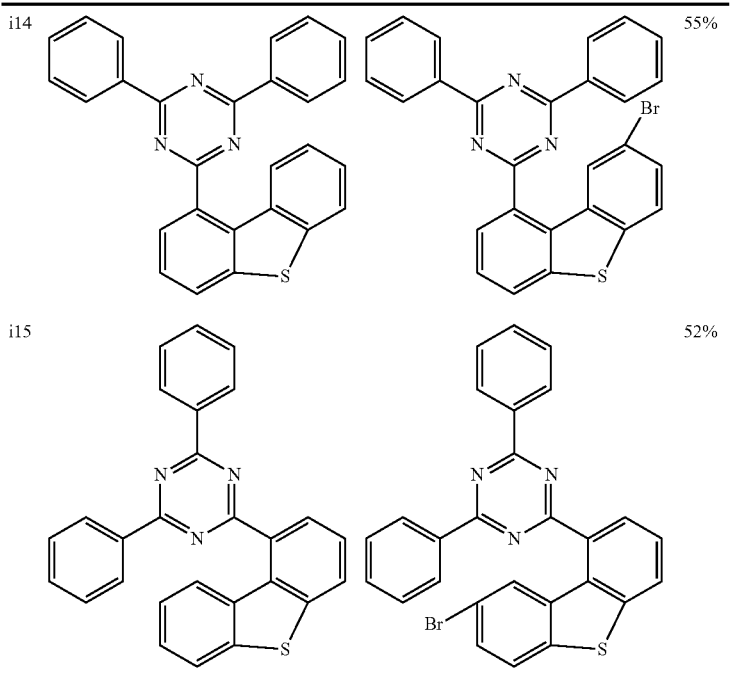

j) 3-[9-(4,6-Diphenyl-1,3,5-triazin-2-yl)dibenzofuran-2-yl]-9-phenyl-9H-carbazole

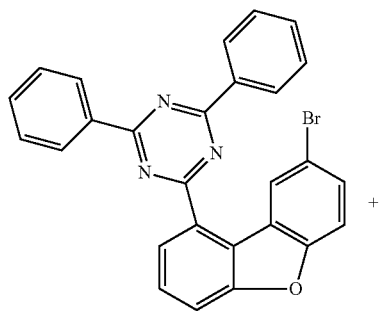

+

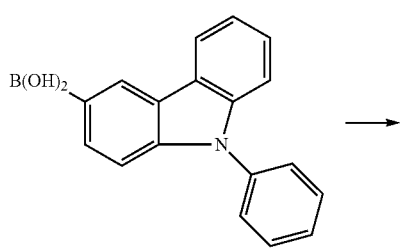

[854952-58-2]

→

-continued

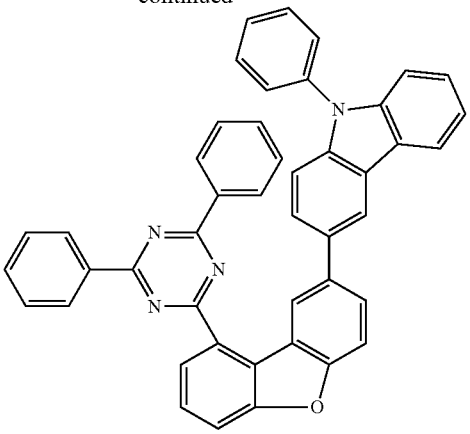

75 g (156 mmol) of 2-(8-bromodibenzofuran-1-yl)-4,6-diphenyl-1,3,5-triazine, 50 g (172 mmol) of N-phenylcarbazole-3-boronic acid and 36 g (340 mmol) of sodium carbonate are suspended in 1000 ml of ethylene glycol diamine ether and 280 ml of water. 1.8 g (1.5 mmol) of tetrakis(triphenylphosphine)palladium(0) are added to this suspension, and the reaction mixture is heated under reflux for 16 h. After cooling, the organic phase is separated off, filtered through silica gel, washed three times with 200 ml of water and subsequently evaporated to dryness. The product is purified by column chromatography on silica gel with toluene/heptane (1:2) and finally sublimed in a high vacuum ($p=5\times10^{-7}$ mbar) (purity 99.9%). The yield is 50 g (78 mmol), corresponding to 50% of theory.

The following compounds are prepared analogously:

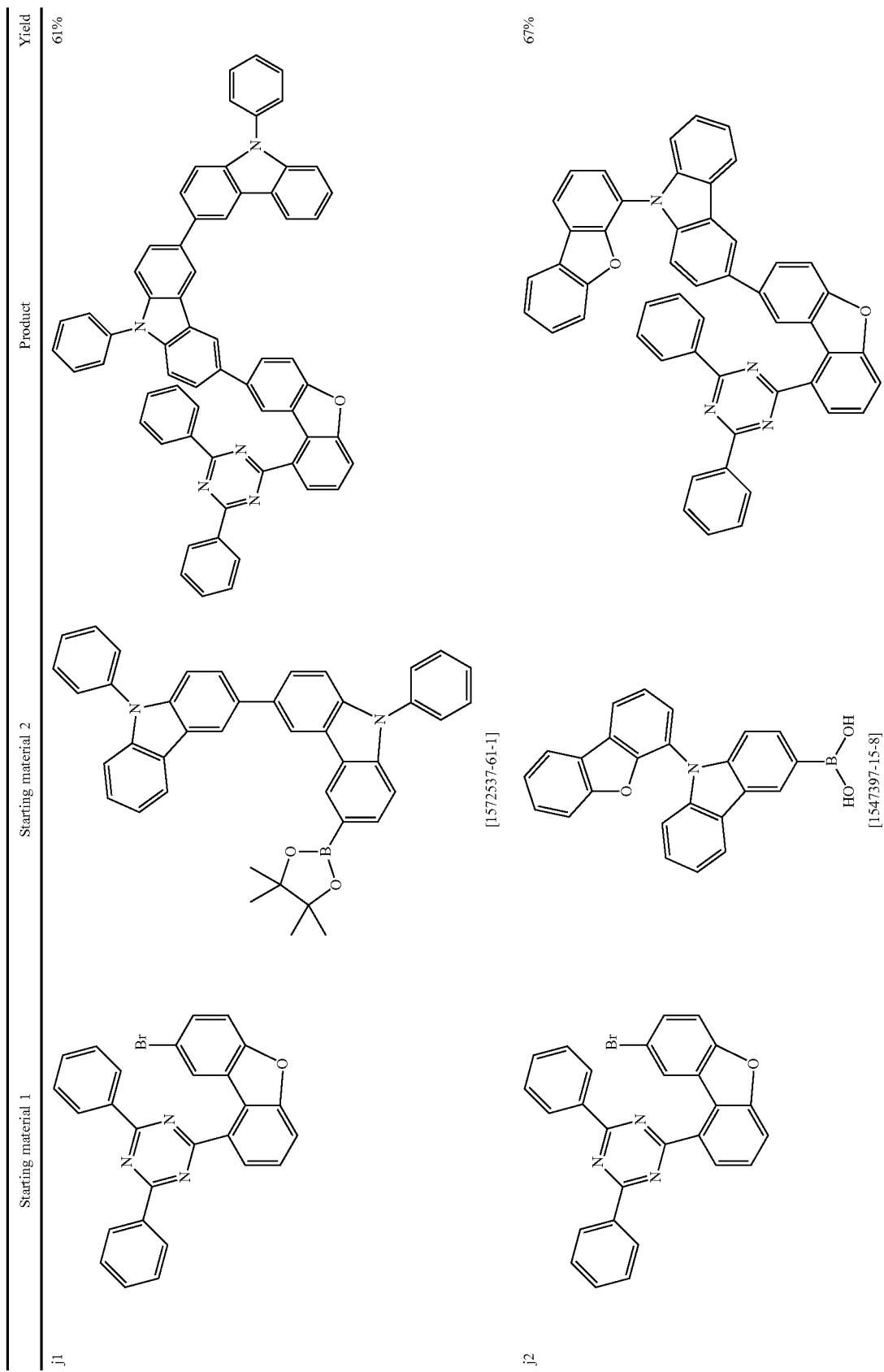

-continued

| Starting material 1 | Starting material 2 | Product | Yield |
|---|---|---|---|
| j3 | [1547492-13-6] | | 65% |
| j4 | [1391729-63-7] | | 53% |

| | Starting material 1 | Starting material 2 | Product | Yield |
|---|---|---|---|---|
| j5 | | [1379585-25-7] | | 58% |
| j6 | | [1373359-67-1] | | 54% |

| | Starting material 1 | Starting material 2 | Product | Yield |
|---|---|---|---|---|
| j7 | (structure with Br-dibenzofuran-triazine-phenyl) | (diindolocarbazole diphenyl boronic acid) [1314019-74-3] | (coupled product) | 65% |
| j8 | (structure with Br-dibenzofuran-triazine-phenyl) | (N-phenylcarbazole-phenyl-B(OH)₂) 854952-60-6 | (coupled product) | 71% |

| | Starting material 1 | Starting material 2 | Product | Yield |
|---|---|---|---|---|
| j9 |  | 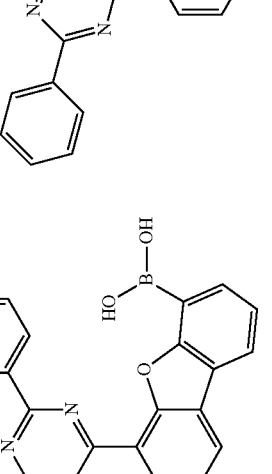 [1449739-29-0] | 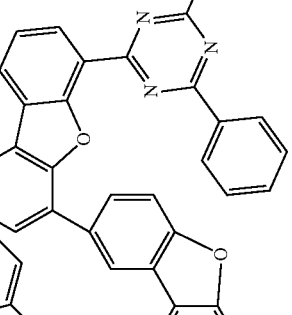 | 56% |
| j10 |  | 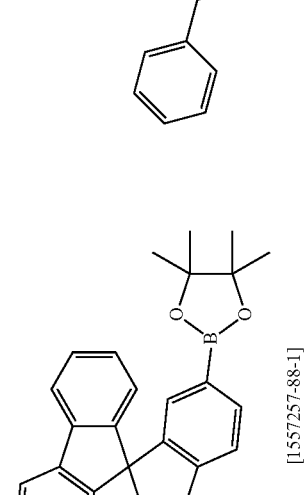 [1557257-88-1] | 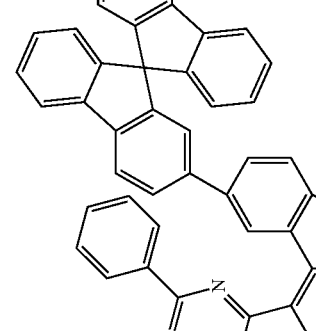 | 79% |
| j11 | 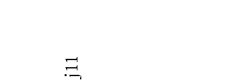 | 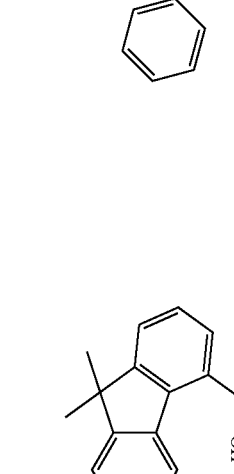 [1246022-50-3] | 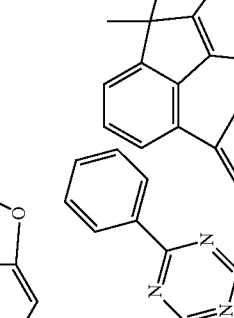 | 70% |

-continued

| | Starting material 1 | Starting material 2 | Product | Yield |
|---|---|---|---|---|
| j12 | | [402936-15-6] | | 82% |
| j13 | | [162607-19-4] | | 69% |

-continued

| | Starting material 1 | Starting material 2 | Product | Yield |
|---|---|---|---|---|
| j14 | | | | 65% |
| j15 | | | | 77% |

-continued

| Starting material 1 | Starting material 2 | Product | Yield |
|---|---|---|---|
| j16 | 854952-58-2 | | 82% |
| j17 | 854952-58-2 | | 54% |

| | Starting material 1 | Starting material 2 | Product | Yield |
|---|---|---|---|---|
| j18 | 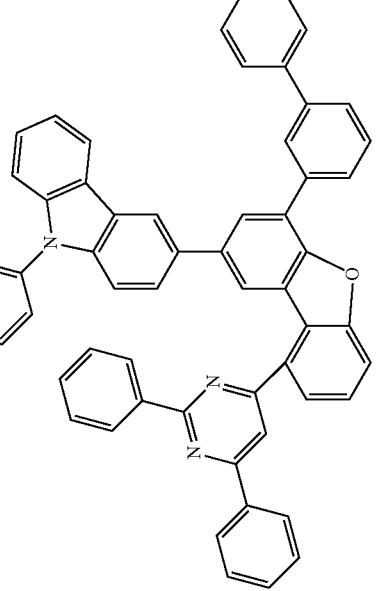 | 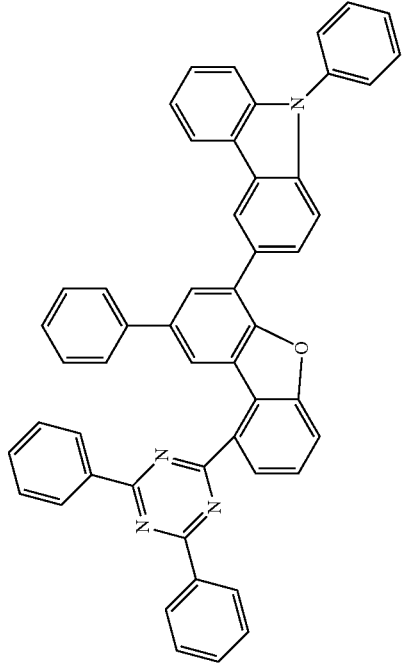 854952-58-2 | 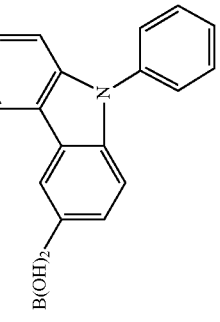 | 67% |
| j19 | 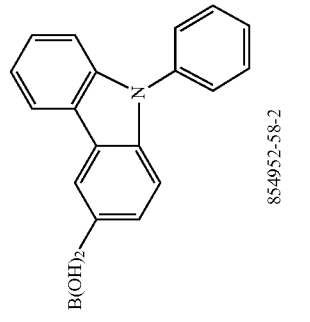 | 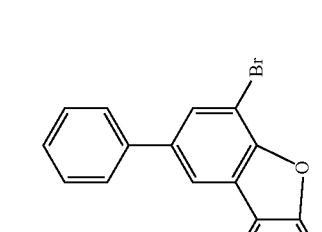 854952-58-2 | | 65% |

-continued

| Starting material 1 | Starting material 2 | Product | Yield |
|---|---|---|---|
| j20 | 854952-58-2 | | 63% |
| j21 | 854952-58-2 | | 79% |

| | Starting material 1 | Starting material 2 | Product | Yield |
|---|---|---|---|---|
| j22 | (triazine-fluorene-Ph2 with Br) | 854952-58-2 (N-phenylcarbazole boronic acid) | (coupled product) | 65% |
| j23 | (triazine-fluorene-(p-tolyl)2 with Br) | 854952-58-2 (N-phenylcarbazole boronic acid) | (coupled product) | 55% |

| | Starting material 1 | Starting material 2 | Product | Yield |
|---|---|---|---|---|
| j24 | | 854952-58-2 | | 67% |
| j25 | | [162607-19-4] | | 73% |

-continued

| | Starting material 1 | Starting material 2 | Product | Yield |
|---|---|---|---|---|
| j26 | | 854952-58-2 | | 66% |
| j27 | | 854952-58-2 | | 59% |

-continued
| | Starting material 1 | Starting material 2 | Product | Yield |
|---|---|---|---|---|
| j28 | 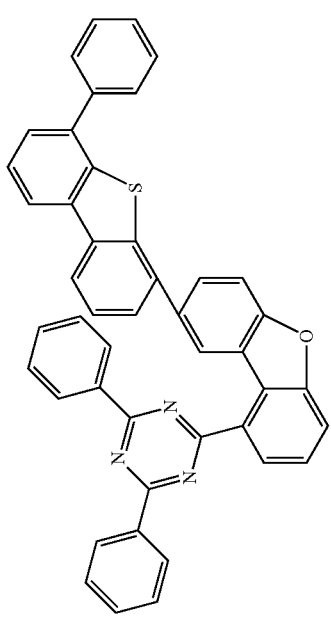 | 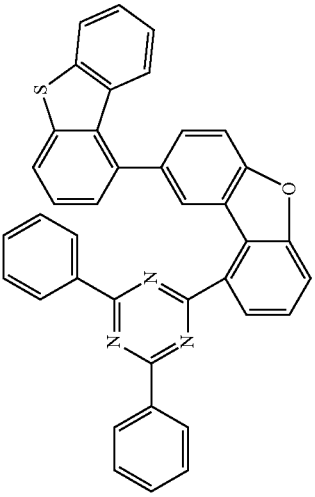  [1556069-50-1] | 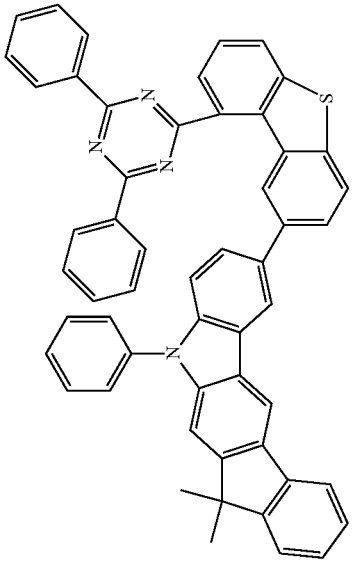 | 64% |
| j29 | 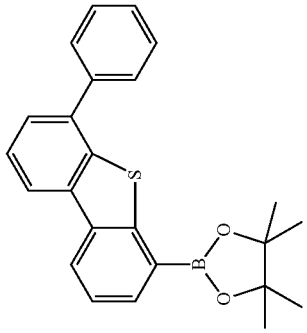 | 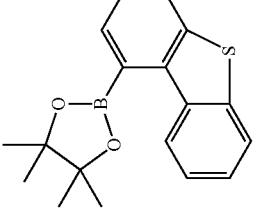  [1434286-69-7] | 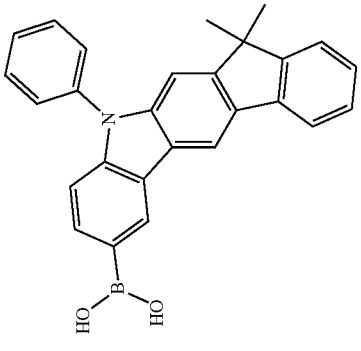 | 71% |
| j30 | 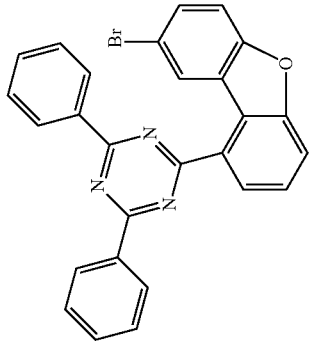 | 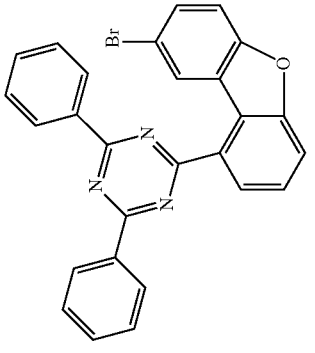  [1379585-25-7] | 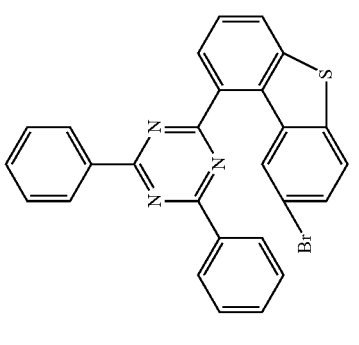 | 62% |

The following compounds are prepared analogously using 0.5 equivalent of the corresponding bromide:
| j31 cmpn. | 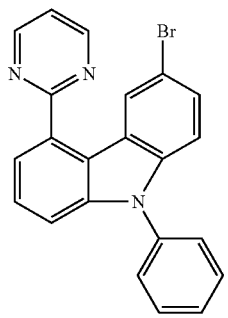 [SMILES: Brc1ccc2c(c1)c1c(-c3ncccn3)cccc1n2-c1ccccc1] | 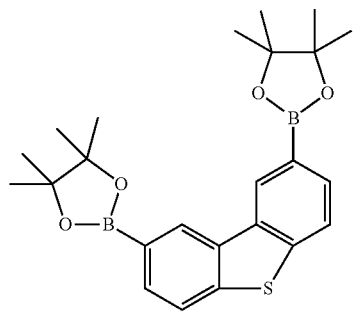 [552855-12-6] |
|---|---|---|
| j32 cmpn. | 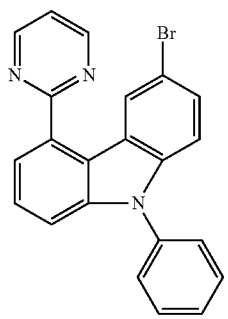 [SMILES: Brc1ccc2c(c1)c1c(-c3ncccn3)cccc1n2-c1ccccc1] | 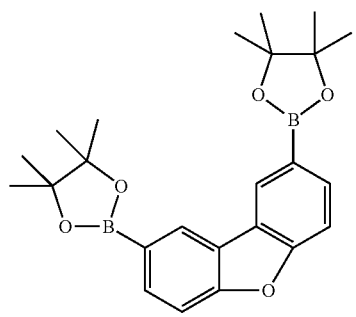 [1197989-83-5] |
| j33 | 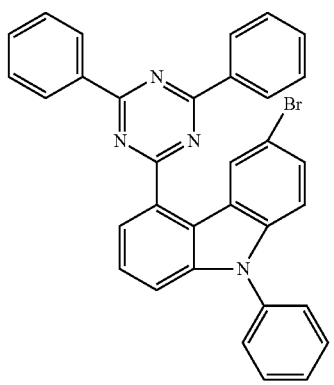 [SMILES: Brc1ccc2c(c1)c1c(-c3nc(-c4ccccc4)nc(-c4ccccc4)n3)cccc1n2-c1ccccc1] | 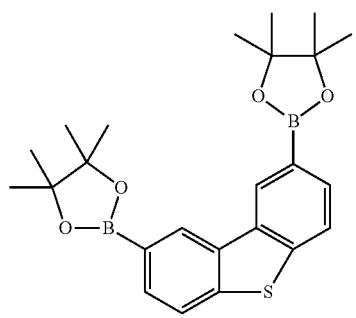 [552855-12-6] |
| j34 | 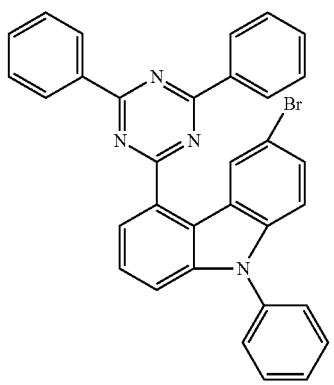 [SMILES: Brc1ccc2c(c1)c1c(-c3nc(-c4ccccc4)nc(-c4ccccc4)n3)cccc1n2-c1ccccc1] | 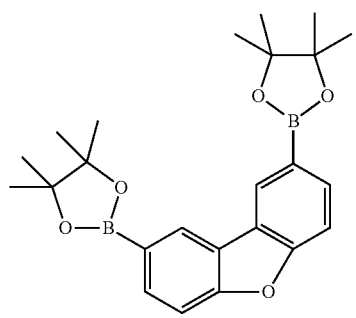 [1197989-83-5] | j31 cmpn. 72%
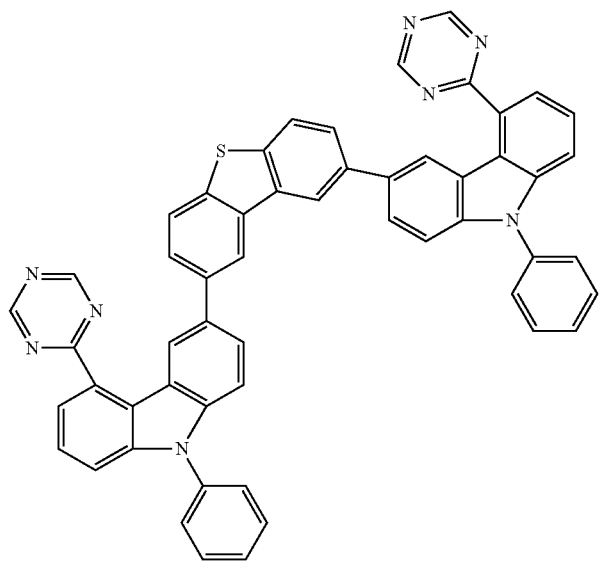 [SMILES: c1ccc(-n2c3ccc(-c4ccc5sc6ccc(-c7ccc8c(c7)c7c(-c9ncncn9)cccc7n8-c7ccccc7)cc6c5c4)cc3c3c(-c4ncncn4)cccc32)cc1]
j32 cmpn. 73%
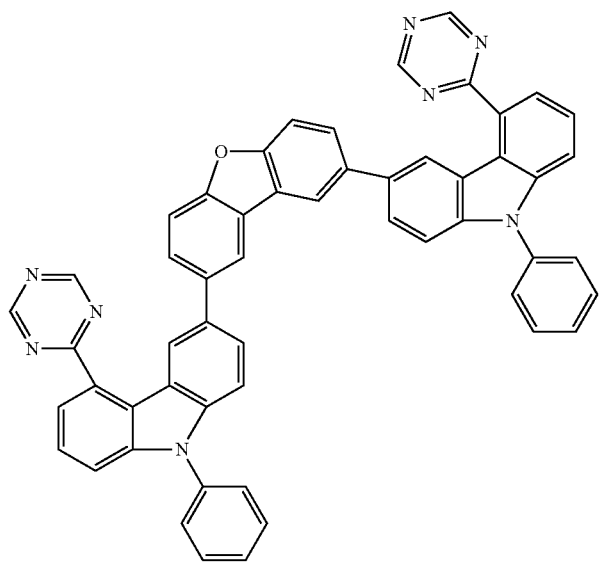 [SMILES: c1ccc(-n2c3ccc(-c4ccc5oc6ccc(-c7ccc8c(c7)c7c(-c9ncncn9)cccc7n8-c7ccccc7)cc6c5c4)cc3c3c(-c4ncncn4)cccc32)cc1]

| | -continued | |
|---|---|---|
| j33 | 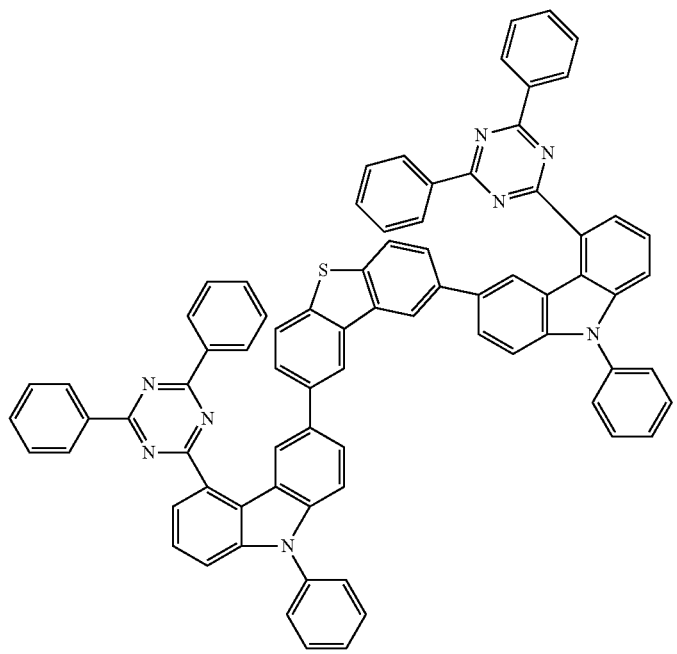 | 74% |
| j34 | 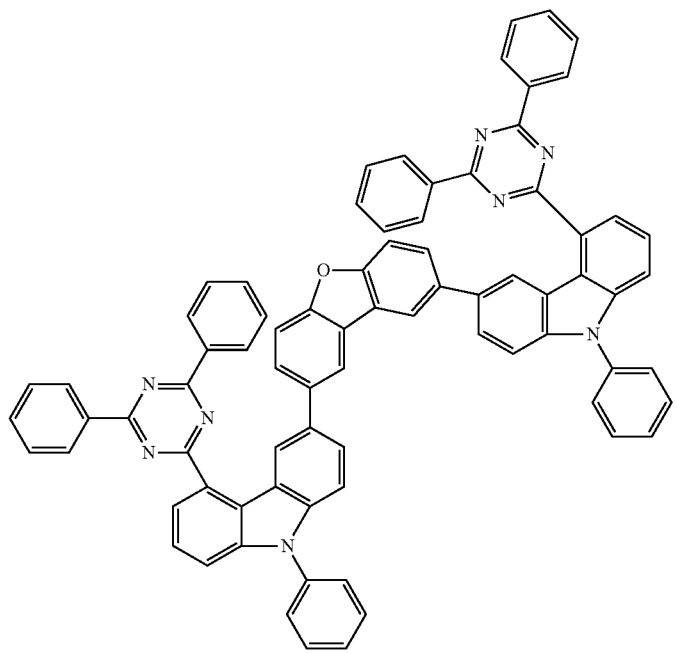 [SMILES: c1ccc(-c2nc(-c3ccccc3)nc(-c3cccc4c3c3cc(-c5ccc6oc7ccc(-c8ccc9c(c8)c8c(-c%10nc(-c%11ccccc%11)nc(-c%11ccccc%11)n%10)cccc8n9-c8ccccc8)cc7c6c5)ccc3n4-c3ccccc3)n2)cc1] | 77% | k) 3-(1-Bromodibenzothiophen-3-yl)-9-phenyl-9H-carbazole

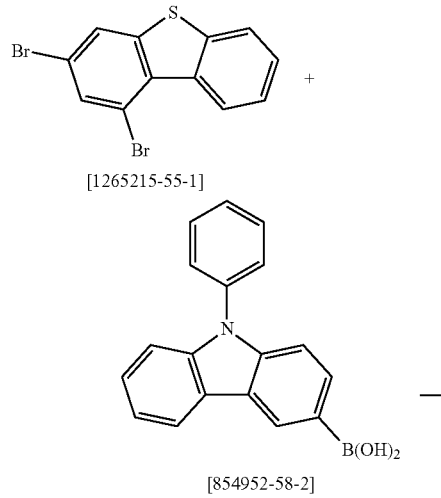

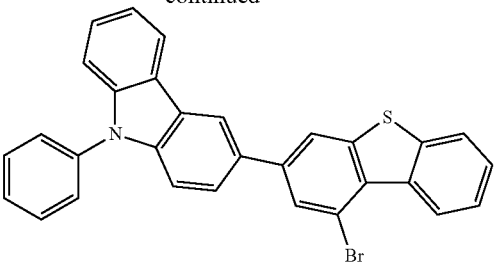

22 g (66 mmol) of 1,3-dibromodibenzothiophene, 17 g (664 mmol) of N-phenylcarbazole-3-boronic acid and 13.7 g (100 mmol) of sodium tetraborate are dissolved in 100 ml of THF and 60 ml of water and degassed. 0.9 g (1.3 mmol) of bis(triphenylphosphine)palladium(II) chloride and 1 g (20 mmol) of hydrazinium hydroxide are added. The reaction mixture is subsequently stirred at 70° C. under a protective-gas atmosphere for 48 h. The cooled solution is extended with toluene, washed a number of times with water, dried and evaporated. The product is purified by column chromatography on silica gel with toluene/heptane (1:2). Yield: 13.2 g (26 mmol), 40% of theory.

The following compounds are prepared analogously:

| | Starting material 1 | Starting material 2 | Product | Yield |
|---|---|---|---|---|
| k1 | [1225467-30-0] | [854952-58-2] | | 27% |
| k2 | [617707-25-2] | [854952-58-2] | | 29% |

-continued

| | Starting material 1 | Starting material 2 | Product | Yield |
|---|---|---|---|---|
| k3 | [617707-25-2] | [1379585-25-7] | | 34% |
| k4 | [1225467-28-6] | [854952-58-2] | | 24% |
| k5 | [1453088-13-5] | [854952-58-2] | | 31% | l) 1-Bromo-8-iododibenzofuran

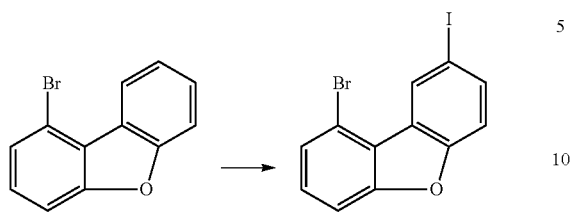

20 g (80 mmol) of dibenzofuran-1-boronic acid, 2.06 g (40.1 mmol) of iodine, 3.13 g (17.8 mmol) of iodic acid, 80 ml of acetic acid, 5 ml of sulfuric acid, 5 ml of water and 2 ml of chloroform are stirred at 65° C. for 3 h. After cooling, water is added to the mixture, and the solid which has precipitated out is filtered off with suction and washed three times with water. The residue is recrystallised from toluene and from dichloromethane/25 heptane. The yield is 25.6 g (68 mmol), corresponding to 85% of theory.

The following compounds are prepared analogously:

| | Starting material 1 | Product | Yield |
|---|---|---|---|
| I1 | [65642-94-6] | | 81% |
| I2 | | | 84% |
| I3 | | | 78% | m) 3-(9-Bromodibenzofuran-2-yl)-9-phenyl-9H-carbazole

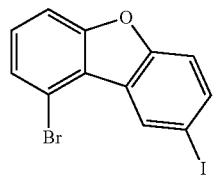

+

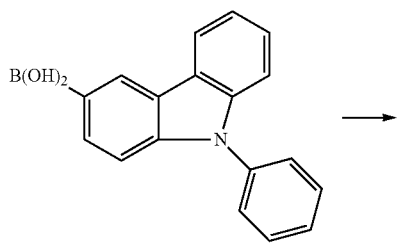

→

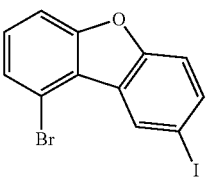 [SMILES: Brc1cccc2oc3ccc(I)cc3c12]

58 g (156 mmol) of 1-bromo-8-iododibenzofuran, 50 g (172 mmol) of N-phenylcarbazole-3-boronic acid and 36 g (340 mmol) of sodium carbonate are suspended in 1000 ml of ethylene glycol diamine ether and 280 ml of water. 1.8 g (1.5 mmol) of tetrakis(triphenylphosphine)palladium(0) are added to this suspension, and the reaction mixture is heated under reflux for 16 h. After cooling, the organic phase is separated off, filtered through silica gel, washed three times with 200 ml of water and subsequently evaporated to dryness. The yield is 48 g (89 mmol), corresponding to 64% of theory.

The following compounds are prepared analogously:

| Starting material 1 | Starting material 2 |
|---|---|
| m1 | |

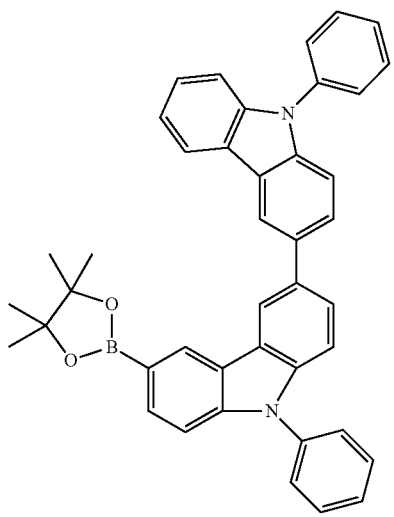

[1572537-61-1]

| | | |
|---|---|---|
| m2 | 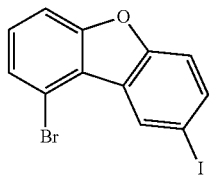 [SMILES: Brc1cccc2oc3ccc(I)cc3c12] | 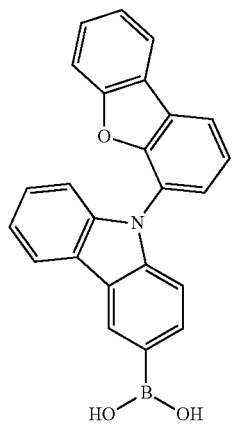
[1547397-15-8] |
| m3 | 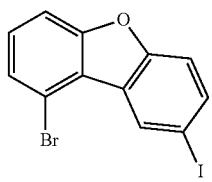 [SMILES: Brc1cccc2oc3ccc(I)cc3c12] | 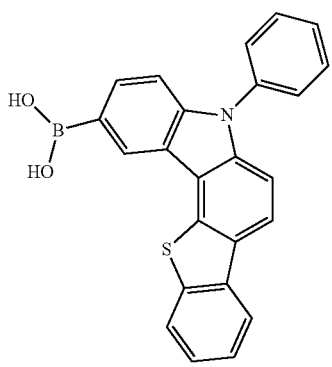
[1391729-63-7] |
| m4 | 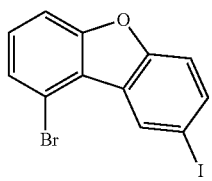 [SMILES: Brc1cccc2oc3ccc(I)cc3c12] | 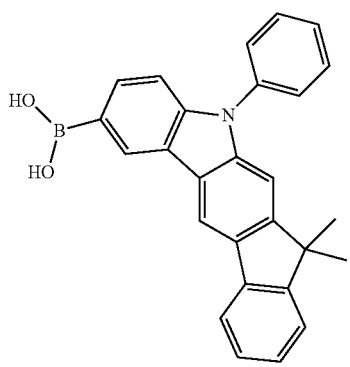
[1379585-25-7] |

| | | |
|---|---|---|
| m5 | 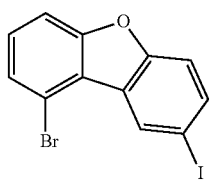 [SMILES: Brc1cccc2oc3ccc(I)cc3c12] | 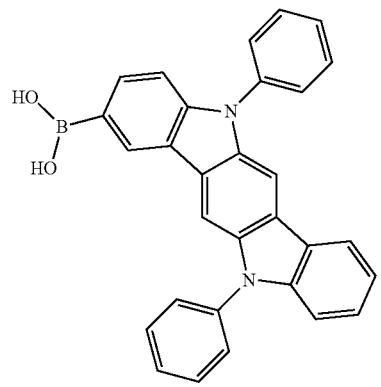<br>[1314019-74-3] |
| m6 | 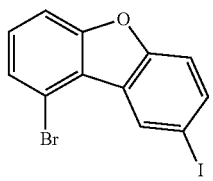 [SMILES: Brc1cccc2oc3ccc(I)cc3c12] | 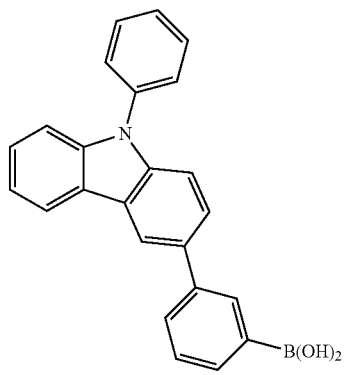<br>[854952-60-6] |
| m7 | 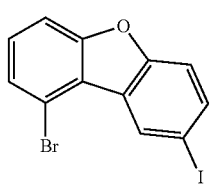 [SMILES: Brc1cccc2oc3ccc(I)cc3c12] | 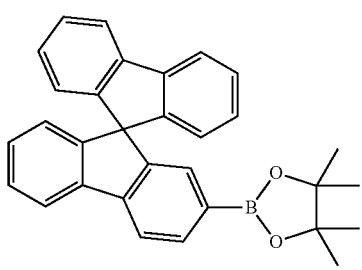<br>[1557257-88-1] |
| m8 | 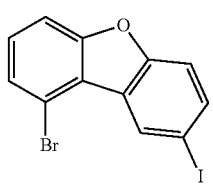 [SMILES: Brc1cccc2oc3ccc(I)cc3c12] | 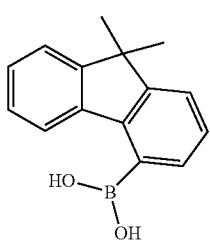<br>[1246022-50-3] |

| | | |
|---|---|---|
| m9 | 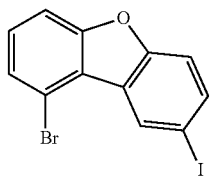 [SMILES: Brc1cccc2oc3ccc(I)cc3c12] | 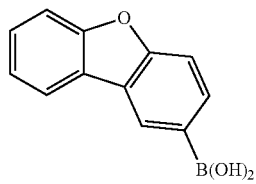<br>[402936-15-6] |
| m10 | 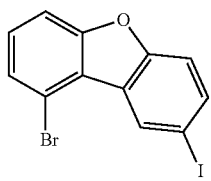 [SMILES: Brc1cccc2oc3ccc(I)cc3c12] | 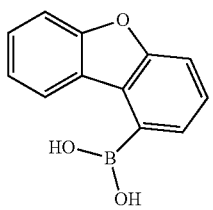<br>[162607-19-4] |
| m11 | 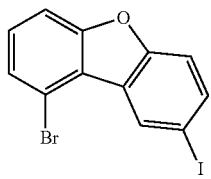 [SMILES: Brc1cccc2oc3ccc(I)cc3c12] | 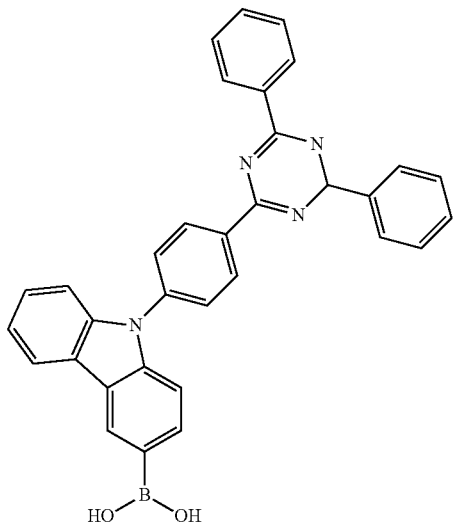 [SMILES: OB(O)c1ccc2c(c1)c1ccccc1n2-c1ccc(C2=NC(c3ccccc3)NC(c3ccccc3)=N2)cc1] |
| m12 | 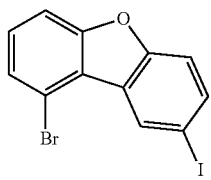 [SMILES: Brc1cccc2oc3ccc(I)cc3c12] | 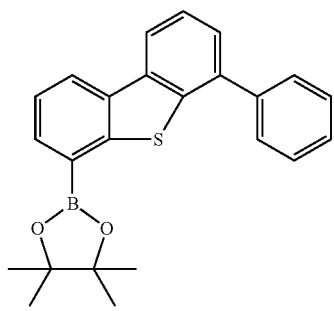<br>[1556069-50-1] |

| | | |
|---|---|---|
| m13 | 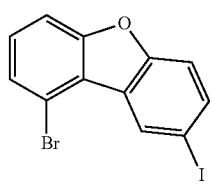 [SMILES: Brc1cccc2oc3ccc(I)cc3c12] | 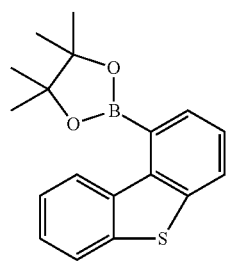<br>[1434286-69-7] |
| m14 | 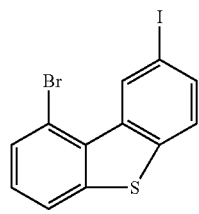 [SMILES: Brc1cccc2sc3ccc(I)cc3c12] | 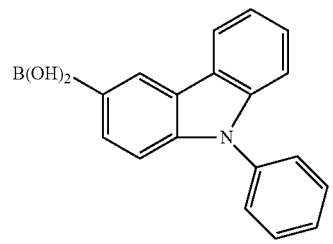<br>854952-58-2 |
| m15 | 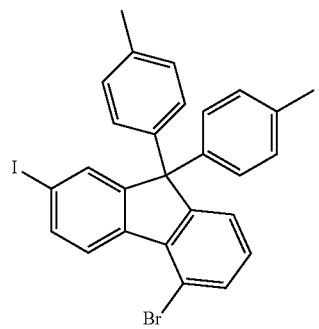 [SMILES: Cc1ccc(C2(c3ccc(C)cc3)c3cc(I)ccc3-c3c(Br)cccc32)cc1] | 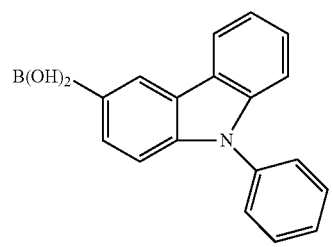<br>854952-58-2 |
| m16 | 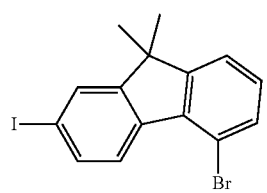 [SMILES: CC1(C)c2cc(I)ccc2-c2c(Br)cccc21] | 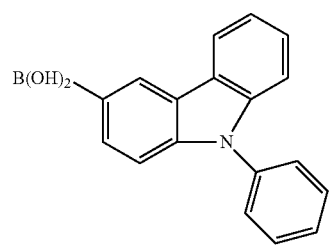<br>854952-58-2 |

-continued

| Product | | Yield |
|---|---|---|
| m1 | (structure) | 60% |
| m2 | (structure) | 62% |
| m3 | (structure) | 54% |
| m4 | (structure) | 50% |

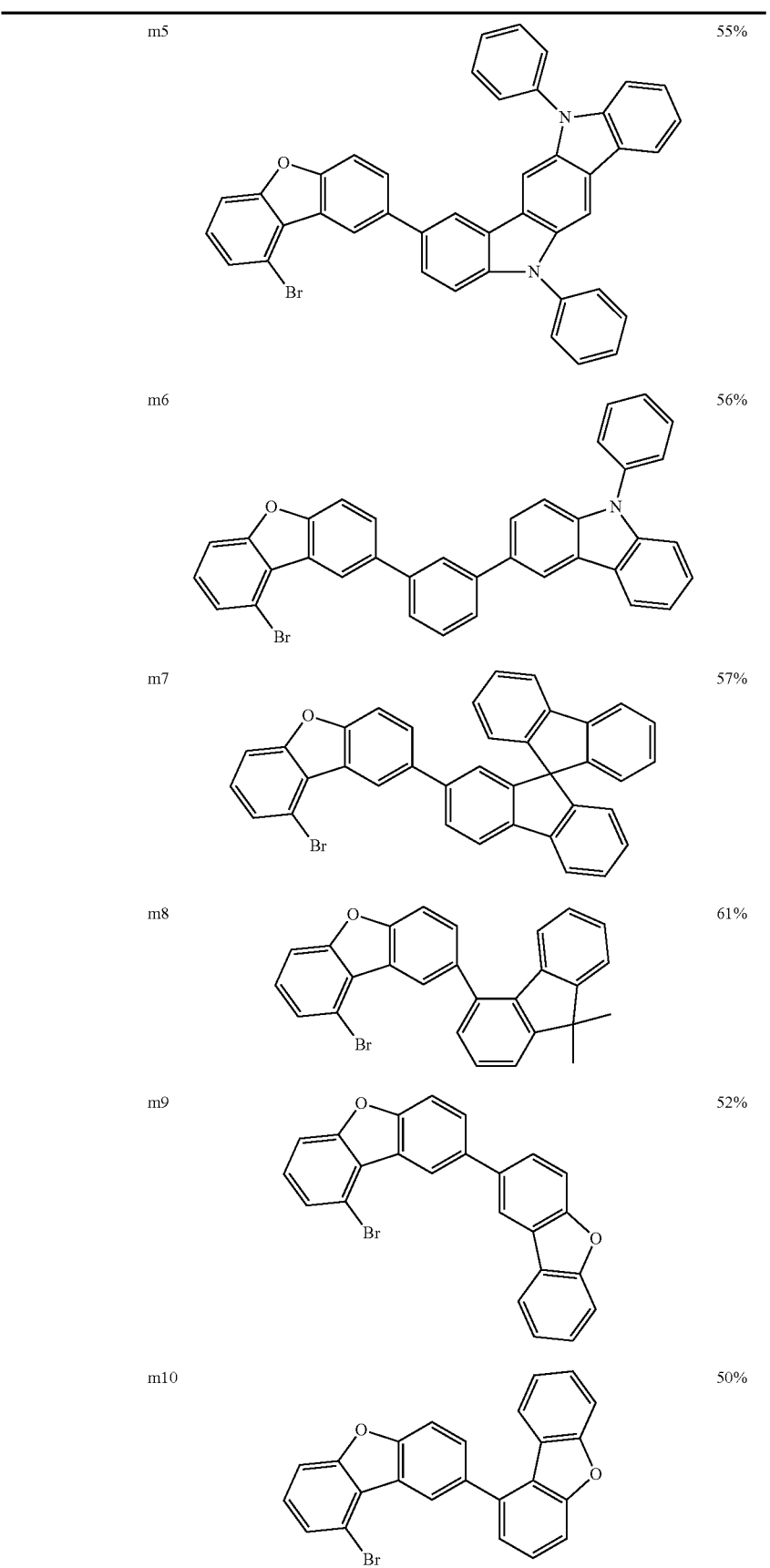

-continued
m11 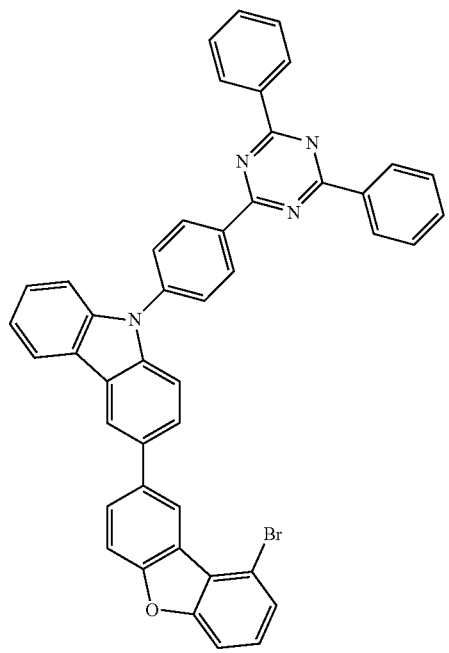 48%
m12 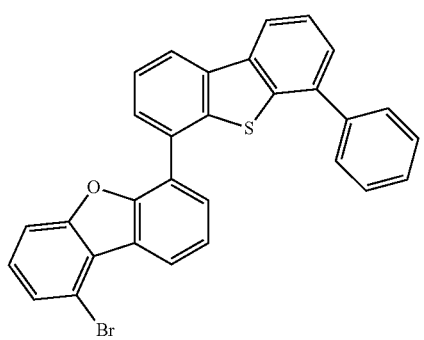 [SMILES: Brc1cccc2oc3c(-c4cccc5c4sc4c(-c6ccccc6)cccc45)cccc3c12] 52%
m13 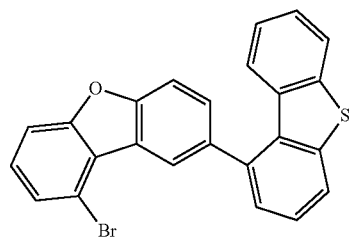 [SMILES: Brc1cccc2oc3ccc(-c4cccc5sc6ccccc6c45)cc3c12] 54%
m14 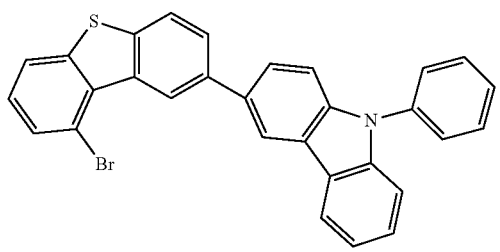 [SMILES: Brc1cccc2sc3ccc(-c4ccc5c(c4)c4ccccc4n5-c4ccccc4)cc3c12] 57%

| | |
|---|---|
| m15 | 48% |

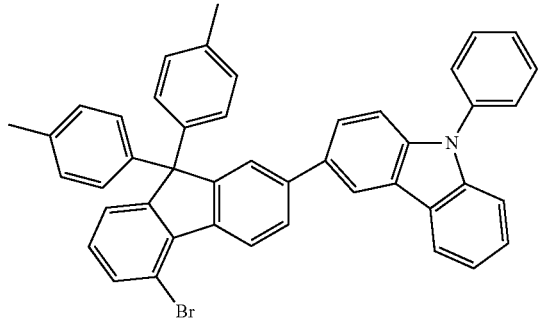 [SMILES: Cc1ccc(C2(c3ccc(C)cc3)c3cc(-c4ccc5c(c4)c4ccccc4n5-c4ccccc4)ccc3-c3c(Br)cccc32)cc1]

| | |
|---|---|
| m16 | 46% |

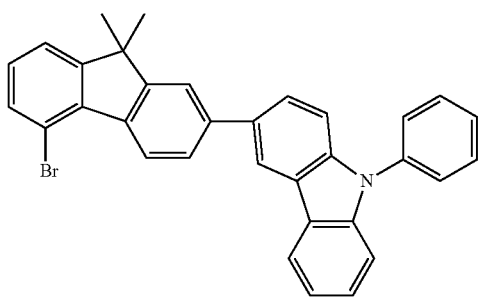

o) 8-(9-Phenyl-9H-carbazol-3-yl)dibenzofuran-1-boronic acid

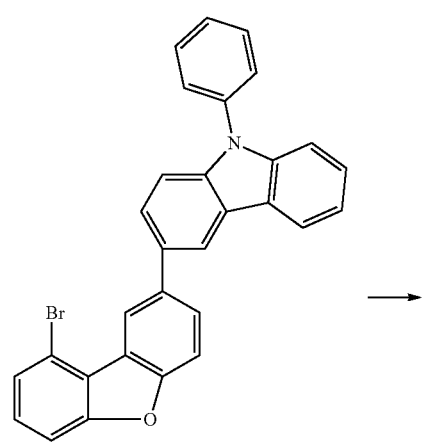

→

-continued

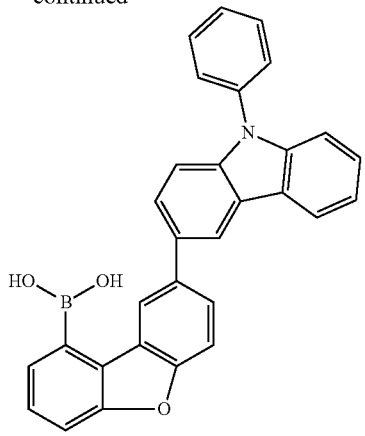

20 g (182 mmol) of 3-(9-bromodibenzofuran-2-yl)-9-phenyl-9H-carbazole are dissolved in 400 ml of dry THF and cooled to −78° C. At this temperature, 77 ml (190 mmol/2.5 M in hexane) of n-butyllithium are added over the course of about 5 min., and the mixture is subsequently stirred at −78° C. for a further 2.5 h. At this temperature, 38 g (365 mmol) of trimethyl borate are added as rapidly as possible, and the reaction is allowed to come slowly to room temperature (about 18 h). The reaction solution is washed with water, the solid which has precipitated out is filtered off and the organic phase are dried azeotropically with toluene. The crude product is washed by stirring with toluene/methylene chloride at about 40° C. and filtered off with suction. Yield: 16.7 g (690 mmol), 90% of theory.

The following compounds are prepared analogously:

| Starting material | Product | Yield |
|---|---|---|
| o1 | | 81% |
| o2 | | 84% |
| o3 | | 82% |

-continued
| | Starting material | Product | Yield |
|---|---|---|---|
| o4 | 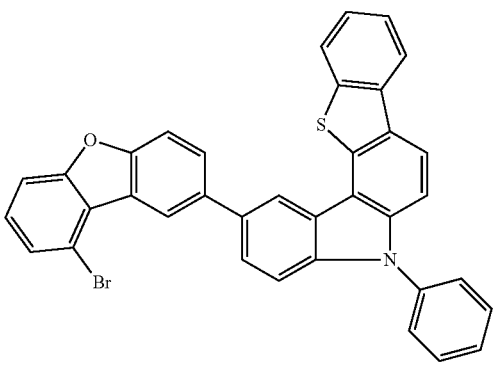 [SMILES: Brc1cccc2oc3ccc(-c4ccc5c(c4)c4c6sc7ccccc7c6ccc4n5-c4ccccc4)cc3c12] | | 81% |
| o5 | 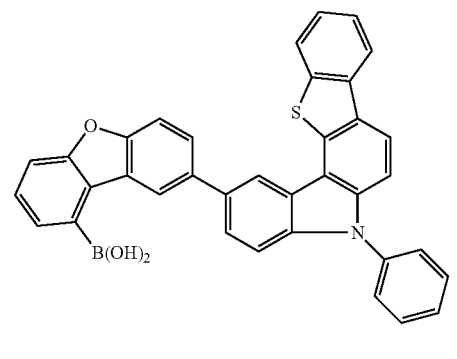 [SMILES: OB(O)c1cccc2oc3ccc(-c4ccc5c(c4)c4c6sc7ccccc7c6ccc4n5-c4ccccc4)cc3c12] | | 79% |
| o6 | 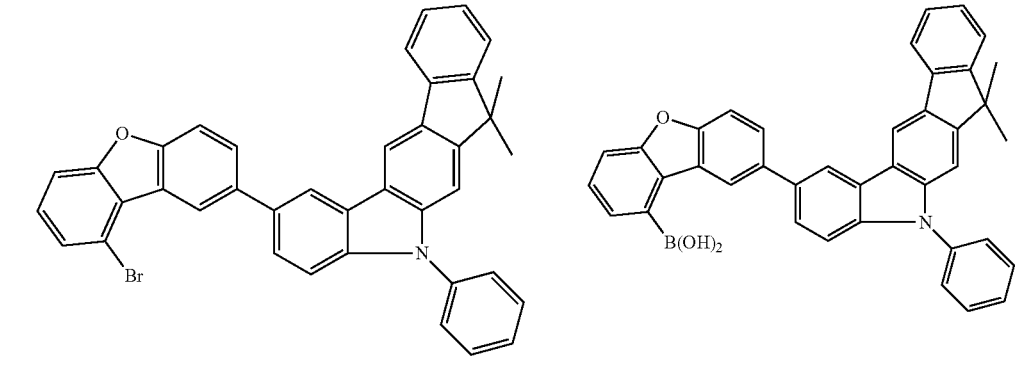 | | 77% |
| o7 | 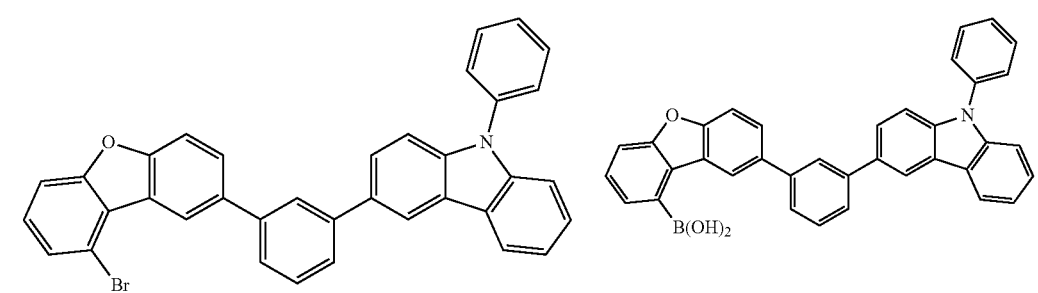 | | 75% |

-continued

| | Starting material | Product | Yield |
|---|---|---|---|
| o8 | | | 78% |
| o9 | | | 76% |
| o10 | | | 81% |
| o11 | | | 80% |
| o12 | | | 71% |

-continued

| | Starting material | Product | Yield |
|---|---|---|---|
| o13 | | | 69% |
| o14 | | | 88% |
| o15 | | | 78% |
| o16 | | | 77% | p) 3-{9-[3-(4,6-Diphenyl-1,3,5-triazin-2-yl)phenyl]dibenzofuran-2-yl}-9-phenyl-9H-carbazole

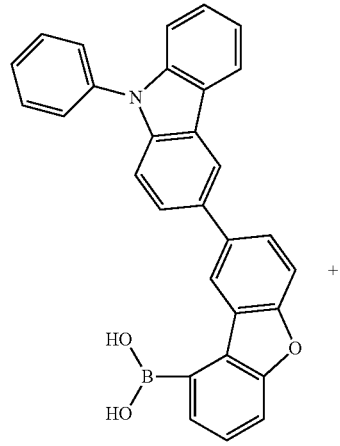

+

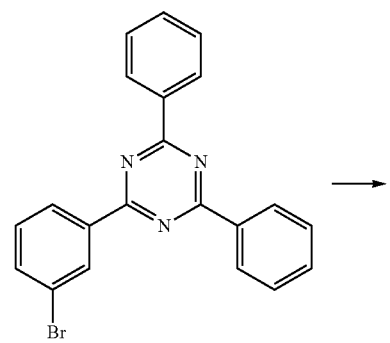

→

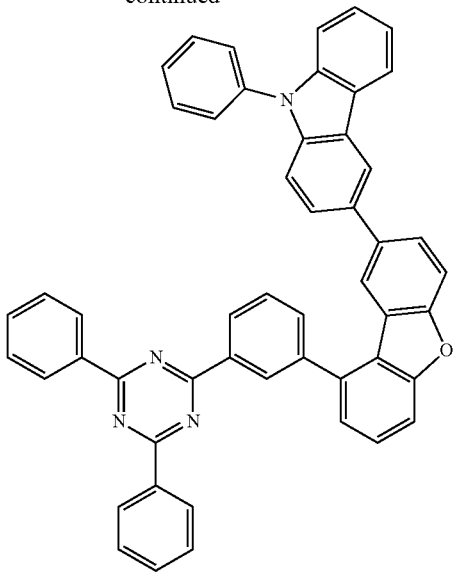

49.8 g (110.0 mmol) of 8-(9-phenyl-9H-carbazol-3-yl)dibenzofuran-1-boronic acid, 42.6 g (110.0 mmol) of 2-(3-bromophenyl)-4,6-diphenyl-1,3,5-triazine and 26 g (210.0 mmol) of sodium carbonate are suspended in 500 ml of ethylene glycol dimethyl ether and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The product is purified by column chromatography on silica gel with toluene/heptane (1:2) and finally sublimed in a high vacuum (p=5×10⁻⁷ mbar) (purity 99.9%). The yield is 52 g (72 mmol), corresponding to 78% of theory.

The following compounds are prepared analogously:

| Starting material 1 | Starting material 2 |
|---|---|
| p1 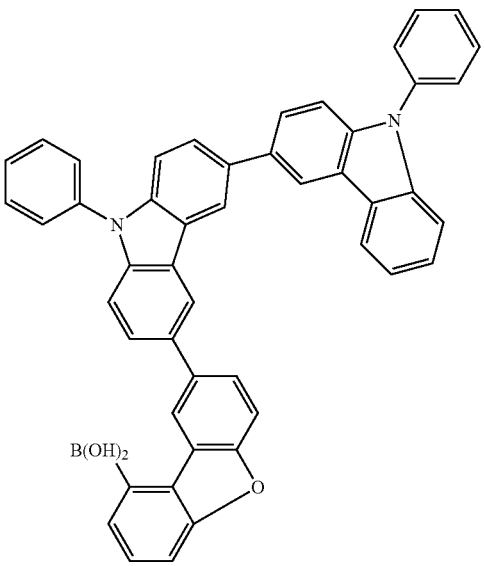 [SMILES: OB(O)c1cccc2oc3ccc(-c4ccc5c(c4)c4cc(-c6ccc7c(c6)c6ccccc6n7-c6ccccc6)ccc4n5-c4ccccc4)cc3c12] | 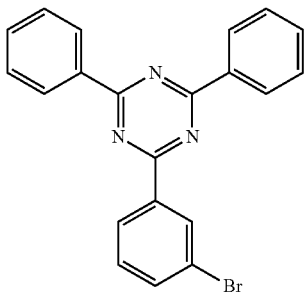 864377-31-1] |

311 312
-continued
p2 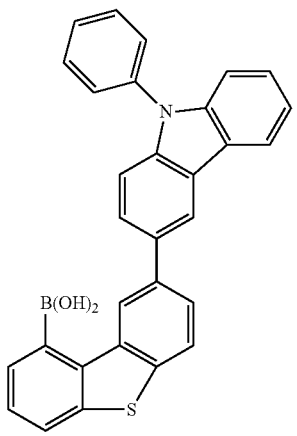 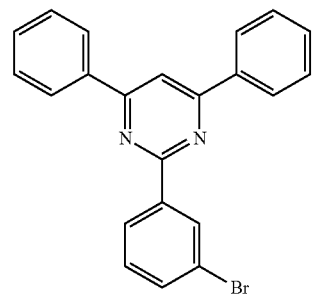
[864377-22-0]
p3 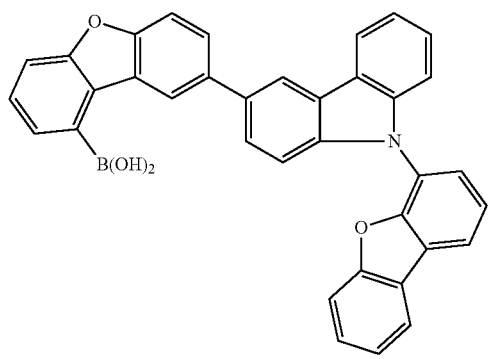 [SMILES: OB(O)c1cccc2oc3ccc(-c4ccc5c(c4)c4ccccc4n5-c4cccc5c4oc4ccccc45)cc3c12] 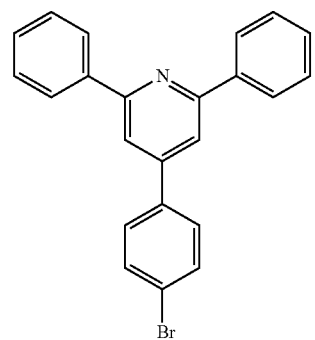
[1498-81-3]
p4 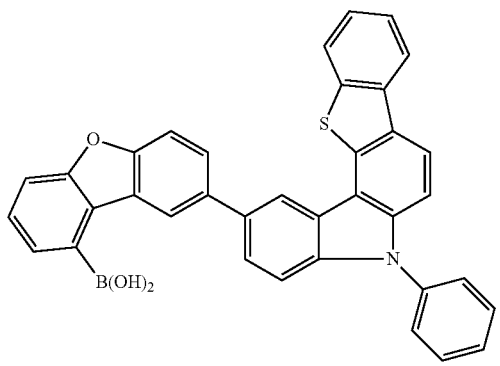 [SMILES: OB(O)c1cccc2oc3ccc(-c4ccc5c(c4)c4c6sc7ccccc7c6ccc4n5-c4ccccc4)cc3c12] 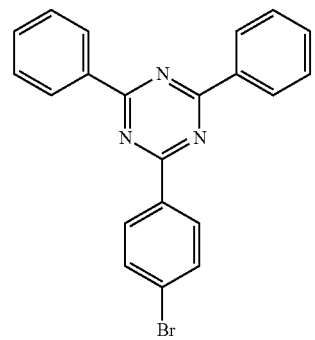
[23449-08-3]
p5 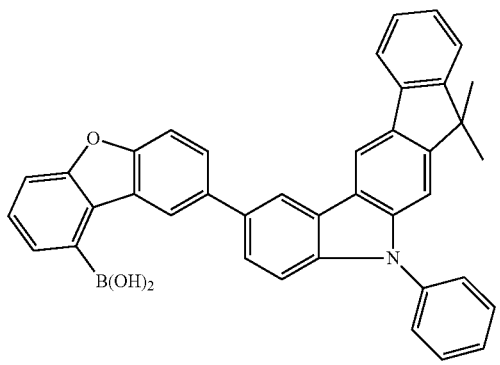 [SMILES: CC1(C)c2ccccc2-c2cc3c4cc(-c5ccc6oc7cccc(B(O)O)c7c6c5)ccc4n(-c4ccccc4)c3cc21] 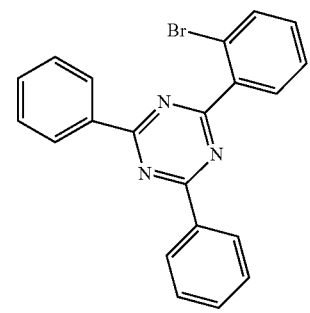
[77989-15-2]

| | | |
|---|---|---|
| p6 | 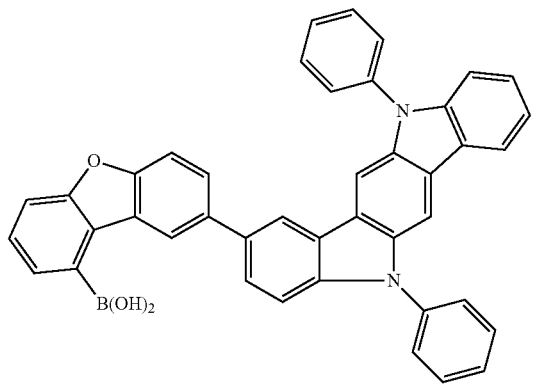 [SMILES: OB(O)c1cccc2oc3ccc(-c4ccc5c(c4)c4cc6c(cc4n5-c4ccccc4)c4ccccc4n6-c4ccccc4)cc3c12] | 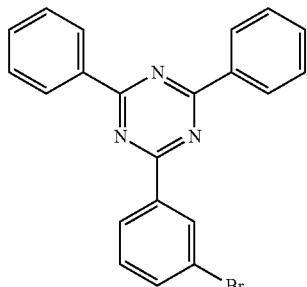
864377-31-1] |
| p7 | 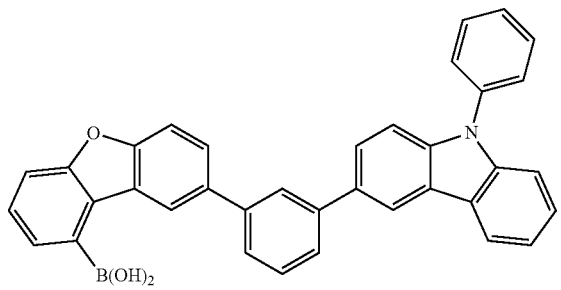 [SMILES: OB(O)c1cccc2oc3ccc(-c4cccc(-c5ccc6c(c5)c5ccccc5n6-c5ccccc5)c4)cc3c12] | 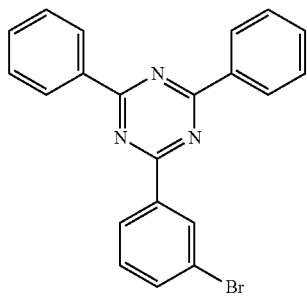
864377-31-1] |
| p8 | 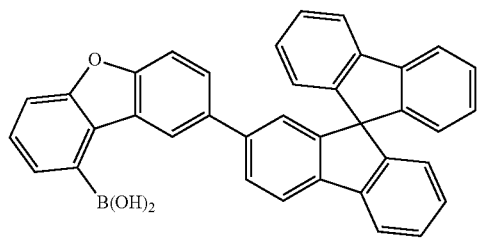 [SMILES: OB(O)c1cccc2oc3ccc(-c4ccc5c(c4)C4(c6ccccc6-c6ccccc64)c4ccccc4-5)cc3c12] | 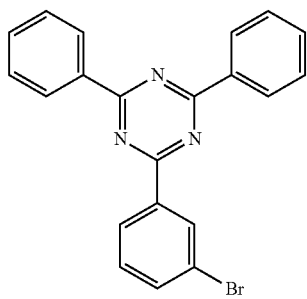
864377-31-1] |
| p9 | 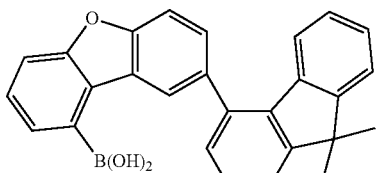 | 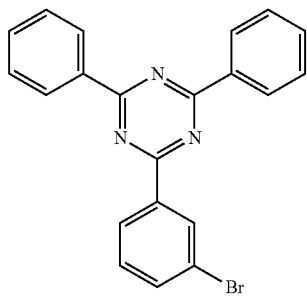
864377-31-1] |

-continued
p10 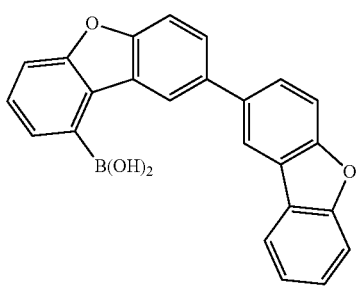 [SMILES: OB(O)c1cccc2oc3ccc(-c4ccc5oc6ccccc6c5c4)cc3c12] 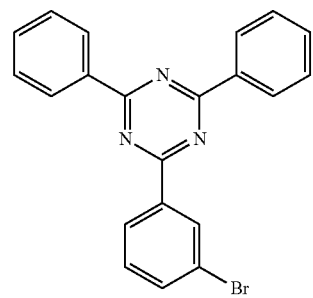
864377-31-1]
p11 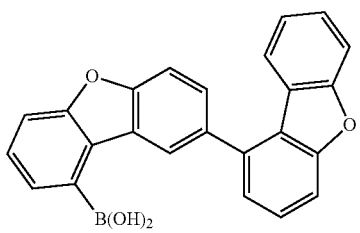 [SMILES: OB(O)c1cccc2oc3ccc(-c4cccc5oc6ccccc6c45)cc3c12] 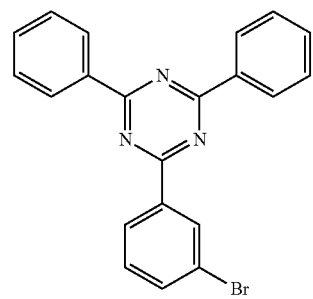
864377-31-1]
p12 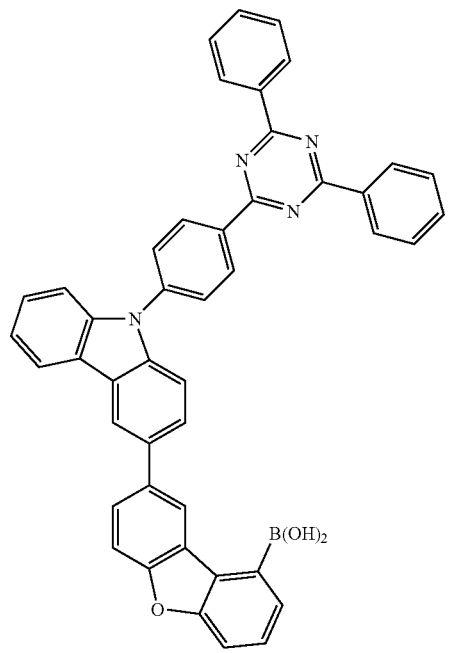 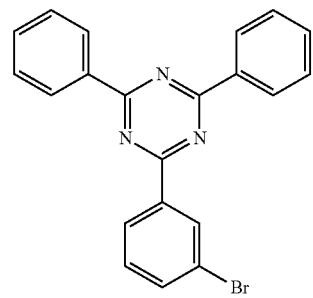
864377-31-1]

-continued
p13
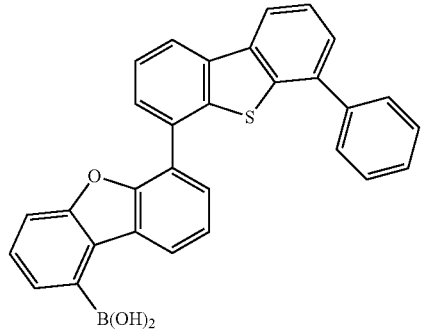 [SMILES: OB(O)c1cccc2oc3c(-c4cccc5c4sc4c(-c6ccccc6)cccc45)cccc3c12]
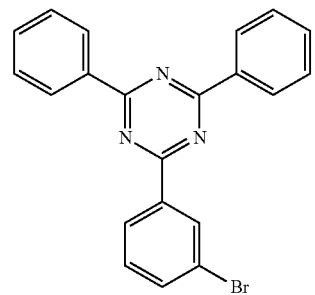
864377-31-1]
p14
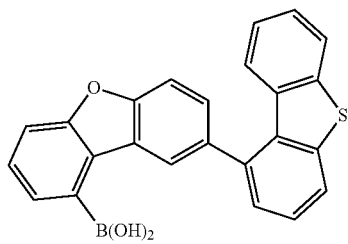 [SMILES: OB(O)c1cccc2oc3ccc(-c4cccc5sc6ccccc6c45)cc3c12]
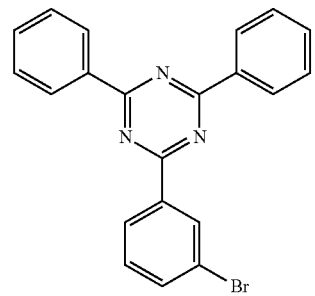
864377-31-1]
p15
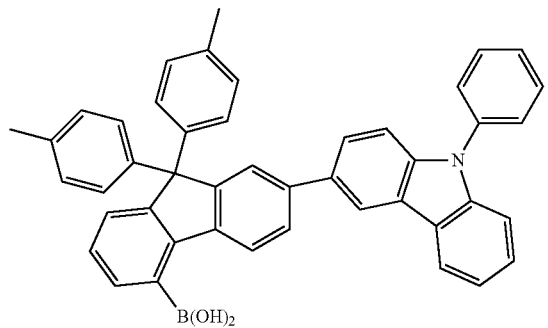 [SMILES: Cc1ccc(C2(c3ccc(C)cc3)c3cc(-c4ccc5c(c4)c4ccccc4n5-c4ccccc4)ccc3-c3c(B(O)O)cccc32)cc1]
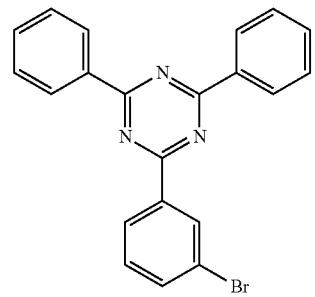
864377-31-1]
p16
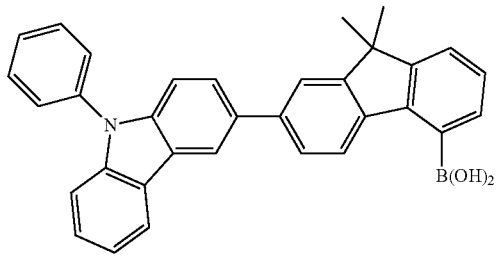 [SMILES: CC1(C)c2cc(-c3ccc4c(c3)c3ccccc3n4-c3ccccc3)ccc2-c2c(B(O)O)cccc21]
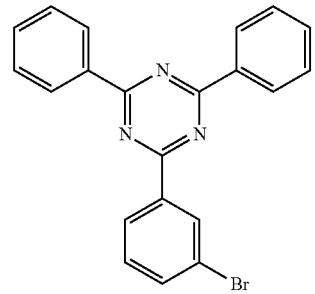
864377-31-1]

-continued
p17
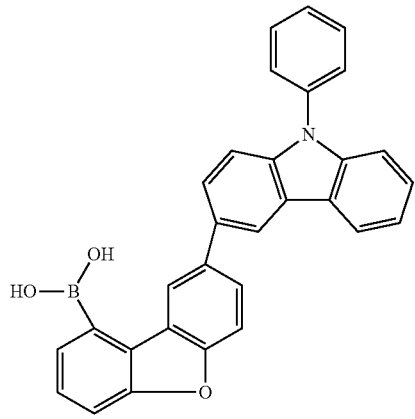 [SMILES: OB(O)c1cccc2oc3ccc(-c4ccc5c(c4)c4ccccc4n5-c4ccccc4)cc3c12]
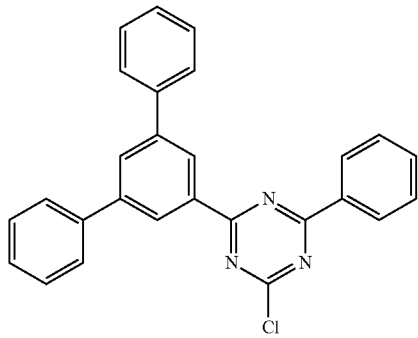
[1616231-77-2]
p18
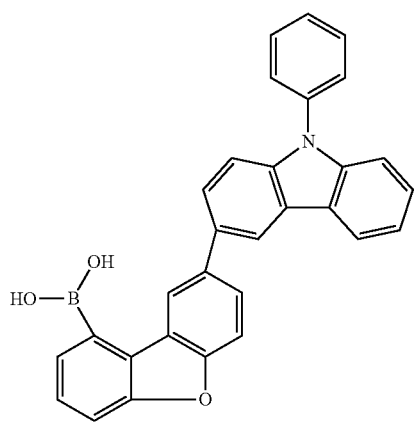 [SMILES: OB(O)c1cccc2oc3ccc(-c4ccc5c(c4)c4ccccc4n5-c4ccccc4)cc3c12]
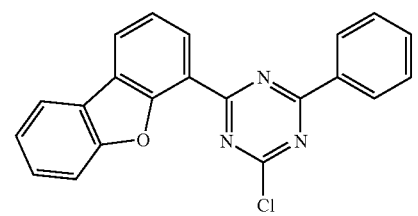
[1616231-51-8]
p19
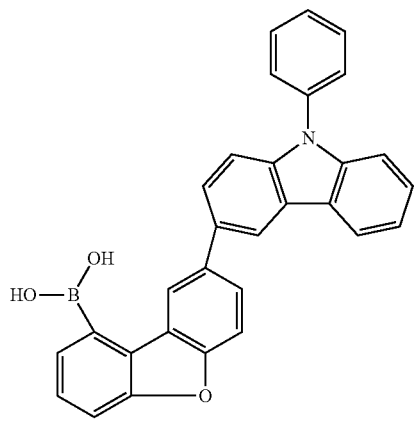 [SMILES: OB(O)c1cccc2oc3ccc(-c4ccc5c(c4)c4ccccc4n5-c4ccccc4)cc3c12]
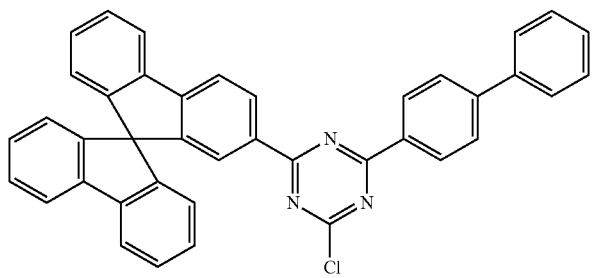
[1616231-53-8]

| | |
|---|---|
| p20 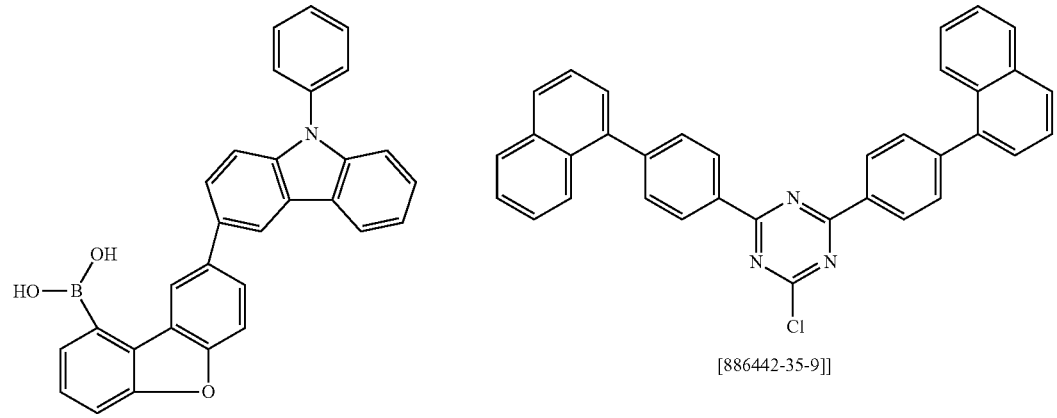 | [886442-35-9] |
| | Product | Yield |
|---|---|---|
| p1 | 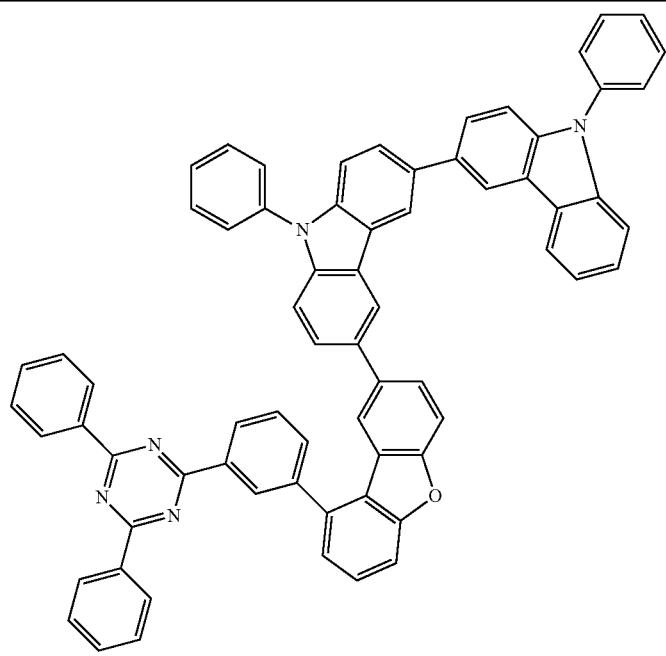 | 59% |
| p2 | | 67% |

| | | |
|---|---|---|
| p3 | 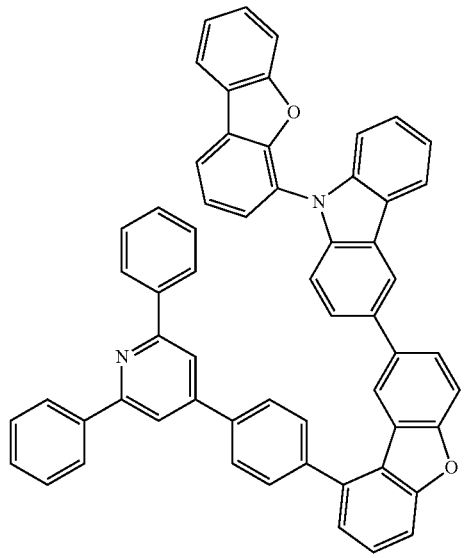 [SMILES: c1ccc(-c2cc(-c3ccc(-c4cccc5oc6ccc(-c7ccc8c(c7)c7ccccc7n8-c7cccc8c7oc7ccccc78)cc6c45)cc3)cc(-c3ccccc3)n2)cc1] | 62% |
| p4 | 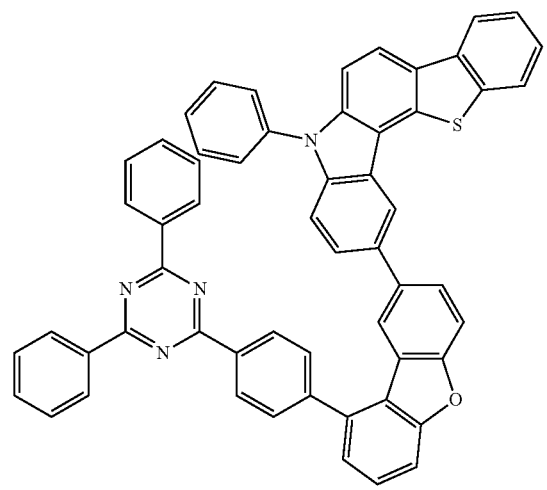 [SMILES: c1ccc(-c2nc(-c3ccccc3)nc(-c3ccc(-c4cccc5oc6ccc(-c7ccc8c(c7)c7c9sc%10ccccc%10c9ccc7n8-c7ccccc7)cc6c45)cc3)n2)cc1] | 69% |
| p5 | 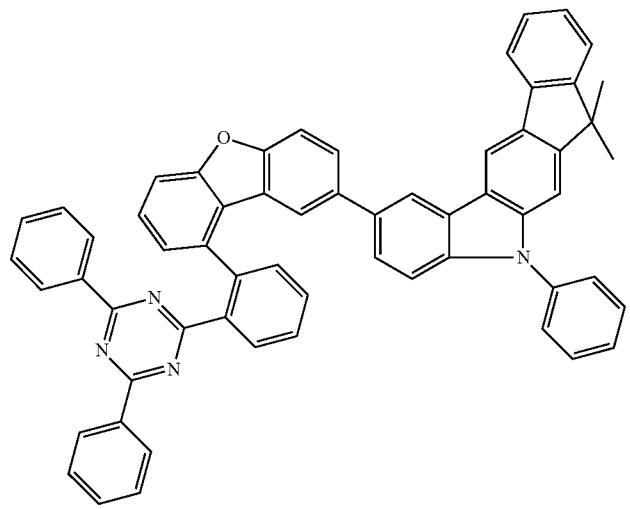 [SMILES: CC1(C)c2ccccc2-c2cc3c4cc(-c5ccc6oc7cccc(-c8ccccc8-c8nc(-c9ccccc9)nc(-c9ccccc9)n8)c7c6c5)ccc4n(-c4ccccc4)c3cc21] | 67% |

| | | |
|---|---|---|
| p6 | 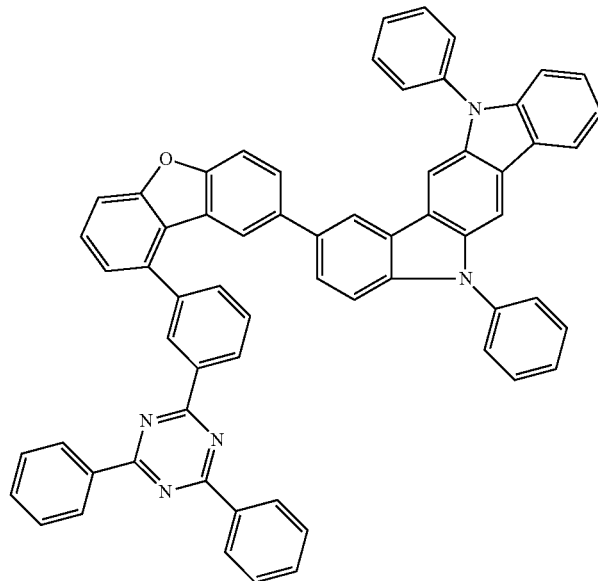 [SMILES: c1ccc(-c2nc(-c3ccccc3)nc(-c3cccc(-c4cccc5oc6ccc(-c7ccc8c(c7)c7cc9c(cc7n8-c7ccccc7)c7ccccc7n9-c7ccccc7)cc6c45)c3)n2)cc1] | 68% |
| p7 | 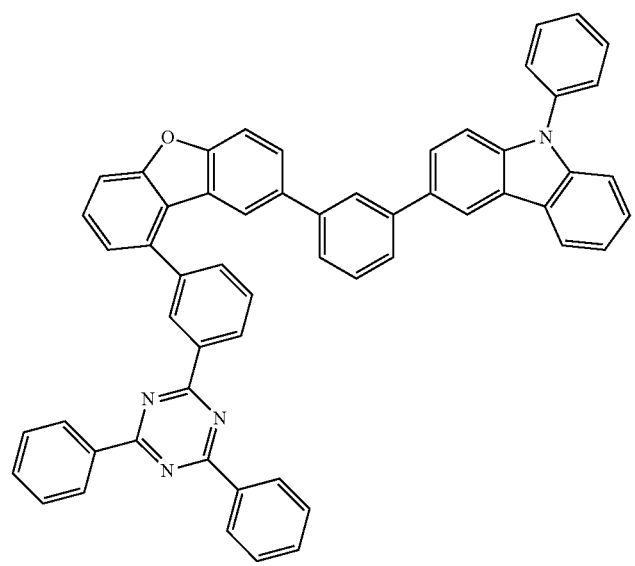 [SMILES: c1ccc(-c2nc(-c3ccccc3)nc(-c3cccc(-c4cccc5oc6ccc(-c7cccc(-c8ccc9c(c8)c8ccccc8n9-c8ccccc8)c7)cc6c45)c3)n2)cc1] | 69% |
| p8 | 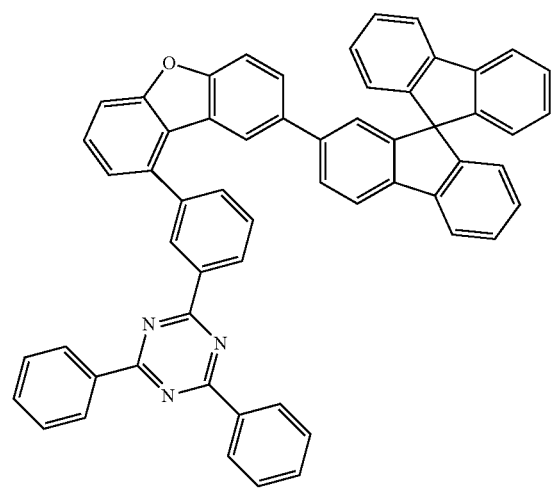 [SMILES: c1ccc(-c2nc(-c3ccccc3)nc(-c3cccc(-c4cccc5oc6ccc(-c7ccc8c(c7)C7(c9ccccc9-c9ccccc97)c7ccccc7-8)cc6c45)c3)n2)cc1] | 60% |

-continued
| | | |
|---|---|---|
| p9 | 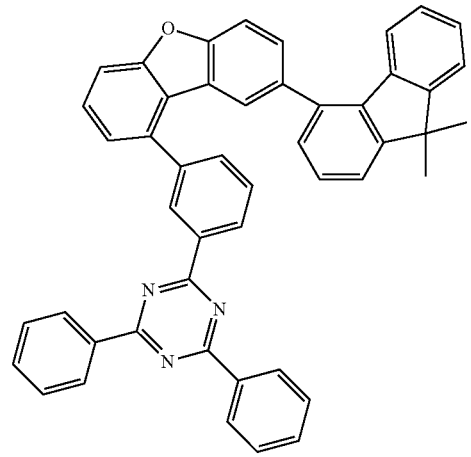 [SMILES: CC1(C)c2ccccc2-c2c(-c3ccc4oc5cccc(-c6cccc(-c7nc(-c8ccccc8)nc(-c8ccccc8)n7)c6)c5c4c3)cccc21] | 63% |
| p10 | 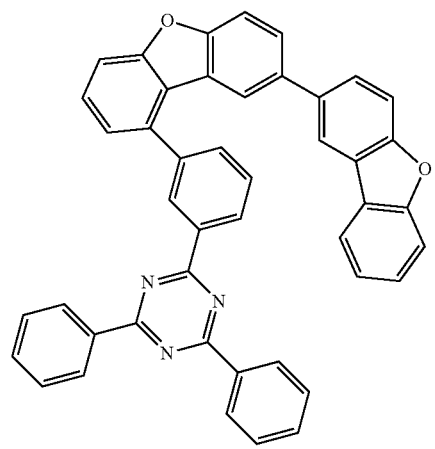 [SMILES: c1ccc(-c2nc(-c3ccccc3)nc(-c3cccc(-c4cccc5oc6ccc(-c7ccc8oc9ccccc9c8c7)cc6c45)c3)n2)cc1] | 66% |
| p11 | 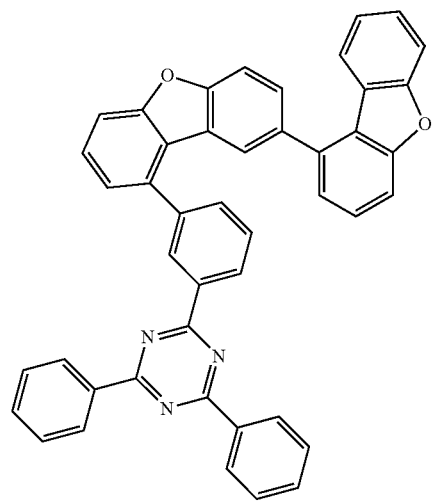 [SMILES: c1ccc(-c2nc(-c3ccccc3)nc(-c3cccc(-c4cccc5oc6ccc(-c7cccc8oc9ccccc9c78)cc6c45)c3)n2)cc1] | 60% |

| p12 | 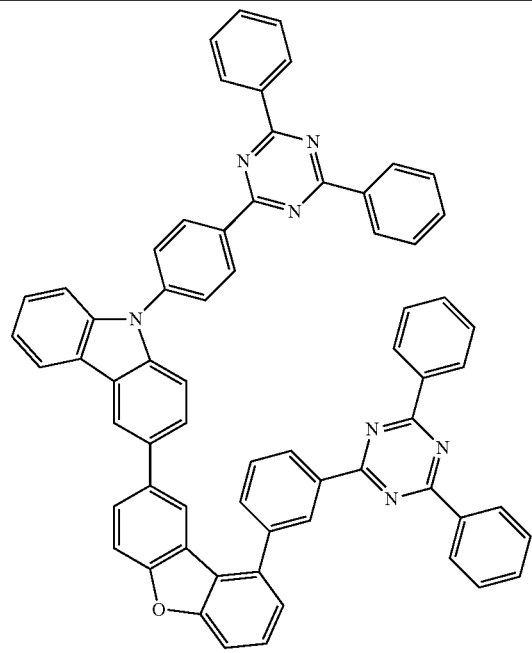 | 61% |
|---|---|---|
| p13 | 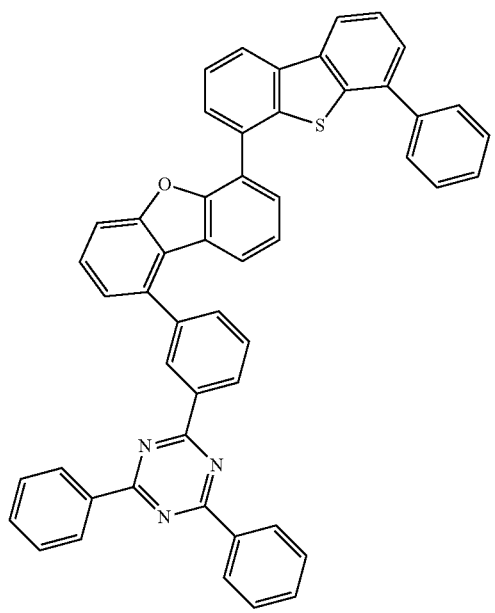 [SMILES: c1ccc(-c2nc(-c3ccccc3)nc(-c3cccc(-c4cccc5oc6c(-c7cccc8c7sc7c(-c9ccccc9)cccc78)cccc6c45)c3)n2)cc1] | 65% |

| | | |
|---|---|---|
| p14 | 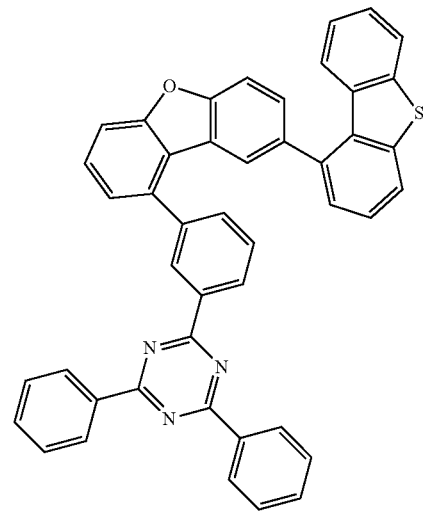 [SMILES: c1ccc(-c2nc(-c3ccccc3)nc(-c3cccc(-c4cccc5oc6ccc(-c7cccc8sc9ccccc9c78)cc6c45)c3)n2)cc1] | 63% |
| p15 | 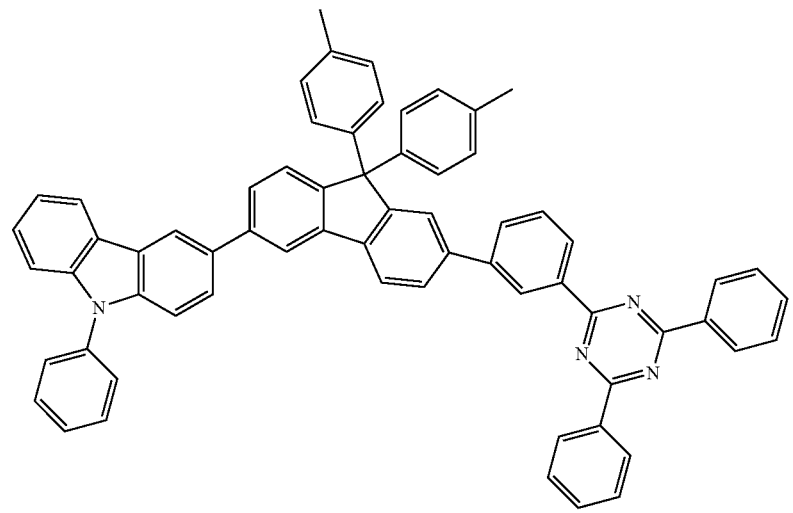 [SMILES: Cc1ccc(C2(c3ccc(C)cc3)c3ccc(-c4ccc5c(c4)c4ccccc4n5-c4ccccc4)cc3-c3ccc(-c4cccc(-c5nc(-c6ccccc6)nc(-c6ccccc6)n5)c4)cc32)cc1] | 65% |
| p16 | 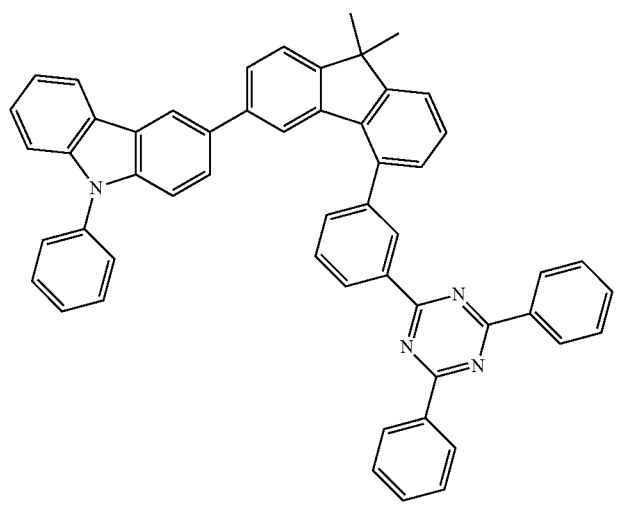 [SMILES: CC1(C)c2ccc(-c3ccc4c(c3)c3ccccc3n4-c3ccccc3)cc2-c2c(-c3cccc(-c4nc(-c5ccccc5)nc(-c5ccccc5)n4)c3)cccc21] | 63% | p17 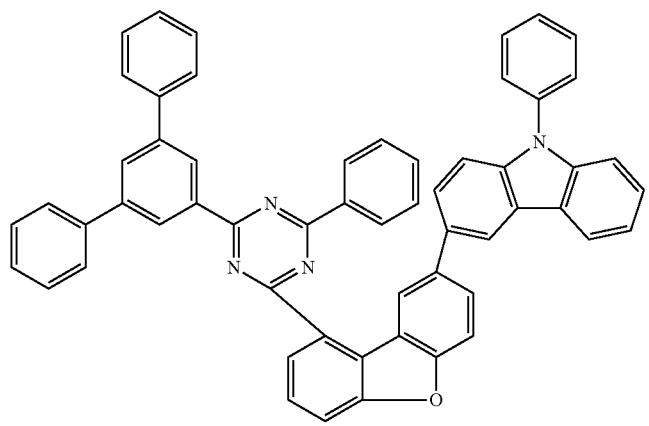 [SMILES: c1ccc(-c2cc(-c3ccccc3)cc(-c3nc(-c4ccccc4)nc(-c4cccc5oc6ccc(-c7ccc8c(c7)c7ccccc7n8-c7ccccc7)cc6c45)n3)c2)cc1] 65%
p18 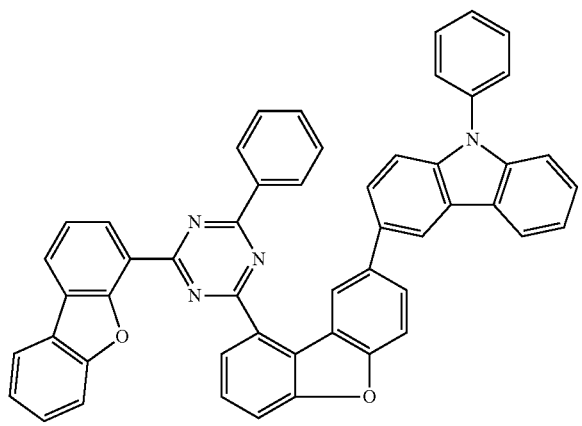 [SMILES: c1ccc(-c2nc(-c3cccc4c3oc3ccccc34)nc(-c3cccc4oc5ccc(-c6ccc7c(c6)c6ccccc6n7-c6ccccc6)cc5c34)n2)cc1] 67%
p19 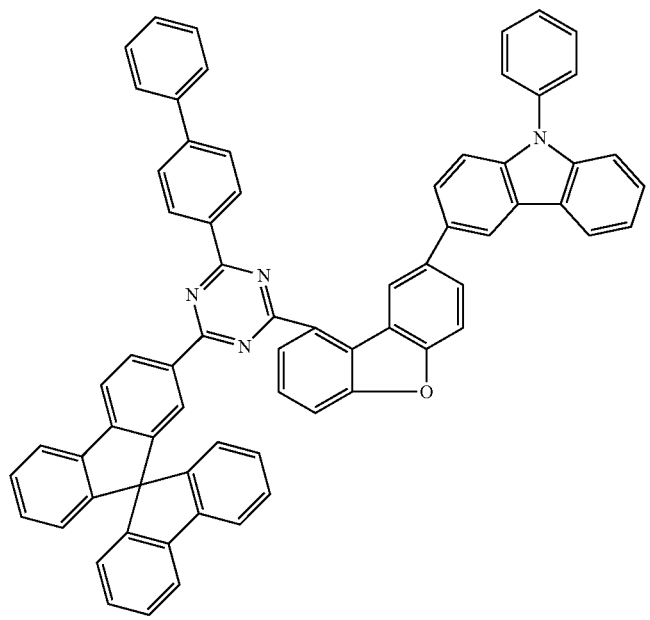 [SMILES: c1ccc(-c2ccc(-c3nc(-c4ccc5c(c4)C4(c6ccccc6-c6ccccc64)c4ccccc4-5)nc(-c4cccc5oc6ccc(-c7ccc8c(c7)c7ccccc7n8-c7ccccc7)cc6c45)n3)cc2)cc1] 72%

| p20 | 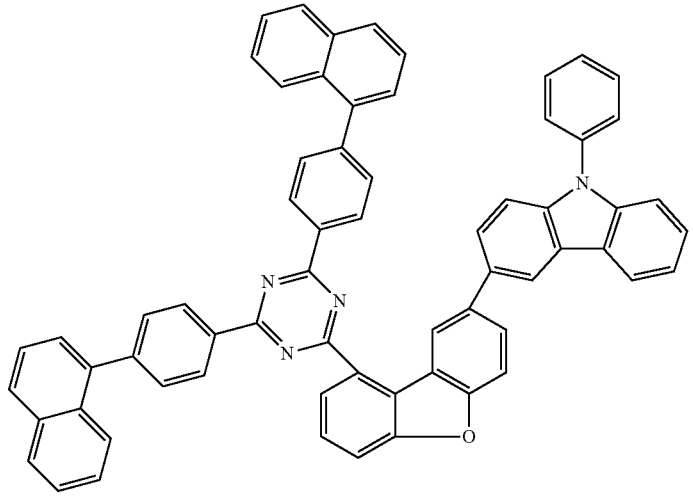 [SMILES: c1ccc(-n2c3ccccc3c3cc(-c4ccc5oc6cccc(-c7nc(-c8ccc(-c9cccc%10ccccc9%10)cc8)nc(-c8ccc(-c9cccc%10ccccc9%10)cc8)n7)c6c5c4)ccc32)cc1] | 66% |

Production of the OLEDs

The data of various OLEDs are presented in the following Examples V1 to E37 (see Tables 1 and 2).

Pre-treatment for Examples V1-E37: Glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH Germany, applied by spin coating from aqueous solution) for improved processing. These coated glass plates form the substrates to which the OLEDs are applied. The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:IC3:TEG1 (55%:35%:10%) here means that material IC1 is present in the layer in a proportion by volume of 55%, IC3 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m 2, and the CIE 1931 x and y colour coordinates are calculated therefrom. The term U1000 in Table 2 denotes the voltage required for a luminous density of 1000 cd/m 2. CE1000 and PE1000 denote the current and power efficiency respectively which are achieved at 1000 cd/m 2. Finally, EQE1000 denotes the external quantum efficiency at an operating luminous density of 1000 cd/m 2. The lifetime LT is defined as the time after which the luminous density drops from the initial luminous density to a certain proportion L1 on operation at constant current. An expression of L0;j0=4000 cd/m 2 and L1=70% in Table 2 means that the lifetime indicated in column LT corresponds to the time after which the initial luminous density drops from 4000 cd/m 2 to 2800 cd/m$^2$. Analogously, L0;j0=20 mA/cm$^2$, L1=80%, means that the luminous density drops to 80% of its initial value after time LT on operation at 20 mA/cm$^2$.

The data of the various OLEDs are summarised in Table 2. Examples V1-V6 are comparative examples in accordance with the prior art, Examples E1-E37 show data of OLEDs according to the invention.

Some of the examples are explained in greater detail below in order to illustrate the advantages of the OLEDs according to the invention.

Use of Mixtures According to the Invention in the Emission Layer of Phosphorescent OLEDs On use as matrix materials in phosphorescent OLEDs, the materials according to the invention give rise to significant improvements over the prior art with respect to the lifetime of the components. Use of compounds EG1 to EG4 according to the invention in combination with the green-emitting dopant TEG1 enables an increase in the lifetime by more than 200% compared with the prior art to be observed (comparison of Examples V1 with E1, E6 and V2 with E2 as well as V3 with E3 and V4, V5 with E4).

TABLE 1

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| V1 | SpA1 70 nm | HATCN 5 nm | SpMA1 90 nm | SdT1:TEG1 (90%:10%) 30 nm | ST2 10 nm | ST2:LiQ (50%:50%) 30 nm | — |
| V2 | SpA1 70 nm | HATCN 5 nm | SpMA1 90 nm | SdT2:TEG1 (90%:10%) 30 nm | ST2 10 nm | ST2:LiQ (50%:50%) 30 nm | — |
| V3 | SpA1 70 nm | HATCN 5 nm | SpMA1 90 nm | SdT3:TEG1 (90%:10%) 30 nm | ST2 10 nm | ST2:LiQ (50%:50%) 30 nm | — |
| V4 | SpA1 70 nm | HATCN 5 nm | SpMA1 90 nm | SdT4:TEG1 (90%:10%) 30 nm | ST2 10 nm | ST2:LiQ (50%:50%) 30 nm | — |
| V5 | SpA1 70 nm | HATCN 5 nm | SpMA1 90 nm | SdT5:TEG1 (90%:10%) 30 nm | ST2 10 nm | ST2:LiQ (50%:50%) 30 nm | — |
| V6 | SpA1 70 nm | HATCN 5 nm | SpMA1 90 nm | SdT6:TEG1 (90%:10%) 30 nm | ST2 10 nm | ST2:LiQ (50%:50%) 30 nm | — |
| E1 | SpA1 70 nm | HATCN 5 nm | SpMA1 90 nm | EG1:TEG1 (90%:10%) 30 nm | ST2 10 nm | ST2:LiQ (50%:50%) 30 nm | — |
| E2 | SpA1 70 nm | HATCN 5 nm | SpMA1 90 nm | EG2:TEG1 (90%:10%) 30 nm | ST2 10 nm | ST2:LiQ (50%:50%) 30 nm | — |
| E3 | SpA1 70 nm | HATCN 5 nm | SpMA1 90 nm | EG3:TEG1 (90%:10%) 30 nm | ST2 10 nm | ST2:LiQ (50%:50%) 30 nm | — |
| E4 | SpA1 70 nm | HATCN 5 nm | SpMA1 90 nm | EG4:TEG1 (90%:10%) 30 nm | ST2 10 nm | ST2:LiQ (50%:50%) 30 nm | — |
| E5 | SpA1 90 nm | HATCN 5 nm | SpMA1 130 nm | EG5:TER1 (92%:8%) 30 nm | — | ST2:LiQ (50%:50%) 40 nm | — |
| E6 | SpA1 90 nm | HATCN 5 nm | SpMA1 130 nm | EG6:TER1 (92%:8%) 30 nm | — | ST2:LiQ (50%:50%) 40 nm | — |
| E7 | SpA1 70 nm | HATCN 5 nm | SpMA1 90 nm | EG7:TEG1 (90%:10%) 30 nm | — | ST2:LiQ (50%:50%) 40 nm | — |
| E8 | SpA1 70 nm | HATCN 5 nm | SpMA1 90 nm | EG8:TEG1 (90%:10%) 30 nm | — | ST2:LiQ (50%:50%) 40 nm | — |
| E9 | SpA1 70 nm | HATCN 5 nm | SpMA1 90 nm | EG9:IC3:TEG1 (45%:45%:10%) 30 nm | IC1 10 nm | ST2:LiQ (50%:50%) 30 nm | — |
| E10 | SpA1 70 nm | HATCN 5 nm | SpMA1 90 nm | EG10:IC3:TEG1 (45%:45%:10%) 30 nm | IC1 10 nm | ST2:LiQ (50%:50%) 30 nm | — |
| E11 | SpA1 70 nm | HATCN 5 nm | SpMA1 90 nm | EG11:IC3:TEG1 (45%:45%:10%) 30 nm | IC1 10 nm | ST2:LiQ (50%:50%) 30 nm | — |
| E12 | SpA1 70 nm | HATCN 5 nm | SpMA1 90 nm | IC1:TEG1 (90%:10%) 30 nm | — | EG12 40 nm | LiQ 3 nm |
| E13 | SpA1 70 nm | HATCN 5 nm | SpMA1 90 nm | IC1:TEG1 (90%:10%) 30 nm | IC1 10 nm | EG13:LiQ (50%:50%) 30 nm | — |
| E14 | SpA1 70 nm | HATCN 5 nm | SpMA1 90 nm | EG14:IC3:TEG1 (65%:25%:10%) 30 nm | IC1 10 nm | ST2:LiQ (50%:50%) 30 nm | — |
| E15 | SpA1 70 nm | HATCN 5 nm | SpMA1 90 nm | IC1:TEG1 (90%:10%) 30 nm | EG15 10 nm | ST2:LiQ (50%:50%) 30 nm | — |
| E16 | HATCN 5 nm | SpMA1 70 nm | SpMA2 15 nm | EG16:L1:TEY1 (45%:45%:10%) 25 nm | — | ST1 45 nm | LiQ 3 nm |
| E17 | SpA1 70 nm | HATCN 5 nm | SpMA1 90 nm | EG17:TEG1 (90%:10%) 30 nm | ST2 10 nm | ST2:LiQ (50%:50%) 30 nm | — |
| E18 | SpA1 70 nm | HATCN 5 nm | SpMA1 90 nm | EG18:IC3:TEG1 (45%:45%:10%) 30 nm | IC1 10 nm | ST2:LiQ (50%:50%) 30 nm | — |
| E19 | HATCN 5 nm | SpMA1 70 nm | SpMA2 15 nm | EG19:L1:TEY1 (45%:45%:10%) 25 nm | — | ST1 45 nm | LiQ 3 nm |

TABLE 1-continued

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| E20 | SpA1 70 nm | HATCN 5 nm | SpMA1 90 nm | IC1:TEG1 (90%:10%) 30 nm | EG20 10 nm | ST2:LiQ (50%:50%) 30 nm | — |
| E21 | SpA1 70 nm | HATCN 5 nm | SpMA1 90 nm | EG21:TEG1 (90%:10%) 30 nm | — | ST2:LiQ (50%:50%) 40 nm | — |
| E22 | SpA1 70 nm | HATCN 5 nm | SpMA1 90 nm | EG22:TEG1 (90%:10%) 30 nm | — | ST2:LiQ (50%:50%) 30 nm | — |
| E23 | SpA1 70 nm | HATCN 5 nm | SpMA1 90 nm | IC1:TEG1 (90%:10%) 30 nm | — | EG23:ST1 40 nm | LiQ 3 nm |
| E24 | SpA1 70 nm | HATCN 5 nm | SpMA1 90 nm | EG24:TEG1 (90%:10%) 30 nm | — | ST2:LiQ (50%:50%) 30 nm | — |
| E25 | SpA1 70 nm | HATCN 5 nm | SpMA1 90 nm | EG25:IC3:TEG1 (50%:40%:10%) 30 nm | ST2 10 nm | ST2:LiQ (50%:50%) 30 nm | — |
| E26 | SpA1 70 nm | HATCN 5 nm | SpMA1 90 nm | EG26:IC3:TEG1 (55%:35%:10%) 30 nm | ST2 10 nm | ST2:LiQ (50%:50%) 30 nm | — |
| E27 | SpA1 70 nm | HATCN 5 nm | SpMA1 90 nm | EG27:IC3:TEG1 (45%:45%:10%) 30 nm | ST2 10 nm | ST2:LiQ (50%:50%) 30 nm | — |
| E28 | SpA1 70 nm | HATCN 5 nm | SpMA1 90 nm | IC1:TEG1 (90%:10%) 30 nm | IC1 10 nm | EG28:LiQ (50%:50%) 30 nm | — |
| E29 | SpA1 90 nm | HATCN 5 nm | SpMA1 130 nm | EG29:TER1 (92%:8%) 30 nm | — | ST2:LiQ (50%:50%) 40 nm | — |
| E30 | SpA1 70 nm | HATCN 5 nm | SpMA1 90 nm | EG30:IC3:TEG1 (45%:45%:10%) 30 nm | ST2 10 nm | ST2:LiQ (50%:50%) 30 nm | — |
| E31 | SpA1 70 nm | HATCN 5 nm | SpMA1 90 nm | EG1:IC3:TEG1 (50%:40%:10%) 30 nm | ST2 10 nm | ST2:LiQ (50%:50%) 30 nm | — |
| E32 | SpA1 70 nm | HATCN 5 nm | SpMA1 90 nm | EG1:IC4:TEG1 (40%:45%:15%) 30 nm | ST2 10 nm | ST2:LiQ (50%:50%) 30 nm | — |
| E33 | SpA1 70 nm | HATCN 5 nm | SpMA1 90 nm | EG1:IC5:TEG1 (70%:25%:5%) 30 nm | ST2 10 nm | ST2:LiQ (50%:50%) 30 nm | — |
| E34 | SpA1 70 nm | HATCN 5 nm | SpMA1 90 nm | EG1:IC6:TEG1 (45%:45%:10%) 30 nm | ST2 10 nm | ST2:LiQ (50%:50%) 30 nm | — |
| E35 | SpA1 70 nm | HATCN 5 nm | SpMA1 90 nm | EG1:IC7:TEG1 (40%:50%:10%) 30 nm | ST2 10 nm | ST2:LiQ (50%:50%) 30 nm | — |
| E36 | SpA1 70 nm | HATCN 5 nm | SpMA1 90 nm | EG1:IC8:TEG1 (30%:50%:20%) 30 nm | ST2 10 nm | ST2:LiQ (50%:50%) 30 nm | — |
| E37 | SpA1 70 nm | HATCN 5 nm | SpMA1 90 nm | EG1:L1:TEG1 (25%:55%:20%) 30 nm | ST2 10 nm | ST2:LiQ (50%:50%) 30 nm | — |

TABLE 2

Data of the OLEDs

| Ex. | U1000 (V) | CE1000 (cd/A) | PE1000 (lm/W) | EQE 1000 | CIE x/y at 1000 cd/m² | $L_0; j_0$ | L1 % | LT (h) |
|---|---|---|---|---|---|---|---|---|
| V1 | 3.6 | 51 | 44 | 13.7% | 0.33/0.63 | 20 mA/cm² | 80 | 95 |
| V2 | 4.2 | 50 | 37 | 14.3% | 0.33/0.62 | 20 mA/cm² | 80 | 10 |
| V3 | 4.3 | 55 | 40 | 14.7% | 0.33/0.64 | 20 mA/cm² | 80 | 15 |
| V4 | 3.5 | 48 | 43 | 12.8% | 0.32/0.64 | 20 mA/cm² | 80 | 190 |
| V5 | 3.7 | 59 | 50 | 15.7% | 0.33/0.64 | 20 mA/cm² | 80 | 125 |
| V6 | 3.4 | 44 | 41 | 11.8% | 0.31/0.65 | 20 mA/cm² | 80 | 20 |
| E1 | 3.5 | 40 | 36 | 11.6% | 0.33/0.62 | 20 mA/cm² | 80 | 290 |
| E2 | 4.3 | 51 | 37 | 14.5% | 0.33/0.62 | 20 mA/cm² | 80 | 20 |
| E3 | 4.4 | 55 | 39 | 15.0% | 0.33/0.63 | 20 mA/cm² | 80 | 35 |

TABLE 2-continued

Data of the OLEDs

| Ex. | U1000 (V) | CE1000 (cd/A) | PE1000 (lm/W) | EQE 1000 | CIE x/y at 1000 cd/m$^2$ | $L_0$; $j_0$ | L1 % | LT (h) |
|---|---|---|---|---|---|---|---|---|
| E4 | 3.6 | 41 | 36 | 11.9% | 0.32/0.63 | 20 mA/cm$^2$ | 80 | 300 |
| E5 | 4.4 | 13 | 9 | 12.4% | 0.66/0.34 | 4000 cd/m$^2$ | 80 | 340 |
| E6 | 4.6 | 11 | 8 | 11.4% | 0.67/0.34 | 4000 cd/m$^2$ | 80 | 370 |
| E7 | 3.4 | 59 | 55 | 15.9% | 0.33/0.63 | 20 mA/cm$^2$ | 80 | 115 |
| E8 | 3.6 | 56 | 49 | 15.2% | 0.33/0.62 | 20 mA/cm$^2$ | 80 | 125 |
| E9 | 3.4 | 62 | 57 | 16.5% | 0.34/0.63 | 20 mA/cm$^2$ | 80 | 240 |
| E10 | 3.5 | 60 | 54 | 16.1% | 0.33/0.63 | 20 mA/cm$^2$ | 80 | 350 |
| E11 | 3.6 | 57 | 50 | 15.5% | 0.33/0.63 | 20 mA/cm$^2$ | 80 | 290 |
| E12 | 3.3 | 64 | 61 | 17.1% | 0.33/0.63 | 20 mA/cm$^3$ | 80 | 125 |
| E13 | 3.7 | 62 | 53 | 16.5% | 0.34/0.63 | 20 mA/cm$^2$ | 80 | 165 |
| E14 | 3.3 | 60 | 57 | 16.7% | 0.32/0.63 | 20 mA/cm$^2$ | 80 | 270 |
| E15 | 3.5 | 59 | 53 | 16.0% | 0.34/0.63 | 20 mA/cm$^2$ | 80 | 145 |
| E16 | 2.9 | 75 | 81 | 22.4% | 0.44/0.55 | 50 mA/cm$^2$ | 90 | 85 |
| E17 | 3.4 | 41 | 37 | 11.7% | 0.33/0.63 | 20 mA/cm$^2$ | 80 | 140 |
| E18 | 3.5 | 60 | 53 | 16.3% | 0.33/0.63 | 20 mA/cm$^2$ | 80 | 260 |
| E19 | 2.8 | 77 | 86 | 23.1% | 0.45/0.55 | 50 mA/cm$^2$ | 90 | 100 |
| E20 | 3.7 | 59 | 50 | 15.8% | 0.33/0.63 | 20 mA/cm$^2$ | 80 | 155 |
| E21 | 3.7 | 55 | 47 | 14.7% | 0.36/0.61 | 20 mA/cm$^2$ | 80 | 135 |
| E22 | 3.8 | 58 | 48 | 15.6% | 0.33/0.63 | 20 mA/cm$^2$ | 80 | 140 |
| E23 | 3.4 | 62 | 57 | 17.0% | 0.31/0.64 | 20 mA/cm$^2$ | 80 | 130 |
| E24 | 3.8 | 56 | 46 | 15.3% | 0.33/0.63 | 20 mA/cm$^2$ | 80 | 125 |
| E25 | 3.6 | 60 | 52 | 16.0% | 0.35/0.62 | 20 mA/cm$^2$ | 80 | 360 |
| E26 | 3.7 | 57 | 48 | 15.2% | 0.33/0.63 | 20 mA/cm$^2$ | 80 | 275 |
| E27 | 3.6 | 54 | 47 | 15.5% | 0.34/0.61 | 20 mA/cm$^2$ | 80 | 255 |
| E28 | 3.6 | 60 | 52 | 16.4% | 0.34/0.62 | 20 mA/cm$^2$ | 80 | 170 |
| E29 | 4.5 | 13 | 9 | 11.6% | 0.67/0.33 | 4000 cd/m$^2$ | 80 | 340 |
| E30 | 3.5 | 58 | 52 | 15.6% | 0.33/0.63 | 20 mA/cm$^2$ | 80 | 270 |
| E31 | 3.4 | 59 | 55 | 15.9% | 0.32/0.64 | 20 mA/cm$^2$ | 80 | 380 |
| E32 | 3.4 | 61 | 56 | 16.2% | 0.33/0.64 | 20 mA/cm$^2$ | 80 | 360 |
| E33 | 3.3 | 59 | 56 | 15.7% | 0.33/0.63 | 20 mA/cm$^2$ | 80 | 335 |
| E34 | 3.5 | 61 | 55 | 16.3% | 0.33/0.63 | 20 mA/cm$^2$ | 80 | 355 |
| E35 | 3.4 | 62 | 57 | 16.6% | 0.31/0.64 | 20 mA/cm$^2$ | 80 | 340 |
| E36 | 3.4 | 59 | 55 | 16.1% | 0.33/0.63 | 20 mA/cm$^2$ | 80 | 345 |
| E37 | 3.3 | 54 | 51 | 15.0% | 0.32/0.63 | 20 mA/cm$^2$ | 80 | 395 |

TABLE 3

Structural formulae of the materials for the OLEDs

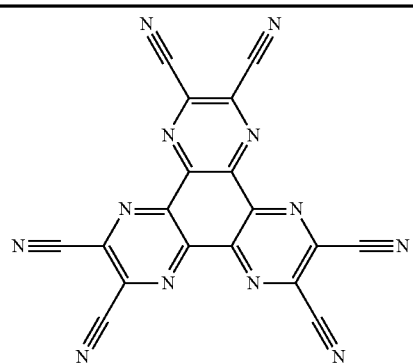

HATCN

TABLE 3-continued
Structural formulae of the materials for the OLEDs
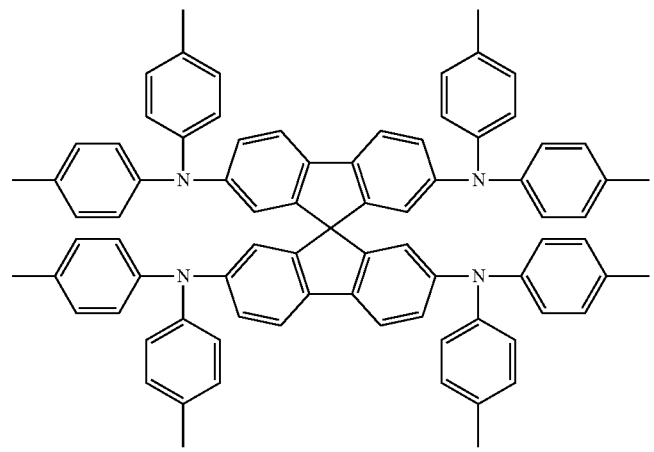
SpA1
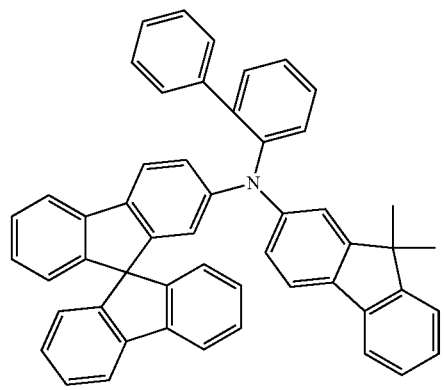 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
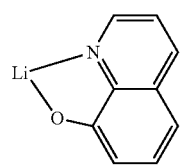
LiQ
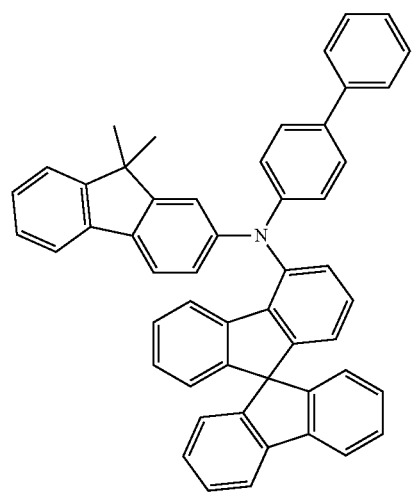 [SMILES: CC1(C)c2ccccc2-c2ccc(N(c3ccc(-c4ccccc4)cc3)c3cccc4c3-c3ccccc3C43c4ccccc4-c4ccccc43)cc21]

TABLE 3-continued
Structural formulae of the materials for the OLEDs
SpMA2
TER1
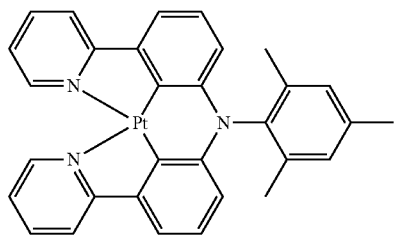
L1
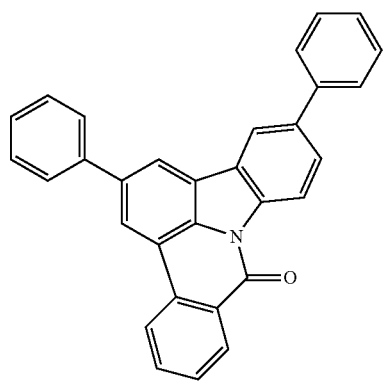 [SMILES: O=c1c2ccccc2c2cc(-c3ccccc3)cc3c4cc(-c5ccccc5)ccc4n1c23]
TEY1
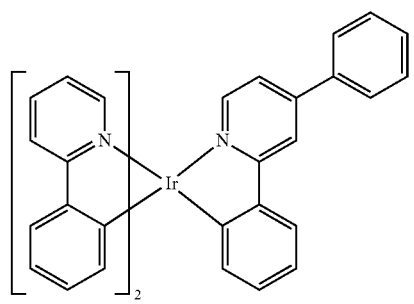
IC1
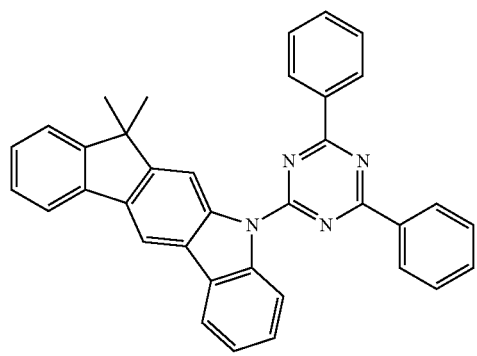 [SMILES: CC1(C)c2ccccc2-c2cc3c4ccccc4n(-c4nc(-c5ccccc5)nc(-c5ccccc5)n4)c3cc21]

TABLE 3-continued
Structural formulae of the materials for the OLEDs
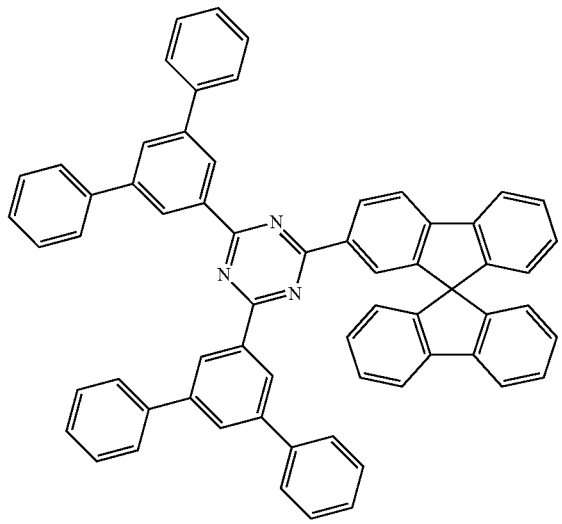 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
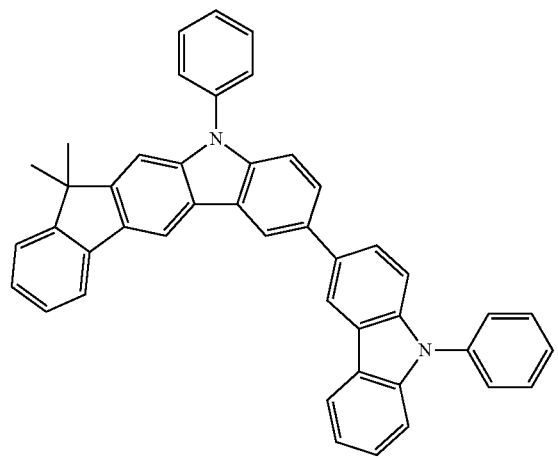 [SMILES: CC1(C)c2ccccc2-c2cc3c4cc(-c5ccc6c(c5)c5ccccc5n6-c5ccccc5)ccc4n(-c4ccccc4)c3cc21]
IC3
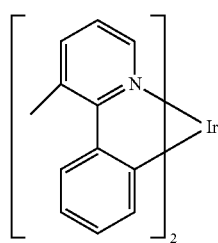
TEG1

TABLE 3-continued
Structural formulae of the materials for the OLEDs
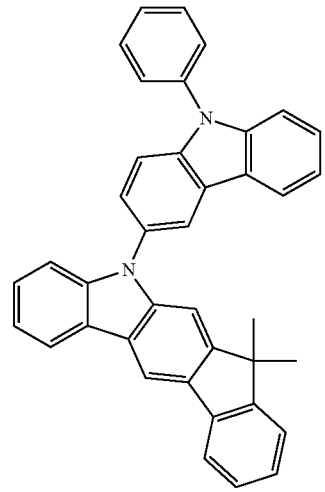 [SMILES: CC1(C)c2ccccc2-c2cc3c4ccccc4n(-c4ccc5c(c4)c4ccccc4n5-c4ccccc4)c3cc21]
IC4
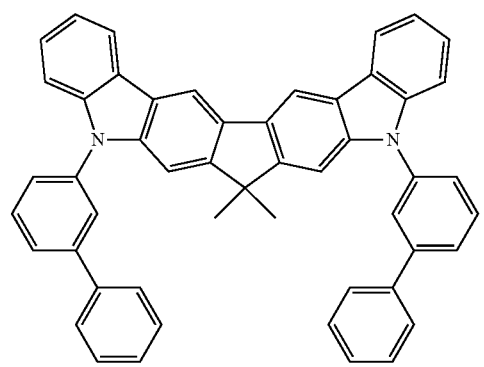 [SMILES: CC1(C)c2cc3c(cc2-c2cc4c5ccccc5n(-c5cccc(-c6ccccc6)c5)c4cc21)c1ccccc1n3-c1cccc(-c2ccccc2)c1]
IC5
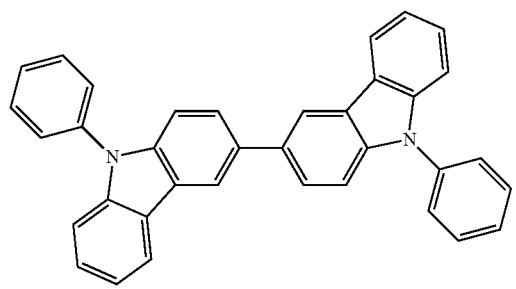 [SMILES: c1ccc(-n2c3ccccc3c3cc(-c4ccc5c(c4)c4ccccc4n5-c4ccccc4)ccc32)cc1]
IC6

TABLE 3-continued
Structural formulae of the materials for the OLEDs
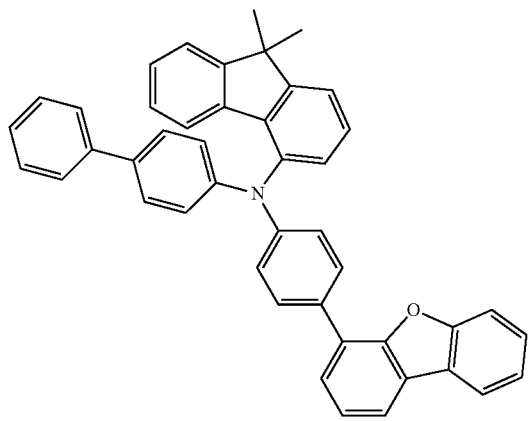 [SMILES: CC1(C)c2ccccc2-c2c(N(c3ccc(-c4ccccc4)cc3)c3ccc(-c4cccc5c4oc4ccccc45)cc3)cccc21]
IC7
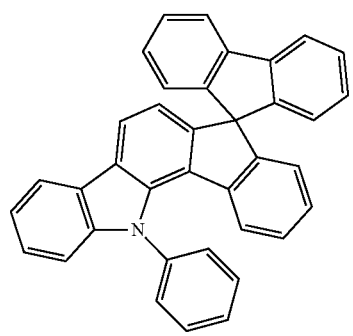 [SMILES: c1ccc(-n2c3ccccc3c3ccc4c(c32)-c2ccccc2C42c3ccccc3-c3ccccc32)cc1]
IC8
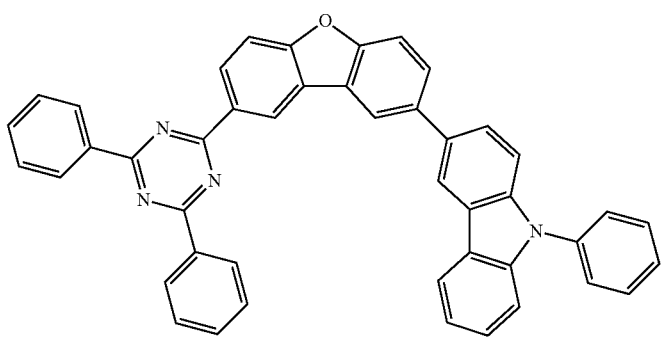 [SMILES: c1ccc(-c2nc(-c3ccccc3)nc(-c3ccc4oc5ccc(-c6ccc7c(c6)c6ccccc6n7-c6ccccc6)cc5c4c3)n2)cc1]
SdT1
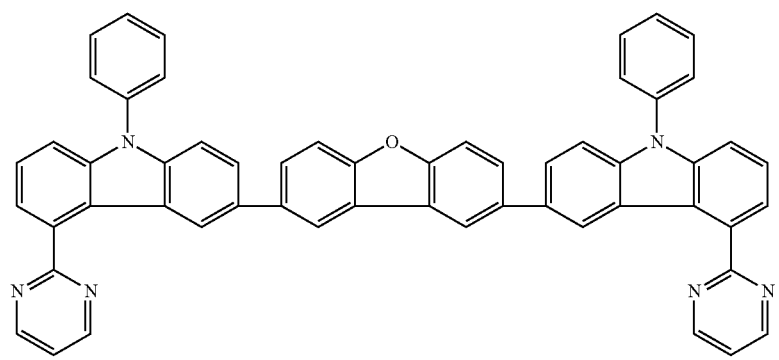
SdT2

TABLE 3-continued
Structural formulae of the materials for the OLEDs
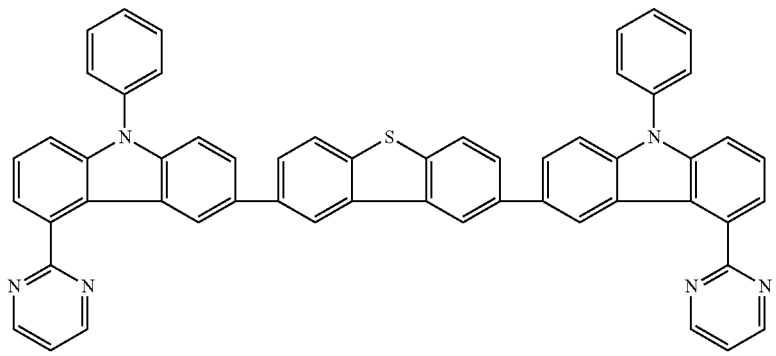 [SMILES: c1ccc(-n2c3ccc(-c4ccc5oc6ccc(-c7ccc8c(c7)c7c(-c9ncccn9)cccc7n8-c7ccccc7)cc6c5c4)cc3c3c(-c4ncccn4)cccc32)cc1]
SdT3
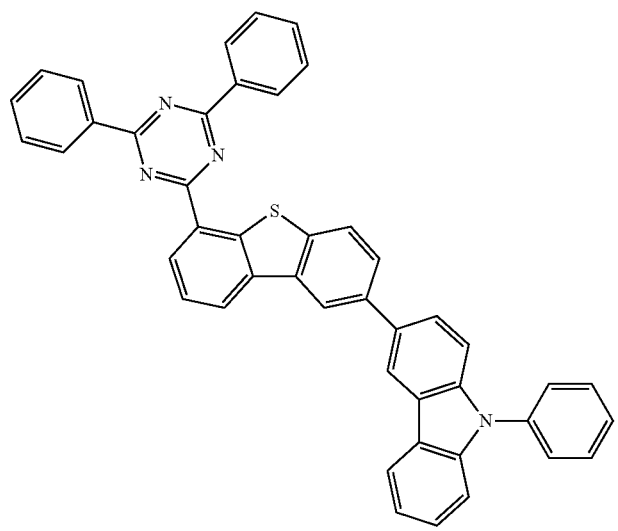 [SMILES: c1ccc(-c2nc(-c3ccccc3)nc(-c3cccc4c3sc3ccc(-c5ccc6c(c5)c5ccccc5n6-c5ccccc5)cc34)n2)cc1]
SdT4
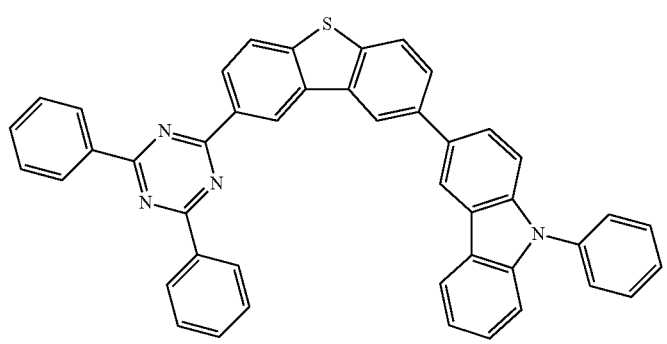 [SMILES: c1ccc(-c2nc(-c3ccccc3)nc(-c3ccc4sc5ccc(-c6ccc7c(c6)c6ccccc6n7-c6ccccc6)cc5c4c3)n2)cc1]
SdT5

TABLE 3-continued
Structural formulae of the materials for the OLEDs
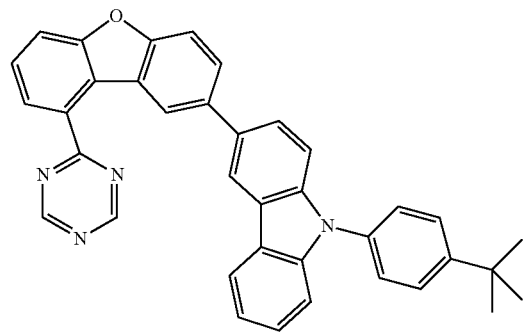 [SMILES: CC(C)(C)c1ccc(-n2c3ccccc3c3cc(-c4ccc5oc6cccc(-c7ncncn7)c6c5c4)ccc32)cc1]
SdT6
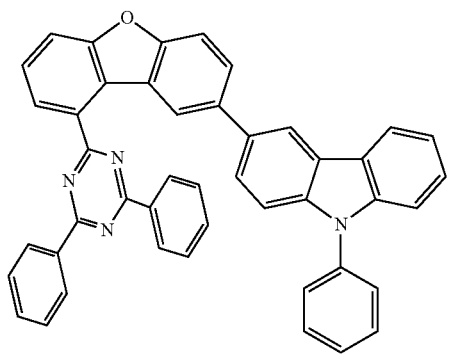 [SMILES: c1ccc(-c2nc(-c3ccccc3)nc(-c3cccc4oc5ccc(-c6ccc7c(c6)c6ccccc6n7-c6ccccc6)cc5c34)n2)cc1]
EG1
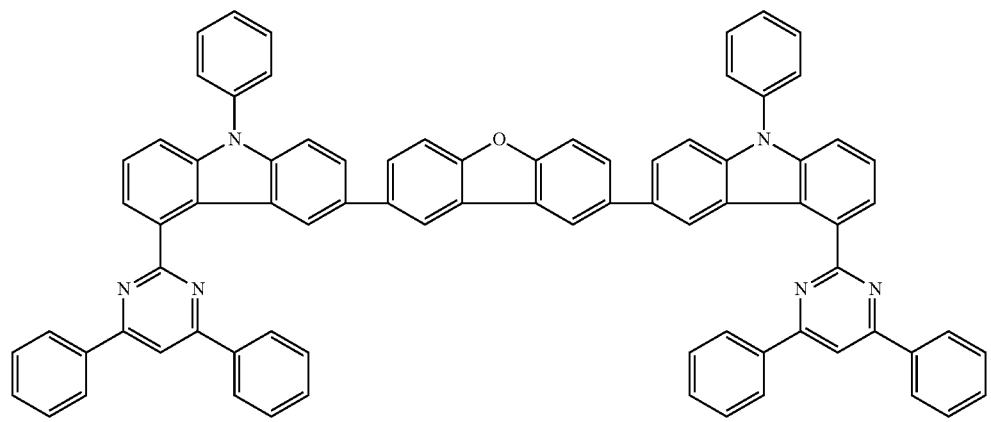
EG2

TABLE 3-continued
Structural formulae of the materials for the OLEDs
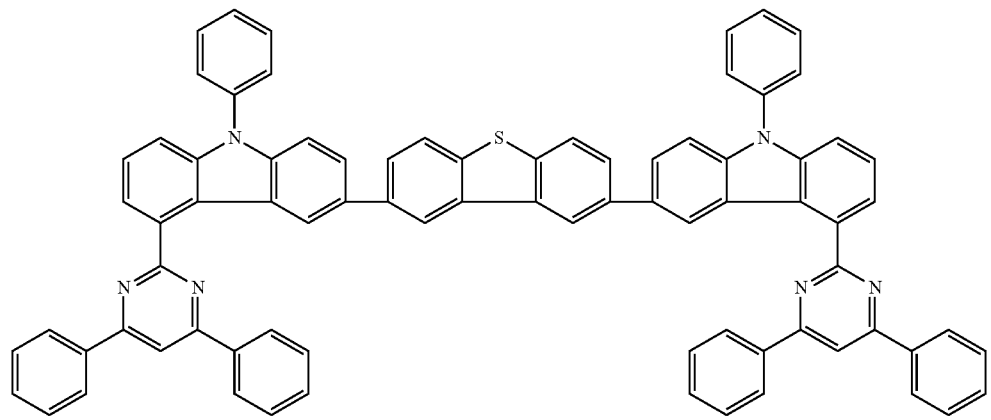 [SMILES: c1ccc(-c2cc(-c3ccccc3)nc(-c3cccc4c3c3cc(-c5ccc6oc7ccc(-c8ccc9c(c8)c8c(-c%10nc(-c%11ccccc%11)cc(-c%11ccccc%11)n%10)cccc8n9-c8ccccc8)cc7c6c5)ccc3n4-c3ccccc3)n2)cc1]
EG3
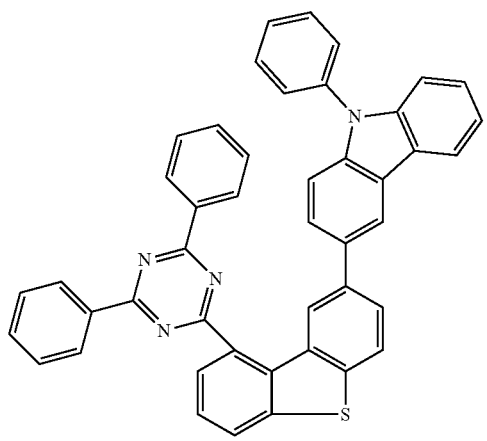 [SMILES: c1ccc(-c2nc(-c3ccccc3)nc(-c3cccc4sc5ccc(-c6ccc7c(c6)c6ccccc6n7-c6ccccc6)cc5c34)n2)cc1]
EG4
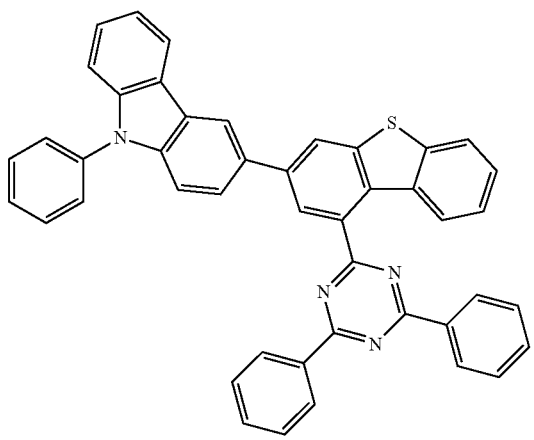 [SMILES: c1ccc(-c2nc(-c3ccccc3)nc(-c3cc(-c4ccc5c(c4)c4ccccc4n5-c4ccccc4)cc4sc5ccccc5c34)n2)cc1]
EG5

TABLE 3-continued
Structural formulae of the materials for the OLEDs
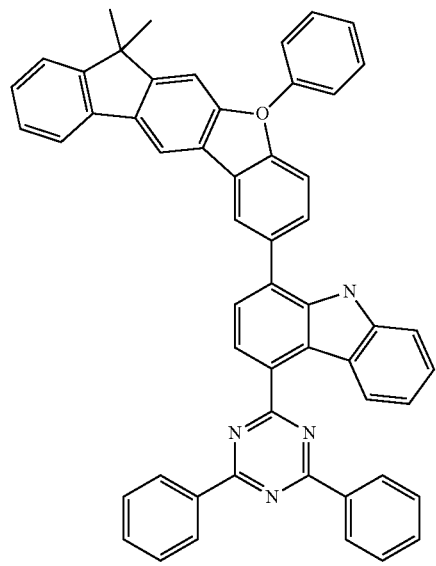
EG6
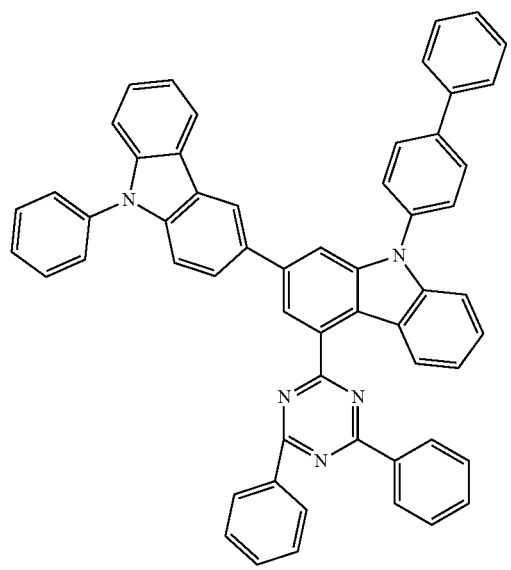 [SMILES: c1ccc(-c2ccc(-n3c4ccccc4c4c(-c5nc(-c6ccccc6)nc(-c6ccccc6)n5)cc(-c5ccc6c(c5)c5ccccc5n6-c5ccccc5)cc43)cc2)cc1]
EG7

TABLE 3-continued
Structural formulae of the materials for the OLEDs
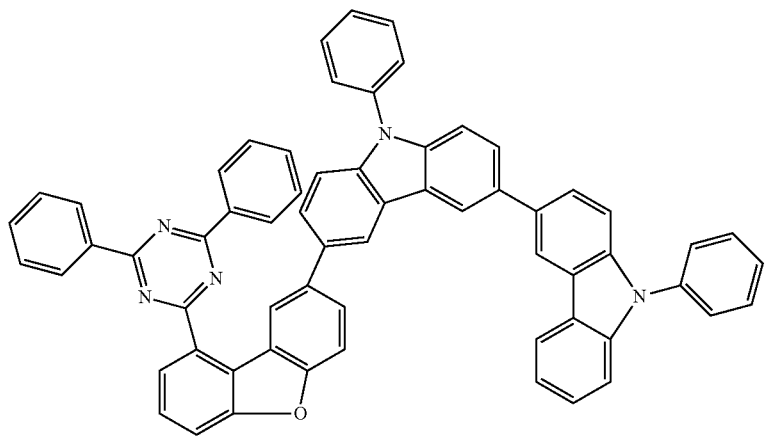 [SMILES: c1ccc(-c2nc(-c3ccccc3)nc(-c3cccc4oc5ccc(-c6ccc7c(c6)c6cc(-c8ccc9c(c8)c8ccccc8n9-c8ccccc8)ccc6n7-c6ccccc6)cc5c34)n2)cc1]
EG8
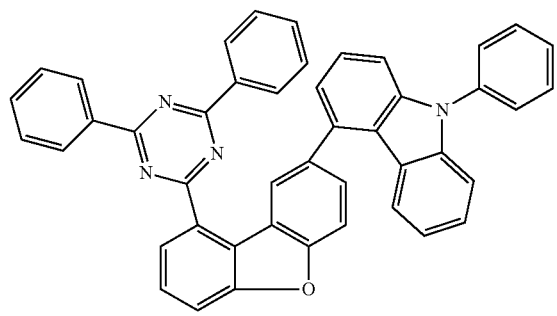 [SMILES: c1ccc(-c2nc(-c3ccccc3)nc(-c3cccc4oc5ccc(-c6cccc7c6c6ccccc6n7-c6ccccc6)cc5c34)n2)cc1]
EG9
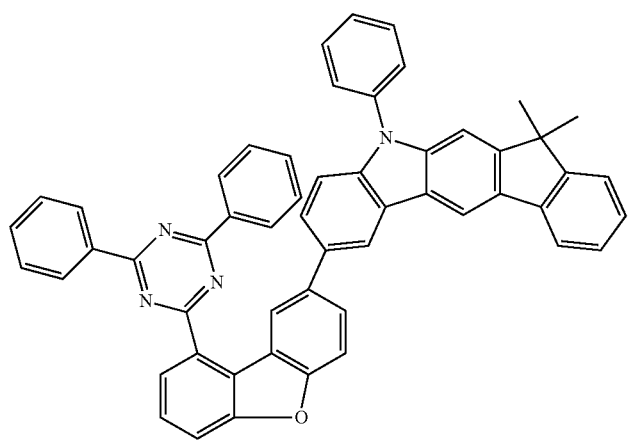 [SMILES: CC1(C)c2ccccc2-c2cc3c4cc(-c5ccc6oc7cccc(-c8nc(-c9ccccc9)nc(-c9ccccc9)n8)c7c6c5)ccc4n(-c4ccccc4)c3cc21]
EG10

TABLE 3-continued
Structural formulae of the materials for the OLEDs
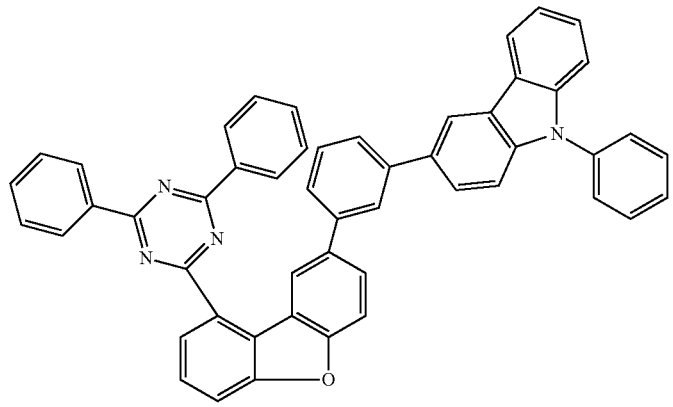 [SMILES: c1ccc(-c2nc(-c3ccccc3)nc(-c3cccc4oc5ccc(-c6cccc(-c7ccc8c(c7)c7ccccc7n8-c7ccccc7)c6)cc5c34)n2)cc1]
EG11
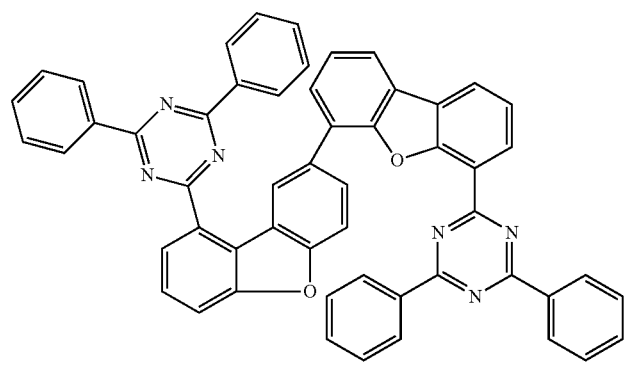 [SMILES: c1ccc(-c2nc(-c3ccccc3)nc(-c3cccc4c3oc3c(-c5ccc6oc7cccc(-c8nc(-c9ccccc9)nc(-c9ccccc9)n8)c7c6c5)cccc34)n2)cc1]
E12
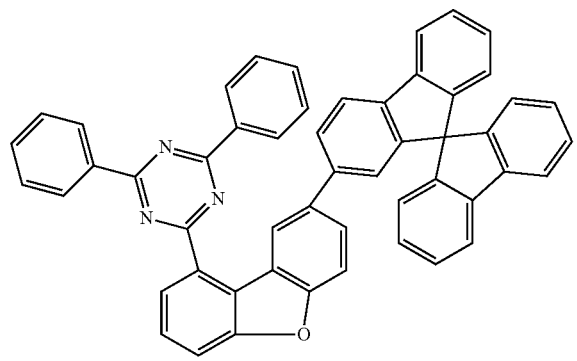 [SMILES: c1ccc(-c2nc(-c3ccccc3)nc(-c3cccc4oc5ccc(-c6ccc7c(c6)C6(c8ccccc8-c8ccccc86)c6ccccc6-7)cc5c34)n2)cc1]
EG13
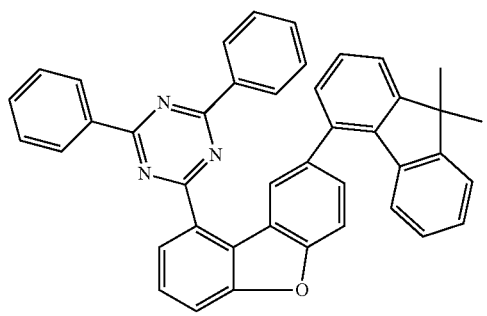 [SMILES: CC1(C)c2ccccc2-c2c(-c3ccc4oc5cccc(-c6nc(-c7ccccc7)nc(-c7ccccc7)n6)c5c4c3)cccc21]
EG14

TABLE 3-continued
Structural formulae of the materials for the OLEDs
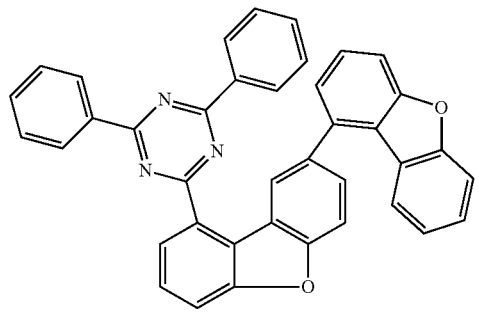 [SMILES: c1ccc(-c2nc(-c3ccccc3)nc(-c3cccc4oc5ccc(-c6cccc7oc8ccccc8c67)cc5c34)n2)cc1]
EG15
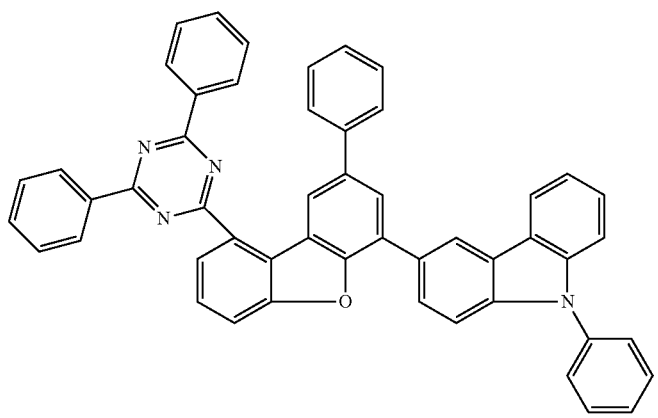 [SMILES: c1ccc(-c2cc(-c3ccc4c(c3)c3ccccc3n4-c3ccccc3)c3oc4cccc(-c5nc(-c6ccccc6)nc(-c6ccccc6)n5)c4c3c2)cc1]
EG16
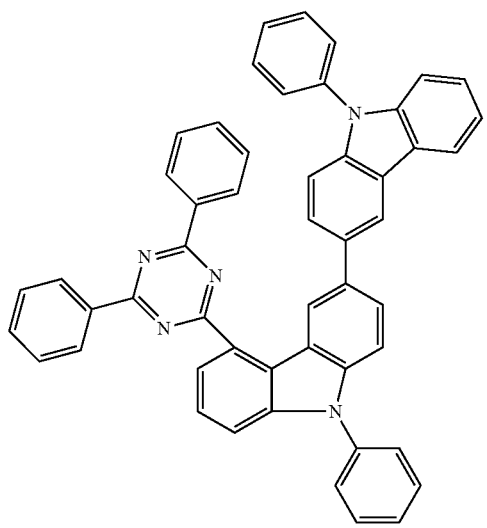 [SMILES: c1ccc(-c2nc(-c3ccccc3)nc(-c3cccc4c3c3cc(-c5ccc6c(c5)c5ccccc5n6-c5ccccc5)ccc3n4-c3ccccc3)n2)cc1]
EG17

TABLE 3-continued
Structural formulae of the materials for the OLEDs
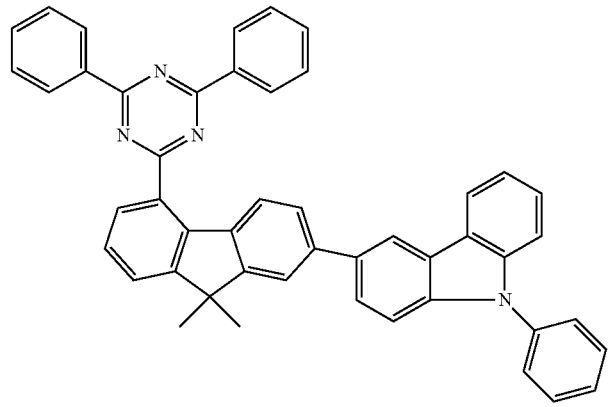 [SMILES: CC1(C)c2cc(-c3ccc4c(c3)c3ccccc3n4-c3ccccc3)ccc2-c2c(-c3nc(-c4ccccc4)nc(-c4ccccc4)n3)cccc21]
EG18
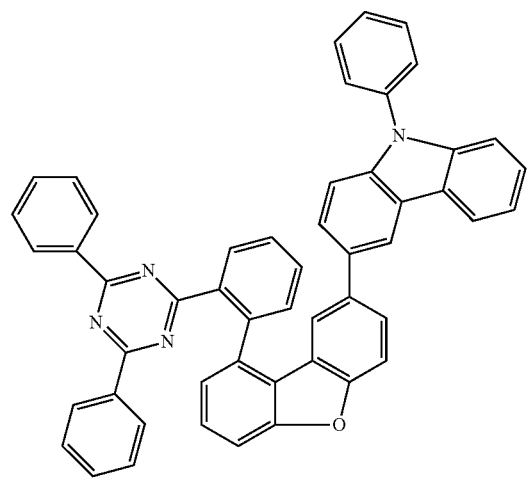 [SMILES: c1ccc(-c2nc(-c3ccccc3)nc(-c3ccccc3-c3cccc4oc5ccc(-c6ccc7c(c6)c6ccccc6n7-c6ccccc6)cc5c34)n2)cc1]
EG19
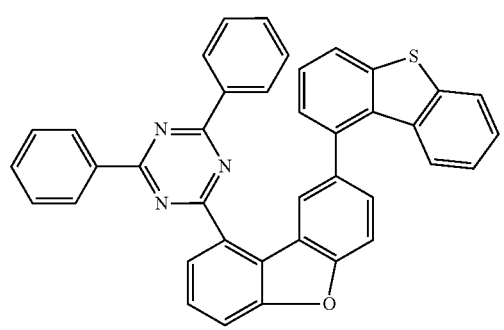 [SMILES: c1ccc(-c2nc(-c3ccccc3)nc(-c3cccc4oc5ccc(-c6cccc7sc8ccccc8c67)cc5c34)n2)cc1]
EG20

TABLE 3-continued
Structural formulae of the materials for the OLEDs
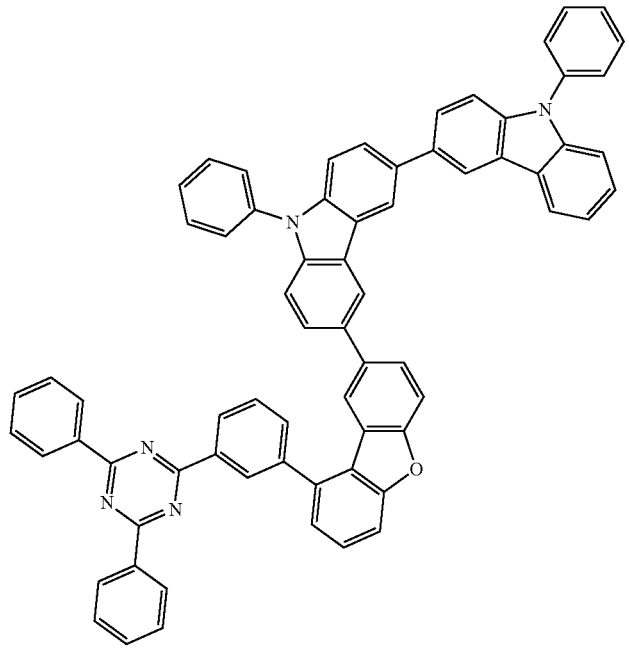 [SMILES: c1ccc(-c2nc(-c3ccccc3)nc(-c3cccc(-c4cccc5oc6ccc(-c7ccc8c(c7)c7cc(-c9ccc%10c(c9)c9ccccc9n%10-c9ccccc9)ccc7n8-c7ccccc7)cc6c45)c3)n2)cc1]
EG21
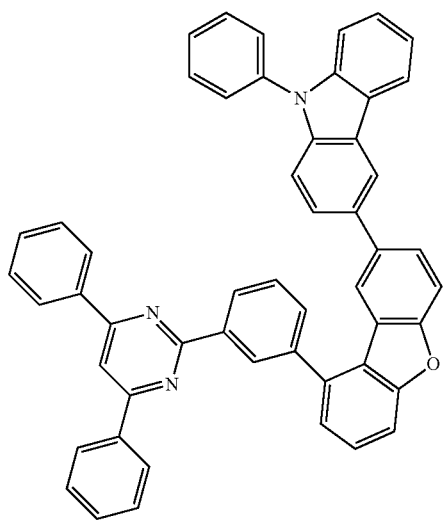 [SMILES: c1ccc(-c2cc(-c3ccccc3)nc(-c3cccc(-c4cccc5oc6ccc(-c7ccc8c(c7)c7ccccc7n8-c7ccccc7)cc6c45)c3)n2)cc1]
EG22

TABLE 3-continued
Structural formulae of the materials for the OLEDs
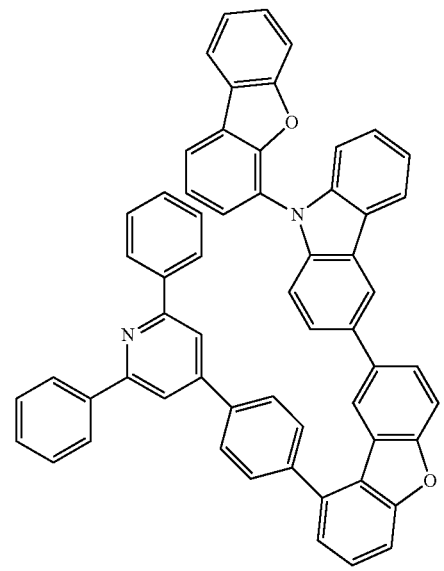 [SMILES: c1ccc(-c2cc(-c3ccc(-c4cccc5oc6ccc(-c7ccc8c(c7)c7ccccc7n8-c7cccc8c7oc7ccccc78)cc6c45)cc3)cc(-c3ccccc3)n2)cc1]
EG23
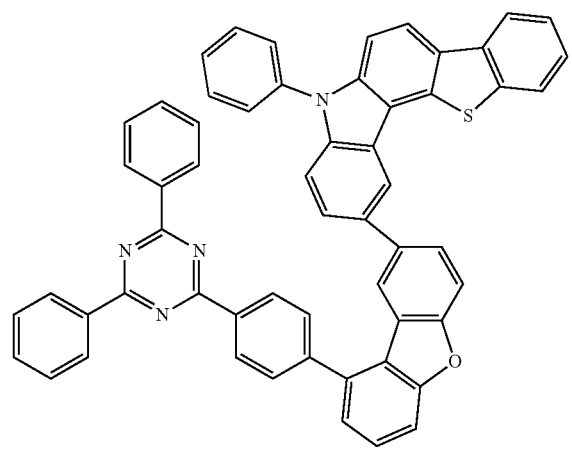 [SMILES: c1ccc(-c2nc(-c3ccccc3)nc(-c3ccc(-c4cccc5oc6ccc(-c7ccc8c(c7)c7c9sc%10ccccc%10c9ccc7n8-c7ccccc7)cc6c45)cc3)n2)cc1]
EG24
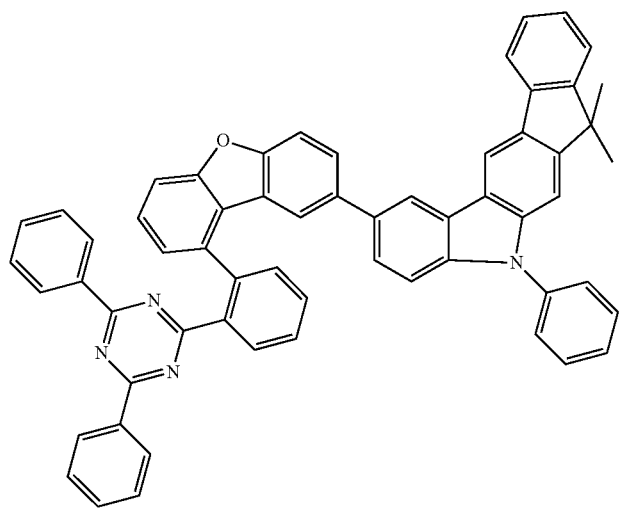 [SMILES: CC1(C)c2ccccc2-c2cc3c4cc(-c5ccc6oc7cccc(-c8ccccc8-c8nc(-c9ccccc9)nc(-c9ccccc9)n8)c7c6c5)ccc4n(-c4ccccc4)c3cc21]

TABLE 3-continued
Structural formulae of the materials for the OLEDs
EG25
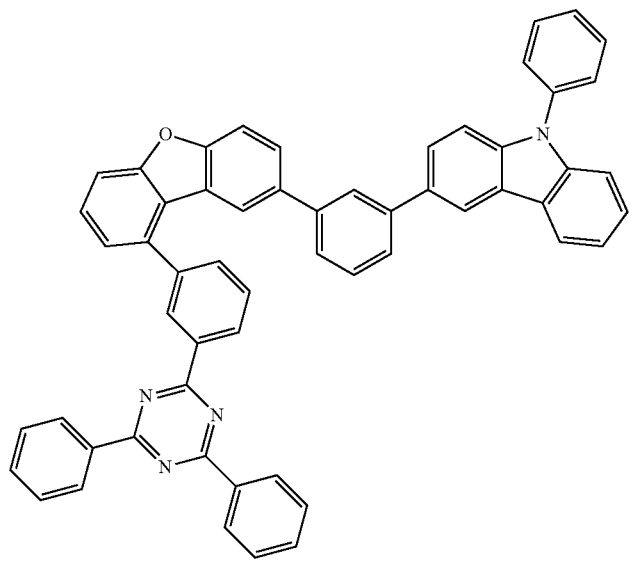 [SMILES: c1ccc(-c2nc(-c3ccccc3)nc(-c3cccc(-c4cccc5oc6ccc(-c7cccc(-c8ccc9c(c8)c8ccccc8n9-c8ccccc8)c7)cc6c45)c3)n2)cc1]
EG26
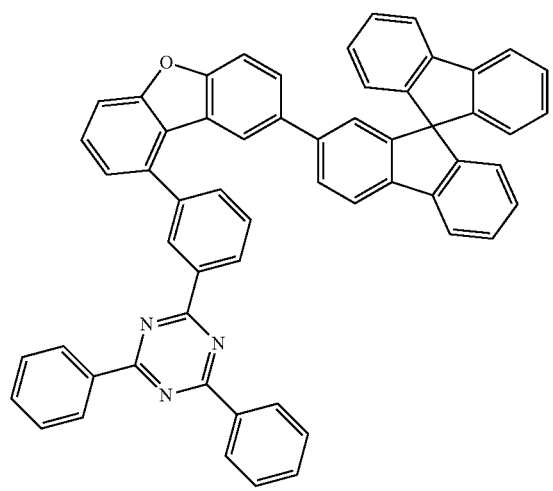 [SMILES: c1ccc(-c2nc(-c3ccccc3)nc(-c3cccc(-c4cccc5oc6ccc(-c7ccc8c(c7)C7(c9ccccc9-c9ccccc97)c7ccccc7-8)cc6c45)c3)n2)cc1]
EG27
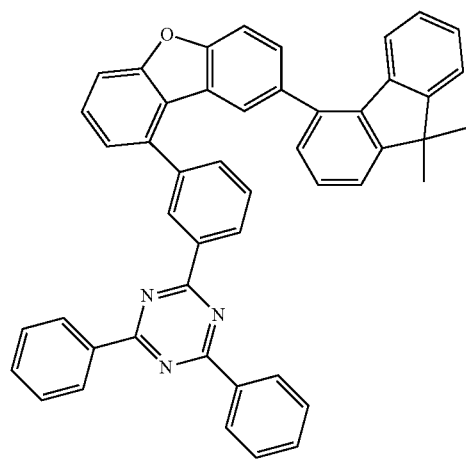 [SMILES: CC1(C)c2ccccc2-c2c(-c3ccc4oc5cccc(-c6cccc(-c7nc(-c8ccccc8)nc(-c8ccccc8)n7)c6)c5c4c3)cccc21]

TABLE 3-continued
Structural formulae of the materials for the OLEDs
EG28
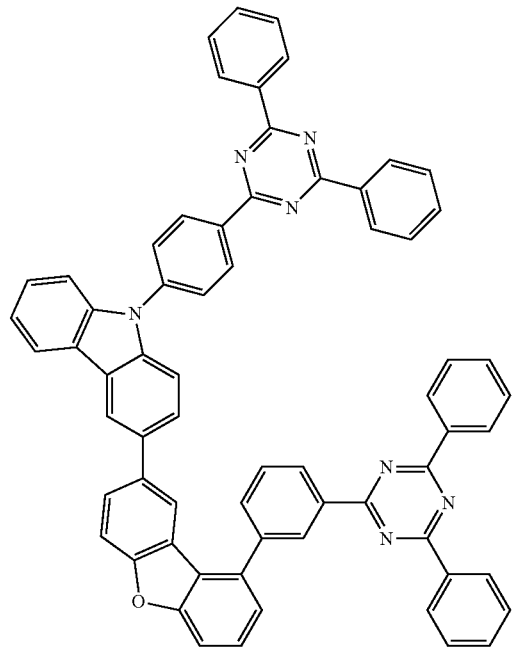 [SMILES: c1ccc(-c2nc(-c3ccccc3)nc(-c3ccc(-n4c5ccccc5c5cc(-c6ccc7oc8cccc(-c9cccc(-c%10nc(-c%11ccccc%11)nc(-c%11ccccc%11)n%10)c9)c8c7c6)ccc54)cc3)n2)cc1]
EG29
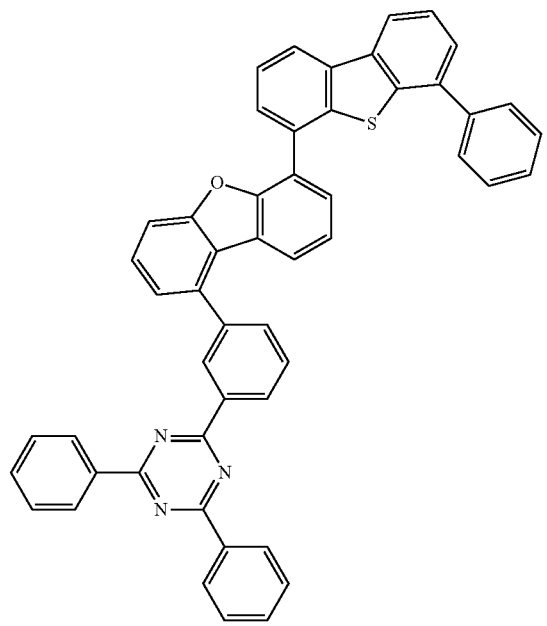 [SMILES: c1ccc(-c2nc(-c3ccccc3)nc(-c3cccc(-c4cccc5oc6c(-c7cccc8c7sc7c(-c9ccccc9)cccc78)cccc6c45)c3)n2)cc1]
EG30

The invention claimed is:
1. A mixture comprising at least one compound of the formula (2a),

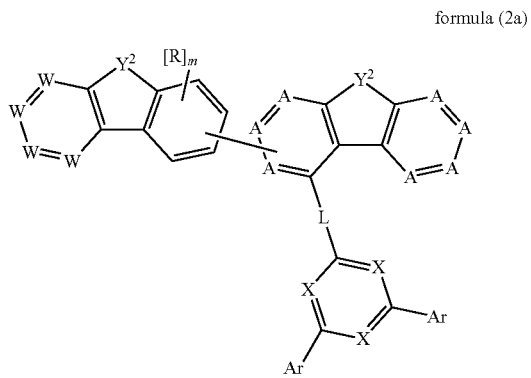

formula (2a)

where the following applies to the symbols and indices used:

A is on each occurrence, identically or differently, CR or N, where a maximum of two groups A per ring stand for N and where A stands for C if the group comprising $Y^2$ is bonded at this position;

W is on each occurrence, identically or differently, CR or N, where a maximum of two groups W stand for N, or two adjacent groups W together stand for a group of the following formula (3), where the compound of the formula (1a) contains a maximum of one group of the formula (3),

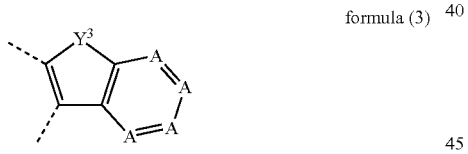

formula (3)

X is on each occurrence, identically or differently, CR or N, with the proviso that at least one group X stands for N;

Ar is on each occurrence, identically or differently, an aromatic or heteroaromatic ring system having 5 to 30 aromatic ring atoms, which may be substituted by one or more radicals R;

$Y^1$, $Y^2$, $Y^3$ are on each occurrence, identically or differently, O, NR, S or $CR^2$, where the radical R which is bonded to N is not equal to H;

L is on each occurrence, identically or differently, a single bond or an aromatic ring system having 5 to 30 aromatic ring atoms, which may be substituted by one or more radicals R;

R is selected on each occurrence, identically or differently, from the group consisting of H, D, F, Cl, Br, I, CN, $NO_2$, $N(Ar^1)_2$, $N(R^1)_2$, $C(=O)Ar^1$, $C(=O)R^1$, $P(=O)(Ar)_2$, $P(Ar^1)_2$, $B(Ar^1)_2$, $Si(Ar^1)_3$, $Si(R^1)_3$, a straight-chain alkyl, alkoxy or thioalkyl group having 1 to 20 C atoms or a branched or cyclic alkyl, alkoxy or thioalkyl group having 3 to 20 C atoms or an alkenyl group having 2 to 20 C atoms, each of which may be substituted by one or more radicals $R^1$, where one or more non-adjacent $CH_2$ groups may be replaced by $R^1C=CR^1$, $Si(R^1)_2$, C=O, C=S, C=NR, P(=O)($R^1$), SO, $SO^2$, $NR^1$, O, S or $CONR^1$ and where one or more H atoms may be replaced by D, F, Cl, Br, I, CN or $NO_2$, an aromatic or heteroaromatic ring system having 5 to 40 aromatic ring atoms, which may in each case be substituted by one or more radicals $R^1$, an aryloxy or heteroaryloxy group having 5 to 40 aromatic ring atoms, which may be substituted by one or more radicals R', or an aralkyl or heteroalkyl group having 5 to 40 aromatic ring atoms, which may be substituted by one or more radicals $R^1$; two substituents R which are bonded to the same carbon atom or to adjacent carbon atoms may optionally form a monocyclic or polycyclic, aliphatic, aromatic or heteroaromatic ring system here, which may be substituted by one or more radicals $R^1$;

$Ar^1$ is on each occurrence, identically or differently, an aromatic or heteroaromatic ring system having 5 to 30 aromatic ring atoms, which may be substituted by one or more non-aromatic radicals $R^1$; two radicals $Ar^1$ which are bonded to the same N atom, P atom or B atom may also be bridged to one another here by a single bond or a bridge selected from N(R'), $C(R^1)_2$, O or S;

m is 0, 1, 2 or 3;

$R^1$ is selected on each occurrence, identically or differently, from the group consisting of H, D, F, CN, an aliphatic hydrocarbon radical having t to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbatoms; two or more adjacent substituents $R^1$ may form a mono- or polycyclic, aliphatic ring system with one another here;

and at least one further compound, wherein the further compound is a matrix material and wherein the matrix material is a hole-transporting compound.

2. The mixture according to claim 1, wherein X is on each occurrence N.

3. The mixture according to claim 1, wherein $Y^1$ is O.

4. The mixture according to claim 1, wherein $Y^1$ is S.

5. The mixture according to claim 1, wherein $Y^1$ is NR.

6. The mixture according to claim 1, wherein $Y^1$ is $CR^2$.

7. The mixture according to claim 1, wherein the hole transporting compound is a carbazole derivative.

8. The mixture according to claim 7, wherein the carbazole derivative is a biscarbazole.

9. The mixture according to claim 1, wherein the compound of formula (2a) is selected from the group of compounds:

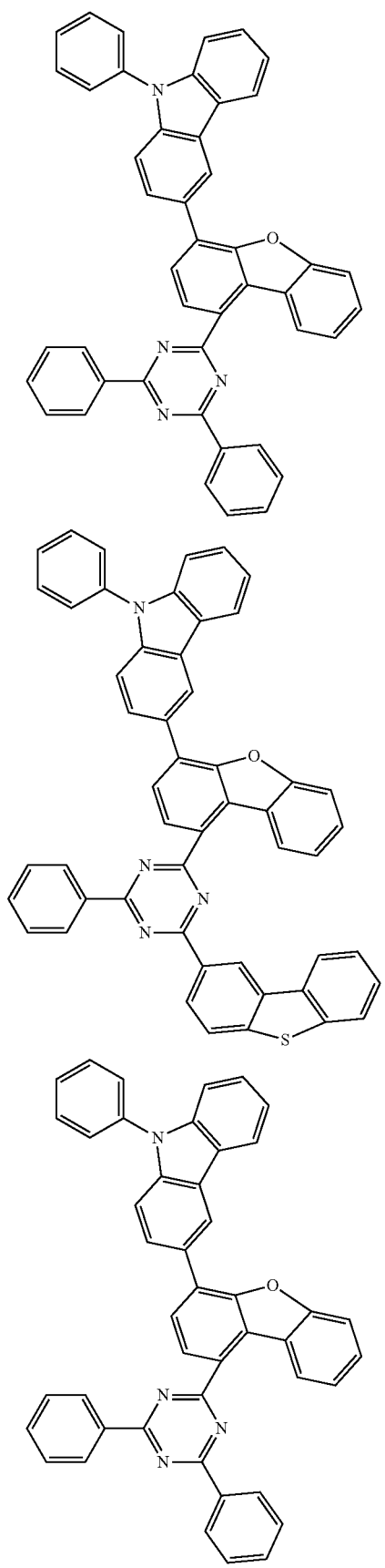

381
-continued
382
-continued
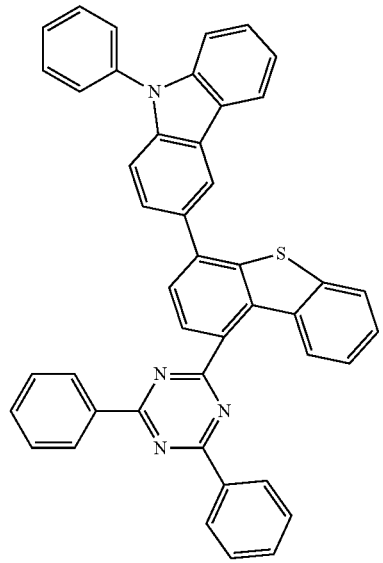
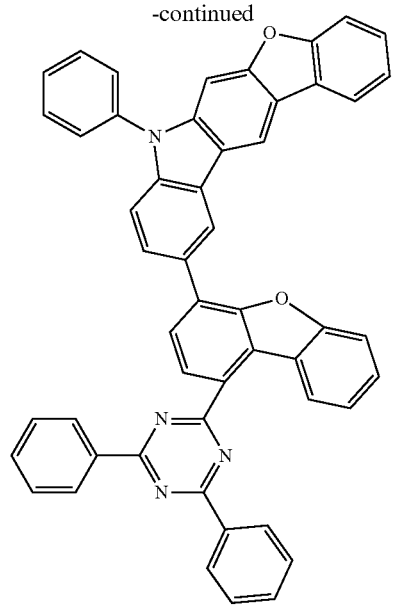
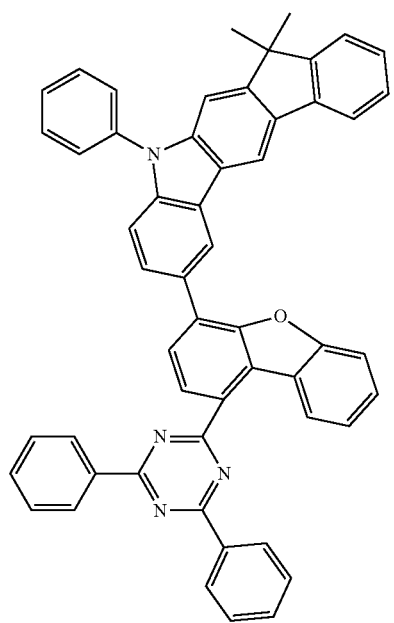
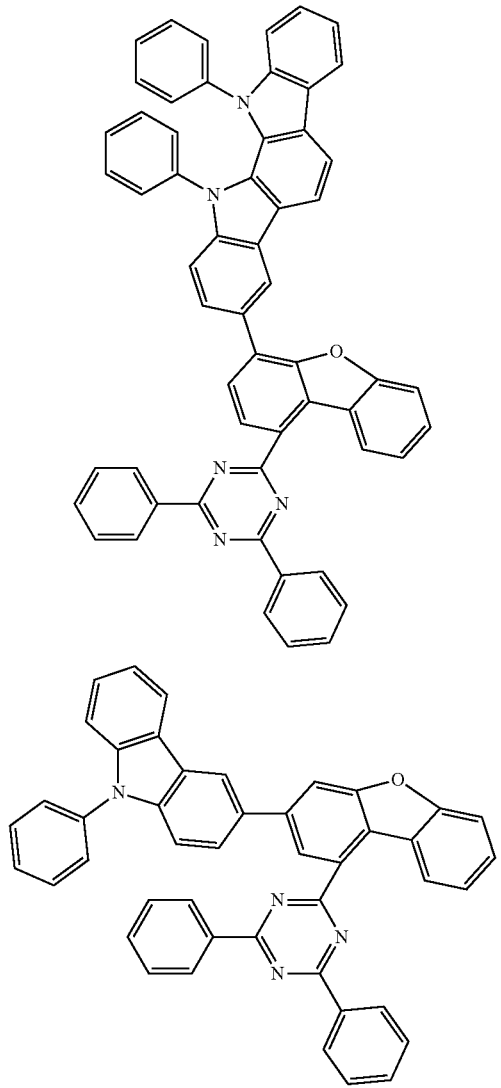

383
-continued
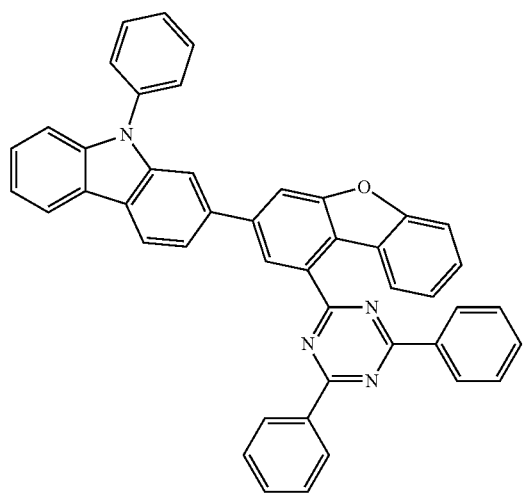
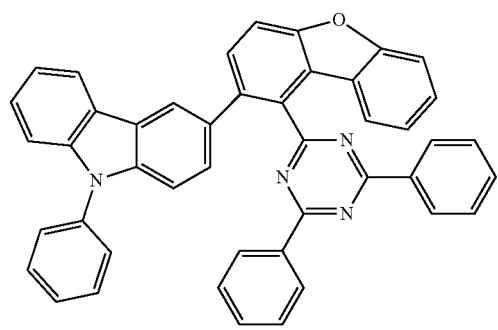
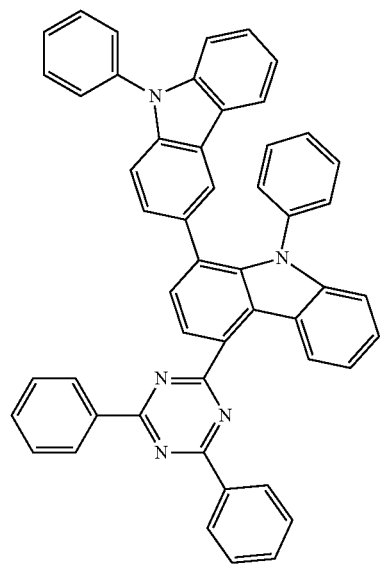
384
-continued
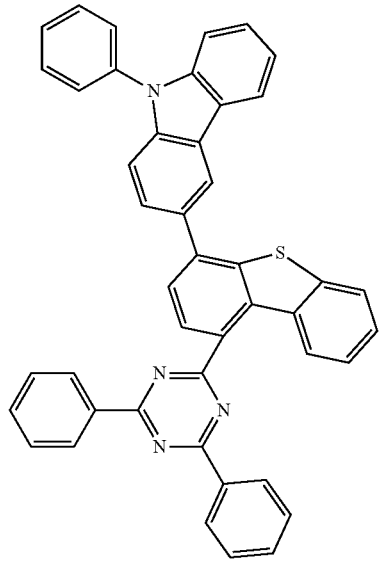
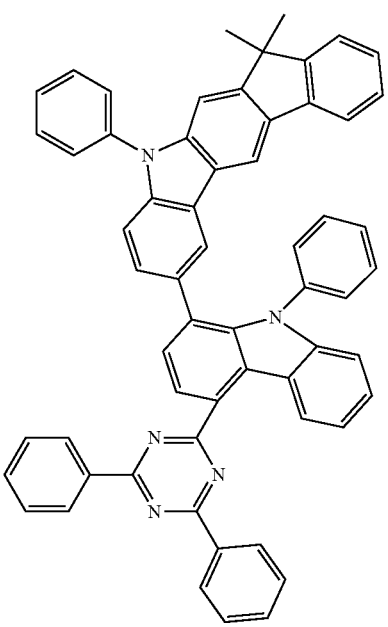

385
-continued
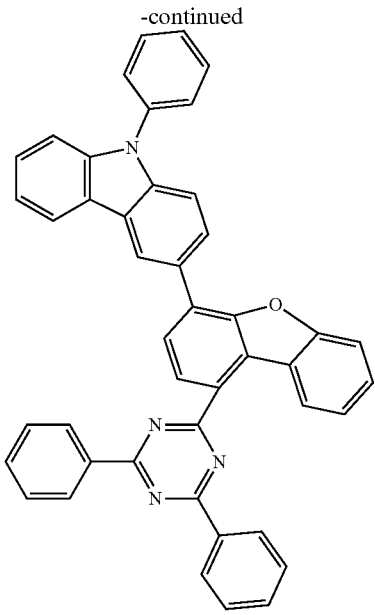
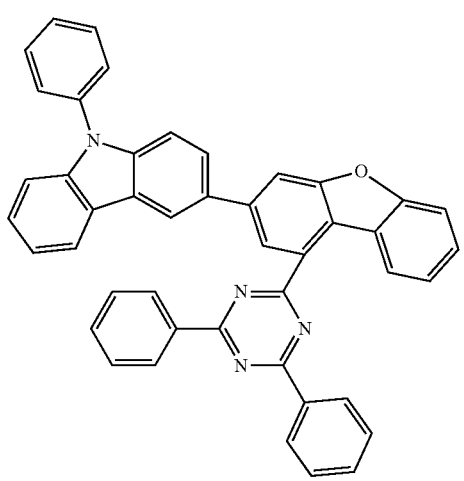
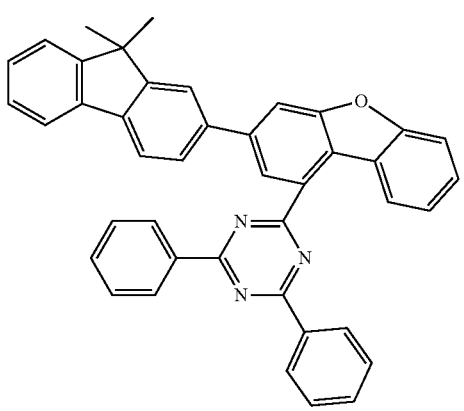
386
-continued
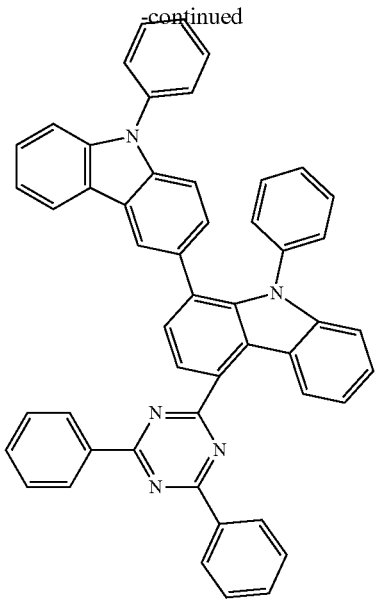
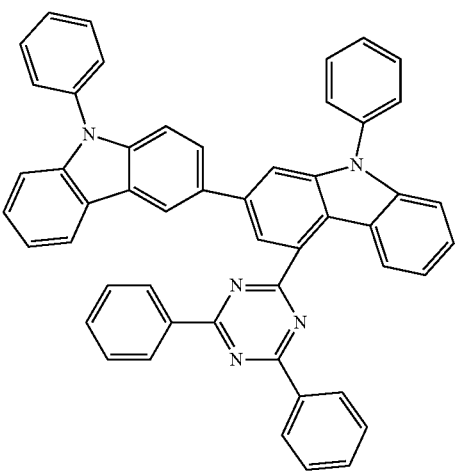
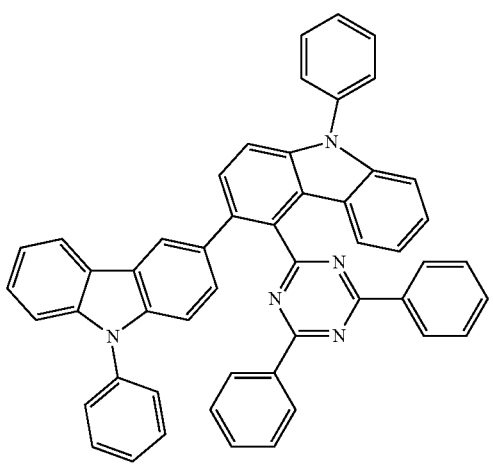

387
-continued
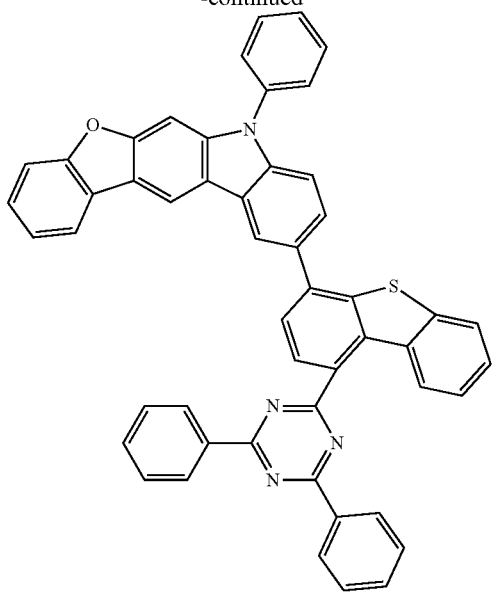
388
-continued
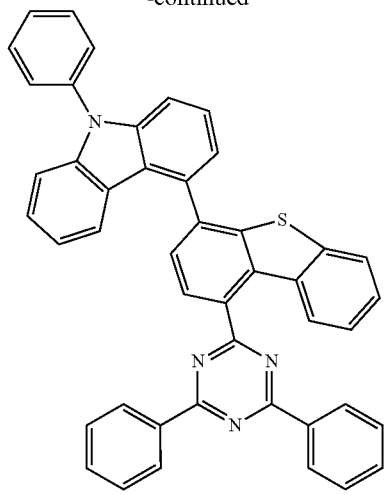
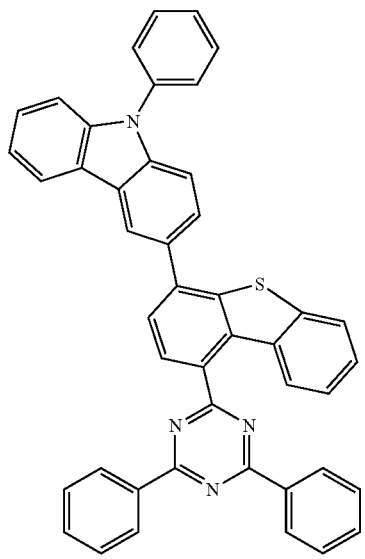
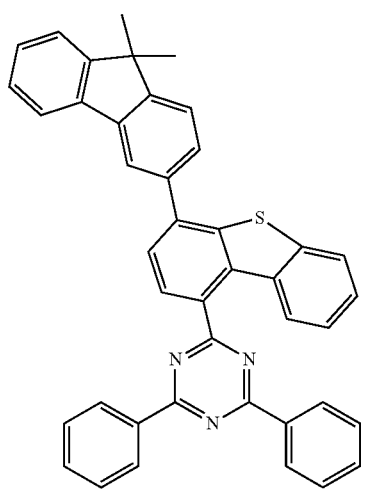

389
-continued
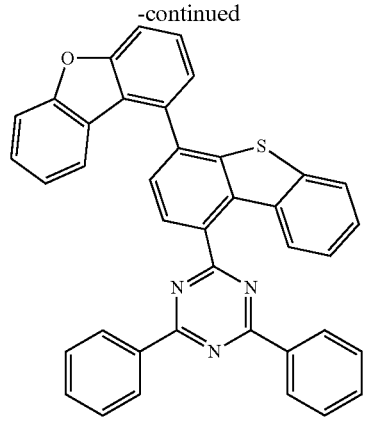
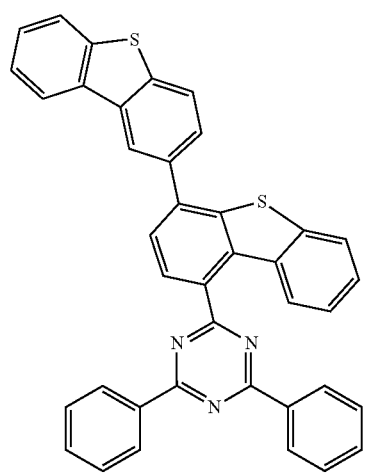
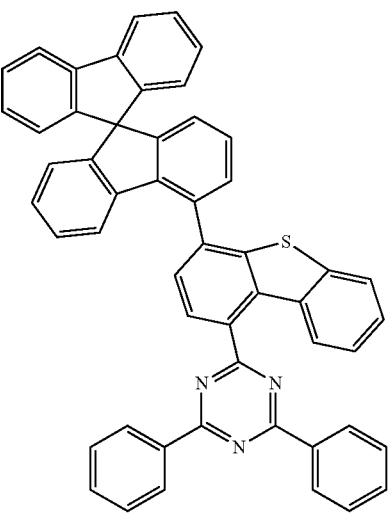
390
-continued
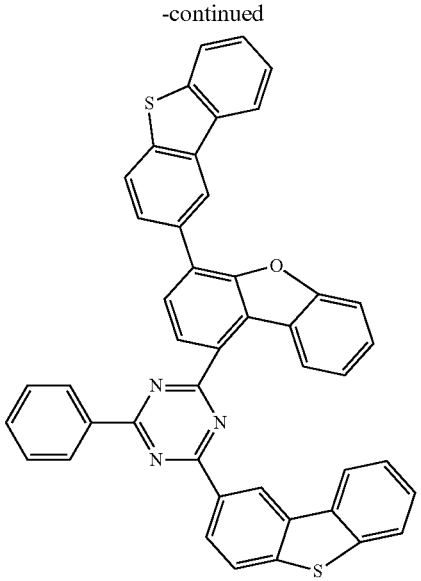
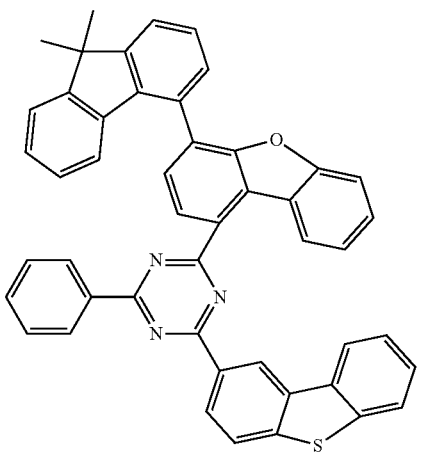
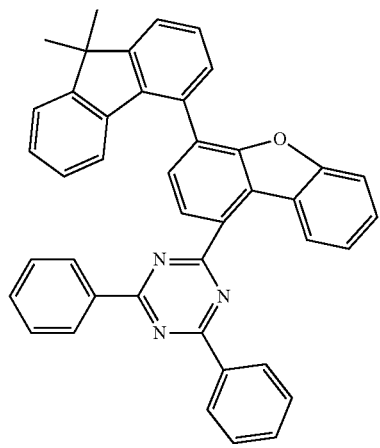

391
-continued
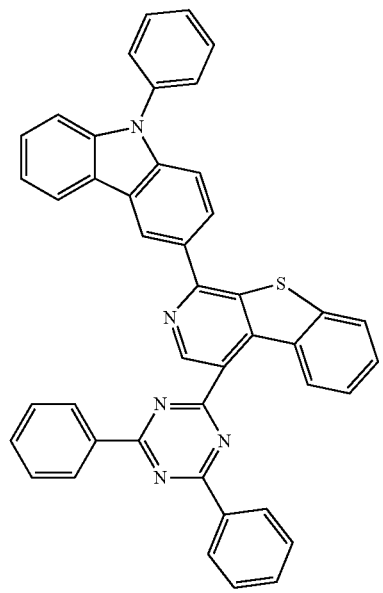
392
-continued
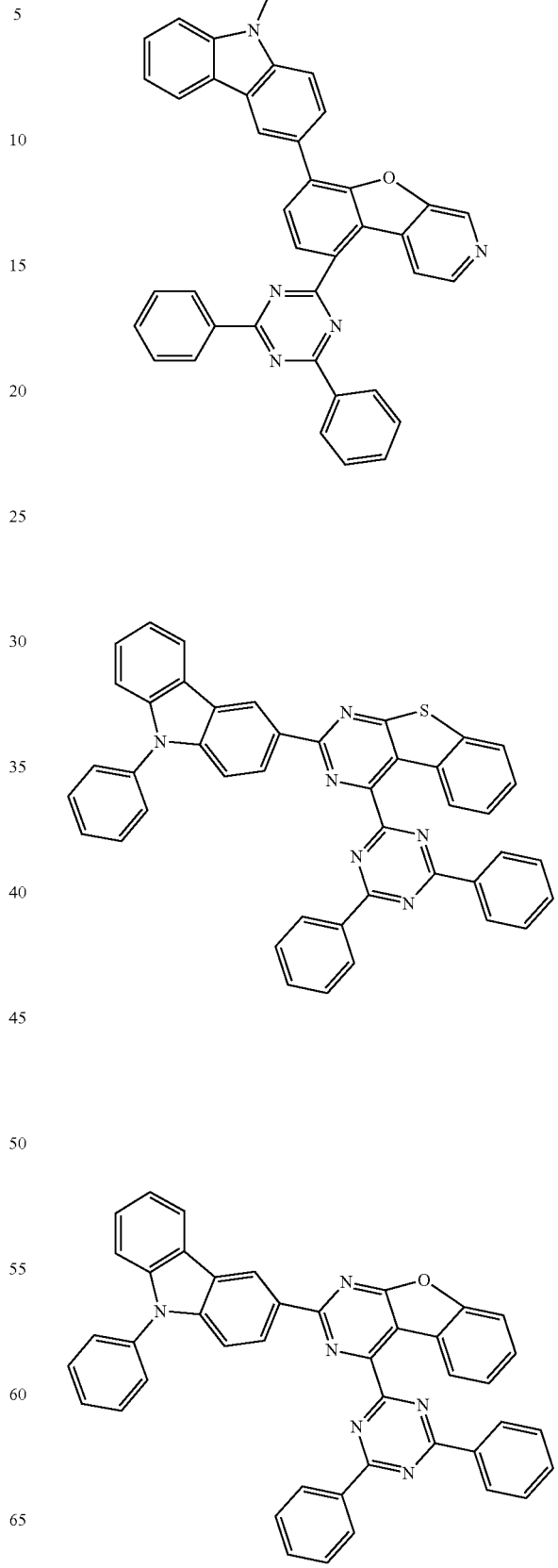

393
-continued
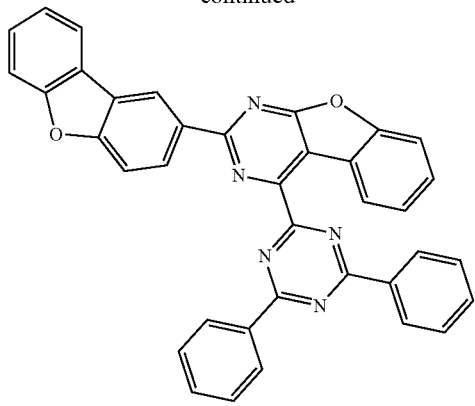
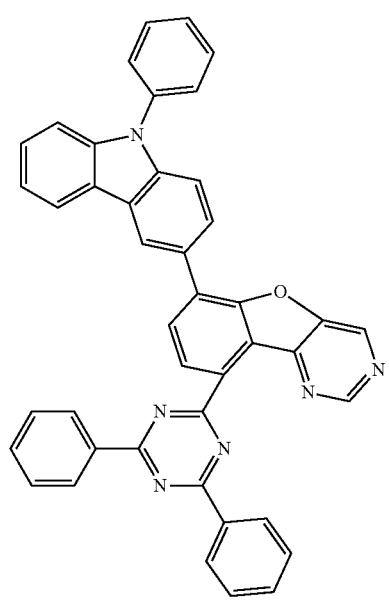
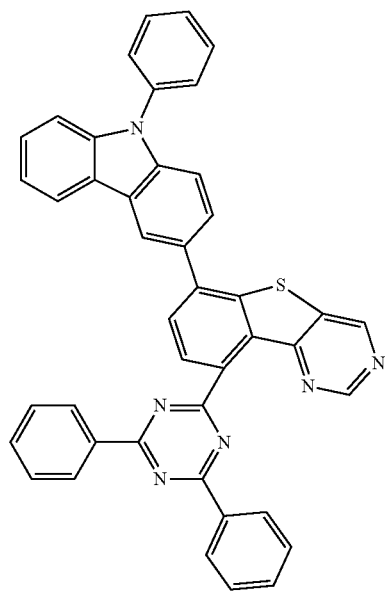
394
-continued
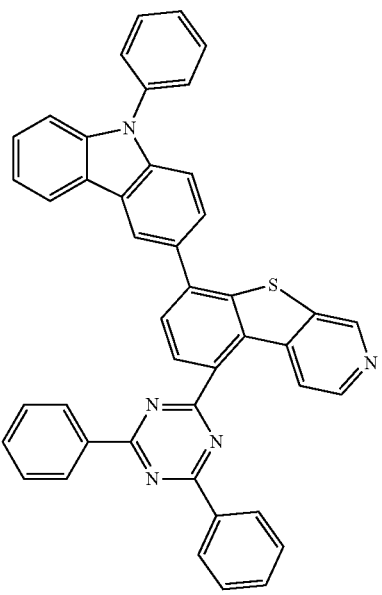
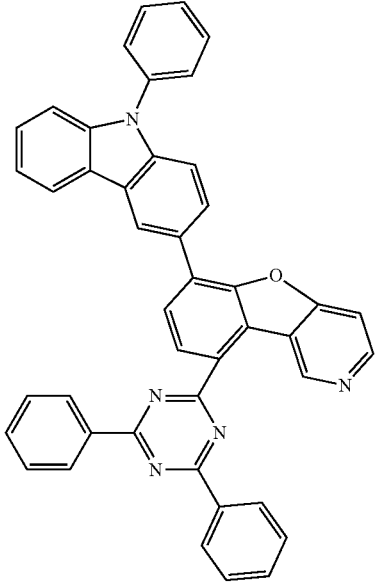

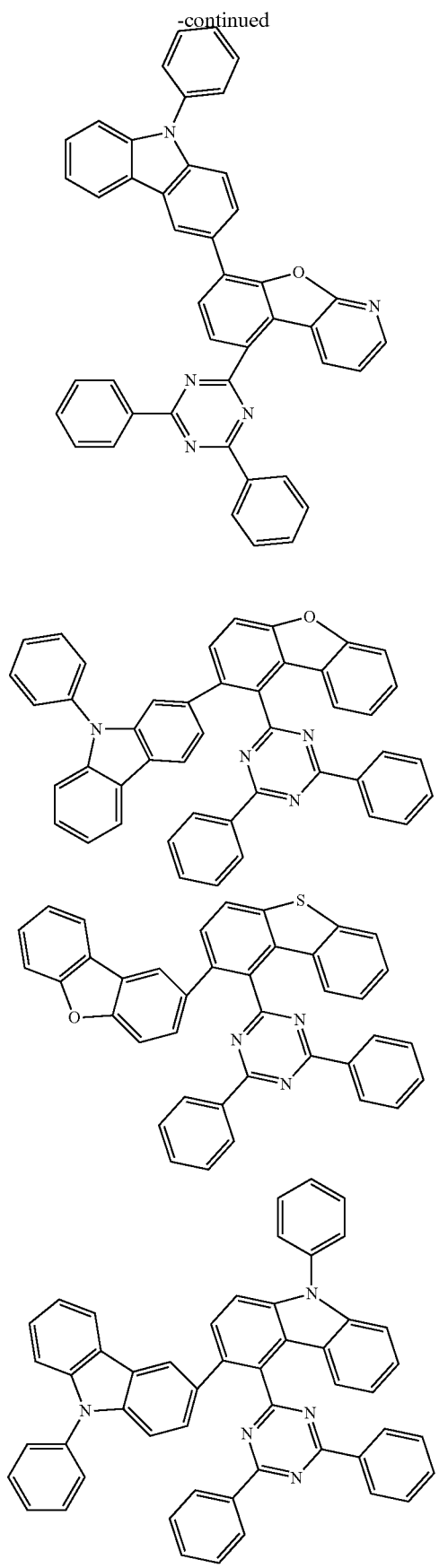
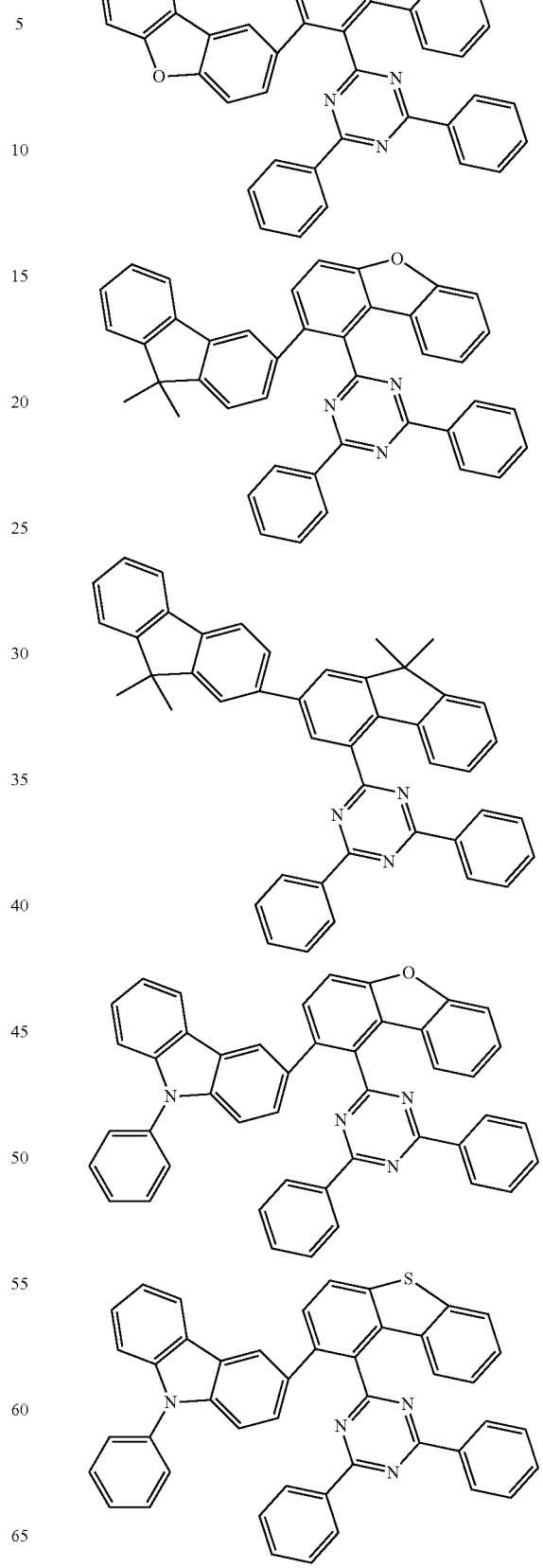

397
-continued
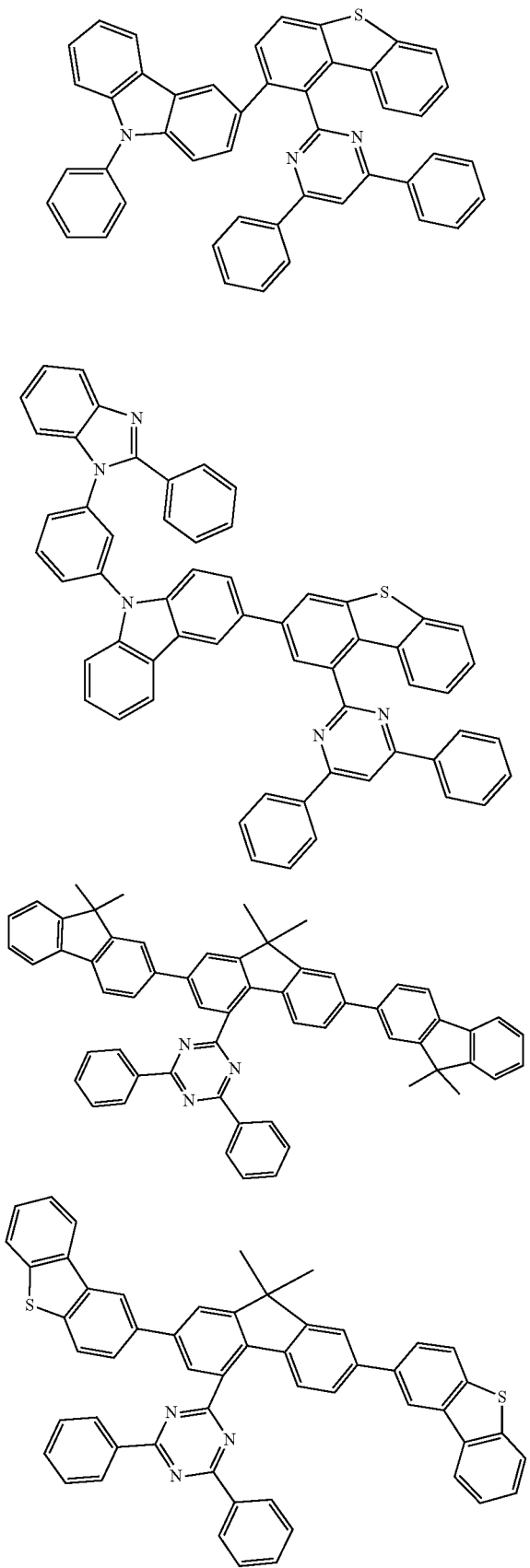
398
-continued
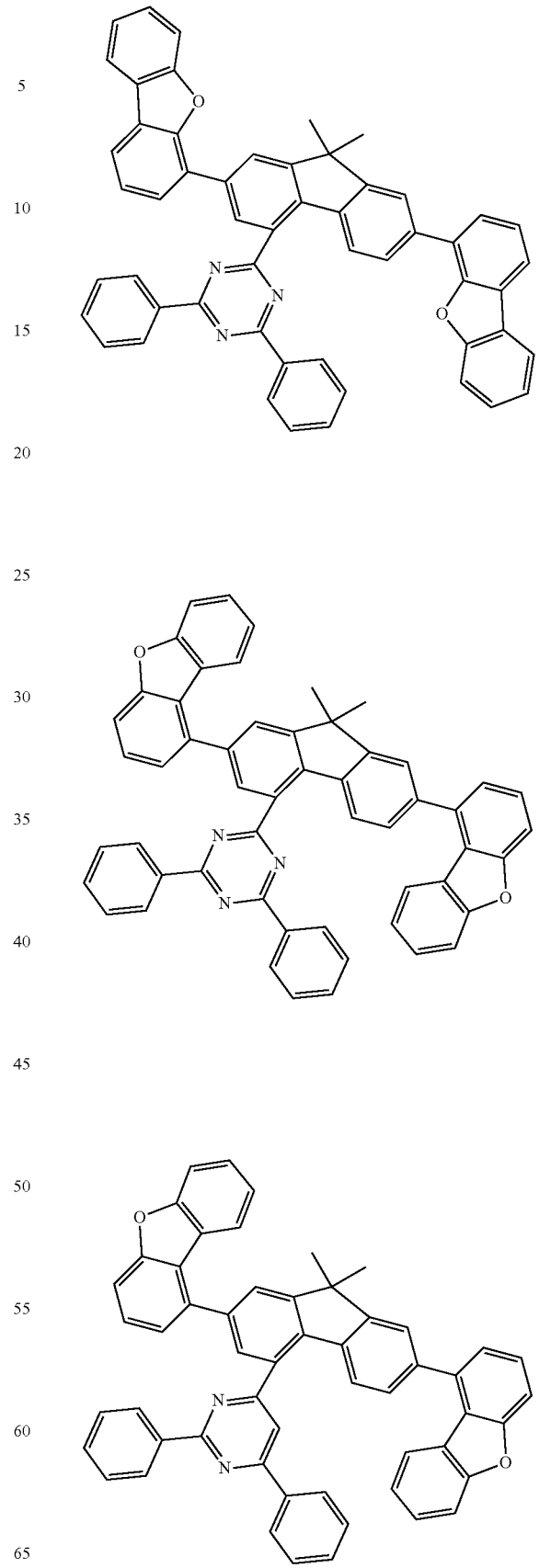

399
-continued
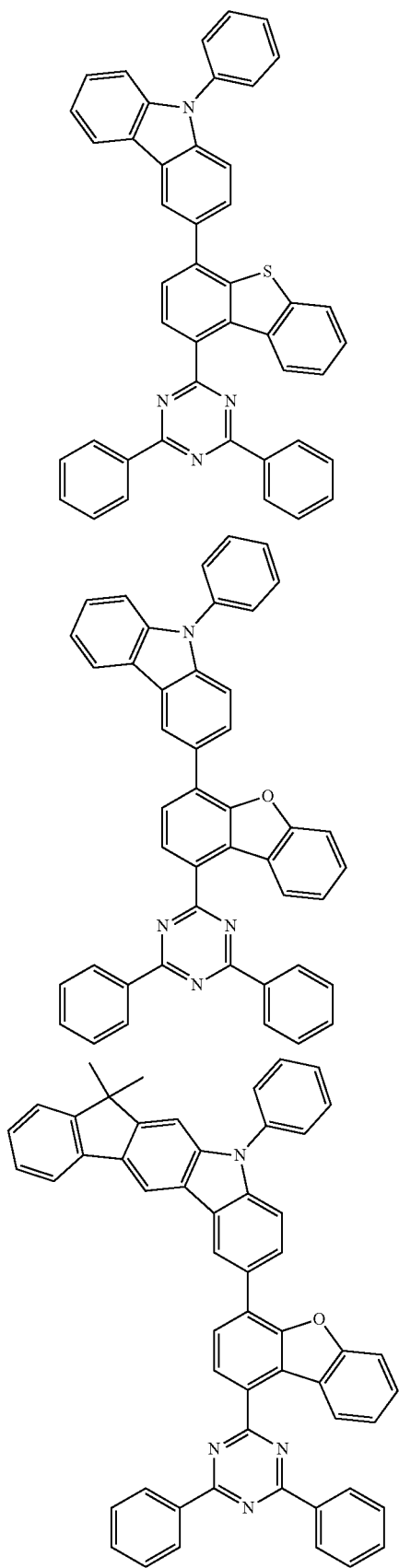
400
-continued
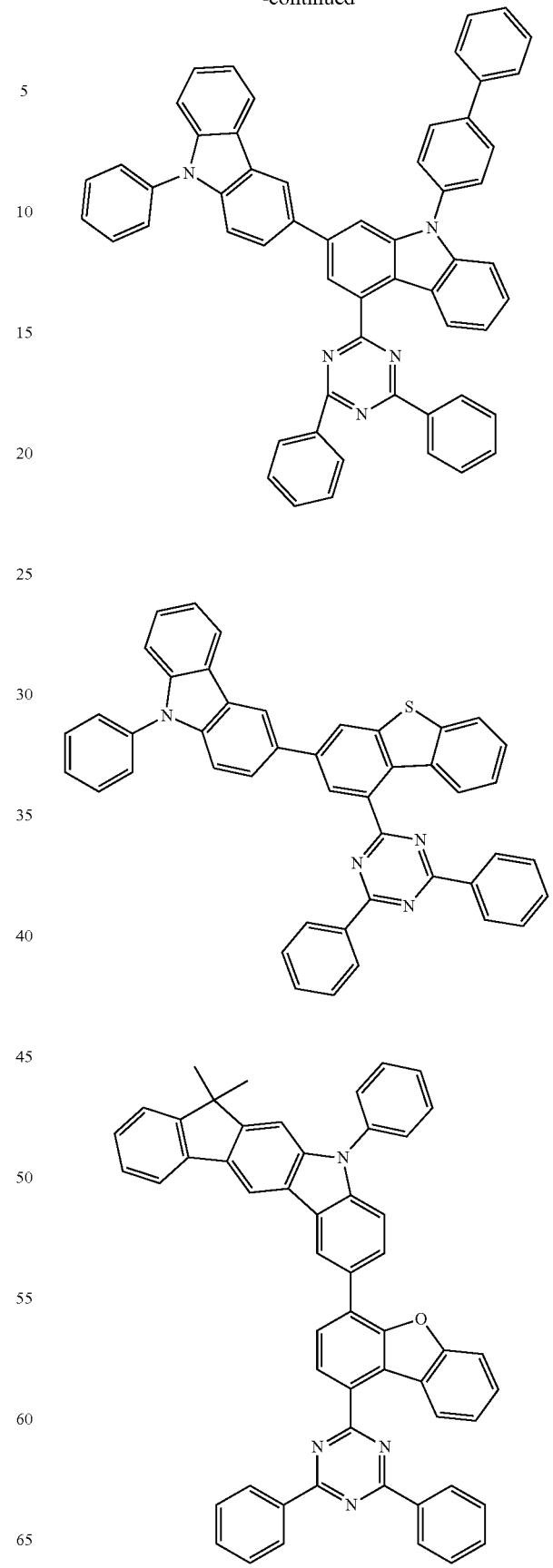

-continued

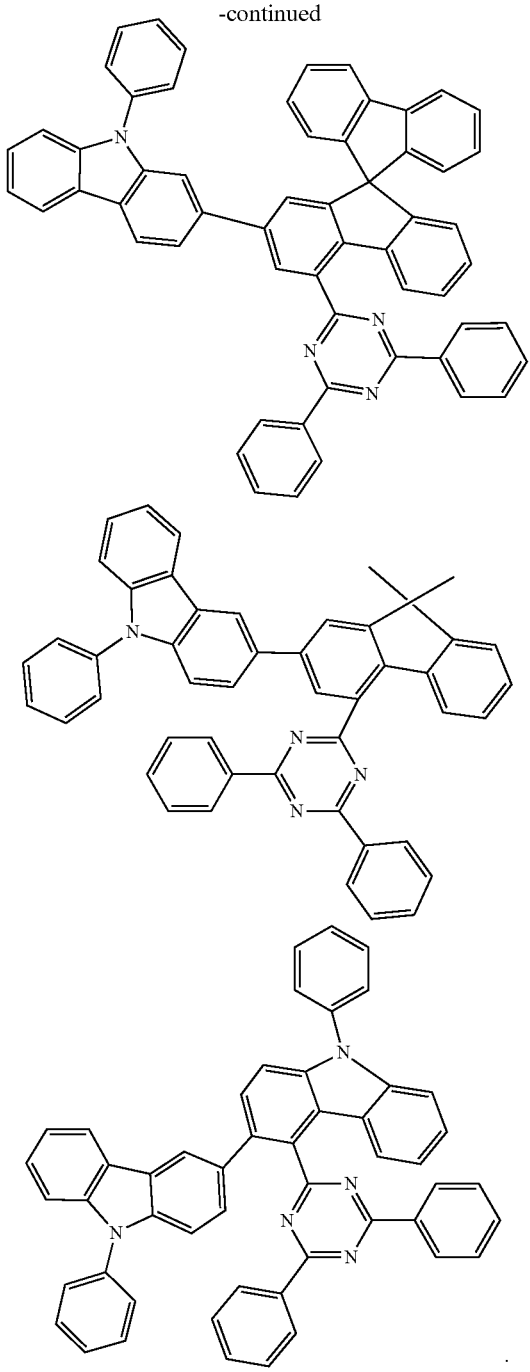

10. An organic electroluminescent device comprising the mixture according to claim 1.
11. An organic electroluminescent device comprising the mixture according to claim 8.
12. An organic electroluminescent device comprising the mixture according to claim 9.
13. An organic electroluminescent device comprising the mixture according to claim 1 wherein the mixture is employed in an emitting layer, in combination with a phosphorescent dopant.
14. An organic electroluminescent device comprising the mixture according to claim 8 wherein the mixture is employed in an emitting layer, in combination with a phosphorescent dopant.
15. An organic electroluminescent device comprising the mixture according g to claim 9 wherein the mixture is employed in an emitting layer, in combination with a phosphorescent dopant.
16. A mixture comprising at least one compound of the formula (2a),

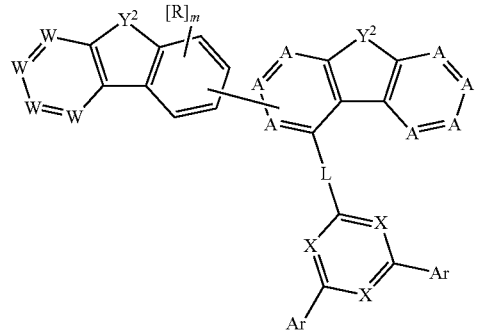

formula (2a)

where the following applies to the symbols and indices used:

A is on each occurrence, identically or differently, CR or N, where a maximum of two groups A per ring stand for N and where A stands for C if the group comprising $Y^2$ is bonded at this position;

W is on each occurrence, identically or differently, CR or N, where a maximum of two groups W stand for N, or two adjacent groups W together stand for a group of the following formula (3), where the compound of the formula (1a) contains a maximum of one group of the formula (3),

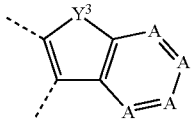

formula (3)

X is on each occurrence, identically or differently, CR or N, with the proviso that at least one group X stands for N;

Ar is on each occurrence, identically or differently, an aromatic or heteroaromatic ring system having 5 to 30 aromatic ring atoms, which may be substituted by one or more radicals R;

$Y^1$ is NR, S or $CR^2$, where the radical R which is bonded to N is not equal to H;

$Y^2$, $Y^3$ are on each occurrence, identically or differently, O, NR, S or $CR^2$, where the radical R which is bonded to N is not equal to H;

L is on each occurrence, identically or differently, a single bond or an aromatic ring system having 5 to 30 aromatic ring atoms, which may be substituted by one or more radicals R;

R is selected on each occurrence, identically or differently, from the group consisting of H, D, F, Cl, Br, I, CN, $NO_2$, $N(Ar^1)_2$, $N(R^1)_2$, $C(=O)Ar^1$, $C(=O)R^1$, $P(=O)(Ar^1)_2$, $P(Ar^1)_2$, $B(Ar^1)_2$, $Si(Ar^1)_3$, $Si(R^1)_3$, a straight-chain alkyl, alkoxy or thioalkyl group having 1 to 20 C atoms or a branched or cyclic alkyl, alkoxy or thioalkyl group having 3 to 20 C atoms or an alkenyl group having 2 to 20 C atoms, each of which may be substituted by one or more radicals $R^1$, where one or more non-adjacent $CH_2$ groups may be replaced by $R^1C$=$CR^1$, $Si(R^1)_2$, C=O, C=S, C=NR, P(=O)($R^1$), SO, $SO^2$, $NR^1$, O, S or $CONR^1$ and where one or more H atoms may be replaced by D, F, Cl, Br, I, CN or $NO_2$, an aromatic or heteroaromatic ring system having 5 to 40 aromatic ring atoms, which may in each case be substituted by one or more radicals $R^1$, an aryloxy or heteroaryloxy group having 5 to 40 aromatic ring atoms, which may be substituted by one or more radicals $R^1$, or an aralkyl or heteroaralkyl group having 5 to 40 aromatic ring atoms, which may be substituted by one or more radicals $R^1$; two substituents R which are bonded to the same carbon atom or to adjacent carbon atoms may optionally form a monocyclic or polycyclic, aliphatic, aromatic or heteroaromatic ring system here, which may be substituted by one or more radicals $R^1$;

$Ar^1$ is on each occurrence, identically or differently, an aromatic or heteroaromatic ring system having 5 to 30 aromatic ring atoms, which may be substituted by one or more non-aromatic radicals $R^1$; two radicals AO which are bonded to the same N atom, P atom or B atom may also be bridged to one another here by a single bond or a bridge selected from $N(R^1)$, $C(R^1)_2$, O or S;

m is 0, 1, 2 or 3;

$R^1$ is selected on each occurrence, identically or differently, from the group consisting of H, D, F, CN, an aliphatic hydrocarbon radical having t to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbatoms; two or more adjacent substituents $R^1$ may form a mono- or polycyclic, aliphatic ring system with one another here;

and at least one further compound, wherein the further compound is a matrix material.

\* \* \* \* \*